(12) United States Patent
Kirby et al.

(10) Patent No.: US 10,470,947 B2
(45) Date of Patent: *Nov. 12, 2019

(54) ABSORBENT ARTICLE WITH A FLUID-ENTANGLED BODY FACING MATERIAL INCLUDING A PLURALITY OF HOLLOW PROJECTIONS

(71) Applicant: KIMBERLY-CLARK WORLDWIDE, INC., Neenah, WI (US)

(72) Inventors: Scott S.C. Kirby, Wahroonga (AU); David Glen Biggs, Neenah, WI (US); Andrew Thomas Hammond, Appleton, WI (US); Eric Donald Johnson, Larsen, WI (US); Candace Dyan Krautkramer, Neenah, WI (US); Robert Lee Popp, Greenville, WI (US); Leila Joy Roberson, Kimberly, WI (US); Daniel Robert Schlinz, Greenville, WI (US); Kendell Jean Williams, Greenville, WI (US); Niall Finn, Lethbridge (AU); Andy R. Butler, Albert Park (AU)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 310 days.

This patent is subject to a terminal disclaimer.

(21) Appl. No.: 15/377,039

(22) Filed: Dec. 13, 2016

(65) Prior Publication Data

US 2017/0112684 A1    Apr. 27, 2017

Related U.S. Application Data

(63) Continuation of application No. 15/232,849, filed on Aug. 10, 2016, which is a continuation of application
(Continued)

(51) Int. Cl.
*A61F 13/512* (2006.01)
*A61F 13/511* (2006.01)
(Continued)

(52) U.S. Cl.
CPC ...... *A61F 13/5125* (2013.01); *A61F 13/5116* (2013.01); *A61F 13/51108* (2013.01);
(Continued)

(58) Field of Classification Search
CPC .......... A61F 13/51104; A61F 13/51108; A61F 13/5116; A61F 13/5123; A61F 13/5125;
(Continued)

(56) References Cited

U.S. PATENT DOCUMENTS 3,485,706 A    12/1969    Evans
3,717,532 A     2/1973    Kamp
(Continued)

FOREIGN PATENT DOCUMENTS

CN    1299258 A    6/2001
CN    1735394 A    2/2006
(Continued)

OTHER PUBLICATIONS

Beaumont, Donald F. and Dr. Kenneth R. Randall, "Rotary Hydraulic Entanglement of Nonwovens," Nonwovens World, vol. 1, No. 3, Nov. 1986, pp. 76-80, reprinted from Insight 86 International Advanced Forming/Bonding Conference.

*Primary Examiner* — Kathryn E Ditmer
(74) *Attorney, Agent, or Firm* — Kimberly-Clark Worldwide, Inc.

(57) ABSTRACT

An absorbent article having improved handling of body exudates. The absorbent article can minimize the amount of
(Continued)

body exudates in contact with a wearer's skin and can minimize the incidence of leakage of body exudates from the absorbent article.

17 Claims, 47 Drawing Sheets

Related U.S. Application Data

No. 13/665,812, filed on Oct. 31, 2012, now Pat. No. 9,474,660.

(51) Int. Cl.
*A61F 13/53* (2006.01)
*A61F 13/51* (2006.01)

(52) U.S. Cl.
CPC .............. *A61F 2013/51014* (2013.01); *A61F 2013/51178* (2013.01); *A61F 2013/5307* (2013.01)

(58) Field of Classification Search
CPC .......... A61F 13/537; A61F 2013/51015; A61F 2013/51178; A61F 2013/5307
See application file for complete search history.

(56) References Cited

U.S. PATENT DOCUMENTS

| | | |
|---|---|---|
| 3,766,922 A | 10/1973 | Krusko |
| 3,855,046 A | 12/1974 | Hansen et al. |
| 4,041,951 A | 8/1977 | Sanford |
| 4,202,868 A | 5/1980 | Hayashi et al. |
| 4,333,979 A | 6/1982 | Sciaraffa et al. |
| 4,614,679 A | 9/1986 | Farrington, Jr. et al. |
| 4,673,402 A | 6/1987 | Weisman et al. |
| 4,704,112 A | 11/1987 | Suzuki et al. |
| 4,718,152 A | 1/1988 | Suzuki et al. |
| 4,741,941 A | 5/1988 | Englebert et al. |
| 4,780,352 A | 10/1988 | Palumbo |
| 4,781,710 A | 11/1988 | Megison et al. |
| 4,805,275 A | 2/1989 | Suzuki et al. |
| 4,868,958 A | 9/1989 | Suzuki et al. |
| 4,879,170 A | 11/1989 | Radwanski et al. |
| 4,931,355 A | 6/1990 | Radwanski et al. |
| 4,939,016 A | 7/1990 | Radwanski et al. |
| 4,950,531 A | 8/1990 | Radwanski et al. |
| 4,970,104 A | 11/1990 | Radwanski |
| 5,019,062 A | 5/1991 | Ryan et al. |
| 5,137,600 A | 8/1992 | Barnes et al. |
| 5,144,729 A | 9/1992 | Austin et al. |
| 5,180,620 A | 1/1993 | Mende |
| 5,242,632 A | 9/1993 | Mende |
| 5,301,401 A | 4/1994 | Suzuki et al. |
| 5,369,858 A | 12/1994 | Gilmore et al. |
| 5,389,202 A | 2/1995 | Everhart et al. |
| 5,407,439 A | 4/1995 | Goulait |
| 5,500,270 A | 3/1996 | Langdon et al. |
| 5,505,720 A | 4/1996 | Hujber et al. |
| 5,527,300 A | 6/1996 | Sauer |
| 5,575,874 A | 11/1996 | Griesbach, III et al. |
| 5,614,281 A | 3/1997 | Jackson et al. |
| 5,624,427 A | 4/1997 | Bergman et al. |
| 5,656,232 A | 8/1997 | Takai et al. |
| 5,858,515 A | 1/1999 | Stokes et al. |
| 5,888,607 A | 3/1999 | Seth et al. |
| 5,906,879 A | 5/1999 | Huntoon et al. |
| 5,928,212 A | 7/1999 | Kline et al. |
| 5,962,112 A | 10/1999 | Haynes et al. |
| 5,990,377 A | 11/1999 | Chen et al. |
| 5,997,981 A | 12/1999 | McCormack et al. |
| 6,022,818 A | 2/2000 | Welchel et al. |
| 6,176,954 B1 | 1/2001 | Tsuji et al. |
| 6,192,556 B1 | 2/2001 | Kikko et al. |
| 6,222,092 B1 | 4/2001 | Hansen et al. |
| 6,228,216 B1 | 5/2001 | Lindsay et al. |
| 6,241,714 B1 | 6/2001 | Raidel et al. |
| 6,242,074 B1 | 6/2001 | Thomas |
| 6,290,685 B1 | 9/2001 | Insley et al. |
| 6,291,050 B1 | 9/2001 | Cree et al. |
| 6,316,687 B1 | 11/2001 | Davis et al. |
| 6,319,455 B1 | 11/2001 | Kauschke et al. |
| 6,331,268 B1 | 12/2001 | Kauschke et al. |
| 6,331,345 B1 | 12/2001 | Kauschke et al. |
| 6,395,957 B1 | 5/2002 | Chen et al. |
| 6,413,344 B2 | 7/2002 | Bodaghi |
| 6,417,427 B1 | 7/2002 | Roxendal et al. |
| 6,436,512 B1 | 8/2002 | Kauschke et al. |
| 6,440,114 B1 | 8/2002 | Bast et al. |
| 6,468,626 B1 | 10/2002 | Takai et al. |
| 6,488,801 B1 | 12/2002 | Bodaghi et al. |
| 6,502,288 B2 | 1/2003 | Black et al. |
| 6,521,555 B1 | 2/2003 | Bodaghi et al. |
| 6,610,173 B1 | 8/2003 | Lindsay et al. |
| 6,610,904 B1 | 8/2003 | Thomas et al. |
| 6,660,362 B1 | 12/2003 | Lindsay et al. |
| 6,689,242 B2 | 2/2004 | Bodaghi |
| 6,725,512 B2 | 4/2004 | Carter |
| 6,733,610 B2 | 5/2004 | Mizutani et al. |
| 6,802,932 B2 | 10/2004 | Kudo et al. |
| 6,822,134 B1 | 11/2004 | Stiehl et al. |
| 6,838,591 B2 | 1/2005 | Waksmundzki et al. |
| 6,888,046 B2 | 5/2005 | Toyoshima et al. |
| 6,911,573 B2 | 6/2005 | Chen et al. |
| 6,911,574 B1 | 6/2005 | Mizutani |
| 6,936,038 B2 | 8/2005 | Tears et al. |
| 6,936,333 B2 | 8/2005 | Shizuno et al. |
| 6,955,847 B1 | 10/2005 | Itou et al. |
| 6,998,017 B2 | 2/2006 | Lindsay et al. |
| 7,105,716 B2 | 9/2006 | Baratian et al. |
| 7,132,585 B2 | 11/2006 | Kudo et al. |
| 7,172,801 B2 | 2/2007 | Hoying et al. |
| 7,194,788 B2 | 3/2007 | Clark et al. |
| 7,267,860 B2 | 9/2007 | Toyoshima et al. |
| 7,294,387 B2 | 11/2007 | Wildeman |
| 7,303,805 B2 | 12/2007 | Seth et al. |
| 7,303,808 B2 | 12/2007 | Taneichi et al. |
| 7,410,683 B2 | 8/2008 | Curro et al. |
| 7,468,114 B2 | 12/2008 | Sato et al. |
| 7,507,463 B2 | 3/2009 | Noda et al. |
| 7,518,032 B2 | 4/2009 | Seyler |
| 7,534,928 B2 | 5/2009 | Sakamoto et al. |
| 7,547,469 B2 | 6/2009 | Provost et al. |
| 7,553,532 B2 | 6/2009 | Turner et al. |
| 7,553,535 B2 | 6/2009 | Noda et al. |
| 7,569,264 B2 | 8/2009 | Toyoshima et al. |
| 7,589,251 B2 | 9/2009 | Roe |
| 7,632,258 B2 | 12/2009 | Misek et al. |
| 7,648,752 B2 | 1/2010 | Hoying et al. |
| 7,662,462 B2 | 2/2010 | Noda et al. |
| 7,678,442 B2 | 3/2010 | Casey et al. |
| 7,682,686 B2 | 3/2010 | Curro et al. |
| 7,686,921 B2 | 3/2010 | Hamed et al. |
| 7,687,681 B2 | 3/2010 | Di Luccio et al. |
| 7,717,150 B2 | 5/2010 | Manabe et al. |
| 7,718,243 B2 | 5/2010 | Curro et al. |
| 7,718,249 B2 | 5/2010 | Russell et al. |
| 7,815,995 B2 | 10/2010 | Clark et al. |
| 7,829,173 B2 | 11/2010 | Turner et al. |
| 7,838,099 B2 | 11/2010 | Curro et al. |
| 7,851,047 B2 | 12/2010 | Sato et al. |
| 7,855,314 B2 | 12/2010 | Hanao et al. |
| 7,884,259 B2 | 2/2011 | Hanao et al. |
| 7,897,240 B2 | 3/2011 | Noda et al. |
| 7,935,861 B2 | 5/2011 | Suzuki |
| 7,942,992 B2 | 5/2011 | Saka et al. |
| 7,954,213 B2 | 6/2011 | Mizutani et al. |
| 7,955,549 B2 | 6/2011 | Noda et al. |
| 7,972,985 B2 | 7/2011 | Hirose et al. |
| 7,981,822 B2 | 7/2011 | Lester, Jr. et al. |
| 7,993,317 B2 | 8/2011 | Hammons et al. |
| 8,075,977 B2 | 12/2011 | Curro et al. |
| 8,105,526 B2 | 1/2012 | Stone et al. |

(56) References Cited

U.S. PATENT DOCUMENTS

| | | | |
|---|---|---|---|
| 8,143,177 B2 | 3/2012 | Noda et al. | |
| 8,153,225 B2 | 4/2012 | Turner et al. | |
| 8,183,431 B2 | 5/2012 | Noda et al. | |
| 8,206,628 B2 | 6/2012 | Stone et al. | |
| 8,235,959 B2 | 8/2012 | Ponomarenko et al. | |
| 8,304,600 B2 | 11/2012 | Noda et al. | |
| 8,393,374 B2 | 3/2013 | Sato et al. | |
| 8,450,557 B2 | 5/2013 | Nishitani et al. | |
| 8,617,449 B2 | 12/2013 | Baker et al. | |
| 8,722,173 B2 | 5/2014 | Oba et al. | |
| 8,748,692 B2 | 6/2014 | Suzuki | |
| 8,765,250 B2 | 7/2014 | Seyler et al. | |
| 9,327,473 B2 | 5/2016 | Finn et al. | |
| 9,474,660 B2 | 10/2016 | Kirby et al. | |
| 9,480,609 B2 | 11/2016 | Kirby et al. | |
| 2001/0027302 A1 | 10/2001 | Glaug et al. | |
| 2002/0034914 A1* | 3/2002 | De Leon | A61F 13/534 |
| | | | 442/384 |
| 2002/0132544 A1 | 9/2002 | Takagaki | |
| 2002/0143311 A1 | 10/2002 | Brisebois | |
| 2003/0003832 A1 | 1/2003 | Childs et al. | |
| 2003/0119410 A1 | 6/2003 | Bodaghi | |
| 2003/0162460 A1 | 8/2003 | Saka et al. | |
| 2003/0181882 A1 | 9/2003 | Toyoshima et al. | |
| 2003/0203162 A1 | 10/2003 | Fenwick et al. | |
| 2003/0211802 A1 | 11/2003 | Keck et al. | |
| 2004/0020579 A1 | 2/2004 | Durrance et al. | |
| 2004/0058607 A1 | 3/2004 | Bodaghi | |
| 2004/0102124 A1 | 5/2004 | Suzuki | |
| 2005/0244619 A1 | 11/2005 | Kauschke et al. | |
| 2005/0261649 A1 | 11/2005 | Cohen | |
| 2005/0261653 A1 | 11/2005 | Digiacomantonio et al. | |
| 2006/0058772 A1 | 3/2006 | Karami | |
| 2006/0069380 A1 | 3/2006 | Chen et al. | |
| 2006/0122572 A1 | 6/2006 | Suarez | |
| 2006/0141217 A1 | 6/2006 | Ellis et al. | |
| 2006/0241558 A1 | 10/2006 | Ramshak | |
| 2007/0020440 A1* | 1/2007 | Wong | A47L 13/16 |
| | | | 428/178 |
| 2007/0026753 A1 | 2/2007 | Neely et al. | |
| 2007/0128411 A1 | 6/2007 | Kawai et al. | |
| 2007/0130713 A1 | 6/2007 | Chen et al. | |
| 2007/0172628 A1 | 7/2007 | Ausen et al. | |
| 2007/0255247 A1 | 11/2007 | Moberg-Alehammar et al. | |
| 2008/0015531 A1 | 1/2008 | Hird et al. | |
| 2008/0085399 A1* | 4/2008 | Noda | B32B 3/30 |
| | | | 428/167 |
| 2008/0108962 A1 | 5/2008 | Furuta et al. | |
| 2008/0172018 A1 | 7/2008 | Chien | |
| 2008/0256768 A1 | 10/2008 | Lampila et al. | |
| 2008/0275415 A1 | 11/2008 | Wheeler et al. | |
| 2008/0300562 A1 | 12/2008 | Ahoniemi et al. | |
| 2009/0030391 A1 | 1/2009 | Hammons et al. | |
| 2009/0221979 A1 | 9/2009 | Huang et al. | |
| 2009/0247977 A1 | 10/2009 | Takeuchi et al. | |
| 2009/0264851 A1 | 10/2009 | Richlen et al. | |
| 2010/0108554 A1 | 5/2010 | Melius et al. | |
| 2010/0209664 A1 | 8/2010 | Sato et al. | |
| 2010/0249740 A1 | 9/2010 | Miyamoto et al. | |
| 2010/0274208 A1* | 10/2010 | Gabrielii | A61F 13/51108 |
| | | | 604/367 |
| 2010/0312211 A1 | 12/2010 | Bond et al. | |
| 2011/0042011 A1 | 2/2011 | Sato et al. | |
| 2011/0151196 A1 | 6/2011 | Schmidt et al. | |
| 2011/0250816 A1 | 10/2011 | Fujiwara et al. | |
| 2012/0059343 A1 | 3/2012 | Kume et al. | |
| 2012/0111483 A1 | 5/2012 | Schneider et al. | |
| 2012/0141742 A1 | 6/2012 | Yamaguchi et al. | |
| 2012/0171408 A1 | 7/2012 | Turner et al. | |
| 2012/0177886 A1 | 7/2012 | Kanya et al. | |
| 2012/0179125 A1 | 7/2012 | Kanya et al. | |
| 2012/0179126 A1 | 7/2012 | Kanya et al. | |
| 2012/0189814 A1 | 7/2012 | Coslett et al. | |
| 2012/0226250 A1 | 9/2012 | Sato et al. | |
| 2012/0310197 A1 | 12/2012 | Thomas | |
| 2012/0330260 A1 | 12/2012 | Bishop et al. | |
| 2013/0034686 A1 | 2/2013 | Mitsuno | |
| 2013/0178811 A1 | 7/2013 | Kikuchi et al. | |
| 2013/0178815 A1 | 7/2013 | Ohashi et al. | |
| 2013/0211358 A1 | 8/2013 | Kikkawa et al. | |
| 2014/0121625 A1 | 5/2014 | Kirby et al. | |

FOREIGN PATENT DOCUMENTS

| | | | |
|---|---|---|---|
| CN | 1937983 A | 3/2007 | |
| CN | 105188630 A | 12/2015 | |
| EP | 0341993 A1 | 11/1989 | |
| EP | 0418954 A2 | 3/1991 | |
| EP | 0432882 A2 | 6/1991 | |
| EP | 0687169 B1 | 11/1999 | |
| EP | 1190690 A2 | 3/2002 | |
| EP | 0863734 B1 | 6/2002 | |
| EP | 1059908 B1 | 10/2004 | |
| EP | 1207829 B1 | 8/2006 | |
| EP | 2157223 A1 | 2/2010 | |
| EP | 1902168 B1 | 7/2010 | |
| EP | 1803429 B1 | 12/2011 | |
| EP | 2159043 B1 | 6/2012 | |
| GB | 1088376 A | 10/1967 | |
| GB | 1395402 A | 5/1975 | |
| JP | 08-109564 A | 4/1996 | |
| JP | 2000-023715 A | 1/2000 | |
| JP | 3181195 B2 | 7/2001 | |
| JP | 2002-173863 A | 6/2002 | |
| JP | 3408078 B2 | 5/2003 | |
| JP | 3453031 B2 | 10/2003 | |
| JP | 2004-113489 A | 4/2004 | |
| JP | 2004-121701 A | 4/2004 | |
| JP | 2005-312547 A | 11/2005 | |
| JP | 2005-334374 A | 12/2005 | |
| JP | 3989476 B2 | 10/2007 | |
| JP | 3989477 B2 | 10/2007 | |
| JP | 2008-148807 A | 7/2008 | |
| JP | 2008-161302 A | 7/2008 | |
| JP | 2008-161319 A | 7/2008 | |
| JP | 2009-153556 A | 7/2009 | |
| JP | 4301999 B2 | 7/2009 | |
| JP | 2010-024573 A | 2/2010 | |
| JP | 2010-115352 A | 5/2010 | |
| JP | 2010-133071 A | 6/2010 | |
| JP | 4566109 B2 | 10/2010 | |
| JP | 4627014 B2 | 2/2011 | |
| JP | 4889273 B2 | 3/2012 | |
| JP | 5074301 B2 | 11/2012 | |
| JP | 5086035 B2 | 11/2012 | |
| JP | 5087419 B2 | 12/2012 | |
| WO | WO 1990/004066 A2 | 4/1990 | |
| WO | WO 1991/011161 A1 | 8/1991 | |
| WO | WO 1998/052458 A1 | 11/1998 | |
| WO | WO 1999/055532 A1 | 11/1999 | |
| WO | WO 2004/059061 A1 | 7/2004 | |
| WO | WO 2005/007952 A2 | 1/2005 | |
| WO | WO-2005007962 A1 * | 1/2005 | ......... A61F 13/5323 |
| WO | WO 2005/065606 A1 | 7/2005 | |
| WO | WO 2006/007307 A1 | 1/2006 | |
| WO | WO 2006/007340 A1 | 1/2006 | |
| WO | WO 2006/011724 A1 | 2/2006 | |
| WO | WO 2010/074205 A1 | 7/2010 | |
| WO | WO 2012/024576 A1 | 2/2012 | |
| WO | WO 2013/047890 A1 | 4/2013 | |
| WO | WO 2013/099624 A1 | 7/2013 | |

* cited by examiner

US 10,470,947 B2

ABSORBENT ARTICLE WITH A FLUID-ENTANGLED BODY FACING MATERIAL INCLUDING A PLURALITY OF HOLLOW PROJECTIONS

CROSS-REFERENCE TO RELATED APPLICATIONS

The present application is a continuation application and claims priority to U.S. patent application Ser. No. 15/232,849 filed, Aug. 10, 2016, which is a continuation application of and claims priority to U.S. patent application Ser. No. 13/665,812, filed Oct. 31, 2012, the contents of which are incorporated herein in their entirety for all purposes.

BACKGROUND

A primary function of personal care absorbent articles is to absorb and retain body exudates such as urine, fecal material, blood, and menses with additional desired attributes including low leakage of the exudates from the absorbent article and a dry feel to the wearer of the absorbent article. To accomplish these tasks, personal care absorbent articles generally have an absorbent core and a cover enclosing the absorbent core. The cover is usually fluid pervious on the body facing side of the absorbent core and fluid impervious on the garment facing side of the absorbent core. Absorbent articles commonly fail, however, to prevent leakage of body exudates. Some body exudates, such as solid and semi-solid fecal material and menses, have difficulty penetrating the body facing material of the absorbent article as easily as low viscosity exudates, such as urine, and tend to spread across the surface of the body facing material. Such spread of body exudates can result in leakage of the body exudates from the absorbent article.

Semi-solid fecal material, such as low viscosity fecal material which can be prevalent with younger children, and menses can be especially difficult to contain in an absorbent article. These exudates can move around on the body facing material of an absorbent article under the influence of gravity, motion, and pressure by the wearer of the absorbent article. The migration of the exudates is often towards the perimeter of the absorbent article, increasing the likelihood of leakage and smears against the skin of the wearer which can make clean-up of the skin difficult.

Attempts have been made in the past to provide body facing material to an absorbent article that can solve the problems described above. One such approach has been the use of various types of embossing to create three-dimensionality in the body facing surface of the absorbent article. This approach, however, requires high basis weight material to create a structure with significant topography. Furthermore, it is inherent in the embossing process that starting thickness of the material is lost due to the fact that embossing is, by its nature, a crushing and bonding process. Additionally, to "set" the embossments in a nonwoven fabric, the densified section is typically fused to create weld points that are typically impervious to the passage of body exudates. Hence, a part of the area for body exudates to transit through the material is lost. Also, "setting" the fabric can cause the material to stiffen and become harsh to the touch.

Another approach has been to form fibrous webs on three-dimensional forming surfaces. The resulting structures typically have little resilience at low basis weights (assuming soft fibers with desirable aesthetic attributes are used) and the topography is significantly degraded when wound on a roll and put through subsequent converting processes. This is partly addressed in the three-dimensional forming process by allowing the three-dimensional shape to fill with fiber. This, however, typically comes at a higher cost due to the usage of more material. This also results in a loss of softness and the resultant material becomes aesthetically unappealing for certain applications.

Another approach has been to aperture a fibrous web. Depending on the process, this can generate a flat two-dimensional web or a web with some three-dimensionality where the displaced fiber is pushed out of the plane of the original web. Typically, the extent of the three-dimensionality is limited and, under sufficient load, the displaced fiber may be pushed back toward its original position resulting in at least partial closure of the aperture. Aperturing processes that attempt to "set" the displaced fiber outside the plane of the original web are also prone to degrading the softness of the starting web. Another problem with apertured materials is that when they are incorporated into end products such as with the use of adhesives, due to their open structure, the adhesives will often readily penetrate through the apertures in the material from its underside to its top, exposed surface, thereby creating unwanted issues such as adhesive build-up in the converting process or creating unintended bonds between layers within the finished product.

There remains a need for an absorbent article that can adequately reduce the incidence of leakage of body exudates from the absorbent article. There remains a need for an absorbent article which can provide improved handling of body exudates. There remains a need for an absorbent article that can minimize the amount of body exudates in contact with the wearer's skin. There remains a need for an absorbent article that can provide physical and emotional comfort to the wearer of the absorbent article.

SUMMARY

In an embodiment, an absorbent article can have an outer cover, an absorbent body, and a body facing material. In such an embodiment, the body facing material can have a support layer and a projection layer. In such an embodiment, the projection layer can have an inner and an outer surface and can have a plurality of hollow projections extending from the outer surface of the projection layer. In various embodiments, the body facing material of the absorbent article can further include a land area with greater than about 1% open area within a chosen area of the body facing material, projections with less than about 1% open area within a chosen area of the body facing material, a plurality of fibers of the projection layer entangled with the support layer, a load of more than about 2 Newtons per 25 mm width at 10% extension in the machine direction, projections having a height greater than about 1 mm, a resiliency of greater than about 70%, and combinations thereof. In various embodiments, the absorbent article can further include a secondary liner positioned between the body facing material and the absorbent body. In various embodiments, the absorbent body can be free from superabsorbent material. In various embodiments, the absorbent body can have greater than about 15% superabsorbent material. In various embodiments, the open area of the projections can be due to interstitial fiber-to-fiber spacing. In various embodiments, the open area of the land area can be due to interstitial fiber-to-fiber spacing.

In an embodiment, an absorbent article can have an outer cover, an absorbent body, a body facing material and a secondary liner positioned between the body facing material and the absorbent body. In such an embodiment, body facing material can have a support layer and a projection layer. In such an embodiment, the projection layer can have an inner and an outer surface and can have a plurality of hollow projections extending from the outer surface of the projection layer. In various embodiments, the body facing material of the absorbent article can further include a land area with greater than about 1% open area within a chosen area of the body facing material, projections with less than about 1% open area within a chosen area of the body facing material, a plurality of fibers of the projection layer entangled with the support layer, a load of more than about 2 Newtons per 25 mm width at 10% extension in the machine direction, projections having a height greater than about 1 mm, a resiliency of greater than about 70%, and combinations thereof. In various embodiments, the absorbent body can be free from superabsorbent material. In various embodiments, the absorbent body can have greater than about 15% superabsorbent material. In various embodiments, the open area of the projections can be due to interstitial fiber-to-fiber spacing. In various embodiments, the open area of the land areas can be due to interstitial fiber-to-fiber spacing.

In an embodiment, an absorbent article can have an outer cover, an absorbent body, and a body facing material. In such an embodiment, the body facing material can have a support layer and a projection layer. In such an embodiment, the projection layer can have an inner and an outer surface and can have a plurality of hollow projections extending from the outer surface of the projection layer. In such an embodiment, the body facing material can further have a load of more than about 2 Newtons per 25 mm width at 10% extension in the machine direction. In various embodiments, the body facing material of the absorbent article can further include a land area with greater than about 1% open area within a chosen area of the body facing material, projections with less than about 1% open area within a chosen area of the body facing material, a plurality of fibers of the projection layer entangled with the support layer, projections having a height greater than about 1 mm, a resiliency of greater than about 70%, and combinations thereof. In various embodiments, the absorbent article can further include a secondary liner positioned between the body facing material and the absorbent body. In various embodiments, the absorbent body can be free from superabsorbent material. In various embodiments, the absorbent body can have greater than about 15% superabsorbent material. In various embodiments, the open area of the projections can be due to interstitial fiber-to-fiber spacing. In various embodiments, the open area of the land areas can be due to interstitial fiber-to-fiber spacing.

In an embodiment, an absorbent article can have an outer cover, an absorbent body, and a body facing material. In such an embodiment, the body facing material can have a support layer and a projection layer. In such an embodiment, the projection layer can have an inner and an outer surface and can have a plurality of hollow projections extending from the outer surface of the projection layer. In such an embodiment, the body facing material can have a resiliency greater than about 70%. In various embodiments, the body facing material of the absorbent article can further include a land area with greater than about 1% open area within a chosen area of the body facing material, projections with less than about 1% open area within a chosen area of the body facing material, a plurality of fibers of the projection layer entangled with the support layer, a load of more than about 2 Newtons per 25 mm width at 10% extension in the machine direction, projections 9 having a height greater than about 1 mm, and combinations thereof. In various embodiments, the absorbent article can further include a secondary liner positioned between the body facing material and the absorbent body. In various embodiments, the absorbent body can be free from superabsorbent material. In various embodiments, the absorbent body can have greater than about 15% superabsorbent material. In various embodiments, the open area of the projections can be due to interstitial fiber-to-fiber spacing. In various embodiments, the open area of the land areas can be due to interstitial fiber-to-fiber spacing.

DETAILED DESCRIPTION

Figure 1:
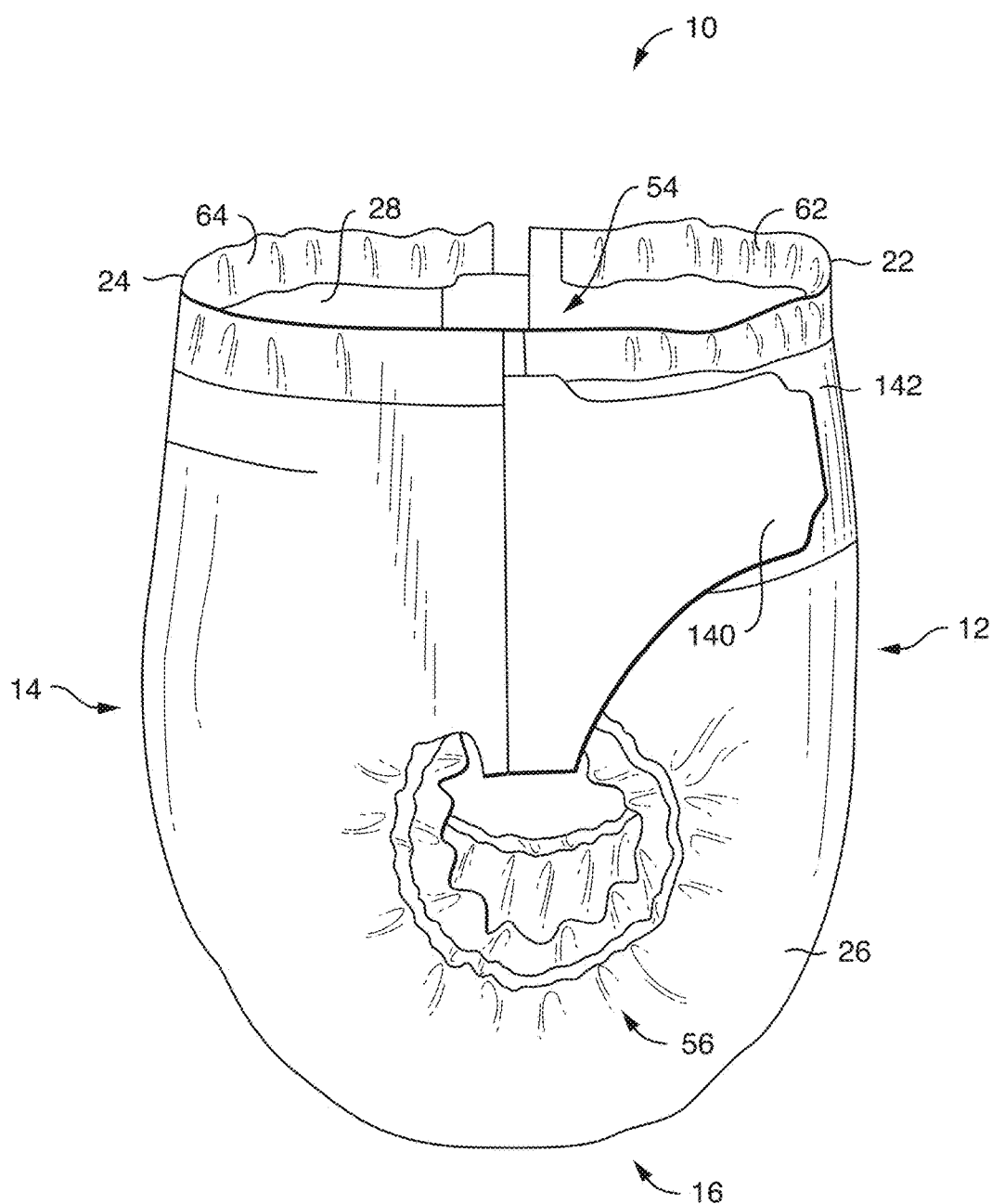
FIG. 1 is a side view illustration of an embodiment of an absorbent article.

In an embodiment, the present disclosure is generally directed towards an absorbent article which can have improved management of body exudates. In an embodiment, the present disclosure is generally directed towards an absorbent article having a body facing material which can have hollow projections extending from a surface of the body facing material. Without being bound by theory, it is believed that multiple attributes can be achieved by providing hollow projections to the body facing material. First, by providing a body facing material with hollow projections, the body facing material can have a higher degree of thickness while minimizing the amount of material used. Increased body facing material thickness can enhance the separation of the skin of the wearer from the absorbent body of an absorbent article, thereby improving the prospect of drier skin. By providing projections, land areas can be created between the projections which can temporarily distance body exudates from the high points of the projections while the body exudates can be absorbed by the absorbent article. Providing projections, therefore, can reduce skin contact with the body exudates and provide better skin benefits. Secondly, by providing projections, the spread of the body exudates on the body facing material of the absorbent article can be reduced thereby exposing less skin to contamination. Thirdly, by reducing overall skin contact, a body facing material with projections can provide a softer feel to the contacted skin thereby enhancing the tactile aesthetics of the body facing material and the absorbent article. Fourthly, when materials with projections are utilized as a body facing material for an absorbent article, the body facing material can also serve the function of acting as a cleaning aid when the absorbent article is removed from the wearer.

Definitions

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, training pants, youth pants, swim pants, feminine hygiene products, including, but not limited to, menstrual pads, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" refers herein to the joining, adhering, connecting, attaching, or the like, of two elements. Two elements will be considered bonded together when they are joined, adhered, connected, attached, or the like, directly to one another or indirectly to one another, such as when each is directly bonded to intermediate elements.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "fluid entangling" and "fluid entangled" refers herein to a formation process for further increasing the degree of fiber entanglement within a given fibrous nonwoven web or between fibrous nonwoven webs and other materials so as to make the separation of the individual fibers and/or the layers more difficult as a result of the entanglement. Generally this is accomplished by supporting the fibrous nonwoven web on some type of forming or carrier surface which has at least some degree of permeability to the impinging pressurized fluid. A pressurized fluid stream (usually multiple streams) can then be directed against the surface of the nonwoven web which is opposite the supported surface of the web. The pressurized fluid contacts the fibers and forces portions of the fibers in the direction of the fluid flow thus displacing all or a portion of a plurality of the fibers towards the supported surface of the web. The result is a further entanglement of the fibers in what can be termed the Z-direction of the web (its thickness) relative to its more planar dimension, its X-Y plane. When two or more separate webs or other layers are placed adjacent one another on the forming/carrier surface and subjected to the pressurized fluid, the generally desired result is that some of the fibers of at least one of the webs are forced into the adjacent web or layer thereby causing fiber entanglement between the interfaces of the two surfaces so as to result in the bonding or joining of the webs/layers together due to the increased entanglement of the fibers. The degree of bonding or entanglement will depend on a number of factors including, but not limited to, the types of fibers being used, the fiber lengths, the degree of pre-bonding or entanglement of the web or webs prior to subjection to the fluid entangling process, the type of fluid being used (liquids, such as water, steam or gases, such as air), the pressure of the fluid, the number of fluid streams, the speed of the process, the dwell time of the fluid and the porosity of the web or webs/other layers and the forming/carrier surface. One of the most common fluid entangling processes is referred to as hydroentangling which is a well-known process to those of ordinary skill in the art of nonwoven webs. Examples of fluid entangling process can be found in U.S. Pat. No. 4,939,016 to Radwanski et al., U.S. Pat. No. 3,485,706 to Evans, and U.S. Pat. Nos. 4,970,104 and 4,959,531 to Radwanski, each of which is incorporated herein in its entirety by reference thereto for all purposes.

The term "g/cc" refers herein to grams per cubic centimeter.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

Absorbent Article:

Referring to FIG. 1, a disposable absorbent article 10 of the present disclosure is exemplified in the form of a diaper. It is to be understood that the present disclosure is suitable for use with various other personal care absorbent articles, such as, for example, feminine hygiene products, without departing from the scope of the present disclosure. While the embodiments and illustrations described herein may generally apply to absorbent articles manufactured in the product longitudinal direction, which is hereinafter called the machine direction manufacturing of a product, it should be noted that one of ordinary skill could apply the information herein to absorbent articles manufactured in the latitudinal direction of the product which hereinafter is called the cross direction manufacturing of a product without departing from the spirit and scope of the disclosure. The absorbent article 10 illustrated in FIG. 1 includes a front waist region 12, a back waist region 14, and a crotch region 16 interconnecting the front and back waist regions, 12 and 14, respectively. The absorbent article 10 has a pair of longitudinal side edges, 18 and 20 (shown in FIG. 2), and a pair of opposite waist edges, respectively designated front waist edge 22 and back waist edge 24. The front waist region 12 can be contiguous with the front waist edge 22 and the back waist region 14 can be contiguous with the back waist edge 24.

Figure 2:
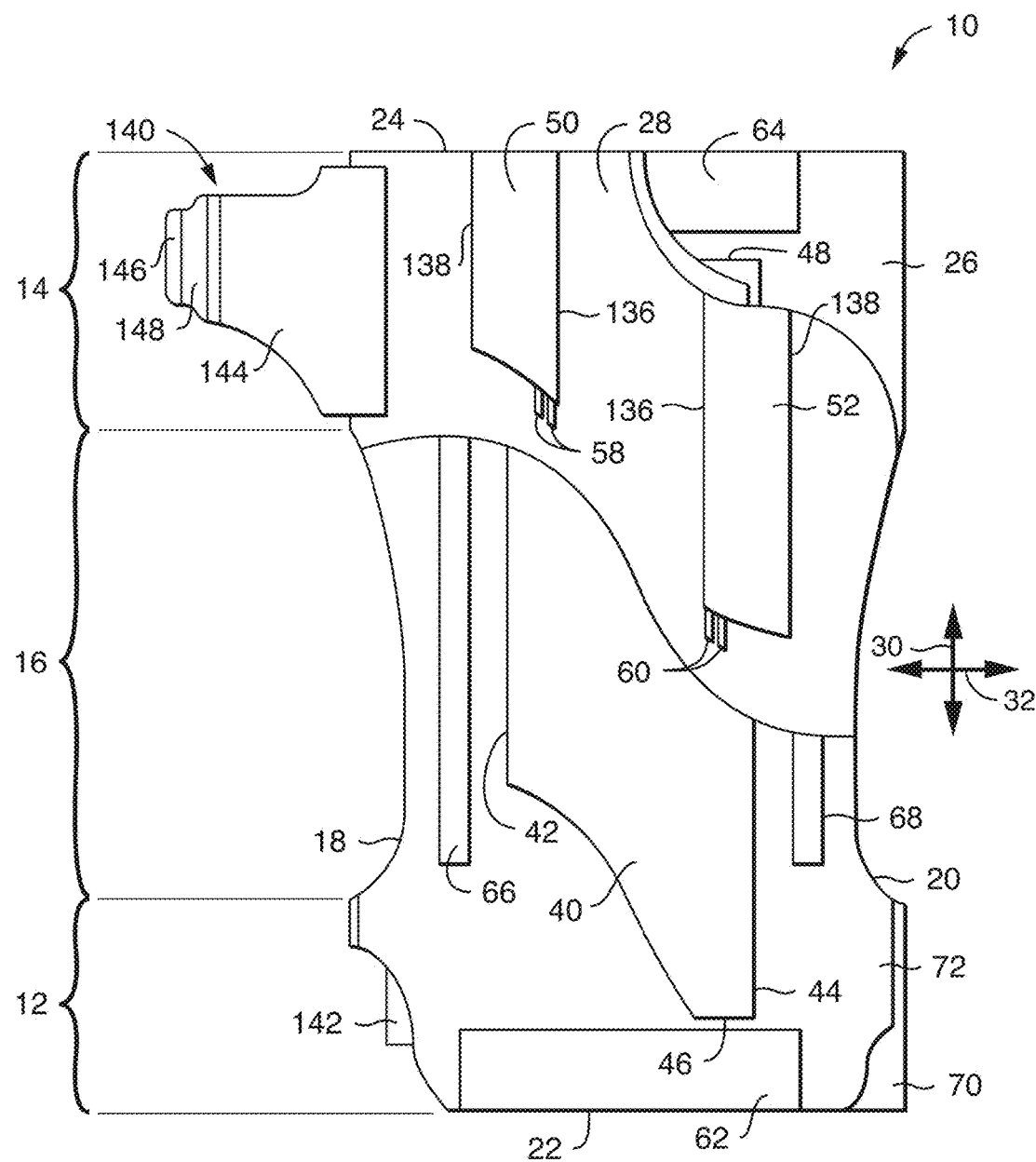
FIG. 2 is a top down view of an embodiment of an absorbent article with portions cut away for clarity.

Referring to FIG. 2, a non-limiting illustration of an absorbent article 10, such as, for example, a diaper, is illustrated in a top down view with portions cut away for clarity of illustration. The absorbent article 10 can include an outer cover 26 and a body facing material 28. In an embodiment, the body facing material 28 can be bonded to the outer cover 26 in a superposed relation by any suitable means such as, but not limited to, adhesives, ultrasonic bonds, thermal bonds, pressure bonds, or other conventional techniques. The outer cover 26 can define a length, or longitudinal direction 30, and a width, or lateral direction 32, which, in the illustrated embodiment, can coincide with the length and width of the absorbent article 10. The longitudinal direction 30 and the lateral direction 32 of the absorbent article 10, and of the materials which form the absorbent article 10, can provide the X-Y planes, respectively, of the absorbent article 10 and of the materials which form the absorbent article 10. The absorbent article 10, and the materials which form the absorbent article 10, can also have a Z-direction. A measurement, taken under pressure, in the Z-direction of a material which forms the absorbent article 10 can provide a measurement of the thickness of the material. A measurement, taken under pressure, in the Z-direction of the absorbent article 10 can provide a measurement of the bulk of the absorbent article 10.

Referring to FIGS. 2-6, an absorbent body 40 can be disposed between the outer cover 26 and the body facing material 28. The absorbent body 40 can have longitudinal edges, 42 and 44, which, in an embodiment, can form portions of the longitudinal side edges, 18 and 20, respectively, of the absorbent article 10 and can have opposite end edges, 46 and 48, which, in an embodiment, can form portions of the waist edges, 22 and 24, respectively, of the absorbent article 10. In an embodiment, the absorbent body 40 can have a length and width that are the same as or less than the length and width of the absorbent article 10. In an embodiment, a pair of containment flaps, 50 and 52, can be present and can inhibit the lateral flow of body exudates.

The front waist region 12 can include the portion of the absorbent article 10 that, when worn, is positioned at least in part on the front of the wearer while the back waist region 14 can include the portion of the absorbent article 10 that, when worn, is positioned at least in part on the back of the wearer. The crotch region 16 of the absorbent article 10 can include the portion of the absorbent article 10, that, when worn, is positioned between the legs of the wearer and can partially cover the lower torso of the wearer. The waist edges, 22 and 24, of the absorbent article 10 are configured to encircle the waist of the wearer and together define the central waist opening 54 (such as shown in FIG. 1). Portions of the longitudinal side edges, 18 and 20, in the crotch region 16 can generally define leg openings 56 (such as shown in FIG. 1) when the absorbent article 10 is worn.

The absorbent article 10 can be configured to contain and/or absorb liquid, solid, and semi-solid body exudates discharged from the wearer. For example, containment flaps, 50 and 52, can be configured to provide a barrier to the lateral flow of body exudates. A flap elastic member, 58 and 60, can be operatively joined to each containment flap, 50 and 52, in any suitable manner known in the art. The elasticized containment flaps, 50 and 52, can define a partially unattached edge that can assume an upright configuration in at least the crotch region 16 of the absorbent article 10 to form a seal against the wearer's body. The containment flaps, 50 and 52, can be located along the absorbent article 10 longitudinal side edges, 18 and 20, and can extend longitudinally along the entire length of absorbent article 10 or can extend partially along the length of the absorbent article 10. Suitable construction and arrangements for containment flaps, 50 and 52, are generally well known to those skilled in the art and are described in U.S. Pat. No. 4,704,116 issued Nov. 3, 1987, to Enloe and U.S. Pat. No. 5,562,650 issued Oct. 8, 1996 to Everett et al., which are incorporated herein by reference.

Figure 4:
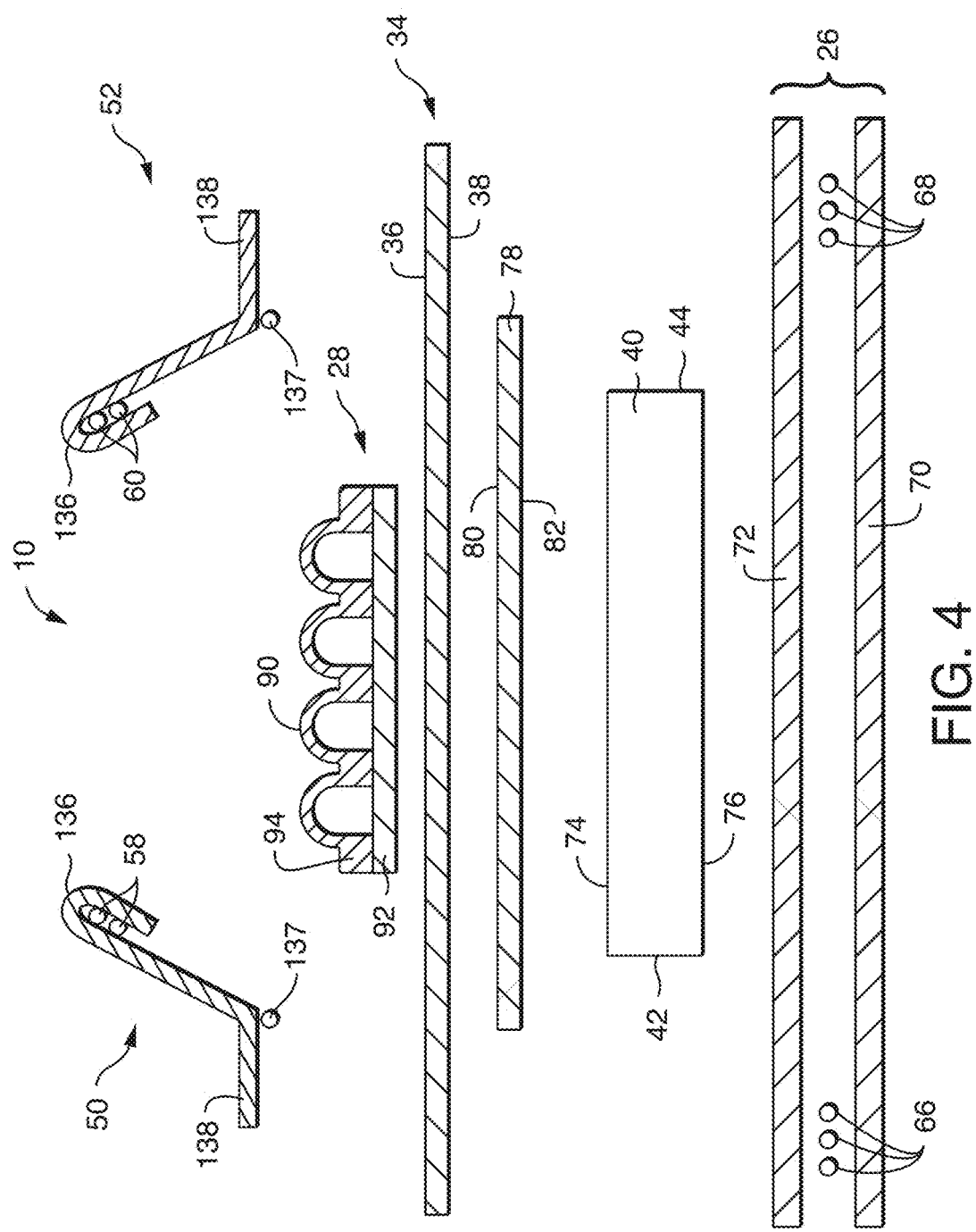
FIG. 4 is an exploded cross-sectional view of another embodiment of an absorbent article.
Figure 6:
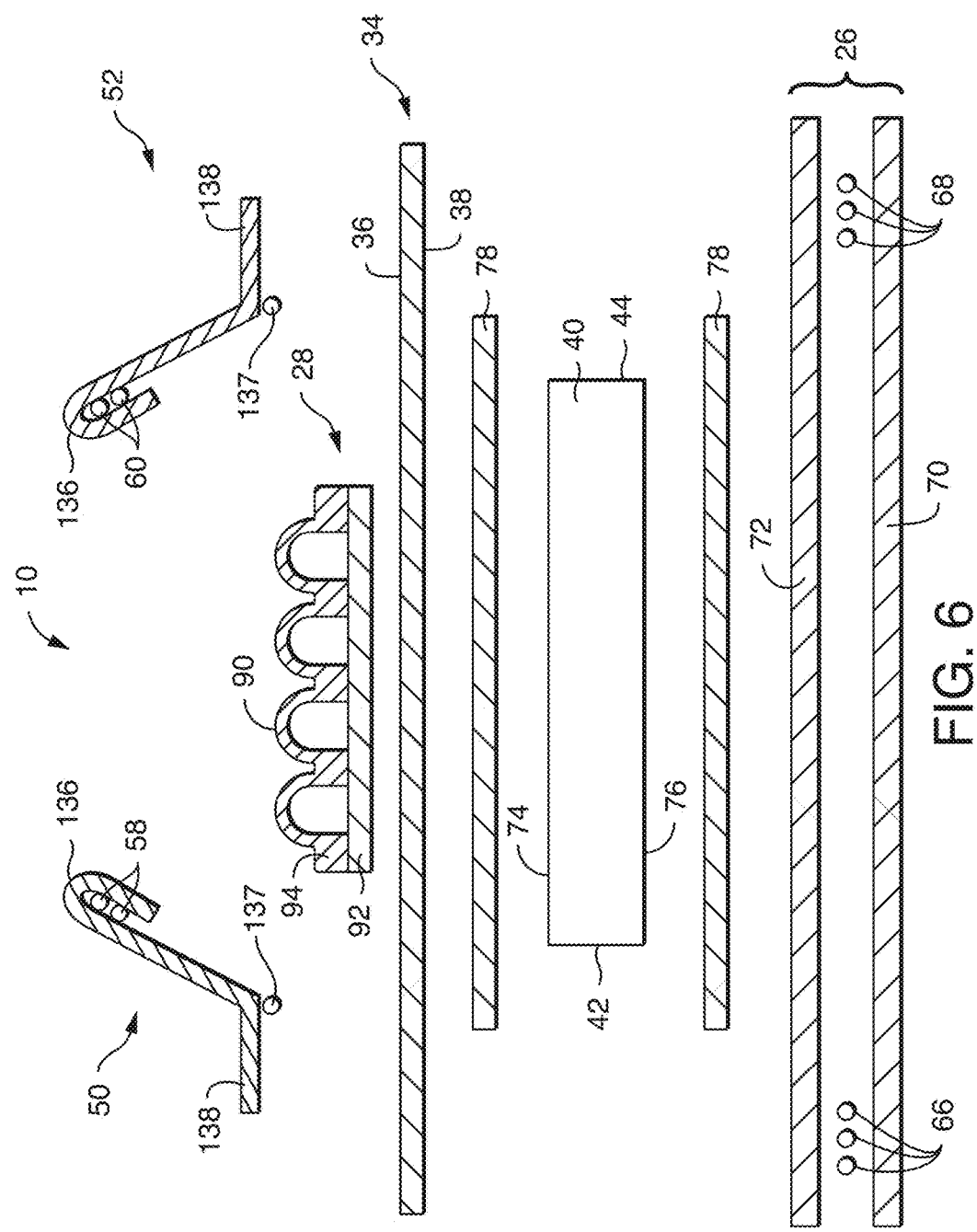
FIG. 6 is an exploded cross-sectional view of another embodiment of an absorbent article.

In various embodiments, the absorbent article 10 can include a secondary liner 34 (such as exemplified in FIG. 4 and FIG. 6). In such embodiments, the secondary liner 34 can have a body facing surface 36 and a garment facing surface 38. In such embodiments, the body facing material 28 can be bonded to the body facing surface 36 of the secondary liner 34.

To further enhance containment and/or absorption of body exudates, the absorbent article 10 can suitably include a front waist elastic member 62, a rear waist elastic member 64, and leg elastic members, 66 and 68, as are known to those skilled in the art. The waist elastic members, 62 and 64, can be attached to the outer cover 26, the body facing material 28, and/or the secondary liner 34 along the opposite waist edges, 22 and 24, and can extend over part or all of the waist edges, 22 and 24. The leg elastic members, 66 and 68, can be attached to the outer cover 26, the body facing material 28, and/or the secondary liner 34 along the opposite longitudinal side edges, 18 and 20, and positioned in the crotch region 16 of the absorbent article 10.

In various embodiments, the body facing material 28 of an absorbent article 10 can have a load of more than about 2 Newtons per 25 mm width at a 10% extension in the machine direction as measured using the Load Versus Percent Extension test method described herein. In various embodiments, the body facing material 28 can have projections which have a height greater than about 1 mm as measured using the Method to Determine Height of Projections test method described herein. In various embodiments, the body facing material 28 of an absorbent article 10 can have a resiliency of greater than about 70% as measured using the Percent Resiliency—One Cycle Compression test method described herein. In various embodiments, the amount of residual fecal material simulant on the body facing material 28 of an absorbent article 10 following insult with fecal material simulant can be less than about 2.5 grams as measured using the Determination of Residual Fecal Material Simulant test method described herein. In various embodiments, the area of spread of fecal material simulant on the body facing material 28 of an absorbent article 10 following insult with fecal material simulant can be less than about 34 cm$^2$ as measured using the Determination of Area of Spread of Fecal Material Simulant test method described herein. In various embodiments, the body facing material 28 can have projections 90 which have less than about 1% open area in a chosen area of the body facing material 28 as measured using the Method to Determine Percent Open Area test method described herein. In various embodiments, the body facing material 28 can have a land area 116 which can have greater than about 1% open area in a chosen area of the body facing material 28 as measured using the Method to Determine Percent Open Area test method described herein. In various embodiments, the intake time for a second intake through a body facing material 28 on an absorbent article 10 following insult with a menses simulant can be less than commercially available absorbent articles as measured using the Intake/Rewet test method described herein. In various embodiments, the intake time for a second intake through a body facing material 28 on an absorbent article 10 can be from about 25 or 30% to about 50, 60 or 70% less than commercially available products following insult with a menses simulant as measured using the Intake/Rewet test method described herein. In various embodiments, the intake time for a second intake through a body facing material 28 on an absorbent article 10 can be less than about 30 seconds following insult of a menses simulant as measured using the Intake/Rewet test method described herein.

In various embodiments, the body facing material 28 can have a land area 116 with a percent open area greater than the percent open area of a projection 90 as measured according to the Method to Determine Percent Open Area test method described herein.

Additional details regarding each of these elements of the absorbent article 10 described herein can be found below and with reference to the Figures.

Outer Cover:

The outer cover 26 can be breathable and/or liquid impermeable. The outer cover 26 can be elastic, stretchable or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material. In an embodiment, the outer cover 26 can be suitably stretchable, and more suitably elastic, in at least the lateral or circumferential direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In an embodiment such as illustrated in FIGS. 3-6, the outer cover 26 may be a two layer construction, including an outer layer 70 material and an inner layer 72 material which can be bonded together such as by a laminate adhesive. Suitable laminate adhesives can be applied continuously or intermittently as beads, a spray, parallel swirls, or the like. Suitable adhesives can be obtained from Bostik Findlay Adhesives, Inc. of Wauwatosa, Wis., U.S.A. It is to be understood that the inner layer 72 can be bonded to the outer layer 70 utilizing ultrasonic bonds, thermal bonds, pressure bonds, or the like.

The outer layer 70 of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer 70 of an outer cover 26 can be a 20 gsm spunbond polypropylene non-woven web. The outer layer 70 may also be constructed of the same materials from which the secondary liner 34 can be constructed as described herein.

The liquid impermeable inner layer 72 of the outer cover 26 (or the liquid impermeable outer cover 26 where the outer cover 26 is of a single-layer construction) can be either vapor permeable (i.e., "breathable") or vapor impermeable. The liquid impermeable inner layer 72 (or the liquid impermeable outer cover 26 where the outer cover 26 is of a single-layer construction) may be manufactured from a thin plastic film, although other liquid impermeable materials may also be used. The liquid impermeable inner layer 72 (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver. An example of a material for a liquid impermeable inner layer 72 (or the liquid impermeable outer cover 26 where the outer cover 26 is of a single-layer construction) can be a printed 19 gsm Berry Plastics XP-8695H film or equivalent commercially available from Berry Plastics Corporation, Evansville, Ind., U.S.A.

Where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Absorbent Body:

The absorbent body 40 can be suitably constructed to be generally compressible, conformable, pliable, non-irritating to the wearer's skin and capable of absorbing and retaining liquid body exudates. The absorbent body 40 can be manufactured in a wide variety of sizes and shapes (for example, rectangular, trapezoidal, T-shape, I-shape, hourglass shape, etc.) and from a wide variety of materials. The size and the absorbent capacity of the absorbent body 40 should be compatible with the size of the intended wearer and the liquid loading imparted by the intended use of the absorbent article 10. Additionally, the size and the absorbent capacity of the absorbent body 40 can be varied to accommodate wearers ranging from infants to adults.

The absorbent body 40 may have a length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm. The absorbent body 40 may have a crotch width ranging from about 30, 40, 50, 55, 60, 65, or 70 mm to about 75, 80, 85, 90, 95, 100, 105, 110, 115, 120, 125, 130, 140, 150, 160, 170 or 180 mm. The width of the absorbent body 40 located within the front waist region 12 and/or the back waist region 14 of the absorbent article 10 may range from about 50, 55, 60, 65, 70, 75, 80, 85, 90, or 95 mm to about 100, 105, 110, 115, 120, 125 or 130 mm. As noted herein, the absorbent body 40 can have a length and width that can be less than or equal to the length and width of the absorbent article 10.

In an embodiment, the absorbent article 10 can be a diaper having the following ranges of lengths and widths of an absorbent body 40 having an hourglass shape: the length of the absorbent body 40 may range from about 170, 180, 190, 200, 210, 220, 225, 240 or 250 mm to about 260, 280, 300, 310, 320, 330, 340, 350, 355, 360, 380, 385, or 390 mm; the width of the absorbent body 40 in the crotch region 16 may range from about 40, 50, 55, or 60 mm to about 65, 70, 75, or 80 mm; the width of the absorbent body 40 in the front waist region 12 and/or the back waist region 14 may range from about 80, 85, 90, or 95 mm to about 100, 105, or 110 mm.

In an embodiment, the absorbent article 10 may be a training pant or youth pant having the following ranges of lengths and widths of an absorbent body 40 having an hourglass shape: the length of the absorbent body 40 may range from about 400, 410, 420, 440 or 450 mm to about 460, 480, 500, 510 or 520 mm; the width of the absorbent body 40 in the crotch region 16 may range from about 50, 55, or 60 mm to about 65, 70, 75, or 80 mm; the width of the absorbent body 40 in the front waist region 12 and/or the back waist region 14 may range from about 80, 85, 90, or 95 mm to about 100, 105, 110, 115, 120, 125, or 130 mm.

In an embodiment, the absorbent article 10 can be an adult incontinence garment having the following ranges of lengths and widths of an absorbent body 40 having a rectangular shape: the length of the absorbent body 40 may range from about 400, 410 or 415 to about 425 or 450 mm; the width of the absorbent body 40 in the crotch region 16 may range from about 90, or 95 mm to about 100, 105, or 110 mm. It should be noted that the absorbent body 40 of an adult incontinence garment may or may not extend into either or both the front waist region 12 or the back waist region 14 of the absorbent article 10.

In an embodiment, the absorbent article 10 can be a feminine hygiene product having the following ranges of lengths and widths of an absorbent body 40 having an hourglass shape: the length of the absorbent body 40 may range from about 150, 160, 170, or 180 mm to about 190, 200, 210, 220, 230, 240, 250, 260, 270, 280, 290, 300, 310 or 320 mm; the width of the absorbent body in the crotch region 16 may range from about 30, 40, or 50 mm to about 60, 70, 80, 90 or 100 mm.

The absorbent body 40 can have two surfaces, 74 and 76, such as a wearer facing surface 74 and a garment facing surface 76. Edges, such as longitudinal side edges, 42 and 44, and such as front and back end edges, 46 and 48, can connect the two surfaces, 74 and 76.

In an embodiment, the absorbent body 40 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 40 can be a matrix of cellulosic fluff and superabsorbent material.

In an embodiment, the absorbent body 40 may be constructed of a single layer of materials, or in the alternative, may be constructed of two layers of materials or more. In an embodiment in which the absorbent body 40 has two layers, the absorbent body 40 can have a wearer facing layer suitably composed of hydrophilic fibers and a garment facing layer suitably composed at least in part of a high absorbency material commonly known as superabsorbent material. In such an embodiment, the wearer facing layer of the absorbent body 40 can be suitably composed of cellulosic fluff, such as wood pulp fluff, and the garment facing layer of the absorbent body 40 can be suitably composed of superabsorbent material, or a mixture of cellulosic fluff and superabsorbent material. As a result, the wearer facing layer can have a lower absorbent capacity per unit weight than the garment facing layer. The wearer facing layer may alternatively be composed of a mixture of hydrophilic fibers and superabsorbent material, as long as the concentration of superabsorbent material present in the wearer facing layer is lower than the concentration of superabsorbent material present in the garment facing layer so that the wearer facing layer can have a lower absorbent capacity per unit weight than the garment facing layer. It is also contemplated that the garment facing layer may be composed solely of superabsorbent material without departing from the scope of this disclosure. It is also contemplated that, in an embodiment, each of the layers, the wearer facing and garment facing layers, can have a superabsorbent material such that the absorbent capacities of the two superabsorbent materials can be different and can provide the absorbent body 40 with a lower absorbent capacity in the wearer facing layer than in the garment facing layer.

Various types of wettable, hydrophilic fibers can be used in the absorbent body 40. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. For example, one suitable type of fiber is a wood pulp that is a bleached, highly absorbent sulfate wood pulp containing primarily soft wood fibers. However, the wood pulp can be exchanged with other fiber materials, such as synthetic, polymeric, or meltblown fibers or with a combination of meltblown and natural fibers. In an embodiment, the cellulosic fluff can include a blend of wood pulp fluff. An example of wood pulp fluff can be "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

The absorbent body 40 can be formed with a dry-forming technique, an air-forming technique, a wet-forming technique, a foam-forming technique, or the like, as well as combinations thereof. A coform nonwoven material may also be employed. Methods and apparatus for carrying out such techniques are well known in the art.

Suitable superabsorbent materials can be selected from natural, synthetic, and modified natural polymers and materials. The superabsorbent materials can be inorganic materials, such as silica gels, or organic compounds, such as cross-linked polymers. Cross-linking may be covalent, ionic, Van der Waals, or hydrogen bonding. Typically, a superabsorbent material can be capable of absorbing at least about ten times its weight in liquid. In an embodiment, the superabsorbent material can absorb more than twenty-four times its weight in liquid. Examples of superabsorbent materials include polyacrylamides, polyvinyl alcohol, ethylene maleic anhydride copolymers, polyvinyl ethers, hydroxypropyl cellulose, carboxymal methyl cellulose, polyvinylmorpholinone, polymers and copolymers of vinyl sulfonic acid, polyacrylates, polyacrylamides, polyvinyl pyrrolidone, and the like. Additional polymers suitable for superabsorbent material include hydrolyzed, acrylonitrile grafted starch, acrylic acid grafted starch, polyacrylates and isobutylene maleic anhydride copolymers and mixtures thereof. The superabsorbent material may be in the form of discrete particles. The discrete particles can be of any desired shape, for example, spiral or semi-spiral, cubic, rod-like, polyhedral, etc. Shapes having a largest greatest dimension/smallest dimension ratio, such as needles, flakes, and fibers are also contemplated for use herein. Conglomerates of particles of superabsorbent materials may also be used in the absorbent body 40.

In an embodiment, the absorbent body 40 can be free of superabsorbent material. In an embodiment, the absorbent body 40 can have at least about 15% by weight of a superabsorbent material. In an embodiment, the absorbent body 40 can have at least about 15, 20, 25, 30, 35, 40, 45, 50, 55, 60, 65, 70, 75, 80, 85, 90, 95, 99 or 100% by weight of a superabsorbent material. In an embodiment, the absorbent body 40 can have less than about 100, 99, 95, 90, 85, 80, 75, 70, 65, 60, 55, 50, 45, 40 35, 30, 25, or 20% by weight of a superabsorbent material. In an embodiment, the absorbent body 40 can have from about 15, 20, 25, 30, 35, 40, 45, 50, 55 or 60% to about 65, 70, 75, 80, 85, 90, 95, 99 or 100% by weight of a superabsorbent material. Examples of superabsorbent material include, but are not limited to, FAVOR SXM-9300 or equivalent available from Evonik Industries, Greensboro, N.C., U.S.A. and HYSORB 8760 or equivalent available from BASF Corporation, Charlotte, N.C., U.S.A.

The absorbent body 40 can be superposed over the inner layer 72 of the outer cover 26, extending laterally between the leg elastic members, 66 and 68, and can be bonded to the inner layer 72 of the outer cover 26, such as by being bonded thereto with adhesive. However, it is to be understood that the absorbent body 40 may be in contact with, and not bonded with, the outer cover 26 and remain within the scope of this disclosure. In an embodiment, the outer cover 26 can be composed of a single layer and the absorbent body 40 can be in contact with the singer layer of the outer cover 26.

In an embodiment, a layer, such as but not limited to, a fluid transfer layer 78, can be positioned between the absorbent body 40 and the outer cover 26.

Figure 3:
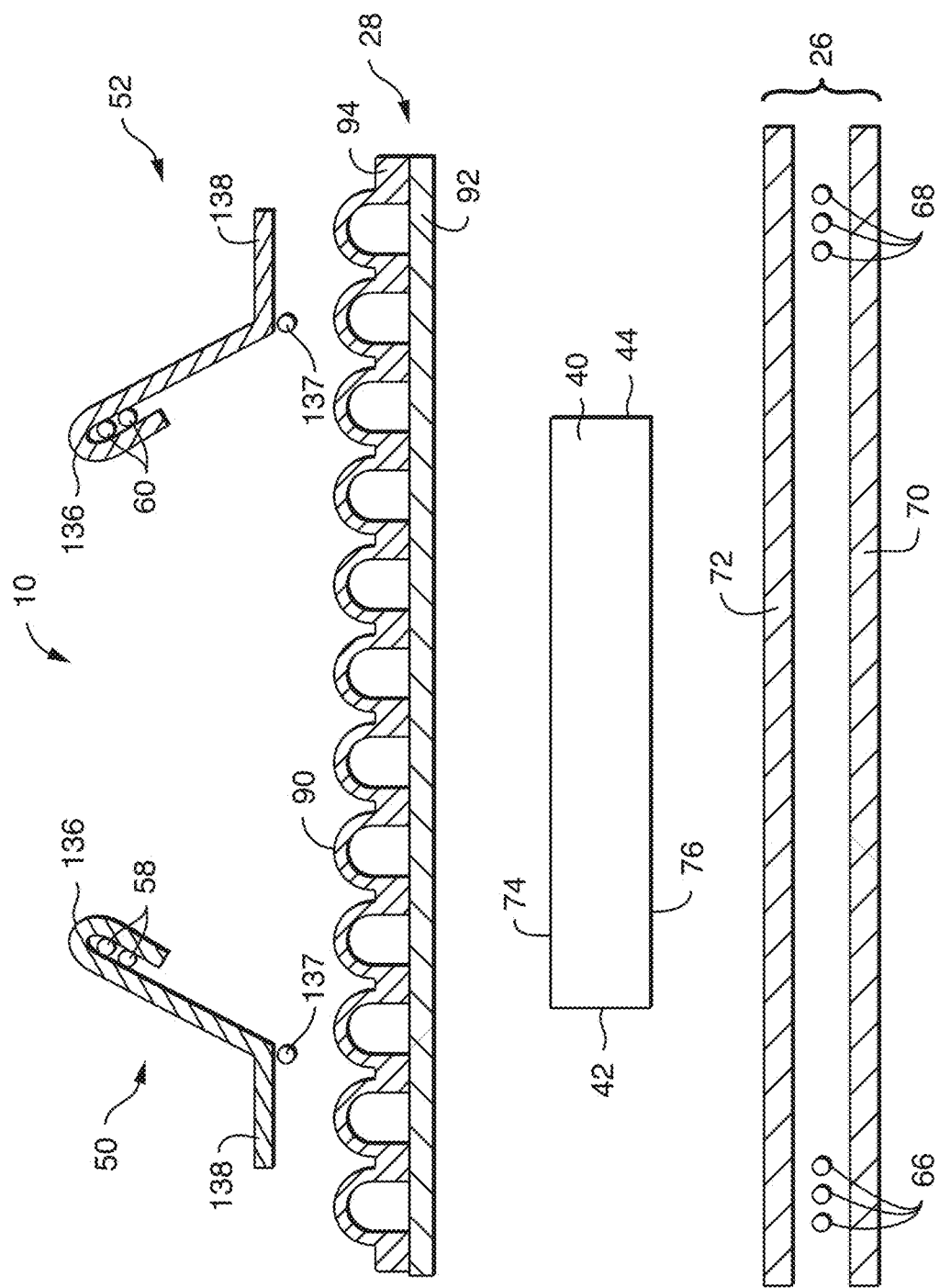
FIG. 3 is an exploded cross-sectional view of an embodiment of an absorbent article.

Fluid Transfer Layer:

In various embodiments, such as illustrated in the non-limiting example of FIG. 3, an absorbent article 10 can be constructed without a fluid transfer layer 78. In various embodiments, such as illustrated in the non-limiting examples of FIGS. 4-6, the absorbent article 10 can have a fluid transfer layer 78. The fluid transfer layer 78 can have a wearer facing surface 80 and a garment facing surface 82. In an embodiment, the fluid transfer layer 78 can be in contact with the absorbent body 40. In an embodiment, the fluid transfer layer 78 can be bonded to the absorbent body 40. Bonding of the fluid transfer layer 78 to the absorbent body 40 can occur via any means known to one of ordinary skill, such as, but not limited to, adhesives. In an embodiment, such as illustrated in the non-limiting example of FIG. 4, a fluid transfer layer 78 can be positioned between the body facing material 28 and the absorbent core 40. In an embodiment, such as illustrated in the non-limiting example of FIG. 5, a fluid transfer layer 78 can completely encompass the absorbent body 40 and can be sealed to itself. In such an embodiment, the fluid transfer layer 78 may be folded over on itself and then sealed using, for example, heat and/or pressure. In an embodiment, such as, for example, in the non-limiting illustration of FIG. 6, a fluid transfer layer 78 may be composed of separate sheets of material which can be utilized to partially or fully encompass the absorbent body 40 and which can be sealed together using a sealing means such as an ultrasonic bonder or other thermochemical bonding means or the use of an adhesive.

In an embodiment, the fluid transfer layer 78 can be in contact with and/or bonded with the wearer facing surface 74 of the absorbent body 40. In an embodiment, the fluid transfer layer 78 can be in contact with and/or bonded with the wearer facing surface 74 and at least one of the edges, 42, 44, 46 and/or 48, of the absorbent body 40. In an embodiment, the fluid transfer layer 78 can be in contact with and/or bonded with the wearer facing surface 74, at least one of the edges, 42, 44, 46 and/or 48, and the garment facing surface 76 of the absorbent body 40. In an embodiment, the absorbent body 40 may be partially or completely encompassed by a fluid transfer layer 78.

The fluid transfer layer 78 can be pliable, less hydrophilic than the absorbent body 40, and sufficiently porous to thereby permit liquid body exudates to penetrate through the fluid transfer layer 78 to reach the absorbent body 40. In an embodiment, the fluid transfer layer 78 can have sufficient structural integrity to withstand wetting thereof and of the absorbent body 40. In an embodiment, the fluid transfer layer 78 can be constructed from a single layer of material or it may be a laminate constructed from two or more layers of material.

In an embodiment, the fluid transfer layer 78 can include, but is not limited to, natural and synthetic fibers such as, but not limited to, polyester, polypropylene, acetate, nylon, polymeric materials, cellulosic materials such as wood pulp, cotton, rayon, viscose, LYOCELL® such as from Lenzing Company of Austria, or mixtures of these or other cellulosic fibers, and combinations thereof. Natural fibers can include, but are not limited to, wool, cotton, flax, hemp, and wood pulp. Wood pulps can include, but are not limited to, standard softwood fluffing grade such as "CoosAbsorb™ S Fluff Pulp" or equivalent available from Abitibi Bowater, Greenville, S.C., U.S.A., which is a bleached, highly absorbent sulfate wood pulp containing primarily southern soft wood fibers.

In various embodiments, the fluid transfer layer 78 can include cellulosic material. In various embodiments, the fluid transfer layer 78 can be creped wadding or a high-strength tissue. In various embodiments, the fluid transfer layer 78 can include polymeric material. In an embodiment, a fluid transfer layer 78 can include a spunbond material. In an embodiment, a fluid transfer layer 78 can include a meltblown material. In an embodiment, the fluid transfer layer 78 can be a laminate of a meltblown nonwoven material having fine fibers laminated to at least one spunbond nonwoven material layer having coarse fibers. In such an embodiment, the fluid transfer layer 78 can be a spunbond-meltblown ("SM") material. In an embodiment, the fluid transfer layer 78 can be a spunbond-meltblown-spunbond ("SMS") material. A non-limiting example of such a fluid transfer layer 78 can be a 10 gsm spunbond-meltblown-spunbond material. In various embodiments, the fluid transfer layer 78 can be composed of at least one material which has been hydraulically entangled into a nonwoven substrate. In various embodiments, the fluid transfer layer 78 can be composed of at least two materials which have been hydraulically entangled into a nonwoven substrate. In various embodiments, the fluid transfer layer 78 can have at least three materials which have been hydraulically entangled into a nonwoven substrate. A non-limiting example of a fluid transfer layer 78 can be a 33 gsm hydraulically entangled substrate. In such an example, the fluid transfer layer 78 can be a 33 gsm hydraulically entangled substrate composed of a 12 gsm spunbond material, a 10 gsm wood pulp material having a length from about 0.6 cm to about 5.5 cm, and an 11 gsm polyester staple fiber material. To manufacture the fluid transfer layer 78 just described, the 12 gsm spunbond material can provide a base layer while the 10 gsm wood pulp material and the 11 gsm polyester staple fiber material can be homogeneously mixed together and deposited onto the spunbond material and then hydraulically entangled with the spunbond material.

In various embodiments, a wet strength agent can be included in the fluid transfer layer 78. A non-limiting example of a wet strength agent can be Kymene 6500 (557LK) or equivalent available from Ashland Inc. of Ashland, Ky., U.S.A. In various embodiments, a surfactant can be included in the fluid transfer layer 78. In various embodiments, the fluid transfer layer 78 can be hydrophilic. In various embodiments, the fluid transfer layer 78 can be hydrophobic and can be treated in any manner known in the art to be made hydrophilic.

In an embodiment, the fluid transfer layer 78 can be in contact with and/or bonded with an absorbent body 40 which is made at least partially of particulate material such as superabsorbent material. In an embodiment in which the fluid transfer layer 78 at least partially or completely encompasses the absorbent body 40, the fluid transfer layer 78 should not unduly expand or stretch as this might cause the particulate material to escape from the absorbent body 40. In an embodiment, the fluid transfer layer 78, while in a dry state, should have respective extension values at peak load in the machine and cross directions of 30 percent or less and 40 percent or less, respectively.

In an embodiment, the fluid transfer layer 78 may have a longitudinal length the same as, greater than, or less than the longitudinal length of the absorbent body 40. The fluid transfer layer 78 can have a longitudinal length ranging from about 150, 160, 170, 180, 190, 200, 210, 220, 225, 230, 240, 250, 260, 270, 280, 290, 300, 310, 320, 330, 340, or 350 mm to about 355, 360, 380, 385, 390, 395, 400, 410, 415, 420, 425, 440, 450, 460, 480, 500, 510, or 520 mm.

Figure 5:
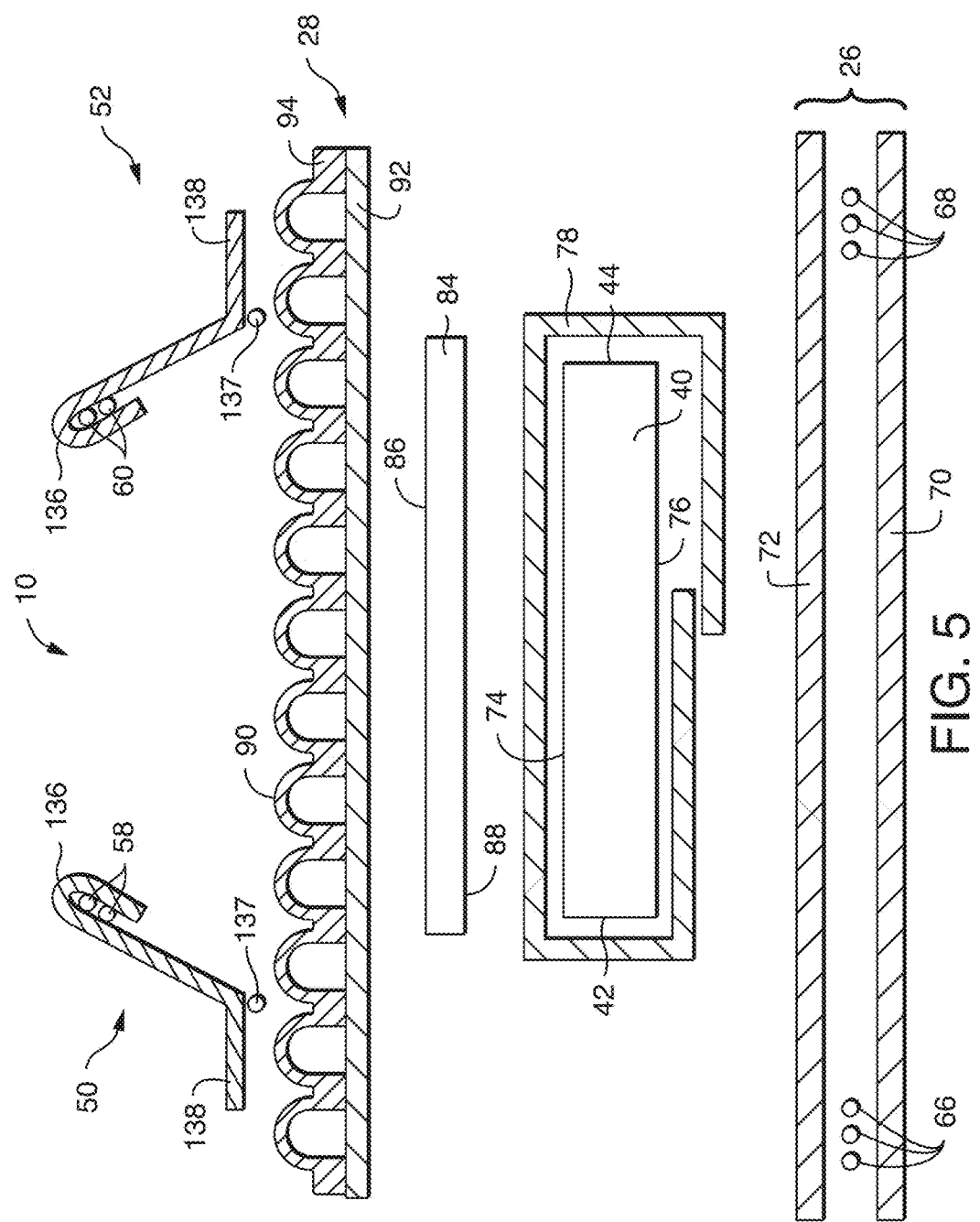
FIG. 5 is an exploded cross-sectional view of another embodiment of an absorbent article.

Acquisition Layer:

In various embodiments, such as illustrated, for example, in FIG. 5, the absorbent article 10 can have an acquisition layer 84. The acquisition layer 84 can help decelerate and diffuse surges or gushes of liquid body exudates penetrating the body facing material 28. In an embodiment, the acquisition layer 84 can be positioned between the body facing material 28 and the absorbent body 40 to take in and distribute body exudates for absorption by the absorbent body 40. In an embodiment, the acquisition layer 84 can be positioned between the body facing material 28 and a fluid transfer layer 78 if a fluid transfer layer 78 is present. In an embodiment, the acquisition layer 84 can be positioned between a secondary liner 34, if present, and the absorbent body 40.

The acquisition layer 84 can have a wearer facing surface 86 and a garment facing surface 88. In an embodiment, the acquisition layer 84 can be in contact with and/or bonded with the body facing material 28. In an embodiment in which the acquisition layer 84 is bonded with the body facing material 28, bonding of the acquisition layer 84 to the body facing material 28 can occur through the use of an adhesive and/or point fusion bonding. The point fusion bonding can be selected from, but is not limited to, ultrasonic bonding, pressure bonding, thermal bonding, and combinations thereof. In an embodiment, the point fusion bonding can be provided in any pattern as deemed suitable.

The acquisition layer 84 may have any longitudinal length dimension as deemed suitable. The acquisition layer 84 may have a longitudinal length from about 120, 130, 140, 150, 160, 170, 180, 190, 200, 210, 220, 225, 230, 240, or 250 mm to about 260, 270, 280, 290, 300, 310, 320, 340, 350, 360, 380, 400, 410, 415, 420, 425, 440, 450, 460, 480, 500, 510 or 520 mm. In an embodiment, the acquisition layer 84 can have any length such that the acquisition layer 84 can be coterminous with the waist edges, 22 and 24, of the absorbent article 10.

In an embodiment, the longitudinal length of the acquisition layer 84 can be the same as the longitudinal length of the absorbent body 40. In such an embodiment the midpoint of the longitudinal length of the acquisition layer 84 can substantially align with the midpoint of the longitudinal length of the absorbent body 40.

In an embodiment, the longitudinal length of the acquisition layer 84 can be shorter than the longitudinal length of the absorbent body 40. In such an embodiment, the acquisition layer 84 may be positioned at any desired location along the longitudinal length of the absorbent body 40. As an example of such an embodiment, the absorbent article 10 may contain a target area where repeated liquid surges typically occur in the absorbent article 10. The particular location of a target area can vary depending on the age and gender of the wearer of the absorbent article 10. For example, males tend to urinate further toward the front region of the absorbent article 10 and the target area may be phased forward within the absorbent article 10. For example, the target area for a male wearer may be positioned about 2¾" forward of the longitudinal midpoint of the absorbent body 40 and may have a length of about ±3" and a width of about ±2". The female target area can be located closer to the center of the crotch region 16 of the absorbent article 10. For example, the target area for a female wearer may be positioned about 1" forward of the longitudinal midpoint of the absorbent body 40 and may have a length of about ±3" and a width of about ±2". As a result, the relative longitudinal placement of the acquisition layer 84 within the absorbent article 10 can be selected to best correspond with the target area of either or both categories of wearers.

In an embodiment, the absorbent article 10 may contain a target area centered within the crotch region 16 of the absorbent article 10 with the premise that the absorbent article 10 would be worn by a female wearer. The acquisition layer 84, therefore, may be positioned along the longitudinal length of the absorbent article 10 such that the acquisition layer 84 can be substantially aligned with the target area of the absorbent article 10 intended for a female wearer. Alternatively, the absorbent article 10 may contain a target area positioned between the crotch region 16 and the front waist region 12 of the absorbent article 10 with the premise that the absorbent article 10 would be worn by a male wearer. The acquisition layer 84, therefore, may be positioned along the longitudinal length of the absorbent article 10 such that the acquisition layer 84 can be substantially aligned with the target area of the absorbent article 10 intended for a male wearer.

In an embodiment, the acquisition layer 84 can have a size dimension that is the same size dimension as the target area of the absorbent article 10 or a size dimension greater than the size dimension of the target area of the absorbent article 10. In an embodiment, the acquisition layer 84 can be in contact with and/or bonded with the body facing material 28 at least partially in the target area of the absorbent article 10.

In various embodiments, the acquisition layer 84 can have a longitudinal length shorter than, the same as or longer than the longitudinal length of the absorbent body 40. In an embodiment in which the absorbent article 10 is a diaper, the acquisition layer 84 may have a longitudinal length from about 120, 130, 140, 150, 160, 170, or 180 mm to about 200, 210, 220, 225, 240, 260, 280, 300, 310 or 320 mm. In such an embodiment, the acquisition layer 84 may be shorter in longitudinal length than the longitudinal length of the absorbent body 40 and may be phased from the front end edge 46 of the absorbent body 40 a distance of from about 15, 20, or 25 mm to about 30, 35 or 40 mm. In an embodiment in which the absorbent article 10 may be a training pant or youth pant, the acquisition layer 84 may have a longitudinal length from about 120, 130, 140, 150, 200, 210, 220, 230, 240 or 250 mm to about 260, 270, 280, 290, 300, 340, 360, 400, 410, 420, 440, 450, 460, 480, 500, 510 or 520 mm. In such an embodiment, the acquisition layer 84 may have a longitudinal length shorter than the longitudinal length of the absorbent body 40 and may be phased a distance of from about 25, 30, 35 or 40 mm to about 45, 50, 55, 60, 65, 70, 75, 80 or 85 mm from the front end edge 46 of the absorbent body 40. In an embodiment in which the absorbent article 10 is an adult incontinence garment, the acquisition layer 84 may have a longitudinal length from about 200, 210, 220, 230, 240, or 250 mm to about 260, 270, 280, 290, 300, 320, 340, 360, 380, 400, 410, 415, 425, or 450 mm. In such an embodiment, the acquisition layer 84 may have a longitudinal length shorter than the longitudinal length of the absorbent body 40 and the acquisition layer 84 may be phased a distance of from about 20, 25, 30 or 35 mm to about 40, 45, 50, 55, 60, 65, 70 or 75 mm from the front end edge 46 of the absorbent body 40.

The acquisition layer 84 may have any width as desired. The acquisition layer 84 may have a width dimension from about 15, 20, 25, 30, 35, 40, 45, 50, 55, 60, or 70 mm to about 80, 90, 100, 110, 115, 120, 130, 140, 150, 160, 170, or 180 mm. The width of the acquisition layer 84 may vary dependent upon the size and shape of the absorbent article 10 within which the acquisition layer 84 will be placed. The acquisition layer 84 can have a width smaller than, the same as, or larger than the width of the absorbent body 40. Within the crotch region 16 of the absorbent article 10, the acquisition layer 84 can have a width smaller than, the same as, or larger than the width of the absorbent body 40.

In an embodiment, the acquisition layer 84 can include natural fibers, synthetic fibers, superabsorbent material, woven material, nonwoven material, wet-laid fibrous webs, a substantially unbounded airlaid fibrous web, an operatively bonded, stabilized-airlaid fibrous web, or the like, as well as combinations thereof. In an embodiment, the acquisition layer 84 can be formed from a material that is substantially hydrophobic, such as a nonwoven web composed of polypropylene, polyethylene, polyester, and the like, and combinations thereof.

In various embodiments, the acquisition layer 84 can have fibers which can have a denier of greater than about 5. In various embodiments, the acquisition layer 84 can have fibers which can have a denier of less than about 5.

In an embodiment, the acquisition layer 84 can be a through-air bonded-carded web such as a 50 gsm through-air bonded-carded web composite having a homogenous blend of about 50% sheath/core bicomponent polyethylene/polypropylene fibers having a fiber diameter of 3 denier and about 50% sheath/core bicomponent polyethylene/polypropylene fibers having a fiber diameter of 1.5 denier. An example of such a composite is a composite having about 50% ES FiberVisions 3 denier ESC-233 bicomponent fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 84 can be a through-air bonded-carded web such as a 50 gsm through-air bonded-carded web composite having a homogenous blend of about 50% Rayon fibers having a fiber diameter of 3 denier and about 50% sheath/core bicomponent polyethylene/polypropylene fibers having a fiber diameter of 1.5 denier. An example of such a composite is a composite having about 50% Kelheim 3 denier Rayon Galaxy fibers and about 50% ES FiberVisions 1.5 denier ESC-215 bicomponent fibers, or equivalent composite, available from ES FiberVisions Corp., Duluth, Ga., U.S.A.

In an embodiment, the acquisition layer 84 can be a through-air bonded-carded web such as a 50 gsm through-air bonded-carded web composite having a homogenous blend of about 40% hollow polypropylene fibers having a fiber diameter of 7 denier and about 60% sheath/core bicomponent polyethylene/polypropylene fibers having a fiber diameter of 17 denier. An example of such a composite is a composite having about 40% ES FiberVisions 7 denier T-118 hollow polypropylene fibers and about 60% ES FiberVisions 17 denier Varde bicomponent fibers, or equivalent composite, available from ES FiberVisions Corp., Duluth, Ga., U.S.A.

In an embodiment, the acquisition layer 84 can be a through-air bonded-carded web such as a 35 gsm through-air bonded-carded web composite having a homogenous mixture of about 35% sheath/core bicomponent polyethylene/polypropylene fibers having a fiber diameter of 6 denier, about 35% sheath/core bicomponent polyethylene/polypropylene fibers having a fiber diameter of 2 denier, and about 30% polyester fibers having a fiber diameter of 6 denier. An example of such a composite is a composite having about 35% Huvis 180-N (PE/PP 6d), about 35% Huvis N-215 (PE/PP 2d), and about 30% Huvis SD-10 PET 6d, or equivalent composite, available from SamBo Company, Ltd, Korea.

In an embodiment, the acquisition layer 84 can be a thermally bonded, stabilized-airlaid fibrous web (e.g. Concert product code DT200.100.D0001) which is available from Glatfelter, a business having offices located in York, Pa., U.S.A.

In an embodiment, the acquisition layer 84 can include a coform/foam material. In an embodiment, the acquisition layer 84 can include a resilient coform material. As used herein, the term "coform" refers to a blend of meltblown fibers and absorbent fibers such as cellulosic fibers that can be formed by air forming a meltblown polymer material while simultaneously blowing air-suspended fibers into the stream of meltblown fibers. The coform material can also include other materials, such as superabsorbent material. The meltblown fibers and absorbent fibers (and other optional materials) can be collected on a forming surface, such as provided by a foraminous belt. The forming surface can include a gas-pervious material that has been placed onto the forming surface. Coform materials are further described in U.S. Pat. Nos. 5,508,102 and 5,350,624 to Georger et al. and U.S. Pat. No. 4,100,324 to Anderson and U.S. Publication No. 2012/0053547 to Schroeder et al., which are incorporated herein in their entirety by reference thereto and to the extent they do not conflict herewith. As used herein, the term "resilient coform" refers to a resilient coform nonwoven layer including a matrix of meltblown fibers and an absorbent material, wherein the meltblown fibers constitute from about 30 wt % to about 99 wt % of the web and the absorbent material constitutes from about 1 wt % to about 70 wt % of the web, and further wherein the meltblown fibers being formed from a thermoplastic composition that contains at least one propylene/α-olefin copolymer having a propylene content of from about 60 mole % to about 99.5 mole % and an α-olefin content of from about 0.5 mole % to about 40 mole %, wherein the copolymer further has a density of from about 0.86 to about 0.90 grams per cubic centimeter and the composition has a melt flow rate of from about 120 to about 6000 grams per 10 minutes, determined at 230° C. in accordance with ASTM Test Method D1238-E, although practical considerations can reduce the high end melt flow rate range.

The acquisition layer 84 may have additional parameters including basis weight and thickness. In an embodiment, the basis weight of the acquisition layer 84 can be at least about 10 or 20 gsm. In an embodiment, the basis weight of the acquisition layer 84 can be from about 10, 20, 30, 40, 50 or 60 gsm to about 65, 70, 75, 80, 85, 90, 100, 110, 120, or 130 gsm. In an embodiment, the basis weight of the acquisition layer 84 can be less than about 130, 120, 110, 100, 90, 85, 80, 75, 70, 65, 60 or 50 gsm. In an embodiment, the acquisition layer 84 can have a thickness, measured at 0.05 psi (0.345 kPa), of less than about 1.5 mm. In an embodiment, such as, for example, when the absorbent article 10 can be a diaper, the acquisition layer 84 can have a thickness, measured at 0.05 psi (0.345 kPa), of less than about 1.5, 1.25, or 1.0 mm. In an embodiment, such as, for example, when the absorbent article can be a feminine hygiene product, the acquisition layer 84 can have a thickness, measured at 0.2 psi (1.379 kPa), of less than about 1.5, 1.25, or 1.0 mm.

Figure 7:
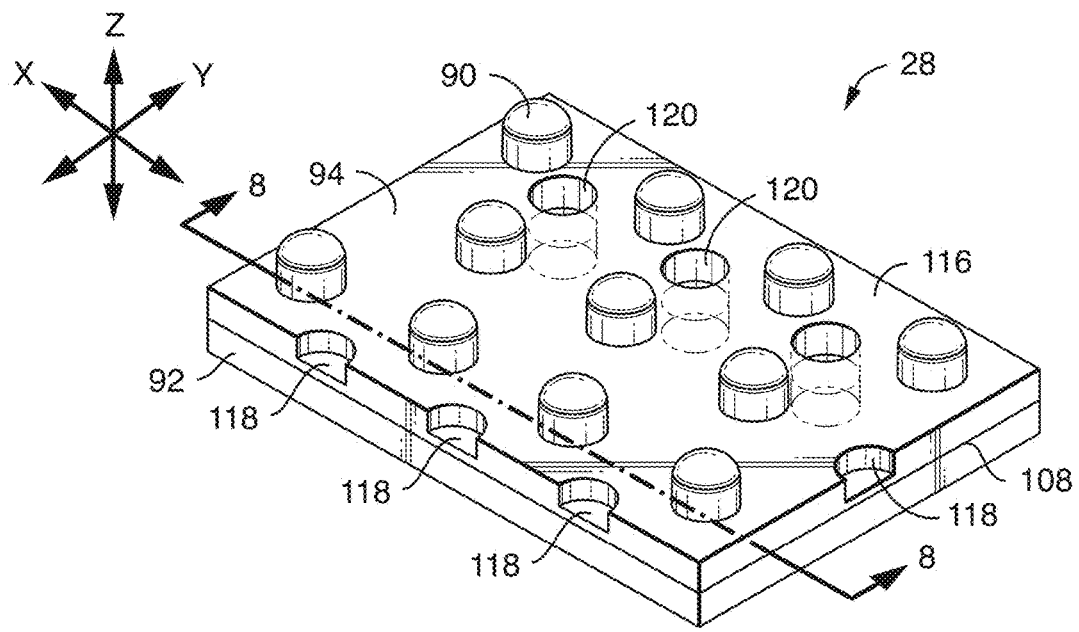
FIG. 7 is a perspective view of an embodiment of a body facing material.
Figure 8:
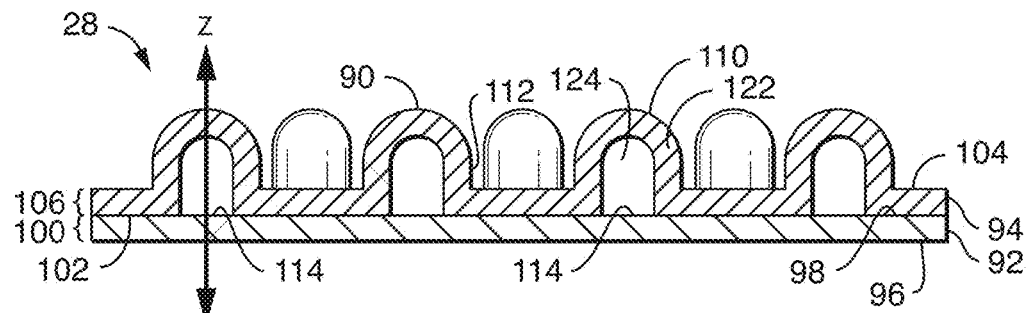
FIG. 8 is a cross-sectional view of the body facing material of FIG. 7 taken along line 8-8.
Figure 9:
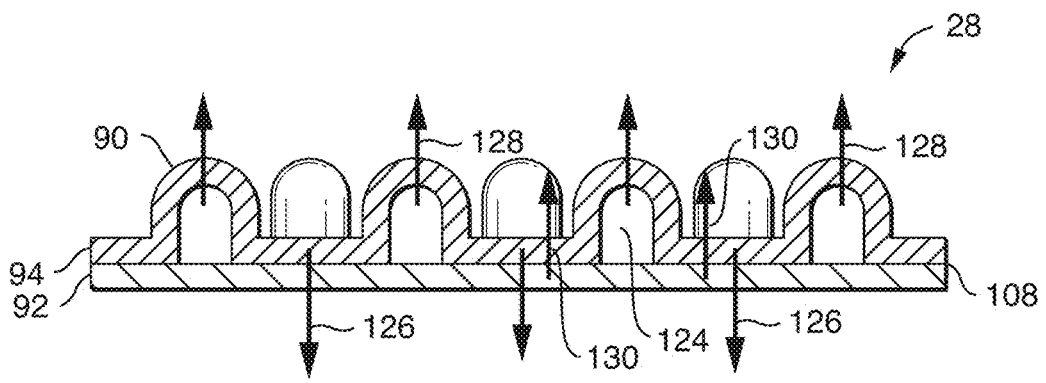
FIG. 9 is a cross-sectional view of the body facing material of FIG. 7 taken along line 8-8 of FIG. 7 showing possible directions of fiber movements within the body facing material due to a fluid entanglement process.

Body Facing Material:

As illustrated in FIGS. 7-9, a body facing material 28 can be a fluid entangled laminate web with projections 90 extending outwardly and away from at least one intended external surface of the laminate web. In an embodiment, the projections 90 can be hollow. The body facing material 28 can have two layers such as a support layer 92 and a projection layer 94. The support layer 92 can have a first surface 96 and an opposed second surface 98 as well as a thickness 100. The projection layer 94 can have an inner surface 102 and an opposed outer surface 104 as well as a thickness 106. An interface 108 can be present between the support layer 92 and the projection layer 94. In an embodiment, fibers of the projection layer 94 can cross the interface 108 and be entangled with and engage the support layer 92 so as to form the body facing material 28. In an embodiment in which the support layer 92 is a fibrous nonwoven web, the fibers of the support layer 92 may cross the interface 108 and be entangled with the fibers in the projection layer 94.

Projections of Body Facing Material

In an embodiment, the projections 90 can be filled with fibers from the projection layer 94 and/or the support layer 92. In an embodiment, the projections 90 can be hollow. The projections 90 can have closed ends 110 which can be devoid of apertures. In some embodiments, however, it may be desirable to increase the pressure and/or dwell time of the impinging fluid jets in the entangling process as described herein to create one or more apertures (not shown) in each of the projections 90. Apertures can also be formed into the body facing material via forming posts (not shown) which can be located on the projection forming surface 156 (such as forming surface 156 in FIGS. 12 and 12A). Such apertures may be formed in the closed ends 110 and/or side walls 112 of the projections 90. Such apertures are to be distinguished from interstitial fiber-to-fiber spacing which is the spacing from one individual fiber to the next individual fiber.

In various embodiments, the projections 90 can have a percentage of open area in which light can pass through the projections 90 unhindered by the material forming the projections 90, such as, for example, fibrous material. The percentage of open area present in the projections 90 encompasses all area of the projection 90 where light can pass through the projection 90 unhindered. Thus, for example, the percentage of open area of a projection 90 can encompass all open area of the projection 90 via apertures, interstitial fiber-to-fiber spacing, and any other spacing within the projection 90 where light can pass through unhindered. In an embodiment, the projections 90 can be formed without apertures and the open area can be due to the interstitial fiber-to-fiber spacing. In various embodiments, the projections 90 can have less than about 1, 0.9, 0.8, 0.7, 0.6, 0.5, 0.4, 0.3, 0.2, or 0.1% open area in a chosen area of the body facing material 28 as measured according to the Method to Determine Percent Open Area test method described herein.

Figure 10:
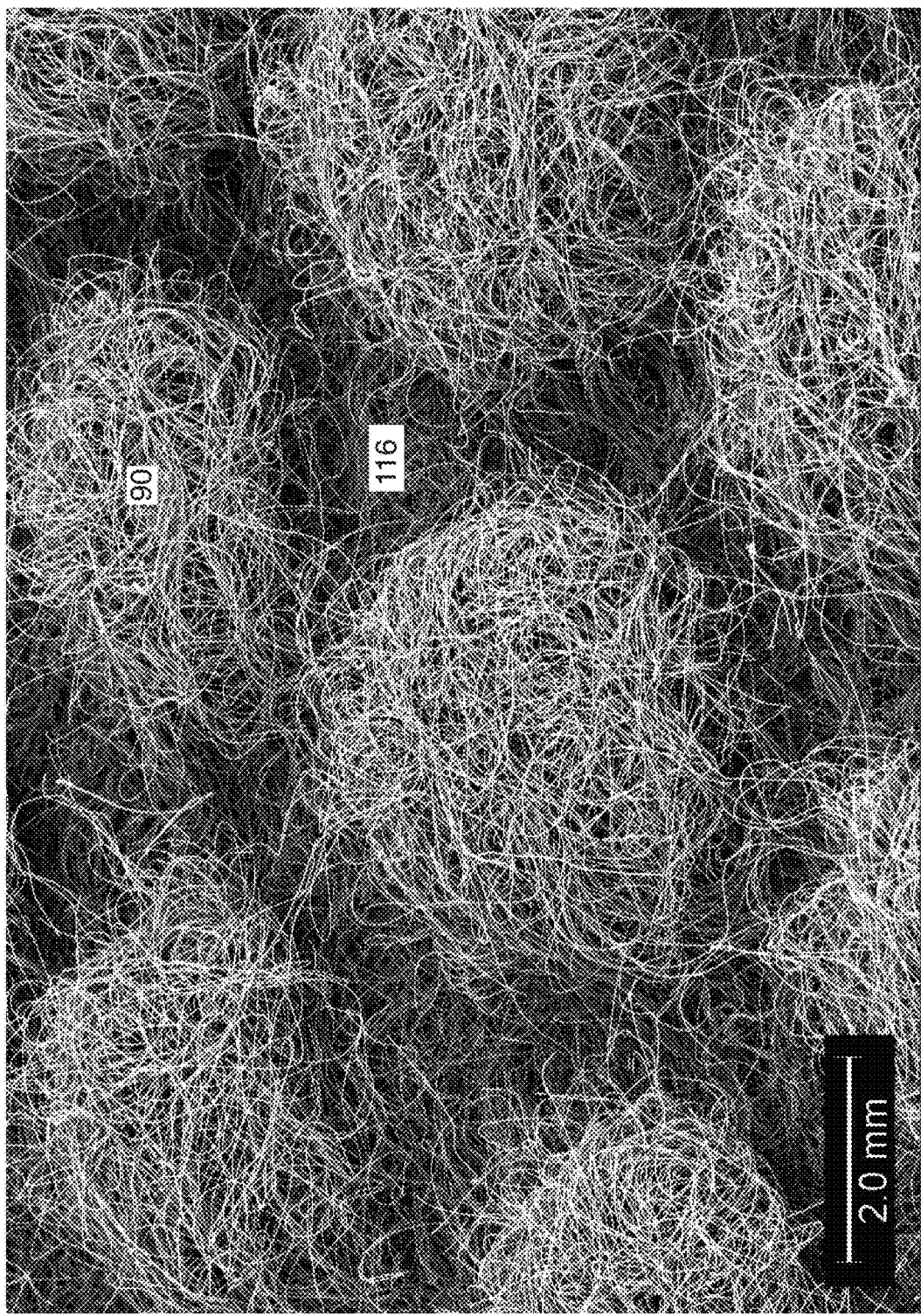
FIG. 10 is a photomicrograph at a 45 degree angle showing a fluid entangled body facing material.
Figure 10A:
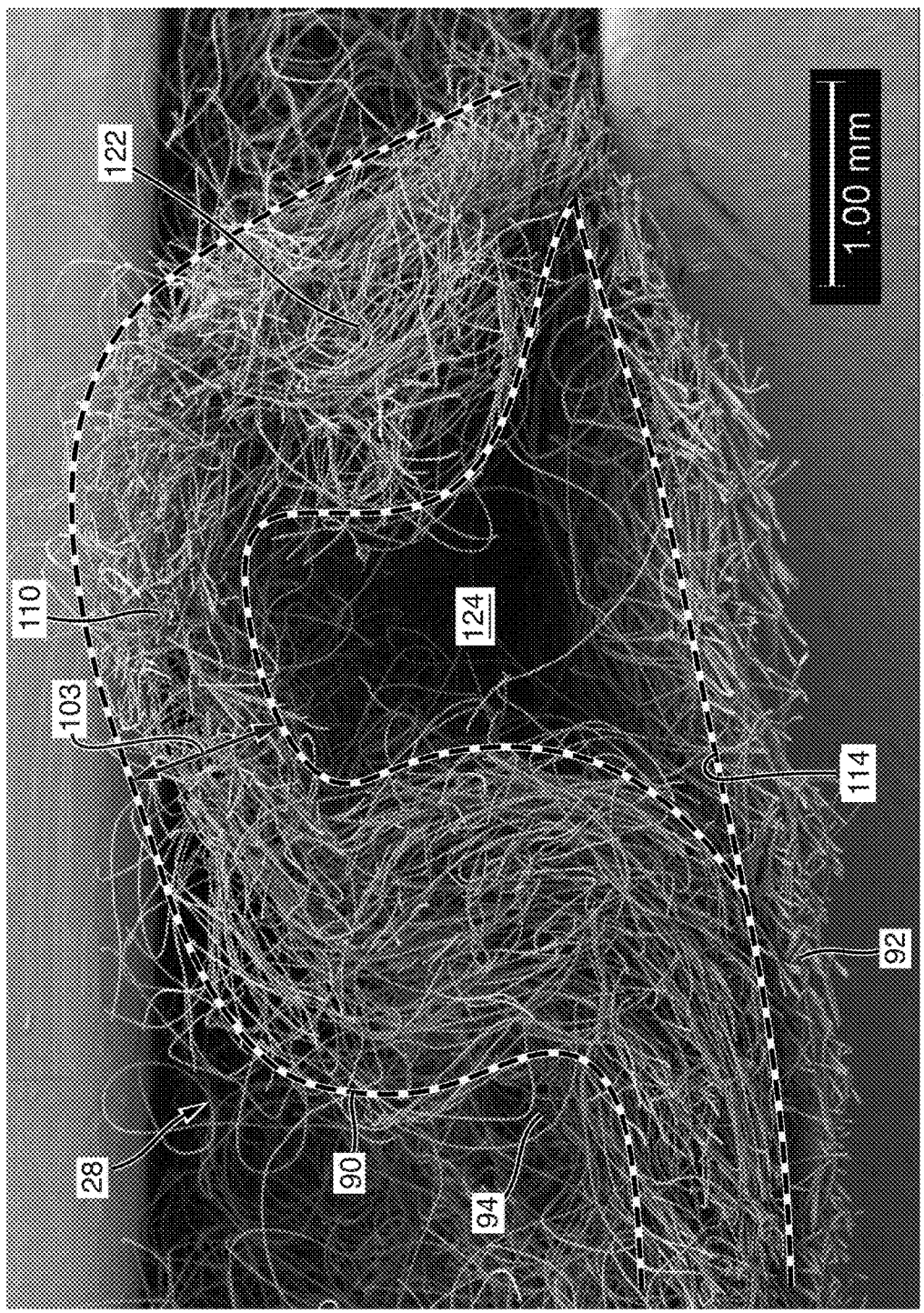
FIGS. 10A and 10B are photomicrographs showing a cross section of a body facing material.
Figure 10B:
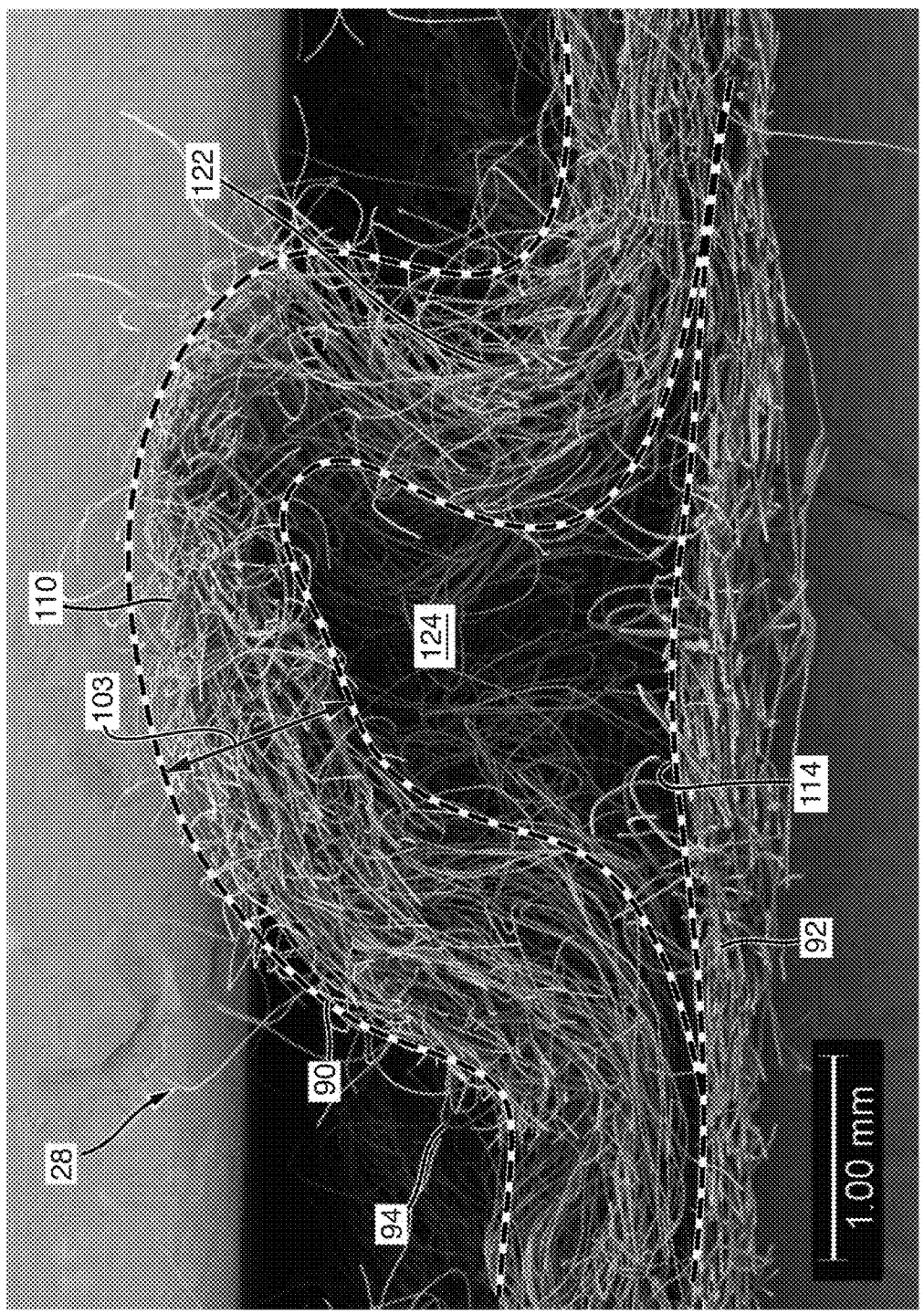

In an embodiment, such as the non-limiting embodiment illustrated in FIG. 10, the projections 90 can be round when viewed from above with somewhat domed or curved tops or closed ends 110, such as seen when viewed in a cross-section such as shown in FIGS. 10A and 10B. The actual shape of the projections 90 can be varied depending on the shape of the forming surface into which the fibers from the projection layer 94 are forced. Thus, while not limiting the variations, the shapes of the projections 90 may be, for example, round, oval, square, rectangular, triangular, diamond-shaped, etc. Both the width and height of the projections 90 can be varied as can be the spacing and pattern of the projections 90. In an embodiment, various shapes, sizes and spacing of the projections 90 can be utilized in the same projection layer 94. In an embodiment, the projections 90 can have a height, measured according to the Method to Determine Percent Open Area test method described herein, of greater than about 1 mm. In an embodiment, the projections 90 can have a height greater than about 1, 2, 3, 4, 5, 6, 7, 8, 9, or 10 mm. In an embodiment, the projections 90 can have a height from about 1, 2, 3, 4, or 5 mm to about 6, 7, 8, 9 or 10 mm.

The projections 90 of the body facing material 28 can be located on and emanate from the outer surface 104 of the projection layer 94. In an embodiment, the projections 90 can extend from the outer surface 104 of the projection layer 94 in a direction away from the support layer 92. In an embodiment in which the projections 90 can be hollow, they can have open ends 114 which can be located towards the inner surface 102 of the projection layer 94 and can be covered by the second surface 98 of the support layer 92 or the inner surface 102 of the projection layer 94 depending upon the amount of fiber that has been used from the projection layer 94 to form the projections 90. The projections 90 can be surrounded by land areas 116 which can be formed from the outer surface 104 of the projection layer 94 though the thickness of the land areas 116 can be comprised of both the projection layer 94 and the support layer 92. The land areas 116 can be relatively flat and planar, as shown in FIGS. 7 and 8, or topographical variability may be built into the land areas 116. For example, in an embodiment, a land area 116 may have a plurality of three-dimensional shapes formed into it by forming the projection layer 94 on a three-dimensionally-shaped forming surface such as is disclosed in U.S. Pat. No. 4,741,941 to Engelbert et al. assigned to Kimberly-Clark Worldwide and incorporated herein by reference in its entirety for all purposes. For example, in an embodiment, a land area 116 may be provided with depressions 118 which can extend all or part way into the projection layer 94 and/or the support layer 92. In addition, a land area 116 may be subjected to embossing which can impart surface texture and other functional attributes to the land area 116. In an embodiment, a land area 116 and the body facing material 28 as a whole may be provided with apertures 120 which can extend through the body facing material 28 so as to further facilitate the movement of fluids (such as the liquids and solids that make up body exudates) into and through the body facing material 28. Such apertures 120 are to be distinguished from interstitial fiber-to-fiber spacing, which is the spacing from one individual fiber to the next individual fiber.

In various embodiments, the land areas 116 can have a percentage of open area in which light can pass through the land areas 116 unhindered by the material forming the land areas 116, such as, for example, fibrous material. The percentage of open area present in the land areas 116 encompasses all area of the land areas 116 where light can pass through the land areas 116 unhindered. Thus, for example, the percentage of open area of a land area 116 can encompass all open area of the land areas 116 via apertures, interstitial fiber-to-fiber spacing, and any other spacing within the land areas 116 where light can pass through unhindered. In various embodiments, the land areas 116 can have greater than about 1% open area in a chosen area of the body facing material 28, as measured according to the Method to Determine Percent Open Area test method described herein. In an embodiment, the land areas 116 can be formed without apertures and the open area can be due to the interstitial fiber-to-fiber spacing. In various embodiments, the land areas 116 can have greater than about 1, 2, 3, 4, 5, 6, 7, 8, 9, 10, 11, 12, 13, 14, 15, 16, 17, 18, 19 or 20% open area in a chosen area of the body facing material 28. In various embodiments, the land areas 116 can have about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20% open area in a chosen area of the body facing material 28. In various embodiments, the land areas 116 can have from about 1, 2 or 3% to about 4 or 5% open area in a chosen area of the body facing material. In various embodiments, the land areas 116 can have from about 5, 6 or 7% to about 8, 9 or 10% open area in a chosen area of the body facing material 28. In various embodiments, the land areas 116 can have from about 10, 11, 12, 13, 14 or 15% to about 16, 17, 18, 19 or 20% open area in a chosen area of the body facing material 28. In various embodiments, the land areas 116 can have greater than about 20% open area in a chosen area of the body facing material 28.

The projections 90 of the body facing material 28 can be provided in any orientation as deemed suitable. In an embodiment, the projections 90 of the body facing material 28 can be provided randomly to the body facing material 28. In an embodiment, the projections 90 can be oriented linearly in the longitudinal direction 30 of the absorbent article 10. In an embodiment, the projections 90 can be oriented linearly in the lateral direction 32 of the absorbent article 10. In an embodiment, the projections 90 can be oriented linearly in a direction which can be at an angle to the longitudinal direction 30 and/or the lateral direction 32 of the absorbent article 10. The land areas 116 of the body facing material 28 can be provided in any orientation as deemed suitable. In an embodiment, the land areas 116 can be oriented linearly in the longitudinal direction 30 of the absorbent article 10. In an embodiment, the land areas 116 can be oriented linearly in the lateral direction 32 of the absorbent article 10. In an embodiment, the land areas 116 can be oriented linearly in a direction which can be at an angle to the longitudinal direction 30 and/or the lateral direction 32 of the absorbent article 10.

In an embodiment, the projections 90 and/or the land areas 116 can be provided such that the projections 90 are located in the crotch region 16 of the absorbent article 10, are located towards the perimeter of the absorbent article 10, and combinations thereof. In an embodiment, the projections 90 can have varying heights in different areas of the absorbent article 10. In such an embodiment, for example, the projections 90 can have a first height in an area of the absorbent article 10 and a different height in a different area of the absorbent article 10. In an embodiment, the projections 90 can have varying diameters in different areas of the absorbent article 10. In such an embodiment, for example, the projections 90 can have a first diameter in an area of the absorbent article 10 and can have a different diameter an another area of the absorbent article 10. In an embodiment, the concentration of projections 90 can vary in the absorbent article 10. In such an embodiment, an area of the absorbent article 10 can have a higher concentration of projections 90 than the concentration of projections 90 in a second area of the absorbent article 10.

In an embodiment, the projections 90 and/or the land areas 116 can be provided in a patterned orientation. Non-limiting examples of patterned orientations can include, but are not limited to, lines, circles, squares, rectangles, triangles, ovals, stars, and hexagons. In an embodiment, a patterned orientation can be provided such that the patterned orientation is parallel with the longitudinal direction 30 and/or the lateral direction 32 of the absorbent article 10. In an embodiment, a patterned orientation can be provided such that the patterned orientation is at an angle to the longitudinal direction 30 and/or the lateral direction 32 of the absorbent article 10. In an embodiment, a projection 90 of the body facing material 28 can be at least partially aligned, completely aligned, or completely non-aligned with another projection 90 of the body facing material 28, such as, for example, an adjacent projection 90. Without being bound by theory, it is believed that the alignment (whether partial, complete alignment or complete non-alignment) of a projection 90 of the body facing material 28 with another projection 90, such as an adjacent projection 90, of the body facing material 28 can result in channels of land areas 116 which can impede further spread of body exudates along the body facing material 28 of the absorbent article 10 and/or can direct the spread of body exudates towards desired locations of the body facing material 28 of the absorbent article 10.

Figure 11A:
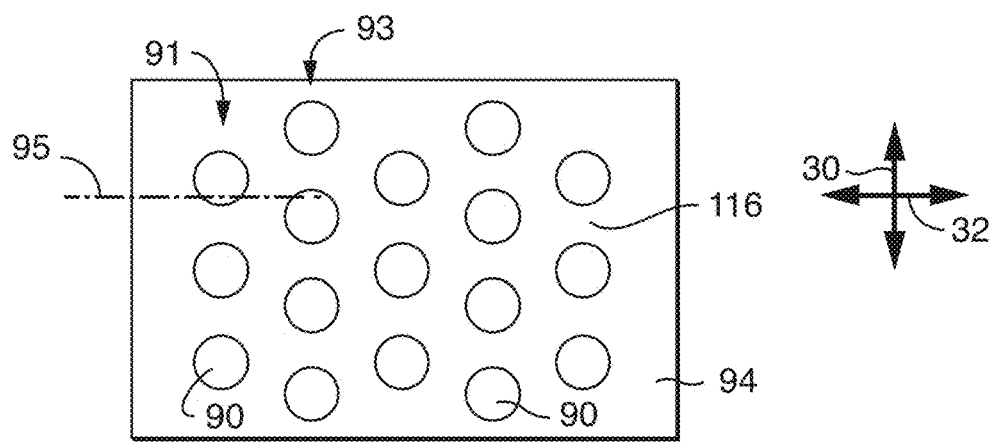
FIG. 11A is a top down view of an illustrative embodiment of a projection layer of a body facing material in which two projections are partially aligned with each other.
Figure 11B:
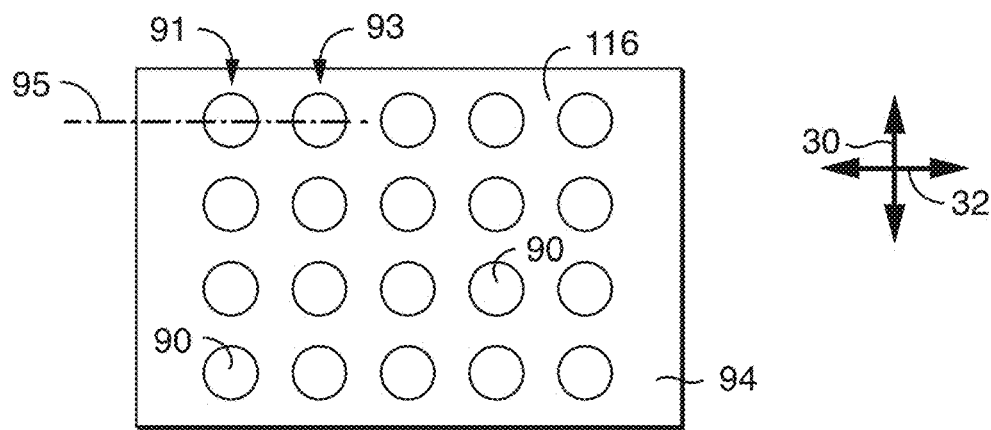
FIG. 11B is a top down view of an illustrative embodiment of a projection layer of a body facing material in which two projections are completely aligned with each other.
Figure 11C:
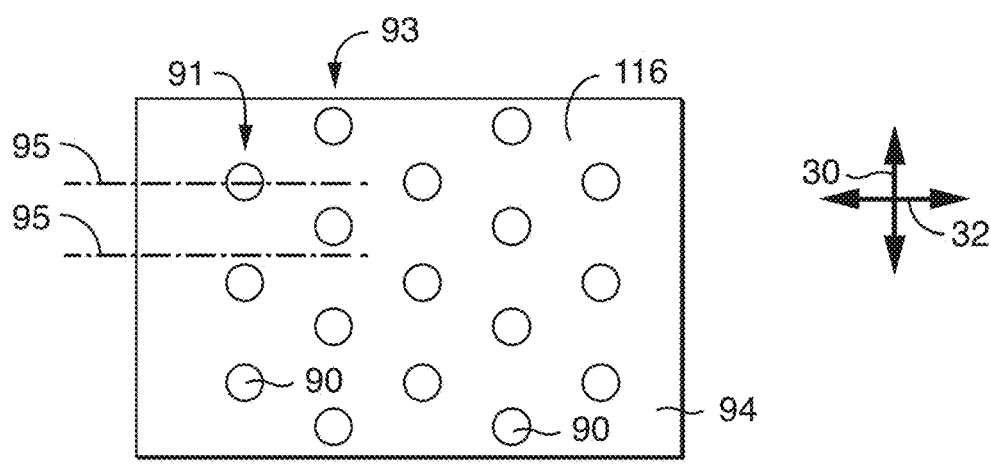
FIG. 11C is a top down view of an illustrative embodiment of a projection layer of a body facing material in which two projections are completely non-aligned with each other.

As illustrative examples, FIGS. 11A, 11B and 11C provide illustrations of an exemplary embodiment of partial alignment, complete alignment and complete non-alignment of two projections in adjacent lines of projection. In the embodiment illustrated, for example, in FIG. 11A, a first line 91 of projections 90 can be arranged linearly in a direction that is parallel with the longitudinal direction 30 of the absorbent article 10. In such an embodiment, a projection 90 of a first line 91 of projections 90 which are oriented in a direction parallel to the longitudinal direction 30 of the absorbent article can be at least partially aligned with a projection 90 of an immediately adjacent second line 93 of projections 90 which are oriented in a direction parallel to the longitudinal direction 30 of the absorbent article. In such an embodiment, a partial alignment of a projection 90 of a first line 91 of projections 90 which are oriented in a direction parallel to the longitudinal direction 30 of the absorbent article 10 with a projection 90 of an immediately adjacent second line 93 of projections 90 which is oriented in a direction parallel to the longitudinal direction 30 of the absorbent article 10 can result in the passage of an imaginary line 95 in the lateral direction 32 of the absorbent article 10 through each of the projections 90 of the first 91 and second 93 lines of projections 90. It should be understood that the passage of the imaginary line 95 through each of the projections 90 of the first 91 and second 93 lines of projections 90 does not necessarily result in a passage through the midpoint of each of the projections 90 of the first 91 and second 93 lines of projections 90. In the embodiment illustrated, for example, in FIG. 11B, a first line 91 of projections 90 can be arranged linearly in a direction that is parallel with the longitudinal direction 30 of the absorbent article 10. In such an embodiment, a projection 90 of a first line 91 of projections 90 which are oriented in a direction parallel to the longitudinal direction 30 of the absorbent article 10 can be completely aligned with a projection 90 of an immediately adjacent second line 93 of projections 90 which are oriented in a direction parallel to the longitudinal direction 30 of the absorbent article 10. In such an embodiment, a complete alignment of a projection 90 of a first line 91 of projections 90 which are oriented in a direction parallel to the longitudinal direction 30 of the absorbent article 10 with a projection 90 of an immediately adjacent second line 93 of projections 90 which is oriented in a direction parallel to the longitudinal direction 30 of the absorbent article 10 can result in the passage of an imaginary line 95 in the lateral direction 32 of the absorbent article 10 through each of the projections 90 of the first 91 and second 93 lines of projections 90. In such an embodiment, the imaginary line 95 could pass through the midpoint of each of the projections 90 of the first 91 and second 93 lines of projections 90. In the embodiment illustrated, for example, in FIG. 11C, a first line 91 of projections 90 can be arranged linearly in a direction that is parallel with the longitudinal direction 30 of the absorbent article 10. In such an embodiment, a projection 90 of a first line 91 of projections 90 which are oriented in a direction parallel to the longitudinal direction 30 of the absorbent article 10 can be completely non-aligned with a projection 90 of an immediately adjacent second line 93 of projections 90 which are oriented in a direction parallel to the longitudinal direction 30 of the absorbent article 10. In such an embodiment, a complete non-alignment of a projection 90 of a first line 91 of projections 90 which are oriented in a direction parallel to the longitudinal direction 30 of the absorbent article 10 with a projection 90 of an immediately adjacent second line 93 of projections 90 which is oriented in a direction parallel to the longitudinal direction 30 of the absorbent article 10 can result in the passage of an imaginary line 95 in the lateral direction 32 of the absorbent article 10 through only one of the projections 90 or through neither of the projections 90 of the first 91 and second lines 93 of projections 90. It should be understood that additional configurations of partial alignment, complete alignment and complete non-alignment can be formed.

While it is possible to vary the density and fiber content of the projections 90, in an embodiment, the projections 90 can be "hollow". Referring to FIGS. 10A and 10B, it can be seen that when the projections 90 are hollow, they can have a shell 122 formed from the fibers of the projection layer 94. The shell 122 can define an interior space 124 which can have a lower density of fibers as compared to the shell 122 of the projections 90. By "density" it is meant the fiber count or content per chosen unit of volume within a portion of the interior space 124 or the shell 122 of the projection 90. The distance 103 between the external facing surface of the shell 122 to the inner facing surface of the shell 122 as well as the density of the shell 122 may vary within a particular or individual projection 90 and it also may vary as between different projections 90. In addition, the size of the hollow interior space 124 as well as its density may vary within a particular or individual projection 90 and it also may vary as between different projections 90. The photomicrographs of FIGS. 10A and 10B reveal a lower density or count of fibers in the interior space 124 as compared to the shell 122 of the illustrated projection 90. As a result, if there is at least some portion of an interior space 124 of a projection 90 that has a lower fiber density than at least some portion of the shell 122 of the same projection 90, then the projection is regarded as being "hollow". In this regard, in some situations, there may not be a well-defined demarcation between the shell 122 and the interior space 124 but, if with sufficient magnification of a cross-section of one of the projections, it can be seen that at least some portion of the interior space 124 of the projection 90 has a lower density than some portion of the shell 122 of the same projection 90, then the projection 90 is regarded as being "hollow". Further, if at least a portion of the projections 90 of a body facing material 28 are hollow, the projection layer 94 and the body facing material 28 are regarded as being "hollow" or as having "hollow projections". In an embodiment, the portion of the projections 90 which are hollow can be greater than or equal to about 50 percent of the projections 90 in a chosen area of the body facing material 28. In an embodiment, greater than or equal to about 70 percent of the projections 90 in a chosen area of the body facing material 28 can be hollow. In an embodiment, greater than or equal to about 90 percent of the projections 90 in a chosen area of the body facing material 28 can be hollow.

As will become more apparent in connection with the description of the processes set forth below, the body facing material 28 can be the result of the movement of the fibers in the projection layer 94 in one and sometimes two or more directions. Referring to FIG. 9, if the forming surface (such as forming surface 156 in FIGS. 12 and 12A) upon which the projection layer 94 is placed is solid except for the forming holes (such as forming holes 170 in FIG. 12A) used to form the projections 90, then the force of the fluid entangling streams hitting and rebounding off the solid surface land areas (such as land areas 172 in FIG. 12A) corresponding to the land areas 116 of the projection layer 94 can cause a migration of fibers adjacent the inner surface 102 of the projection layer 94 into the support layer 92 adjacent its second surface 98. This migration of fibers in the first direction can be represented by the arrows 126 shown in FIG. 9. In order to form the projections 90 extending outwardly from the outer surface 104 of the projection layer 94, there must be a migration of fibers in a second direction as shown by the arrows 128. It is this migration in the second direction which causes fibers from the projection layer 94 to move out and away from the outer surface 104 to form the projections 90.

In an embodiment in which the support layer 92 can be a fibrous nonwoven web, depending on the degree of web integrity and the strength and dwell time of the fluid jets, there also may be a movement of support layer 92 fibers into the projection layer 94 as shown by arrows 130 in FIG. 9. The net result of these fiber movements can be the creation of a body facing material 28 with good overall integrity and lamination of the layers (92 and 94) at their interface 108 thereby allowing further processing and handling of the body facing material 28. As a result of the fluid entanglement processes described herein, it is generally not desirable that the fluid pressure used to form the projections 90 be of sufficient force so as to force fibers from the support layer 92 to be exposed on the outer surface 104 of the projection layer 94.

Support Layer and Projection Layer of Body Facing Material

As the name implies, the support layer 92 can support the projection layer 94 containing the projections 90 and can be made from a number of structures provided the support layer 92 can be capable of supporting the projection layer 94. The primary functions of the support layer 92 can be to protect the projection layer 94 during the formation of the projections 90, to be able to bond to or be entangled with the projection layer 94 and to aid in further processing of the projection layer 94 and the resultant body facing material 28. Suitable materials for the support layer 92 can include, but are not limited to, nonwoven fabrics or webs, scrim materials, netting materials, paper/cellulose/wood pulp-based products which can be considered a subset of nonwoven fabrics or webs as well as foam materials, films and combinations of the foregoing provided the material or materials chosen are capable of withstanding a process of manufacture such as a fluid-entangling process. In an embodiment, the support layer 92 can be a fibrous nonwoven web made from a plurality of randomly deposited fibers which may be staple length fibers such as are used, for example, in carded webs, air laid webs, etc. or they may be more continuous fibers such as are found in, for example, meltblown or spunbond webs. Due to the functions the support layer 92 must perform, the support layer 92 can have a higher degree of integrity than the projection layer 94. In this regard, the support layer 92 can remain substantially intact when it is subjected to the fluid-entangling process discussed in greater detail below. The degree of integrity of the support layer 92 can be such that the material forming the support layer 92 can resist being driven down into and filling the projections 90 of the projection layer 94. As a result, in an embodiment in which the support layer 92 is a fibrous nonwoven web, it should have a higher degree of fiber-to-fiber bonding and/or fiber entanglement than the fibers in the projection layer 94. While it can be desirable to have fibers from the support layer 92 entangle with the fibers of the projection layer 94 adjacent the interface 108 between the two layers, it is generally desired that the fibers of this support layer 92 not be integrated or entangled into the projection layer 94 to such a degree that large portions of these fibers find their way inside the projections 90.

In an embodiment, a function of the support layer 92 can be to facilitate further processing of the projection layer 94. In an embodiment, the fibers used to form the projection layer 94 can be more expensive than those used to form the support layer 92. As a result, in such an embodiment, it can be desirable to keep the basis weight of the projection layer 94 low. In so doing, however, it can become difficult to process the projection layer 94 subsequent to its formation. By attaching the projection layer 94 to an underlying support layer 92, further processing, winding and unwinding, storage and other activities can be done more effectively.

In order to resist the higher degree of fiber movement, as mentioned above, in an embodiment, the support layer 92 can have a higher degree of integrity than the projection layer 94. This higher degree of integrity can be brought about in a number of ways. One can be fiber-to-fiber bonding which can be achieved through thermal or ultrasonic bonding of the fibers to one another with or without the use of pressure as in through-air bonding, point bonding, powder bonding, chemical bonding, adhesive bonding, embossing, calender bonding, etc. In addition, other materials may be added to the fibrous mix such as adhesives and/or bicomponent fibers. Pre-entanglement of a fibrous nonwoven support layer 92 may also be used such as, for example, by subjecting the web to hydroentangling, needlepunching, etc., prior to this support layer 92 being joined to a projection layer 94. Combinations of the foregoing are also possible. Still other materials such as foams, scrims and nettings may have enough initial integrity so as to not need further processing. The level of integrity can in many cases be visually observed due to, for example, the observation with the unaided eye of such techniques as point bonding which is commonly used with fibrous nonwoven webs such as spunbond webs and staple fiber-containing webs. Further magnification of the support layer 92 may also reveal the use of fluid-entangling or the use of thermal and/or adhesive bonding to join the fibers together. Depending on whether samples of the individual layers (92 and 94) are available, tensile testing in either or both of the machine and cross-machine directions may be undertaken to compare the integrity of the support layer 92 to the projection layer 94. See for example ASTM test D5035-11 which is incorporated herein its entirety for all purposes.

The type, basis weight, tensile strength and other properties of the support layer 92 can be chosen and varied depending upon the particular end use of the resultant body facing material 28. When the body facing material 28 is to be used as part of an absorbent article such as a personal care absorbent article, wipe, etc., it can be generally desirable that the support layer 92 be a layer that is fluid pervious, has good wet and dry strength, is able to absorb fluids such as body exudates, possibly retain the fluids for a certain period of time and then release the fluids to one or more subjacent layers. In this regard, fibrous nonwovens such as spunbond webs, meltblown webs and carded webs such as airlaid webs, bonded carded webs and coform materials are well-suited as support layers 92. Foam materials and scrim materials are also well-suited. In addition, the support layer 92 may be a multi-layered material due to the use of several layers or the use of multi-bank formation processes as are commonly used in making spunbond webs and meltblown webs as well as layered combinations of meltblown and spunbond webs. In the formation of such support layers 92, both natural and synthetic materials may be used alone or in combination to fabricate the materials. In various embodiments, the support layer 92 can have a basis weight ranging from about 5 to about 40 or 50 gsm.

The type, basis weight and porosity of the support layer 92 can affect the process conditions necessary to form the projections 90 in the projection layer 94. Heavier basis weight materials can increase the entangling force of the entangling fluid streams needed to form the projections 90 in the projection layer 94. However, heavier basis weight support layers 92 can also provide improved support for the projection layer 94 as it has been determined that the projection layer 94 by itself is too stretchy to maintain the shape of the projections 90 post the formation process. The projection layer 94 by itself can unduly elongate in the machine direction due to the mechanical forces exerted on it by subsequent winding and converting processes and consequently diminish and distort the projections. Also, without the support layer 92, the projections 90 in the projection layer 94 tend to collapse due to the winding pressures and compressive weights the projection layer 94 experiences in the winding process and subsequent conversion and do not recover to the extent they do when a support layer 94 is present.

The support layer 92 may be subjected to further treatment and/or additives to alter or enhance its properties. For example, surfactants and other chemicals may be added both internally and externally to the components forming all or a portion of the support layer 92 to alter or enhance its properties. Compounds commonly referred to as hydrogels or superabsorbents which absorb many times their weight in liquids may be added to the support layer 92 in both particulate and fiber form.

The projection layer 94 can be made from a plurality of randomly deposited fibers which may be staple length fibers such as are used, for example, in carded webs, airlaid webs, coform webs, etc., or they may be more continuous fibers such as are found in, for example, meltblown or spunbond webs.

The fibers in the projection layer 94 can have less fiber-to-fiber bonding and/or fiber entanglement and thus less integrity as compared to the integrity of the support layer 92, especially in embodiments when the support layer 92 is a fibrous nonwoven web. In an embodiment, the fibers in the projection layer 94 may have no initial fiber-to-fiber bonding for purposes of allowing the formation of the projections 90 as will be explained in further detail below in connection with the description of one or more of the embodiments of the process and apparatus for forming the body facing material 28. Alternatively, when both the support layer 92 and the projection layer 94 can both be fibrous nonwoven webs, the projection layer 94 can have less integrity than the support layer 92 due to the projection layer 94 having, for example, less fiber-to-fiber bonding, less adhesive or less pre-entanglement of the fibers forming the projection layer 94.

The projection layer 94 can have a sufficient amount of fiber movement capability to allow the below-described fluid entangling process to be able to move a first plurality of the plurality of fibers of the projection layer 94 out of the X-Y plane of the projection layer 94 and into the perpendicular or Z-direction of the projection layer 94 so as to be able to form the projections 90 (illustrated in FIG. 7). As noted herein, in various embodiments, the projections 90 can be hollow. As described herein, in an embodiment, a second plurality of the plurality of fibers in the projection layer 94 can become entangled with the support layer 92. If more continuous fiber structures are being used such as meltblown or spunbond webs, in an embodiment, there may be little or no pre-bonding of the projection layer 94 prior to the fluid entanglement process. Longer fibers such as are generated in meltblowing and spunbonding processes (which are often referred to as continuous fibers to differentiate them from staple length fibers) will typically require more force to displace the fibers in the Z-direction than will shorter, staple length fibers that typically have fiber lengths less than about 100 mm and more typically fibers lengths in the 10 to 60 mm range. Conversely, staple fiber webs such as carded webs and airlaid webs can have some degree of pre-bonding or entanglement of the fibers due to their shorter length. Such shorter fibers require less fluid force from the fluid entangling streams to move them in the Z-direction to form the projections 90. As a result, a balance must be met between fiber length, degree of pre-fiber bonding, fluid force, web speed and dwell time so as to be able to create the projections 90 without, unless desired, forming apertures in the land areas 116 or the projections 90 or forcing too much material into the interior space 124 of the projections 90 thereby making the projections 90 too rigid for some end-use applications.

In various embodiments, the projection layer 94 can have a basis weight ranging from about 10 gsm to about 60 gsm. Spunbond webs can typically have basis weights of between about 15 and about 50 gsm when being used as the projection layer 94. Fiber diameters can range between about 5 and about 20 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. Hollow fibers may also be used. The fibers may be formed from any polymer formulations typically used to form spunbond webs. Examples of such polymers include, but are not limited to, polypropylene ("PP"), polyester ("PET"), polyamide ("PA"), polyethylene ("PE") and polylactic acid ("PLA"). The spunbond webs may be subjected to post-formation bonding and entangling techniques if necessary to improve the processability of the web prior to its being subjected to the projection forming process.

Meltblown webs can typically have basis weights of between about 20 and about 50 gsm when being used as the projection layer 94. Fiber diameters can range between about 0.5 and about 5 microns. The fibers may be single component fibers formed from a single polymer composition or they may be bicomponent or multicomponent fibers wherein one portion of the fiber can have a lower melting point than the other components so as to allow fiber-to-fiber bonding through the use of heat and/or pressure. The fibers may be formed from any polymer formulations typically used to form spunbond webs. Examples of such polymers include, but are not limited to, PP, PET, PA, PE and PLA.

Carded and airlaid webs can use staple fibers that can typically range in length between about 10 and about 100 millimeters. Fiber denier can range between about 0.5 and about 6 denier depending upon the particular end use. Basis weights can range between about 20 and about 60 gsm. The staple fibers may be made from a wide variety of polymers including, but not limited to, PP, PET, PA, PE, PLA, cotton, rayon, flax, wool, hemp and regenerated cellulose such as, for example, Viscose. Blends of fibers may be utilized too, such as blends of bicomponent fibers and single component fibers as well as blends of solid fibers and hollow fibers. If bonding is desired, it may be accomplished in a number of ways including, for example, through-air bonding, calender bonding, point bonding, chemical bonding and adhesive bonding such as powder bonding. If needed, to further enhance the integrity and processability of a projection layer 94 prior to the projection forming process, the projection layer 94 may be subjected to pre-entanglement processes to increase fiber entanglement within the projection layer 94 prior to the formation of the projections 90. Hydroentangling can be advantageous in this regard.

While the foregoing nonwoven web types and formation processes described herein are suitable for use in conjunction with the projection layer 94, it is anticipated that other webs and formation processes may also be used provided the webs are capable of forming the projections 90.

The support layer 92 and the projection layer 94 each can be made at a variety of basis weights depending upon the particular end application. For example, the body facing material 28 can have an overall basis weight from about 15, 20 or 25 to about 100, 110 or 120 gsm and the support layer 92 can have a basis weight from about 5 to about 40 or 50 gsm while the projection layer 94 can have a basis weight from about 15 or 20 to about 50 or 60 gsm. Such basis weight ranges can be possible due to the manner in which the body facing material 28 can be formed and the use of two different layers with different functions relative to the formation process. As a result, the body facing material 28 can be made in commercial settings which heretofore were not considered possible due to the inability to process the individual webs and form the desired projections 90.

In an embodiment, the body facing material 28 of an absorbent article 10 can have a load of more than about 2 Newtons per 25 mm width at a 10% extension in the machine direction. In an embodiment, the body facing material 28 of an absorbent article 10 can have a load of more than about 4 Newtons per 25 mm width at a 10% extension in the machine direction. In an embodiment, the body facing material 28 of an absorbent article 10 can have a load of more than about 6 Newtons per 25 mm width at a 10% extension in the machine direction. In various embodiments, the body facing material 28 of an absorbent article 10 can have a resiliency of greater than about 70%. In various embodiments, the body facing material 28 of an absorbent article 10 can have a resiliency of greater than about 70, 73, 75, 77, 80, or 83%.

In various embodiments, the absorbent article 10 can be a diaper. In various embodiments, the amount of residual fecal material simulant on the body facing material 28 of an absorbent article 10 following insult with fecal material simulant as measured according to the Determination of Residual Fecal Material Simulant test method described herein can be less than about 2.5, 2.4, 2.3, 2.2, 2.1, 2.0, 1.9, 1.8, 1.7, 1.6, or 1.5 grams. In various embodiments, the area of spread of fecal material simulant on the body facing material 28 of an absorbent article 10 following insult with fecal material simulant as measured according to the Determination of Area of Spread of Fecal Material Simulant test method described herein can be less than about 34, 33, 32, 31, 30, or 29 cm$^2$.

In various embodiments, the absorbent article 10 can be a feminine hygiene product. In various embodiment, the second intake time through a body facing material 28 on an absorbent article 10 following insult with a menses simulant can be less than about 30, 20 or 15 seconds as measured using the Intake/Rewet test method described herein. In various embodiments, the second intake time of menses simulant through a body facing material 28 on an absorbent article 10 can be from about 25 or 30% to about 50, 60 or 70% less than commercially available product following insult with the menses simulant as measured using the Intake/Rewet test method described herein. In various embodiments, the second intake time through a body facing material 28 on an absorbent article 10 can be about 25, 30, 31, 47, 49, 50, 54, 60, 64, 66 or 70% less than commercially available products following insult with a menses simulant as measured using the Intake/Rewet test method described herein.

In various embodiment, the second intake time through a body facing material 28 on an absorbent article 10 following insult with a menses simulant can be less than about 30, 20 or 15 seconds without an increase in rewet amount as measured using the Intake/Rewet test method described herein. In various embodiments, the second intake time of menses simulant through a body facing material 28 on an absorbent article 10 can be from about 25 or 30% to about 50, 60 or 70% less than commercially available product without an increase in rewet amount following insult with the menses simulant as measured using the Intake/Rewet test method described herein. In various embodiments, the second intake time through the body facing material 28 on an absorbent article 10 following insult with menses simulant can be about 25, 30, 31, 47, 49, 50, 54, 60, 64, 66 or 70% less than commercially available products without an increase in rewet amount.

Process for Making Body Facing Material

A fluid entangling process can be employed to form the body facing material 28. Any number of fluids may be used to join the support layer 92 and projection layer 94 together including both liquids and gases. The most common technology used in this regard can be referred to as spunlace or hydroentangling technology which can use pressurized water as the fluid for entanglement.

Figure 12:
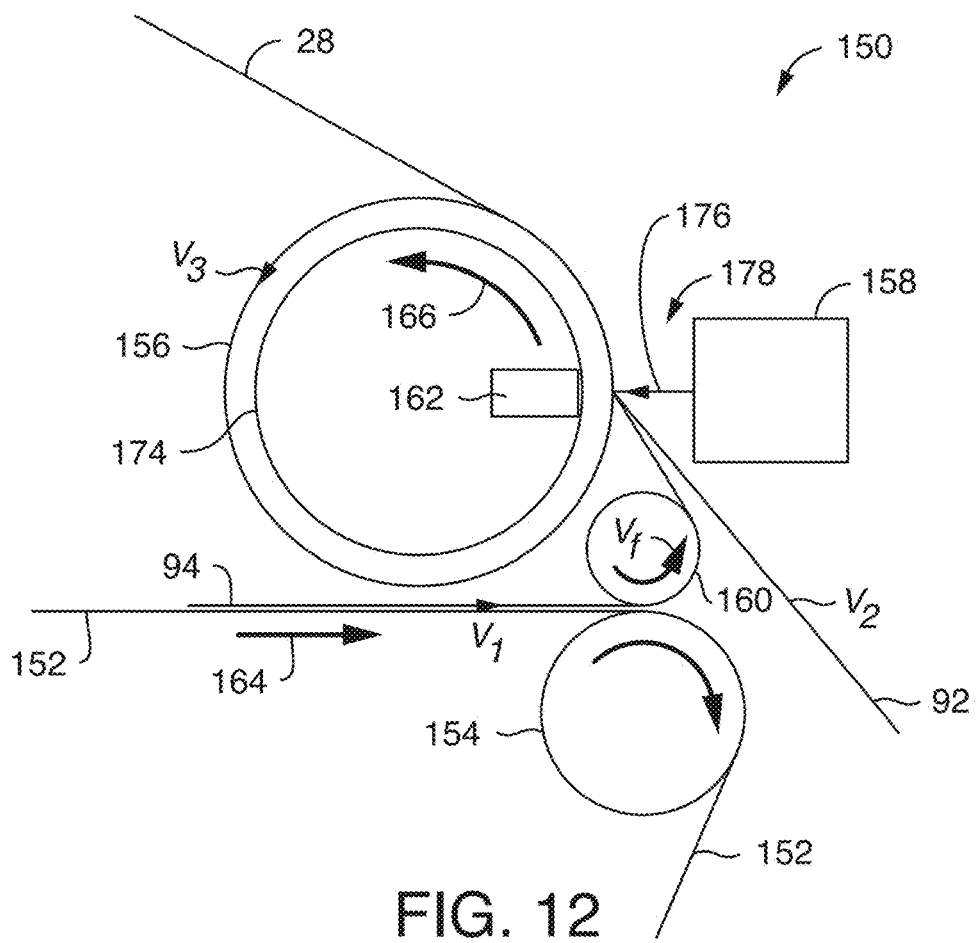
FIG. 12 is a schematic side view of an apparatus and a process for forming a fluid entangled body facing material.

Referring to FIG. 12 there is shown an embodiment of a process and apparatus for forming a fluid-entangled body facing material 28 with projections 90. The apparatus 150 can include a first transport belt 152, a transport belt drive roller 154, a projection forming surface 156, a fluid entangling device 158, an optional overfeed roller 160, and a fluid removal system 162 such as a vacuum or other conventional sucking device. Such vacuum devices and other means are well known to those of ordinary skill in the art. The transport belt 152 can carry the projection layer 94 into the apparatus 150. If any pre-entangling is to be done on the projection layer 94 upstream of the process illustrated in FIG. 12, the transport belt 152 may be porous. The transport belt 152 can travel in a first direction (which is the machine direction) as shown by arrow 164 at a first speed or velocity V1. The transport belt 152 can be driven by a transport belt drive roller 154 or other suitable means as are well known to those of ordinary skill in the art.

Figure 12A:
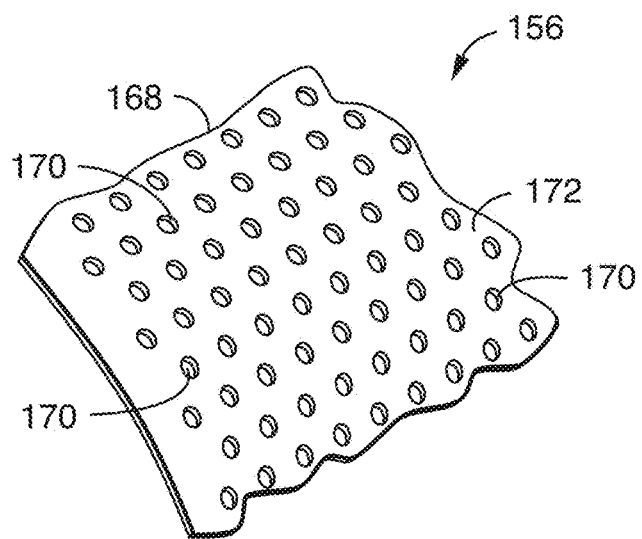
FIG. 12A is an exploded view of a representative portion of a projection forming surface.

The projection forming surface 156 as shown in FIG. 12 can be in the form of a texturizing drum and a partially exploded view of the surface is shown in FIG. 12A. The projection forming surface 156 can move in the machine direction as shown by arrow 166 at a speed or velocity V3. It can be driven and its speed can be controlled by any suitable drive means (not shown) such as electric motors and gearing as are well known to those of ordinary skill in the art. The projection forming surface 156 depicted in FIGS. 12 and 12A can have a forming surface 168 containing a pattern of forming holes 170 that can correspond to the shape and pattern of the desired projections 90 in the projection layer 94 and the forming holes 170 can be separated by a land area 172. The forming holes 170 can be of any shape and any pattern. As can be seen from the Figures depicting the body facing material 28, the forming hole 170 shapes can be round but it should be understood that any number of shapes and combination of shapes can be used depending on the end use application. Examples of possible forming hole 170 shapes include, but are not limited to, ovals, crosses, squares, rectangles, diamond shapes, hexagons and other polygons. Such shapes can be formed in the projection forming surface 156 by casting, punching, stamping, laser-cutting and water-jet cutting. The spacing of the forming holes 170 and, therefore, the degree of land area 172 can also be varied depending upon the particular end application of the body facing material 28. Further, the pattern of the forming holes 170 in the projection forming surface 156 can be varied depending upon the particular end application of the body facing material 28.

The material forming the projection forming surface 156 may be any number of suitable materials commonly used for forming such surfaces including, but not limited to, sheet metal, plastics and other polymer materials, rubber, etc. The forming holes 170 can be formed in a sheet of the material that is then formed into a projection forming surface 156 or the projection forming surface 156 can be molded or cast from suitable materials or printed with 3D printing technology. The projection forming surface 156 can be removably fitted onto and over an optional porous inner drum shell 174 so that different forming surfaces 168 can be used for different end product designs. The porous inner drum shell 174 can interface with the fluid removal system 162 which can facilitate pulling the entangling fluid and fibers down into the forming holes 170 in the outer forming surface 168 thereby forming the projections 90 in the projection layer 94. The porous inner drum shell 174 can also act as a barrier to retard further fiber movement down into the fluid removal system 162 and other portions of the equipment thereby reducing fouling of the equipment. The porous inner drum shell 174 can rotate in the same direction and at the same speed as the projection forming surface 156. In addition, to further control the height of the projections 90, the distance between the inner drum shell 174 and the projection forming surface 156 can be varied. In an embodiment in which a porous inner drum shell is utilized, the distance between the outer facing surface of the inner drum shell 174 and the inner facing surface of the projection forming surface 156 can range from about 0 to about 5 mm.

The cross-sectional dimensions of the forming holes 170 and their depth can influence the cross-section and height of the projections 90 produced in the projection layer 94. In an embodiment, the forming hole 170 depth in the projection forming surface 156 can correspond to the height of the projections 90. In an embodiment, the depth of the forming holes 170 in the projection forming surface 156 can be from about 1 or 3 mm to about 5 or 10 mm. In an embodiment, a forming hole 170 cross-section size may be from about 2 or 3 mm to about 6 or 10 mm as measured along the major axis. In an embodiment, a forming hole 170 spacing on a center-to-center basis can be from about 3 or 4 mm to about 7 or 10 mm. The pattern of the spacing between forming holes 170 may be varied and selected depending upon the particular end use. Some examples of patterns include, but are not limited to, aligned patterns of rows and/or columns, skewed patterns, hexagonal patterns, wavy patterns and patterns depicting pictures, figures and objects. It should be noted that each of the forming holes 170 depth, spacing, size, shape and other parameters may be varied independently of one another and may be varied based upon the particular end use of the body facing material 28 being formed.

The land areas 172 in the forming surface 168 of the projection forming surface 156 can be solid so as to not pass the entangling fluid 176 emanating from the fluid entangling devices 158 but in some instances it may be desirable to make the land areas 172 fluid permeable to further texturize the exposed surface of the projection layer 94. Alternatively, select areas of the forming surface 168 of the projection forming surface 156 may be fluid pervious and other areas impervious. For example, a central zone (not shown) of the projection forming surface 156 may be fluid pervious while lateral regions (not shown) on either side of the central zone may be fluid impervious. In addition, the land areas 172 in the forming surface 168 may have raised areas (not shown) formed in or attached thereto to form optional depressions 118 and/or optional apertures 120 in the projection layer 94 and the body facing material 28.

In the embodiment of the apparatus 150 shown in FIG. 12, the projection forming surface 156 is shown in the form of a texturizing drum. It should be appreciated however that other means may be used to create the projection forming surface 156. For example, a foraminous belt or wire (not shown) may be used which includes forming holes 170 formed in the belt or wire at appropriate locations. Alternatively, flexible rubberized belts which are impervious to the pressurized fluid entangling streams, save the forming holes 170, may be used. Such belts and wires are well known to those of ordinary skill in the art as are the means for driving and controlling the speed of such belts and wires. In an embodiment, a texturizing drum may be more advantageous for formation of a body facing material 28 as described herein because it can be made with land areas 172 which can be smooth and impervious to the entangling fluid 176 and which do not leave a wire weave pattern on the outer surface 104 of the projection layer 94 as wire belts tend to do.

An alternative to a projection forming surface 156 with a forming hole-depth defining the projection height can be a drum shell that is thinner than the desired projection height but which can be spaced away from the porous inner drum 174 surface on which it is wrapped. The spacing may be achieved by any means that preferably does not otherwise interfere with the process of forming the projections 90 and withdrawing the entangling fluid from the equipment. For example, one means can be a hard wire or filament that may be inserted between the projection forming surface 156 and the porous inner drum 174 as a spacer or wrapped around the inner porous drum 174 underneath the projection forming surface 156 to provide the appropriate spacing. A drum shell depth of less than about 2 mm can make it more difficult to remove the projection layer 94 and the body facing material 28 from the projection forming surface 156 because the material of the projection layer 94 can expand or be moved by fluid flow into the overhanging area beneath the projection forming surface 156 which in turn can distort the resultant body facing material 28.

It has been found, however, that by using a support layer 92 in conjunction with the projection layer 94 as part of the formation process, distortion of the resultant two layer fluid entangled body facing material 28 can be greatly reduced and generally facilitates cleaner removal of the body facing material 28 because the less extensible, more dimensionally stable support layer 92 can take the load while the body facing material 28 is removed from the projection forming surface 156. The higher tension that can be applied to the support layer 92, compared to a single projection layer 94, means that as the body facing material 28 moves away from the projection forming surface 156, the projections 90 can exit the forming holes 170 smoothly in a direction roughly perpendicular to the forming surface 168 and co-axially with the forming holes 170 in the projection forming surface 156. In addition, by using the support layer 92, processing speeds can be increased.

To form the projections 90 in the projection layer 94 and to laminate the support layer 92 and the projection layer 94 together, one or more fluid entangling devices 158 can be spaced above the projection forming surface 156. The most common technology used in this regard can be referred to as spunlace or hydroentangling technology which can use pressurized water as the fluid for entanglement. As an unbonded or relatively unbonded web or webs forming the layers (92 and 94) can be fed onto a projection forming surface 156, a multitude of high pressure fluid jets (not shown) from one or more fluid entangling devices 158 can move the fibers of the webs and the fluid turbulence can cause the fibers to entangle. These fluid streams can cause the fibers to be further entangled within the individual webs. The streams can also cause fiber movement and entanglement at the interface of the two or more webs thereby causing the webs to become joined together. Still further, if the fibers in a layer, such as the projection layer 94, are loosely held together, they can be driven out of their X-Y plane and thus into the Z-direction to form the projections 90. Depending on the level of entanglement needed, one or a plurality of such fluid entangling devices 158 can be used.

In FIG. 12, a single fluid entangling device 158 is shown, but in succeeding Figures where multiple devices are used in various regions of the apparatus 150, they are labeled with letter designators such as 158*a*, 158*b*, 158*c*, 158*d*, and 158*e*. When multiple fluid entangling devices 158 are used, the entangling fluid pressure in each subsequent fluid entangling device 158 can be higher than the preceding one so that the energy imparted to the web or webs increases and so the fiber entanglement within or between the webs increases. This reduces disruption of the overall evenness of the areal density of the web by the pressurized fluid jets while achieving the desired level of entanglement and hence bonding of the layers and formation of the projections 90. The entangling fluid 176 of the fluid entangling devices 158 can emanate from injectors via jet-strips (not shown) consisting of a row or rows of pressurized fluid jets with small apertures of a diameter usually from about 0.08 to about 0.15 mm and spacing of around 0.5 mm in the cross-machine direction. The pressure in the jets can be between about 5 bar and 400 bar but typically can be less than about 200 bar except for heavy weight fluid entangled materials and when fibrillation is required. Other jet sizes, spacings, numbers of jets and jet pressures can be used depending upon the particular end application. Such fluid entangling devices 158 are well known to those of ordinary skill in the art and are readily available from such manufactures as Fleissner of Germany and Andritz-Perfojet of France.

The fluid entangling device 158 can be provided with conventional hydroentangling jet-strips. Typically, these jet-strips can be positioned or spaced from about 5 millimeters to about 10 or 20 millimeters from the projection forming surface 156 though the actual spacing can vary depending on the basis weights of the materials being acted upon, the fluid pressure, the number of individual jets being used, the amount of vacuum being used via the fluid removal system 162 and the speed at which the equipment is being run.

In the embodiments shown in FIGS. 12 through 17 the fluid entangling devices 158 can be conventional hydroentangling devices, the construction and operation of which are well known to those of ordinary skill in the art. See for example U.S. Pat. No. 3,485,706 to Evans, the content of which is incorporated herein by reference in its entirety for all purposes. Also see the description of the hydraulic entanglement equipment described by Honeycomb Systems, Inc., Biddeford, Me., in the article entitled "Rotary Hydraulic Entanglement of Nonwovens", reprinted from INSIGHT '86 INTERNATIONAL ADVANCED FORMING/BONDING Conference, the contents of which is incorporated herein by reference in its entirety for all purposes.

Referring to FIG. 12, the projection layer 94 can be fed into the apparatus 150 at a speed V1, the support layer 92 can be fed into the apparatus 150 at a speed V2 and the body facing material 28 can exit the apparatus 150 at a speed V3 which is the speed of the projection forming surface 156. As will be explained in greater detail below, these speeds V1, V2 and V3 may be the same as one another or varied to change the formation process and the properties of the resultant body facing material 28. Feeding both the projection layer 94 and the support layer 92 into the apparatus 150 at the same speed (V1 and V2) can produce a body facing material 28 with the desired projections 90. Feeding both the projection layer 94 and the support layer 92 into the apparatus 150 at the same speed which can be faster than the machine direction speed (V3) of the projection forming surface 156 can also form the desired projections 90.

Also shown in FIG. 12 is an optional overfeed roller 160 which may be driven at a speed Vf. The overfeed roller 160 may be run at the same speed as the speed V1 of the projection layer 94 or it may be run at a faster speed to tension the projection layer 94 upstream of the overfeed roller 160 when overfeed is desired. Overfeed can occur when one or both of the incoming layers (92 and 94) is fed onto the projection forming surface 156 at a greater speed than the speed V3 of the projection forming surface 156. It has been found that improved projection formation in the projection layer 94 can be affected by feeding the projection layer 94 onto the projection forming surface 156 at a higher speed than the incoming speed V2 of the support layer 92. In addition, it has been discovered that improved properties and projection formation can be accomplished by varying the feed speeds of the layers (92 and 94) and by also using the overfeed roller 160 just upstream of the projection forming surface 156 to supply a greater amount of fiber via the projection layer 94 for subsequent movement by the entangling fluid 176 down into the forming holes 170 in the projection forming surface 156. In particular, by overfeeding the projection layer 94 onto the projection forming surface 156, improved projection formation can be achieved including increased projection height.

In order to provide an excess of fiber so that the height of the projections 90 can be maximized, the projection layer 94 can be fed onto the projection forming surface 156 at a greater surface speed (V1) than the projection forming surface 156 is traveling (V3). Referring to FIG. 12, the projection layer 94 can be fed onto the projection forming surface 156 at a speed V1 while the support layer 92 can be fed in at a speed V2 and the projection forming surface 156 can be traveling at a speed V3 which can be slower than V1 and can be equal to V2. The overfeed percent (OF), the ratio at which the projection layer 94 can be fed onto the projection forming surface 156, can be defined as $OF=[(V_1/V_3)-1] \times 100$ where $V_1$ is the input speed of the projection layer 94 and V3 is the output speed of the resultant body facing material 28 and the speed of the projection forming surface 156. (When the overfeed roller 160 is being used to increase the speed of the incoming material onto the projection forming surface 156 it should be noted that the speed V1 of the material after the overfeed roller 160 will be faster than the speed V1 upstream of the overfeed roller 160. In calculating the overfeed ratio, it is this faster speed V1 that should be used.) Good formation of the projections 90 has been found to occur when the overfeed ratio is between about 10 and about 50 percent. Note too, that this overfeeding technique and ratio can be used with respect to not just the projection layer 94 only but to a combination of the projection layer 94 and the support layer 92 as they are collectively fed onto the projection forming surface 156.

In order to minimize the length of projection layer 94 that is supporting its own weight before being subjected to the entangling fluid 176 and to avoid wrinkling and folding of the projection layer 94, the overfeed roller 160 can be used to carry the projection layer 94 at speed V1 to a position close to the texturizing zone 178 on the projection forming surface 156. In the example illustrated in FIG. 12, the overfeed roller 160 can be driven off the transport belt 152 but it is also possible to drive it separately so as to not put undue stress on the incoming projection layer 94. The support layer 92 may be fed into the texturizing zone 178 separately from the projection layer 94 and at a speed V2 that may be greater than, equal to or less than the projection forming surface 156 speed V3 and greater than, equal to, or less than the projection layer 94 speed V1. In an embodiment, the support layer 92 can be drawn into the texturizing zone 178 by its frictional engagement with the projection layer 94 positioned on the projection forming surface 156 and so once on the projection forming surface 156, the support layer 92 can have a surface speed close to the speed V3 of the projection forming surface 156 or it may be positively fed into the texturizing zone 178 at a speed close to the projection forming surface 156 speed of V3. The texturizing process can cause some contraction of the support layer 92 in the machine direction. The overfeed of either the support layer 92 or the projection layer 94 can be adjusted according to the particular materials and the equipment and conditions being used so that the excess material that is fed into the texturizing zone 178 can be used up thereby avoiding any unsightly wrinkling in the resultant body facing material 28. As a result, the two layers (92 and 94) can be under some tension at all times despite the overfeeding process. The take-off speed of the body facing material 28 can be arranged to be close to the projection forming surface 156 speed V3 such that excessive tension is not applied to the body facing material 28 in its removal from the projection forming surface 156. Such excessive tension would be detrimental to the clarity and size of the projections 90.

Figure 13:
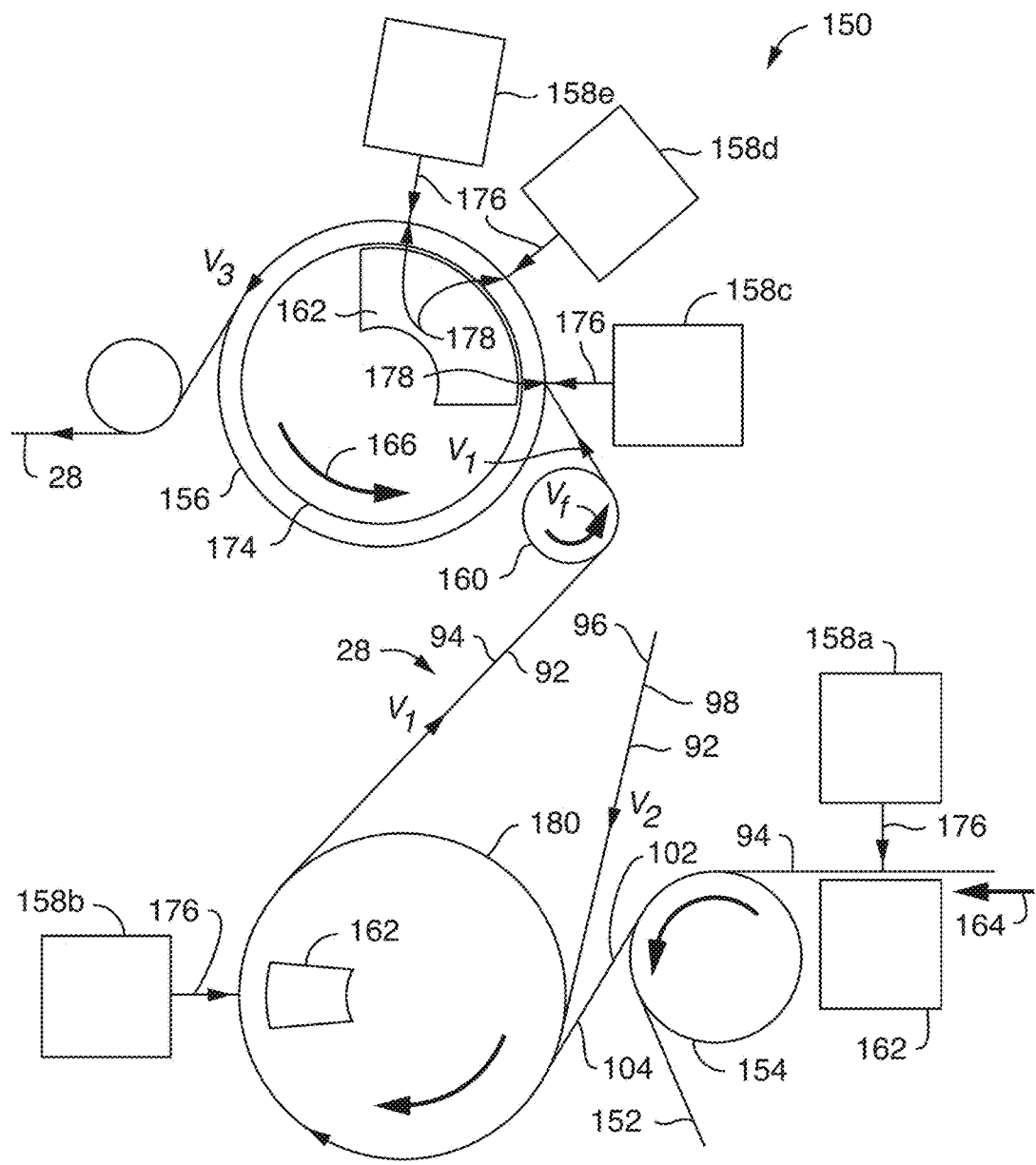
FIG. 13 is a schematic side view of an alternate embodiment of an apparatus and a process for forming a fluid entangled body facing material.

An alternate embodiment of the process and apparatus can be shown in FIG. 13 in which like reference numerals are used for like elements. In this embodiment the main differences relative to the process and apparatus shown in FIG. 12 are a pre-entanglement of the projection layer 94 to improve its integrity prior to further processing via a pre-entanglement fluid entangling device 158a; a lamination of the projection layer 94 to the support layer 92 via a lamination fluid entangling device 158b; and an increase in the number of fluid-entangling devices 158 (referred to as projection fluid entangling devices 158c, 158d, and 158e) and thus an enlargement of the texturizing zone 178 on the projection forming surface 156 in the projection forming portion of the process.

The projection layer 94 can be supplied to the apparatus 150 via the transport belt 152. As the projection layer 94 travels on the transfer belt 152 it can be subjected to a first fluid entangling device 158a to improve the integrity of the projection layer 94. This can be referred to as pre-entanglement of the projection layer 94. As a result, the transport belt 152 can be fluid pervious to allow the entangling fluid 176 to pass through the projection layer 94 and the transport belt 152. To remove the delivered entangling fluid 176, as in FIG. 12, a fluid removal system 162 may be used below the transport belt 152. The fluid pressure from the first fluid entangling device 158a can be in the range from about 10 to about 50 bar.

The support layer 92 and the projection layer 94 can be fed to a lamination forming surface 180 with the first surface 96 of the support layer 92 facing and contacting the lamination forming surface 180 and the second surface 98 of the support layer 92 contacting the inner surface 102 of the projection layer 94. To entangle the two layers (92 and 94) together, one or more fluid entangling devices 158b can be used in connection with the lamination forming surface 180 to affect fiber entanglement between the two layers (92 and 94). A fluid removal system 162 can be used to dispose of the entangling fluid 176. To distinguish the apparatus in this lamination portion of the overall process from the subsequent projection forming portion where the projections are formed, this equipment and process are referred to as lamination equipment as opposed to projection forming equipment. Thus, this portion is referred to as using a lamination forming surface 180 and a lamination fluid entangling device 158b which uses lamination fluid jets as opposed to projection forming jets. The lamination forming surface 180 can be movable in the machine direction of the apparatus 150 at a lamination forming surface speed and should be permeable to the entangling fluid emanating from the lamination fluid jets located in the lamination fluid entangling device 158b. The lamination fluid entangling device 158b can have a plurality of lamination fluid jets which are capable of emitting a plurality of pressurized lamination fluid streams of entangling fluid 176 in a direction towards the lamination forming surface 180. The lamination forming surface 180, when in the configuration of a drum as shown in FIG. 13, can have a plurality of holes in its surface separated by land areas to make it fluid permeable or it can be made from conventional forming wire which is permeable as well. In this portion of the apparatus 150, complete bonding of the two layers (92 and 94) is not necessary. Process parameters for this portion of the equipment are similar to those for the projection forming portion and the description of the equipment and process in connection with FIG. 12. Thus, the speeds of the layers (92 and 94) and the surfaces in the lamination forming portion of the equipment and process may be varied as explained above with respect to the projection forming equipment and process described with respect to FIG. 12.

For example, the projection layer 94 may be fed into the lamination forming process and onto the support layer 92 at a speed that can be greater than the speed the support layer 92 can be fed onto the lamination forming surface 180. Relative to entangling fluid pressures, lower lamination fluid jet pressures can be desired in this portion of the equipment as additional entanglement of the layers can occur during the projection forming portion of the process. As a result, lamination forming pressures from the lamination entangling device 158b can range between about 30 and about 100 bar.

When the plurality of lamination fluid streams 176 in the lamination fluid entangling device 158b are directed in a direction from the outer surface 104 of the projection layer 94 towards the lamination forming surface 180, at least a portion of the fibers in the projection layer 94 can become entangled with the support layer 92 to form a laminate web. Once the projection layer 94 and support layer 92 are joined into a laminate web, the laminate web can leave the lamination portion of the equipment and process (elements 158b and 180) and can be fed into the projection forming portion of the equipment and process (elements 156, 158c, 158d, 158e and optional 160). As with the process shown in FIG. 12, the laminate web may be fed onto the projection forming surface 156 at the same speed as the projection forming surface 156 is traveling or it may be overfed onto the projection forming surface 156 using the overfeed roller 160 or by simply causing the laminate web to travel at a speed V1 which is greater than the speed V3 of the projection forming surface 156. As a result, the process variables described above with respect to FIG. 12 may also be employed with the equipment and process shown in FIG. 13. In addition, as with the apparatus and materials in FIG. 12, if the overfeed roller 160 is used to increase the speed V1 of the laminate web as it comes in contact with the projection forming surface 156, it is this faster speed V1 after the overfeed roller 160 that should be used when calculating the overfeed ratio. The same approach can be used when calculating the overfeed ratio with the remainder of the embodiments shown in FIGS. 14-17 if overfeed of material is being employed.

In the projection forming portion of the equipment, a plurality of pressurized projection fluid streams of entangling fluid 176 can be directed from the projection fluid jets located in the projection fluid entangling devices (158c, 158d, and 158e) into the laminate web in a direction from the first surface 96 of the support layer 92 towards the projection forming surface 156 to cause a first plurality of the fibers of the projection layer 94 in the vicinity of the forming holes 170 located in the projection forming surface 156 to be directed into the forming holes 170 to form the plurality of projections 90 which extend outwardly from the outer surface 104 of the projection layer 94 thereby forming the fluid entangled body facing material 28. As with the other processes, the body facing material 28 can be removed from the projection forming surface 156 and, if desired, can be subjected to the same or different further processing as described with respect to the process and apparatus of FIG. 12 such as drying to remove excess entangling fluid or further bonding or other steps. In the projection forming portion of the equipment and apparatus 150, projection forming pressures from the projection fluid entangling devices, 158c, 158d, and 158e, can range from about 80 to about 200 bar.

Figure 14:
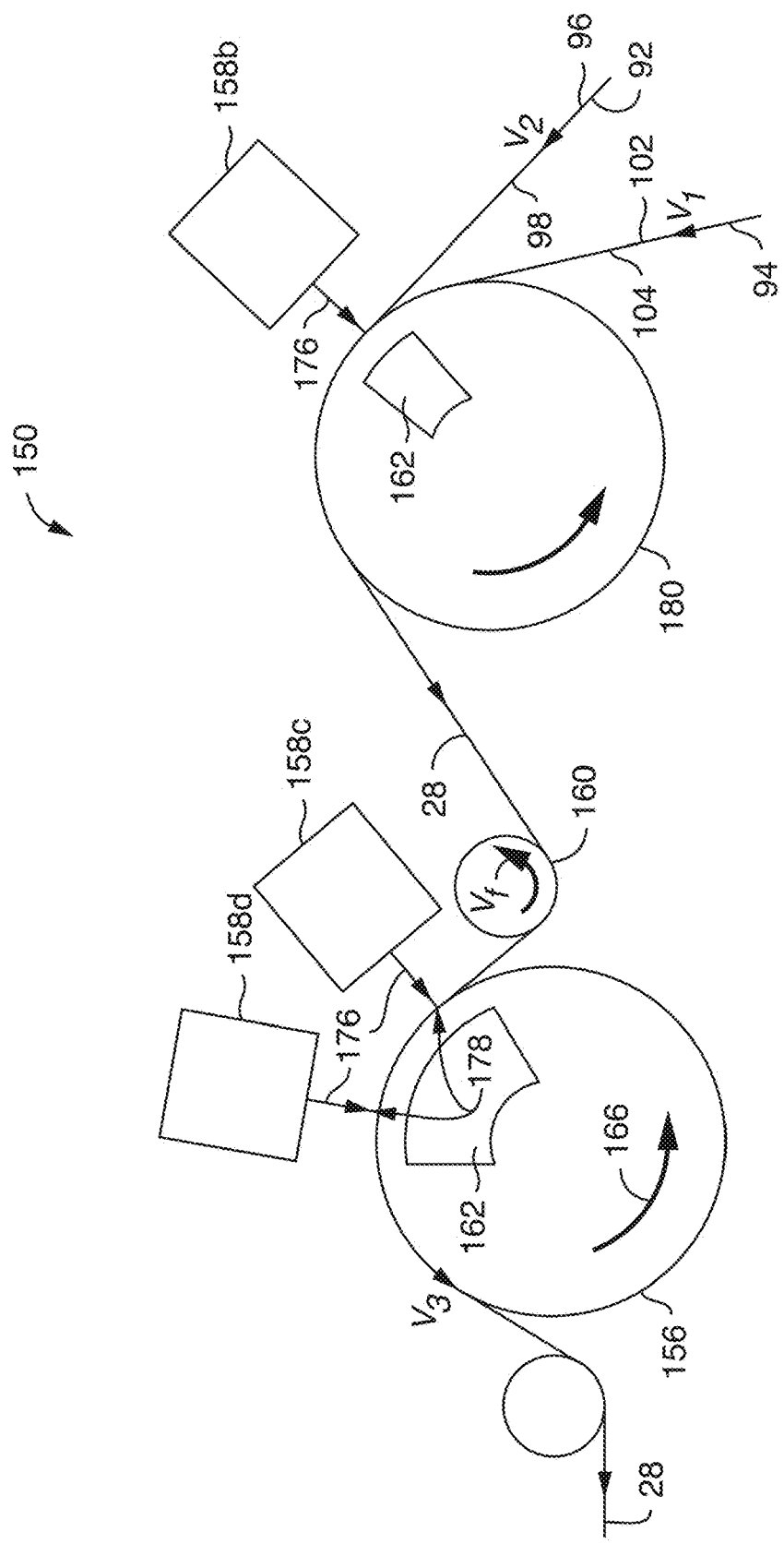
FIG. 14 is a schematic side view of an alternate embodiment of an apparatus and a process for forming a fluid entangled body facing material. The apparatus and process illustrated in FIG. 14 is an adaptation of the apparatus and process illustrated in FIG. 13 as well as subsequent FIGS. 15 and 17.

A further modification of the process and apparatus 150 of FIG. 13 can be illustrated in FIG. 14. In FIG. 13, as well as the embodiments illustrated in FIGS. 15 and 17, the fluid entangled body facing material 28 can be subjected to a pre-lamination step by way of the lamination forming surface 180 and a lamination fluid entangling device(s) 158b. In each of these configurations (FIGS. 13, 15 and 17), the material that is in direct contact with the lamination forming surface 180 is the first surface 96 of the support layer 92. However, it is also possible to invert the support layer 92 and the projection layer 94 such as is shown in FIG. 14 such that the outer surface 104 of the projection layer 94 is the side that is in direct contact with the lamination forming surface 180.

Figure 15:
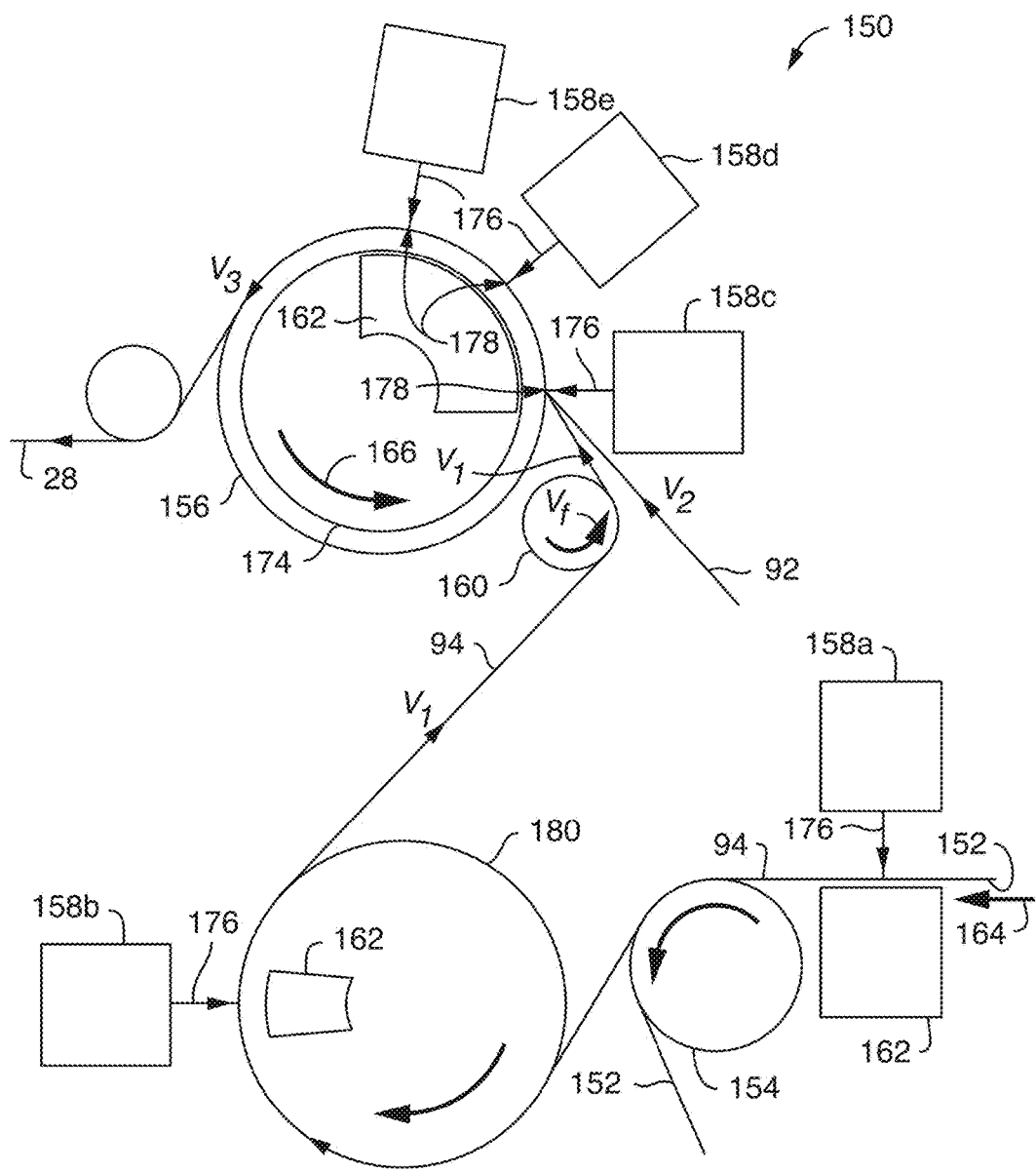
FIG. 15 is a schematic side view of an alternate embodiment of an apparatus and a process for forming a fluid entangled body facing material.

Another embodiment of the process and apparatus can be illustrated in FIG. 15. This embodiment can be similar to that shown in FIG. 13 except that only the projection layer 94 may be subjected to pre-entanglement using the fluid entangling devices 158a and 158b prior to the projection layer 94 being fed into the projection forming portion of the equipment. In addition, the support layer 92 can be fed into the texturizing zone 178 on the projection forming surface 156 in the same manner as in FIG. 12 though the texturizing zone 178 can be supplied with multiple fluid entangling devices (158c, 158d and 158e).

Figure 16:
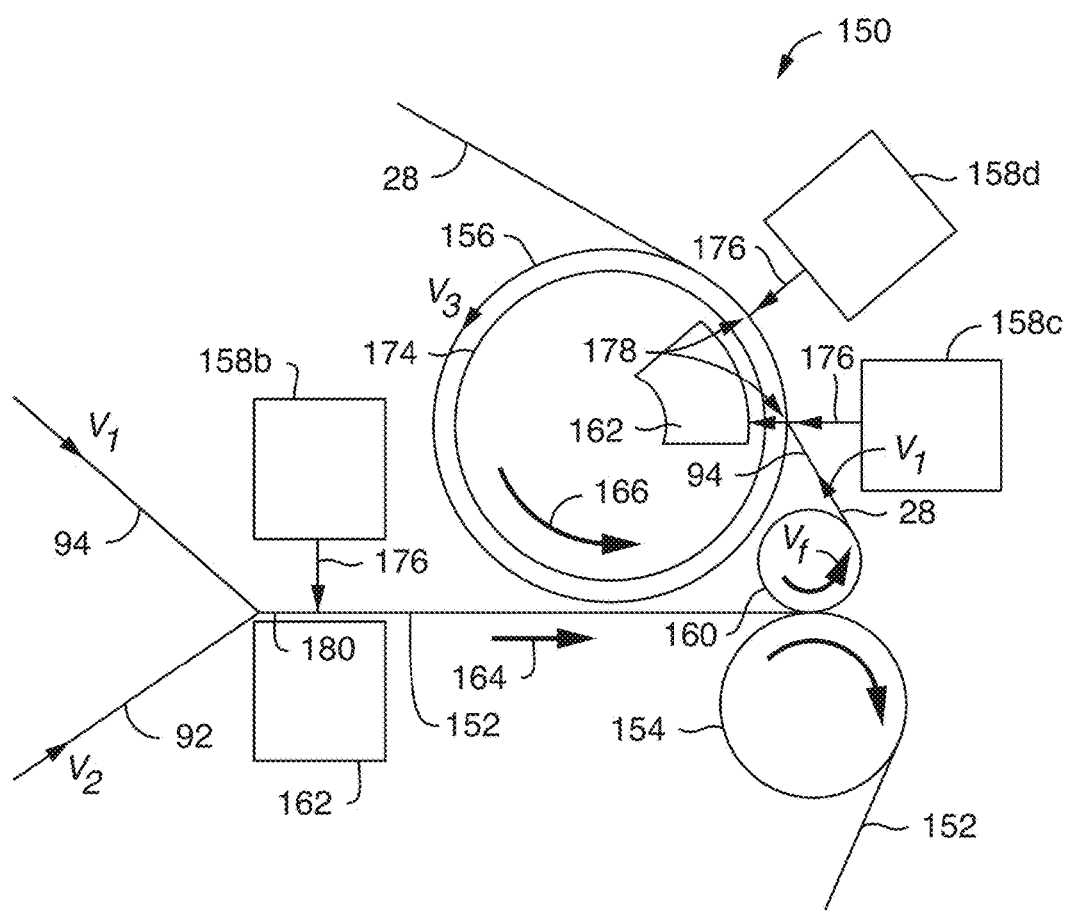
FIG. 16 is a schematic side view of an alternate embodiment of an apparatus and a process for forming a fluid entangled body facing material.

FIG. 16 depicts another embodiment of the process and apparatus which, like FIG. 13, can bring the projection layer 94 and the support layer 92 into contact with one another for a lamination treatment in a lamination portion of the equipment and process utilizing a lamination forming surface 180 (which can be the same element as the transport belt 152) and a lamination fluid entanglement device 158b. In addition, like the embodiment of FIG. 13, in the texturizing zone 178 of the projection forming portion of the process and apparatus 150, multiple projection fluid entangling devices (158c and 158d) can be used.

Figure 17:
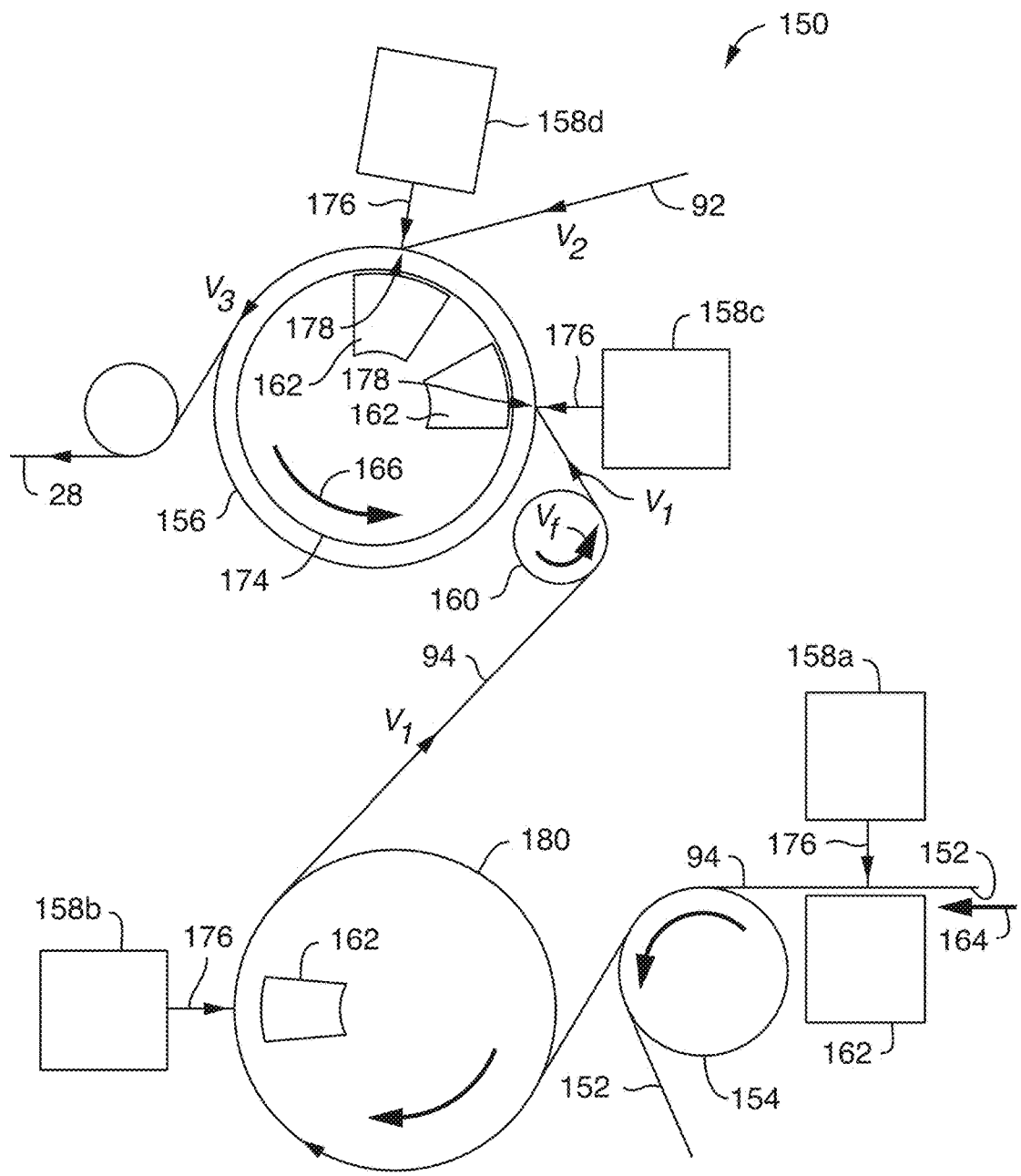
FIG. 17 is a schematic side view of an alternate embodiment of an apparatus and a process for forming a fluid entangled body facing material.

FIG. 17 depicts another embodiment of the process and apparatus 150. In FIG. 17, the primary difference is that the projection layer 94 can undergo a first treatment with entangling fluid 176 via a projection fluid entangling device 158c in the texturizing zone 178 before the second surface 98 of the support layer 92 is brought into contact with the inner surface 102 of the projection layer 94 for fluid entanglement via the projection fluid entangling device 158d. In this manner, an initial formation of the projections 90 can begin without the support layer 92 being in place. As a result, it may be desirable that the projection fluid entangling device 158c be operated at a lower pressure than the fluid entangling device 158d. For example, the projection fluid entangling device 158c may be operated in a pressure range of about 100 to about 140 bar whereas the projection fluid entangling device 158d may be operated in a pressure range of about 140 to about 200 bar. Other combinations and ranges of pressures can be chosen depending upon the operating conditions of the equipment and the types and basis weights of the materials being used for the projection layer 94 and the support layer 92.

In each of the embodiments of the process and apparatus 150, the fibers in the projection layer 94 can be sufficiently detached and mobile within the projection layer 94 such that the entangling fluid 176 emanating from the projection fluid jets in the texturizing zone 178 can move a sufficient number of the fibers out of the X-Y plane of the projection layer 94 in the vicinity of the forming holes 170 in the projection forming surface 156 and force the fibers down into the forming holes 170 thereby forming the projections 90 in the projection layer 94 of the body facing material 28. In addition, by overfeeding at least the projection layer 94 into the texturizing zone 178, enhanced projection formation can be achieved as shown by the examples and photomicrographs.

Secondary Liner:

In various embodiments, the body facing material 28 of the absorbent article 10 can overlay the absorbent body 40 and the outer cover 26 and can isolate the wearer's skin from liquid waste retained by the absorbent body 40. In various embodiments, the body facing material 28 can overlay a secondary liner 34. In such embodiments, the secondary liner 34 can overlay the absorbent body 40. In various embodiments, a fluid transfer layer 78 can be positioned between the secondary liner 34 and the absorbent body 40. In various embodiments, an acquisition layer 84 can be positioned between the secondary liner 34 and the absorbent body 40 or a fluid transfer layer 78, if present. In various embodiments, the secondary liner 34 can be bonded to the acquisition layer 84, or the fluid transfer layer 78 if no acquisition layer 84 is present, via adhesive and/or by a point fusion bonding. The point fusion bonding may be selected from ultrasonic, thermal, pressure bonding, and combinations thereof.

In an embodiment, the secondary liner 34 can extend beyond the absorbent body 40 and/or a fluid transfer layer 78, and/or an acquisition layer 84 to overlay a portion of the outer cover 26 and can be bonded thereto by any method deemed suitable, such as, for example, by being bonded thereto by adhesive, to substantially enclose the absorbent body 40 between the outer cover 26 and the secondary liner 34. The secondary liner 34 may be narrower than the outer cover 26, but it is to be understood that the secondary liner 34 and the outer cover 26 may be of the same dimensions. It is also contemplated that the secondary liner 34 may not extend beyond the absorbent body 40 and/or may not be secured to the outer cover 26. The secondary liner 34 can be suitably compliant, soft feeling, and non-irritating to the wearer's skin and can be the same as or less hydrophilic than the absorbent body 40 to permit body exudates to readily penetrate through to the absorbent body 40 and provide a relatively dry surface to the wearer.

The secondary liner 34 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the secondary liner 34. The secondary liner 34 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof.

For example, the secondary liner 34 can be composed of a meltblown or spunbond web of polyolefin fibers. Alternatively, the secondary liner 34 can be a bonded-carded web composed of natural and/or synthetic fibers. The secondary liner 34 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire secondary liner 34 or it can be selectively applied to particular sections of the secondary liner 34. In an embodiment, the secondary liner 34 can be treated with a modifier which can increase the surface energy of the material surface or reduce the viscoelastic properties of body exudates, such as menses.

In an embodiment, a secondary liner 34 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a secondary liner 34 can be a spunbond substrate with a basis weight from about 10 or 12 to about 15 or 20 gsm. In an embodiment, a secondary liner 34 can be a 12 gsm spunbond-meltblown-spunbond substrate having 10% meltblown content applied between the two spunbond layers.

Although the outer cover 26 and secondary liner 34 can include elastomeric materials, it is contemplated that the outer cover 26 and the secondary liner 34 can be composed of materials which are generally non-elastomeric. In an embodiment, the secondary liner 34 can be stretchable, and more suitably elastic. In an embodiment, the secondary liner 34 can be suitably stretchable and more suitably elastic in at least the lateral or circumferential direction of the absorbent article 10. In other aspects, the secondary liner 34 can be stretchable, and more suitably elastic, in both the lateral and the longitudinal directions.

Containment Flaps:

In an embodiment, containment flaps, 50 and 52, can be secured to the body facing material 28 and/or, if present, the secondary liner 34, of the absorbent article 10 in a generally parallel, spaced relation with each other laterally inward of the leg openings 56 to provide a barrier against the flow of body exudates to the leg openings 56. In an embodiment, the containment flaps, 50 and 52, can extend longitudinally from the front waist region 12 of the absorbent article 10, through the crotch region 16 to the back waist region 14 of the absorbent article 10. The containment flaps, 50 and 52, can be bonded to the body facing material 28 and/or the secondary liner 34 by a seam of adhesive 137 to define a fixed proximal end 138 of the containment flaps, 50 and 52.

The containment flaps, 50 and 52, can be constructed of a fibrous material which can be similar to the material forming the body facing material 28 and/or the secondary liner 34, if present. Other conventional material, such as polymer films, can also be employed. Each containment flap, 50 and 52, can have a moveable distal end 136 which can include flap elastics, such as flap elastics 58 and 60, respectively. Suitable elastic materials for the flap elastic, 58 and 60, can include sheets, strands or ribbons of natural rubber, synthetic rubber, or thermoplastic elastomeric materials.

The flap elastics, 58 and 60, as illustrated, can have two strands of elastomeric material extending longitudinally along the distal ends 136 of the containment flaps, 50 and 52, in generally parallel, spaced relation with each other. The elastic strands can be within the containment flaps, 50 and 52, while in an elastically contractible condition such that contraction of the strands gathers and shortens the distal ends 136 of the containment flaps, 50 and 52. As a result, the elastic strands can bias the distal ends 136 of each containment flap, 50 and 52, toward a position spaced from the proximal end 138 of the containment flaps, 50 and 52, so that the containment flaps, 50 and 52, can extend away from the body facing material 28 and/or the secondary liner 34 in a generally upright orientation of the containment flaps, 50 and 52, especially in the crotch region 16 of the absorbent article 10, when the absorbent article 10 is fitted on the wearer. The distal end 136 of the containment flaps, 50 and 52, can be connected to the flap elastics, 58 and 60, by partially doubling the containment flap, 50 and 52, material back upon itself by an amount which can be sufficient to enclose the flap elastics, 58 and 60. It is to be understood, however, that the containment flaps, 50 and 52, can have any number of strands of elastomeric material and may also be omitted from the absorbent article 10 without departing from the scope of this disclosure.

Leg Elastics:

Leg elastic members, 66 and 68, can be secured between the outer and inner layers, 70 and 72, respectively, of the outer cover 26, such as by being bonded therebetween by laminate adhesive, generally adjacent the lateral outer edges of the inner layer 72 of the outer cover 26. Alternatively, the leg elastic members, 66 and 68, may be disposed between other layers of the absorbent article 10. A wide variety of elastic materials may be used for the leg elastic members, 66 and 68. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate.

Fastening System:

In an embodiment, the absorbent article 10 can include a fastener system. The fastener system can include one or more back fasteners 140 and one or more front fasteners 142. Portions of the fastener system may be included in the front waist region 12, back waist region 14, or both. The fastener system can be configured to secure the absorbent article 10 about the waist of the wearer and maintain the absorbent article 10 in place during use. In an embodiment, the back fasteners 140 can include one or more materials bonded together to form a composite ear as is known in the art. For example, the composite fastener may be composed of a stretch component 144, a nonwoven carrier or hook base 146, and a fastening component 148.

Waist Elastic Members:

In an embodiment, the absorbent article 10 can have waist elastic members, 62 and 64, which can be formed of any suitable elastic material. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist elastic members, 62 and 64, may be omitted from the absorbent article 10 without departing from the scope of this disclosure.

Figure 18:
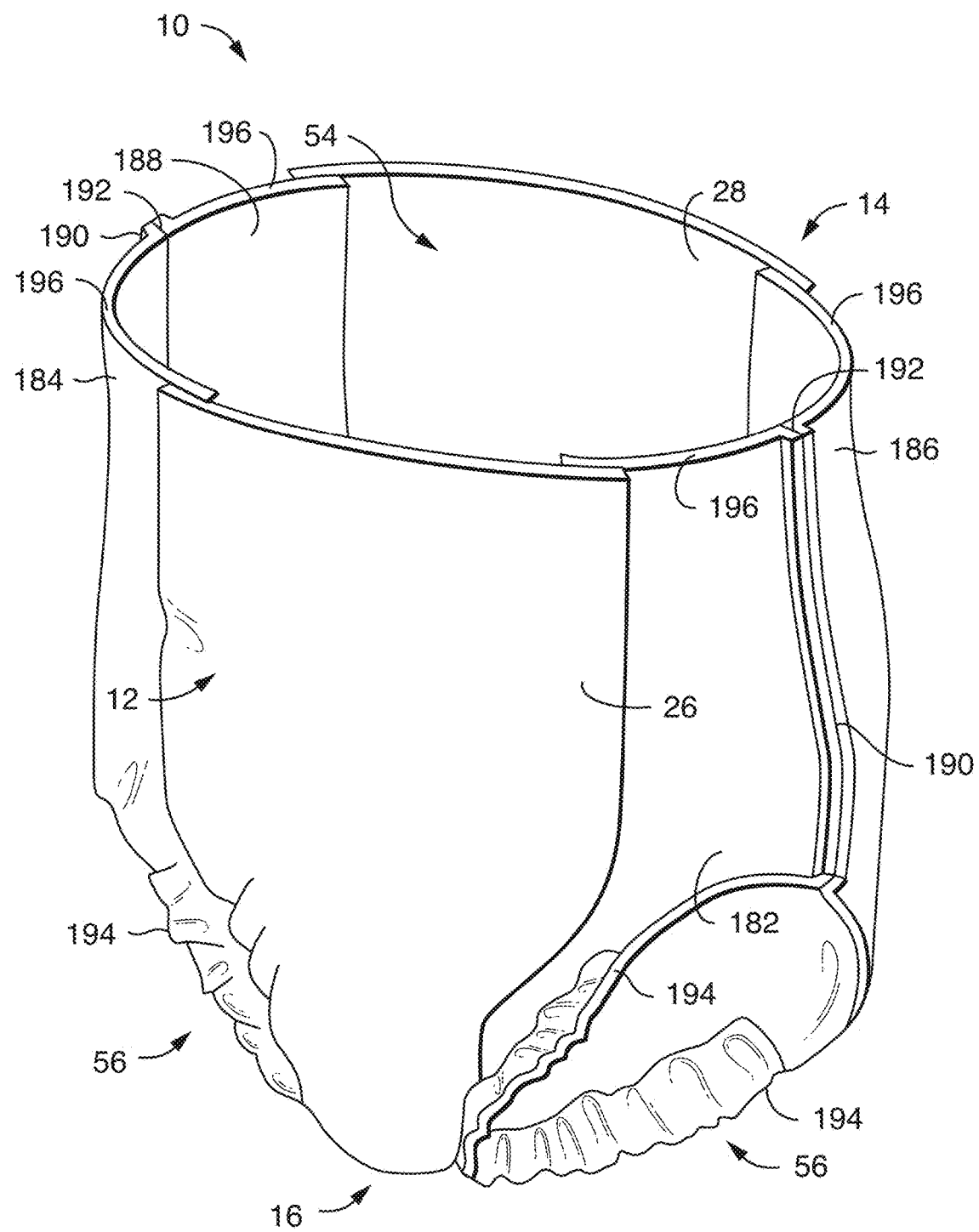
FIG. 18 is a perspective view of an embodiment of an absorbent article.

Side Panels:

In an embodiment in which the absorbent article 10 can be a training pant, youth pant, diaper pant, or adult absorbent pant, the absorbent article 10 may have front side panels, 182 and 184, and rear side panels, 186 and 188. FIG. 18 provides a non-limiting illustration of an absorbent article 10 that can have side panels, such as front side panels, 182 and 184, and rear side panels, 186 and 188. The front side panels 182 and 184 and the rear side panels 186 and 188 of the absorbent article 10 can be bonded to the absorbent article 10 in the respective front and back waist regions, 12 and 14, and can extend outwardly beyond the longitudinal side edges, 18 and 20, of the absorbent article 10. In an example, the front side panels, 182 and 184, can be bonded to the inner layer 72 of the outer cover 26, such as being bonded thereto by adhesive, by pressure bonding, by thermal bonding or by ultrasonic bonding. These front side panels, 182 and 184, may also be bonded to the outer layer 70 of the outer cover 26, such as by being bonded thereto by adhesive, by pressure bonding, by thermal bonding, or by ultrasonic bonding. The back side panels, 186 and 188, may be secured to the outer and inner layers, 70 and 72 respectively, of the outer cover 26 at the back waist region 14 of the absorbent article 10 in substantially the same manner as the front side panels, 182 and 184. Alternatively, the front side panels, 182 and 184, and the back side panels, 186 and 188, may be formed integrally with the absorbent article 10, such as by being formed integrally with the outer cover 26, the body facing material 28, the secondary liner 34 or other layers of the absorbent article 10.

For improved fit and appearance, the front side panels, 182 and 184, and the back side panels, 186 and 188, can suitably have an average length measured parallel to the longitudinal axis of the absorbent article 10 that is about 20 percent or greater, and more suitably about 25 percent or greater, of the overall length of the absorbent article 10, also measured parallel to the longitudinal axis. For example, absorbent articles 10 having an overall length of about 54 centimeters, the front side panels, 182 and 184, and the back side panels, 186 and 188, suitably have an average length of about 10 centimeters or greater, and more suitably have an average length of about 15 centimeters. Each of the front side panels, 182 and 184, and back side panels, 186 and 188, can be constructed of one or more individual, distinct pieces of material. For example, each front side panel, 182 and 184, and back side panel, 186 and 188, can include first and second side panel portions (not shown) joined at a seam (not shown), with at least one of the portions including an elastomeric material. Alternatively, each individual front side panel, 182 and 184, and back side panel, 186 and 188, can be constructed of a single piece of material folded over upon itself along an intermediate fold line (not shown).

The front side panels, 182 and 184, and back side panels, 186 and 188, can each have an outer edge 190 spaced laterally from the engagement seam 192, a leg end edge 194 disposed toward the longitudinal center of the absorbent article 10, and a waist end edge 196 disposed toward a longitudinal end of the absorbent article 10. The leg end edge 194 and waist end edge 196 can extend from the longitudinal side edges, 18 and 20, of the absorbent article 10 to the outer edges 190. The leg end edges 194 of the front side panels, 182 and 184, and back side panels, 186 and 188, can form part of the longitudinal side edges, 18 and 20, of the absorbent article 10. The leg end edges 194 of the illustrated absorbent article 10 can be curved and/or angled relative to the transverse axis to provide a better fit around the wearer's legs. However, it is understood that only one of the leg end edges 194 can be curved or angled, such as the leg end edge 194 of the back waist region 14, or neither of the leg end edges 194 can be curved or angled, without departing from the scope of this disclosure. The waist end edges 196 can be parallel to the transverse axis. The waist end edges 196 of the front side panels, 182 and 184, can form part of the front waist edge 22 of the absorbent article 10, and the waist end edges 196 of the back side panels, 186 and 188, can form part of the back waist edge 24 of the absorbent article 10.

The front side panels, 182 and 184, and back side panels, 186 and 188, can include an elastic material capable of stretching laterally. Suitable elastic materials, as well as one described process for incorporating elastic front side panels, 182 and 184, and back side panels, 186 and 188, into an absorbent article 10 are described in the following U.S. Pat. No. 4,940,464 issued Jul. 10, 1990 to Van Gompel et al., U.S. Pat. No. 5,224,405 issued Jul. 6, 1993 to Pohjola, U.S. Pat. No. 5,104,116 issued Apr. 14, 1992 to Pohjola, and U.S. Pat. No. 5,046,272 issued Sep. 10, 1991 to Vogt et al.; all of which are incorporated herein by reference. As an example, suitable elastic materials include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Morman, and European Patent Application No. EP 0 217 032 published on Apr. 8, 1987, in the names of Taylor et al., and PCT Application WO 01/88245 in the name of Welch et al., all of which are incorporated herein by reference. Other suitable materials are described in U.S. patent application Ser. No. 12/649,508 to Welch et al. and Ser. No. 12/023,447 to Lake et al., all of which are incorporated herein by reference. Alternatively, the front side panels, 182 and 184, and back side panels, 186 and 188, may include other woven or non-woven materials, such as those described above as being suitable for the outer cover 26 or secondary liner 34, mechanically pre-strained composites, or stretchable but inelastic materials.

Figure 19:
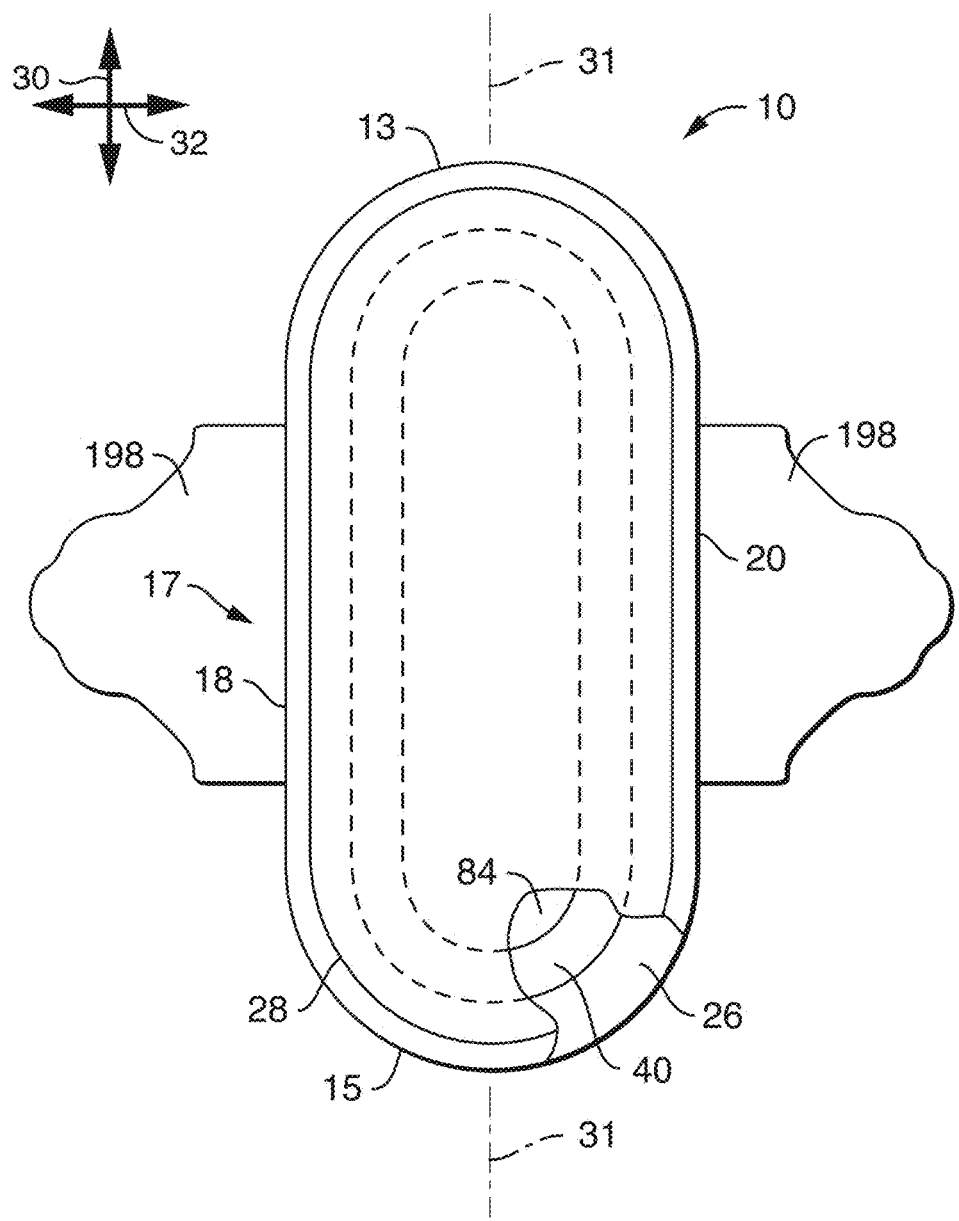
FIG. 19 is a top down view of an embodiment of an absorbent article.

Feminine Hygiene Product:

FIG. 19 provides a non-limiting illustration of an absorbent article 10 in the form of a feminine hygiene product such as a menstrual pad or feminine adult incontinence product. The absorbent article 10 can have a lengthwise, longitudinal direction 30 which can extend along an appointed x-axis of the absorbent article 10, and a transverse, lateral direction 32 which can extend along an appointed y-axis of the absorbent article 10. Additionally, the absorbent article 10 can include first and second longitudinally opposed end portions, 13 and 15, and an intermediate region 17 located between the end portions, 13 and 15. The absorbent article 10 can have first and second longitudinal side edges, 18 and 20, which can be the longitudinal sides of the elongated absorbent article 10. The longitudinal side edges, 18 and 20, can be contoured to match the shape of the absorbent article 10. The absorbent article 10 can have any desired shape such as, for example, a dog bone shape, a race track shape, an hourglass shape, or the like. Additionally, the absorbent article 10 can be substantially longitudinally symmetric, or may be longitudinally asymmetric, as desired.

As representatively shown, the longitudinal dimension of the absorbent article 10 can be relatively larger than the transverse lateral dimension of the absorbent article 10. Configurations of the absorbent article 10 can include a body facing material 28 and an outer cover 26, such as described herein. An absorbent body 40, such as described herein, can be positioned between the body facing material 28 and the outer cover 26. As representatively shown, for example, the peripheries of the body facing material 28 and the outer cover 26 can be substantially entirely coterminous or the peripheries of the body facing material 28 and the outer cover 26 can be partially or entirely non-coterminous. In an embodiment, the absorbent article 10 can include a secondary liner 34 such as described herein. In an embodiment, the absorbent article 10 can include an acquisition layer 84 such as described herein.

In an embodiment in which the absorbent article 10 can be a feminine hygiene product, the absorbent article 10 can include laterally extending wing portions 198 that can be integrally connected to the side edges, 18 and 20, of the absorbent article 10 in the intermediate region 17 of the absorbent article 10. For example, the wing portions 198 may be separately provided members that are subsequently attached or otherwise operatively joined to the intermediate region 17 of the absorbent article 10. In other configurations, the wing portions 198 may be unitarily formed with one or more components of the absorbent article 10. As an example, a wing portion 198 may be formed from a corresponding, operative extension of the body facing material 28, a secondary liner 34, if present, an outer cover 26, and combinations thereof.

The wing portions 198 can have an appointed storage position (not shown) in which the wing portions 198 are directed generally inwardly toward the longitudinally extending centerline 31. In various embodiments, the wing portion 198 that is connected to one side edge, such as side edge 18, may have sufficient cross-directional length to extend and continue past the centerline 31 to approach the laterally opposite side edge 20 of the absorbent article 10. The storage position of the wing portions 198 can ordinarily represent an arrangement observed when the absorbent article 10 is first removed from a wrapper or packaging. Prior to placing the absorbent article 10, such as the feminine hygiene product, into a bodyside of an undergarment prior to use, the wing portions 198 can be selectively arranged to extend laterally from the side edges, 18 and 20, of the absorbent article 10 intermediate region 17. After placing the absorbent article 10 into the undergarment, the wing portions 198 can be operatively wrapped and secured around the side edges of the undergarment to help hold the absorbent article 10 in place, in a manner well known in the art.

The wing portions 198 can have any operative construction and can include a layer of any operative material. Additionally, each wing portion 198 can comprise a composite material. For example, the wing portions 198 can include a spunbond fabric material, a bicomponent spunbond material, a necked spunbond material, a neck-stretched-bonded laminate (NBL) material, a meltblown fabric material, a bonded carded web, a thermal bonded carded web, a through-air bonded carded web, or the like, as well as combinations thereof.

Each wing portion 198 can include a panel-fastener component (not shown) which can be operatively joined to an appointed engagement surface of its associated wing portion 198. The panel-fastener component can include a system of interengaging mechanical fasteners, a system of adhesive fasteners, or the like, as well as combinations thereof. In an embodiment, either or both wing portions 198 can include a panel-fastener system which incorporates an operative adhesive. The adhesive may be a solvent based adhesive, a hot melt adhesive, a pressure-sensitive adhesive, or the like, as well as combinations thereof.

In an embodiment, a garment attachment mechanism (not shown), such as a garment attachment adhesive, can be distributed onto the garment side of the absorbent article 10. In an embodiment, the garment adhesive can be distributed over the garment side of the absorbent article 10 of the outer cover 26, and one or more layers or sheets of release material can be removably placed over the garment adhesive for storage prior to use. In an embodiment, the garment attachment mechanism can include an operative component of a mechanical fastening system. In such an embodiment, the garment attachment mechanism can include an operative component of a hook-and-loop type of fastening system.

Decolorizing Composition:

In an embodiment, a chemical treatment may be employed to alter the color of bodily exudates captured by the absorbent article 10. In an embodiment, for example, the treatment may be a decolorizing composition that agglutinates (agglomerates) red blood cells in blood and menses and limits the extent that the red color of menses is visible. One such composition includes a surfactant, such as described in U.S. Pat. No. 6,350,711 to Potts, et al., which is incorporated herein in its entirety by reference thereto. Non-limiting examples of such surfactants include Pluronic® surfactants (tri-block copolymer surfactant), inorganic salts that contain a polyvalent anion (e.g., divalent, trivalent, etc.), such as sulfate ($SO_4^{2-}$), phosphate ($PO_4^{3-}$), carbonate ($CO_3^{2-}$), oxide ($O^{2-}$), etc., and a monovalent cation, such as sodium ($Na^+$), potassium ($K^+$), lithium ($Li^+$), ammonium ($NH_4^+$), etc. Alkali metal cations are also beneficial. Some examples of salts formed from such ions include, but are not limited to, disodium sulfate ($Na_2SO_4$), dipotassium sulfate ($K_2SO_4$), disodium carbonate ($Na_2CO_3$), dipotassium carbonate ($K_2CO_3$), monosodium phosphate ($NaH_2PO_4$), disodium phosphate ($Na_2HPO_4$), monopotassium phosphate ($KH_2PO_4$), dipotassium phosphate ($K_2HPO_4$), etc. Mixtures of the aforementioned salts may also be effective in facilitating physical separation of red blood cells. For example, a mixture of disodium sulfate ($Na_2SO_4$) and monopotassium phosphate ($KH_2PO_4$) may be employed.

Besides agglutinating agents, the decolorizing composition may alter the chemical structure of hemoglobin to change its color. Examples of such compositions are described in U.S. Patent Application Publication No. 2009/0062764 to MacDonald, et al., which is incorporated herein in its entirety by reference thereto. In an embodiment, the composition can include an oxidizing agent that can be generally capable of oxidizing hemoglobin or other substances responsible for unwanted color of the bodily exudates. Some examples of oxidizing agents include, but are not limited to, peroxygen bleaches (e.g., hydrogen peroxide, percarbonates, persulphates, perborates, peroxyacids, alkyl hydroperoxides, peroxides, diacyl peroxides, ozonides, supereoxides, oxo-ozonides, and periodates); hydroperoxides (e.g., tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide); peroxides (e.g., lithium peroxide, sodium peroxide, potassium peroxide, ammonium peroxide, calcium peroxide, rubidium peroxide, cesium peroxide, strontium peroxide, barium peroxide, magnesium peroxide, mercury peroxide, silver peroxide, zirconium peroxide, hafnium peroxide, titanium peroxide, phosphorus peroxide, sulphur peroxide, rhenium peroxide, iron peroxide, cobalt peroxide, and nickel peroxide); perborates (e.g., sodium perborate, potassium perborate, and ammonium perborate); persulphates (e.g., sodium persulphate, potassium dipersulphate, and potassium persulphate); and so forth. Other suitable oxidizing agents include, but are not limited to omega-3 and -6 fatty acids, such as linoleic acids, α-linoleic acid, arachidonic acid, eicosapentaenoic acid, docosahexaenoic acid, eicosadienoinc acid, eicosatrienoic acid, etc.

The decolorizing composition may be applied to any liquid permeable layer of the absorbent article 10 where it can contact aqueous fluids exuded by the body, such as, for example, menses, such as the body facing layer 28, secondary liner 34, acquisition layer 84, fluid transfer layer 78, absorbent body 40, outer cover 26, and combinations thereof. In an embodiment, the decolorizing composition may be applied to only a portion of the surface of the layer(s) to which it is applied to ensure that the layer(s) is still capable of retaining sufficient absorbent properties. In an embodiment, it may be desired that the decolorizing composition is positioned closer to the absorbent body 40. In an embodiment, an additional layer (not shown) may be employed in the absorbent article 10 and may be applied with the decolorizing composition that is in contact with the absorbent body 40. The additional layer may be formed from a variety of different porous materials, such as a perforated film, nonwoven web (e.g., cellulosic web, spunbond web, meltblown web, etc.), foams, etc. In an embodiment, the additional layer may be in the form of a hollow enclosure (e.g., sachet, bag, etc.) that is folded so that it partially or completely surrounds the absorbent body 40. The decolorizing composition may be disposed within this enclosure so that it remains sealed therein prior to use.

Non-Limiting Examples of Embodiments of Absorbent Articles:

In an embodiment, an absorbent article 10 can have an outer cover 26, an absorbent body 40, and a body facing material 28. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the body facing material 28 of the absorbent article 10 can further include a land area 116 with greater than about 1% open area within a chosen area of the body facing material 28, projections 90 with less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent article 10 can further include a secondary liner 34 positioned between the body facing material 28 and the absorbent body 40. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land area 116 can be due to interstitial fiber-to-fiber spacing.

In an embodiment, an absorbent article 10 can have an outer cover 26, an absorbent body 40, a body facing material 28 and a secondary liner 34 positioned between the body facing material 28 and the absorbent body 40. In such an embodiment, body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the body facing material 28 of the absorbent article 10 can further include a land area 116 with greater than about 1% open area within a chosen area of the body facing material 28, projections 90 with less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing.

In an embodiment, an absorbent article 10 can have an outer cover 26, an absorbent body 40, and a body facing material 28. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In such an embodiment, the body facing material 28 can further have a load of more than about 2 Newtons per 25 mm width at 10% extension in the machine direction. In various embodiments, the body facing material 28 of the absorbent article 10 can further include a land area 116 with greater than about 1% open area within a chosen area of the body facing material 28, projections with less than about 1% open area within a chosen area of the body facing material 28, a plurality of fibers of the projection layer 94 entangled with the support layer 92, projections 90 having a height greater than about 1 mm, a resiliency of greater than about 70%, and combinations thereof. In various embodiments, the absorbent article 10 can further include a secondary liner 34 positioned between the body facing material 28 and the absorbent body 40. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing.

In an embodiment, an absorbent article 10 can have an outer cover 26, an absorbent body 40, and a body facing material 28. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In such an embodiment, the body facing material 28 can have a resiliency greater than about 70%. In various embodiments, the body facing material 28 of the absorbent article 10 can further include a land area 116 with greater than about 1% open area within a chosen area of the body facing material 28, projections with less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, and combinations thereof. In various embodiments, the absorbent article 10 can further include a secondary liner 34 positioned between the body facing material 28 and the absorbent body 40. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing.

In an embodiment, an absorbent article 10 can have an outer cover 26, an absorbent body 40, and a body facing material 28 which can have a support layer 92 and a projection layer 94. The projection layer 94 can have an inner 102 and an outer 104 surface and can have a plurality of hollow projections 90 extending from the outer surface 104 of the projection layer 94. In such an embodiment, the body facing material 28 can have a land area 116 which can have greater than about 1% open area within a chosen area of the body facing material 28 and projections 90 having less than about 1% open area within a chosen area of the body facing material 28. In various embodiments, the body facing material 28 of the absorbent article 10 can further include a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent article 10 can further include a secondary liner 34 positioned between the body facing material 28 and the absorbent body 40. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing. In various embodiments, the amount of residual fecal material simulant remaining on the body facing material 28 following insult with fecal material simulant according to the test method described herein is less than about 2.5 grams.

In an embodiment, an absorbent article 10 can have an outer cover 26, an absorbent body 40, a body facing material 28, and a fluid transfer layer 78 positioned between the absorbent body 40 and the body facing material 28. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the fluid transfer layer can contain a polymeric material. In various embodiments, the body facing material 28 of the absorbent article 10 can further include a land area 116 with greater than about 1% open area within a chosen area of the body facing material 28, projections 90 having less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing. In various embodiments, the amount of residual fecal material simulant remaining on the body facing material 28 following insult with fecal material simulant according to the test method described herein is less than about 2.5 grams.

In an embodiment, an absorbent article 10 can have an outer cover 26, an absorbent body 40, a body facing material 28, an acquisition layer 84 positioned between the absorbent body 40 and the body facing material 28, and a fluid transfer layer 78 positioned between the acquisition layer 84 and the absorbent body 40. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the acquisition layer 84 can have fibers with a denier less than about 5. In various embodiments, the fluid transfer layer 78 can contain a cellulosic material. In various embodiments, the body facing material 28 of the absorbent article 10 can further include a land area 116 with greater than about 1% open area within a chosen area of the body facing material 28, projections 90 having less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing. In various embodiments, the amount of residual fecal material simulant remaining on the body facing material 28 following insult with fecal material simulant according to the test method described herein is less than about 2.5 grams.

In an embodiment, an absorbent article 10 can have an outer cover 26, an absorbent body 40, a body facing material 28 which can have a support layer 92 and a projection layer 94, and a fluid transfer layer 78 positioned between the absorbent body 40 and the body facing material 28. The projection layer 94 can have an inner 102 and an outer 104 surface and can have a plurality of hollow projections 90 extending from the outer surface 104 of the projection layer 94. In such an embodiment, the body facing material 28 can have a land area 116 which can have greater than about 10% open area within a chosen area of the body facing material 28 and projections 90 having less than about 1% open area within a chosen area of the body facing material 28. In various embodiments, the body facing material 28 of the absorbent article 10 can further include a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing. In various embodiments, the amount of residual fecal material simulant remaining on the body facing material 28 following insult with fecal material simulant according to the test method described herein is less than about 2.5 grams.

In an embodiment, an absorbent article 10 can have an outer cover 26, an absorbent body 40, a body facing material 28, an acquisition layer 84 positioned between the absorbent body 40 and the body facing material 28, and a fluid transfer layer 78 positioned between the acquisition layer 84 and the absorbent body 40. In such an embodiment, the fluid transfer layer 78 can include a polymeric material. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the acquisition layer 84 can have fibers with a denier greater than about 5. In various embodiments, the body facing material 28 of the absorbent article 10 can further include a land area 116 with greater than about 1% open area within a chosen area of the body facing material 28, projections 90 having less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land areas 116 can be due to interstitial fiber-to-fiber spacing. In various embodiments, the area of spread of fecal material simulant on the body facing material 28 following insult with fecal material simulant according to the test method described herein can be less than about 34 $cm^2$.

In an embodiment, an absorbent article 10 can have an outer cover 26, an absorbent body 40, a body facing material 28 with a land area 116 having greater than about 5% open area within a chosen area of the body facing material 28, an acquisition layer 84 positioned between the absorbent body 40 and the body facing material 28, and a fluid transfer layer 78 positioned between the acquisition layer 84 and the absorbent body 40. In such an embodiment, the fluid transfer layer 78 can contain a cellulosic material. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94 wherein the projections have less than about 1% open area within a chosen area of the body facing material. In various embodiments, the acquisition layer 84 can have fibers with a denier greater than about 5. In various embodiments, the acquisition layer 84 can have fibers with a denier less than about 5. In various embodiments, the body facing material 28 of the absorbent article 10 can further include a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70%, and combinations thereof. In various embodiments, the absorbent body 40 can be free from superabsorbent material. In various embodiments, the absorbent body 40 can have greater than about 15% superabsorbent material. In various embodiments, the open area of the projections 90 can be due to interstitial fiber-to-fiber spacing. In various embodiments, the open area of the land area 116 can be due to interstitial fiber-to-fiber spacing. In various embodiments, the area of spread of fecal material simulant on the body facing material 28 following insult with fecal material simulant according to the test method described herein can be less than about 34 cm$^2$.

In an embodiment, an absorbent article 10 can have an outer cover 26, an absorbent body 40, a body facing material 28, an acquisition layer 84 positioned between the absorbent body 40 and the body facing material 28, and a fluid transfer layer 78 positioned between the acquisition layer 84 and the absorbent body 40. In such an embodiment, the fluid transfer layer 78 can contain a cellulosic material. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In various embodiments, the acquisition layer 84 can have fibers with a denier greater than about 5. In various embodiments, the acquisition layer 84 can have fibers with a denier less than about 5. In various embodiments, the body facing material 28 of the absorbent article 10 can further include a plurality of fibers of the projection layer 94 entangled with the support layer 92, a load of more than about 2 Newtons per 25 mm width at 10% extension in the machine direction, projections 90 having a height greater than about 1 mm, projections having less than about 1% open area within a chosen area of the body facing material 28, a resiliency of greater than about 70%, and combinations thereof. In various embodiments, the body facing material 28 can have a land area 116 and the land area 116 can have an open area greater than about 1% within a chosen area of the body facing material 28. In various embodiments, the absorbent body 40 can be free from superabsorbent material. In various embodiments, the absorbent body 40 can have greater than about 15% superabsorbent material. In various embodiments, the open area of the projections 90 is due to interstitial fiber-to-fiber spacing. In various embodiments, the open area of the land areas 116 is due to interstitial fiber-to-fiber spacing. In various embodiments, the area of spread of fecal material simulant on the body facing material 28 following insult with fecal material simulant according to the test method described herein can be less than about 34 cm$^2$.

In an embodiment, an absorbent article 10 can have an outer cover 26, an absorbent body 40, and a body facing material 28. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In such an embodiment, the absorbent article 10 can have a second intake time of simulated menses through the body facing material 28 of less than about 30 seconds following insult with simulated menses according to the Intake/Rewet test method described herein. In various embodiments, the body facing material 28 can further include a land area 116 with greater than about 1% open area within a chosen area of the body facing material 28, projections 90 with less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70% and combinations thereof. In various embodiments, the absorbent article 10 can further include a secondary liner 34 positioned between the body facing material 28 and the absorbent body 40. In various embodiments, the absorbent body 40 can be free from superabsorbent material. In various embodiments, the absorbent body 40 can have greater than about 15% superabsorbent material. In various embodiments, the open area of the land area 116 can be due to interstitial fiber-to-fiber spacing.

In an embodiment, an absorbent article 10 can have an outer cover 26, an absorbent body 40, a body facing material 28, and a secondary liner 34 positioned between the body facing material 28 and the absorbent body 40. In such an embodiment, the body facing material 28 can have a support layer 92 and a projection layer 94. In such an embodiment, the projection layer 94 can have an inner 102 and an outer 104 surface and can have a plurality of hollow projections 90 extending from the outer surface 104 of the projection layer 94. In such an embodiment, the absorbent article 10 can have a second intake time of simulated menses through the body facing material 28 of less than about 30 seconds following insult with simulated menses according to the Intake/Rewet test method described herein. In various embodiments, the body facing material 28 can further include a land area 116 with greater than about 1% open area within a chosen area of the body facing material 28, projections 90 with less than about 1% open area within a chosen area of the body facing material 28, a plurality of fibers of the projection layer 94 entangled with the support layer 92, a load of more than about 2 Newtons per 25 mm width at 10% extension in the machine direction, projections 90 having a height greater than about 1 mm, a resiliency of greater than about 70% and combinations thereof. In various embodiments, the absorbent body 40 can be free from superabsorbent material. In various embodiments, the absorbent body 40 can have greater than about 15% superabsorbent material. In various embodiments, the open area of the land area 116 can be due to interstitial fiber-to-fiber spacing.

Method to Determine Percent Open Area

The percentage of open area can be determined by using the image analysis measurement method described herein. In this context, the open area is considered the regions within a material where light transmitted from a light source passes directly thru those regions unhindered in the material of interest. Generally, the image analysis method determines a numeric value of percent open area for a material via specific image analysis measurement parameters such as area. The percent open area method is performed using conventional optical image analysis techniques to detect open area regions in both land areas and projections separately and then calculating their percentages in each. To separate land areas and projections for subsequent detection and measurement, incident lighting is used along with image processing steps. An image analysis system, controlled by an algorithm, performs detection, image processing and measurement and also transmits data digitally to a spreadsheet database. The resulting measurement data are used to determine the percent open area of materials possessing land areas and projections.

Figure 20:
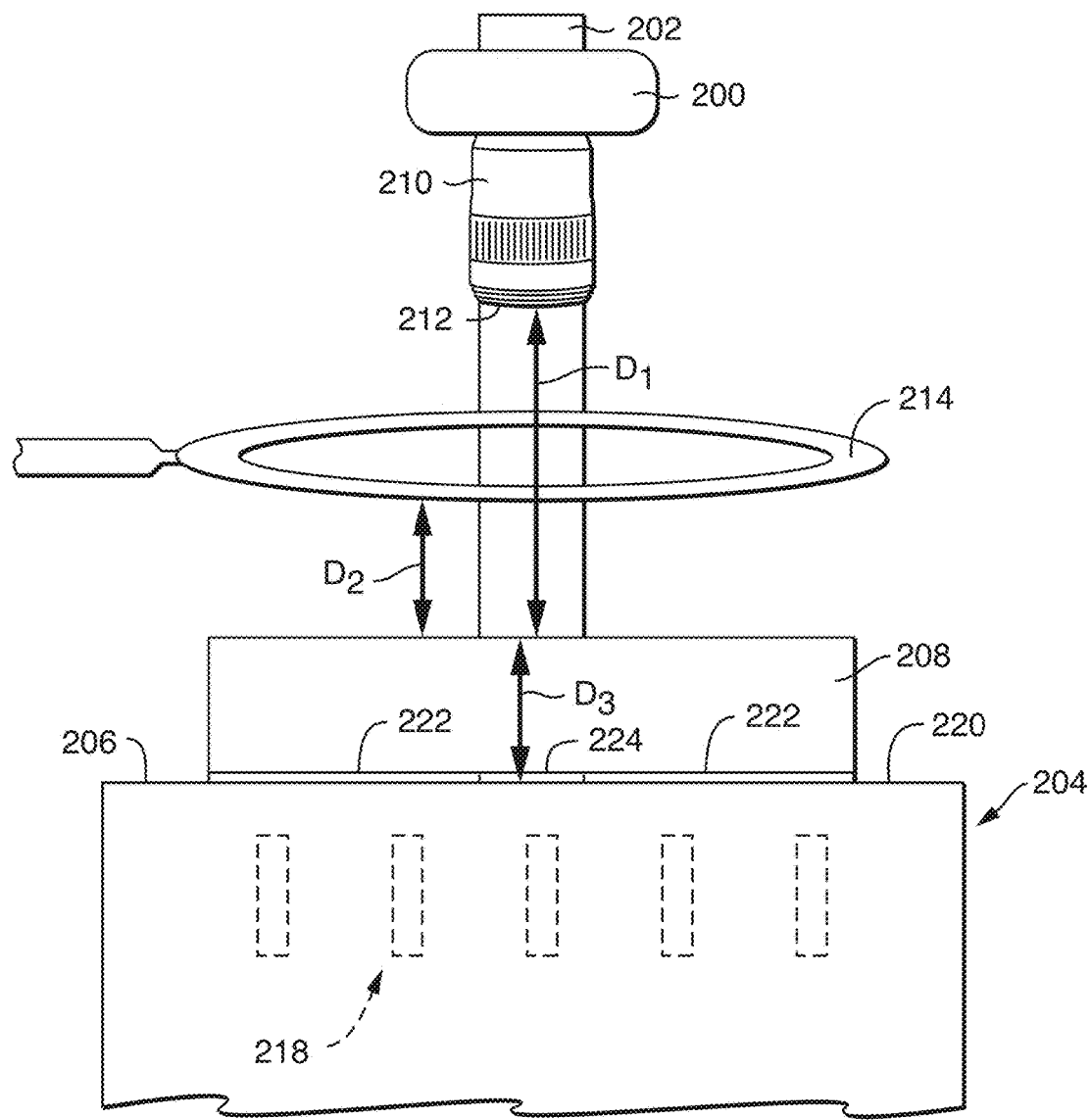
FIG. 20 is a perspective view of an exemplary illustration of a set-up of an imaging system used for determining the percent open area.

The method for determining the percent open area in both land areas and projections of a given material includes the step of acquiring two separate digital images of the material. An exemplary setup for acquiring the image is representatively illustrated in FIG. 20. Specifically, a CCD video camera 200 (e.g., a Leica DFC 310 FX video camera operated in gray scale mode and available from Leica Microsystems of Heerbrugg, Switzerland) is mounted on a standard support 202 such as a Polaroid MP-4 Land Camera standard support or equivalent available from Polaroid Resource Center in Cambridge, Miss. The standard support 202 is attached to a macro-viewer 204 such as a KREONITE macro-viewer available from Dunning Photo Equipment, Inc., having an office in Bixby, Okla. An auto stage 208 is placed on the upper surface 206 of the macro-viewer 204. The auto stage 208 is used to automatically move the position of a given material for viewing by the camera 200. A suitable auto stage is Model H112, available from Prior Scientific Inc., having an office in Rockland, Mass.

The material possessing land areas and projections is placed on the auto stage 208 under the optical axis of a 60 mm Nikon AF Micro Nikkor lens 210 with an f-stop setting of 4. The Nikon lens 210 is attached to the Leica DFC 310 FX camera 200 using a c-mount adaptor. The distance D1 from the front face 212 of the Nikon lens 210 to the material is 21 cm. The material is laid flat on the auto stage 208 and any wrinkles removed by gentle stretching and/or fastening it to the auto stage 208 surface using transparent adhesive tape at its outer edges. The material is oriented so the machine-direction (MD) runs in the horizontal direction of the resulting image. The material surface is illuminated with incident fluorescent lighting provided by a 16 inch diameter, 40 watt, GE Circline fluorescent lamp 214. The lamp 214 is contained in a fixture that is positioned so it is centered over the material and under the video camera above and is a distance D2 of 3 inches above the material surface. The illumination level of the lamp 214 is controlled with a Variable Auto-transformer, type 3PN1010, available from Staco Energy Products Co. having an office in Dayton, Ohio Transmitted light is also provided to the material from beneath the auto stage 208 by a bank of five 20 watt fluorescent lights 218 covered with a diffusing plate 220. The diffusing plate 220 is inset into, and forms a portion of, the upper surface 206 of the macro-viewer 204. The diffusing plate 220 is overlaid with a black mask 222 possessing a 3-inch by 3-inch opening 224. The opening 224 is positioned so that it is centered under the optical axis of the Leica camera and lens system. The distance D3 from the opening 224 to the surface of the auto stage 208 is approximately 17 cm. The illumination level of the fluorescent light bank 218 is also controlled with a separate Variable Auto-transformer.

The image analysis software platform used to perform the percent open area measurements is a QWIN Pro (Version 3.5.1) available from Leica Microsystems, having an office in Heerbrugg, Switzerland. The system and images are also calibrated using the QWIN software and a standard ruler with metric markings at least as small as one millimeter. The calibration is performed in the horizontal dimension of the video camera image. Units of millimeters per pixel are used for the calibration.

The method for determining the percent open area of a given material includes the step of performing several area measurements from both incident and transmitted light images. Specifically, an image analysis algorithm is used to acquire and process images as well as perform measurements using Quantimet User Interactive Programming System (QUIPS) language. The image analysis algorithm is reproduced below.

```
NAME = % Open Area - Land vs Projection Regions-1
PURPOSE = Measures % open area on 'land' and 'projection' regions via 'sandwich' lighting
technique
DEFINE VARIABLES & OPEN FILES
Open File ( C:\Data\39291\% Open Area\data.xls, channel #1 )
MFLDIMAGE = 2
TOTCOUNT = 0
TOTFIELDS = 0
SAMPLE ID AND SET UP
Configure ( Image Store 1392 × 1040, Grey Images 81, Binaries 24 )
Enter Results Header
File Results Header ( channel #1 )
File Line ( channel #1 )
Image Setup DC Twain [PAUSE] ( Camera 1, AutoExposure Off, Gain 0.00,
ExposureTime 34.23 msec, Brightness 0, Lamp 38.83 )
Measure frame ( x 31, y 61, Width 1330, Height 978 )
Image frame ( x 0, y 0, Width 1392, Height 1040 )
-- Calvalue = 0.0231 mm/px
CALVALUE = 0.0231
Calibrate ( CALVALUE CALUNITS$ per pixel )
Clear Accepts
For ( SAMPLE = 1 to 1, step 1 )
Clear Accepts
File ( "Field No.", channel #1, field width: 9, left justified )
File ( "Land Area", channel #1, field width: 9, left justified )
File ( "Land Open Area", channel #1, field width: 13, left justified )
File ( "%Open Land Area", channel #1, field width: 15, left justified )
File ( "Proj. Area", channel #1, field width: 9, left justified )
File ( "Proj. Open Area", channel #1, field width: 13, left justified )
File ( "% Open Proj. Area", channel #1, field width: 15, left justified )
File ( "Total % Open Area", channel #1, field width: 14, left justified )
```

```
File Line ( channel #1 )
Stage ( Define Origin )
Stage ( Scan Pattern, 5 × 1 fields, size 82500.000000 × 82500.000000 )
IMAGE ACQUISITION 1 - Projection isolation
For ( FIELD = 1 to 5, step 1 )
 Display ( Image0 (on), frames (on,on), planes (off,off,off,off,off,off), lut 0, x 0, y 0, z
  1, Reduction off )
 PauseText ( "Ensure incident lighting is correct (WL = 0.88 - 0.94) and acquire
   image." )
 Image Setup DC Twain [PAUSE] ( Camera 1, AutoExposure Off, Gain 0.00,
   ExposureTime 34.23 msec, Brightness 0, Lamp 38.83 )
 Acquire ( into Image0 )
  DETECT - Projections only
  PauseText ( "Ensure that threshold is set at least to the right of the left gray-level
   histogram peak which corresponds to the 'land' region." )
 Detect [PAUSE] ( whiter than 127, from Image0 into Binary0 delineated )
BINARY IMAGE PROCESSING
Binary Amend (Close from Binary0 to Binary1, cycles 10, operator Disc, edge erode on)
Binary Identify ( FillHoles from Binary1 to Binary1 )
Binary Amend (Open from Binary1 to Binary2, cycles 20, operator Disc, edge erode on)
Binary Amend (Close from Binary2 to Binary3, cycles 8, operator Disc, edge erode on )
PauseText ("Toggle <control> and <b> keys to check bump detection and correct if
  necessary." )
 Binary Edit [PAUSE] ( Draw from Binary3 to Binary3, nib Fill, width 2 )
 Binary Logical ( copy Binary3, inverted to Binary4 )
IMAGE ACQUISITION 2 - % Open Area
Display ( Image0 (on), frames (on,on), planes (off,off,off,off,off,off), lut 0, x 0, y 0, z
  1, Reduction off )
PauseText ( "Turn off incident light & ensure transmitted lighting is correct (WL =
0.97) and acquire image." )
Image Setup DC Twain [PAUSE] ( Camera 1, AutoExposure Off, Gain 0.00,
  ExposureTime 34.23 msec, Brightness 0, Lamp 38.83 )
 Acquire ( into Image0 )
 DETECT - Open areas only
 Detect ( whiter than 210, from Image0 into Binary10 delineated )
 BINARY IMAGE PROCESSING
 Binary Logical ( C = A AND B : C Binary11, A Binary3, B Binary10 )
 Binary Logical ( C = A AND B : C Binary12, A Binary4, B Binary10 )
 MEASURE AREAS - Land, projections, open area within each
 -- Land Area
 MFLDIMAGE = 4
 Measure field ( plane MFLDIMAGE, into FLDRESULTS(1), statistics into
  FLDSTATS(7,1) ) Selected parameters:  Area
 LANDAREA = FLDRESULTS(1)
 -- Projection Area
 MFLDIMAGE = 3
 Measure field ( plane MFLDIMAGE, into FLDRESULTS(1), statistics into
  FLDSTATS(7,1) ) Selected parameters:  Area
 BUMPAREA = FLDRESULTS(1)
 -- Open Projection area
 MFLDIMAGE = 11
 Measure field ( plane MFLDIMAGE, into FLDRESULTS(1), statistics into
  FLDSTATS(7,1) ) Selected parameters:  Area
 APBUMPAREA = FLDRESULTS(1)
 -- Open land area
 MFLDIMAGE = 12
 Measure field ( plane MFLDIMAGE, into FLDRESULTS(1), statistics into
  FLDSTATS(7,1) ) Selected parameters:  Area
 APLANDAREA = FLDRESULTS(1)
 -- Total % open area
 MFLDIMAGE = 10
 Measure field ( plane MFLDIMAGE, into FLDRESULTS(1), statistics into
  FLDSTATS(7,1) ) Selected parameters: Area%
 TOTPERCAPAREA = FLDRESULTS(1)
 CALCULATE AND OUTPUT AREAS
 PERCAPLANDAREA = APLANDAREA/LANDAREA*100
 PERCAPBUMPAREA = APBUMPAREA/BUMPAREA*100
 File ( FIELD, channel #1, 0 digits after '.' )
 File ( LANDAREA, channel #1, 2 digits after '.' )
 File ( APLANDAREA, channel #1, 2 digits after '.' )
 File ( PERCAPLANDAREA, channel #1, 1 digit after '.' )
 File ( BUMPAREA, channel #1, 2 digits after '.' )
 File ( APBUMPAREA, channel #1, 4 digits after '.' )
 File ( PERCAPBUMPAREA, channel #1, 5 digits after '.' )
 File ( TOTPERCAPAREA, channel #1, 2 digits after '.' )
 File Line ( channel #1 )
 Stage ( Step, Wait until stopped + 1100 msecs )
Next ( FIELD )
 PauseText ( "If no more samples, enter '0.'" )
```

-continued

```
Input ( FINISH )
If ( FINISH=0 )
  Goto OUTPUT
Endif
PauseText ( "Place the next replicate specimen on the auto-stage, turn on incident light
  and turn-off and/or block sub-stage lighting." )
Image Setup DC Twain [PAUSE] ( Camera 1, AutoExposure Off, Gain 0.00,
  ExposureTime 34.23 msec, Brightness 0, Lamp 38.83 )
File Line (channel #1)
Next ( SAMPLE )
OUTPUT:
Close File ( channel #1 )
END
```

The QUIPS algorithm is executed using the QWIN Pro software platform. The analyst is initially prompted to enter the material set information which is sent to the EXCEL file.

The analyst is next prompted by a live image set up window on the computer monitor screen to place a material onto the auto-stage 208. The material should be laid flat and gentle force applied at its edges to remove any macro-wrinkles that may be present. It should also be aligned so that the machine direction runs horizontally in the image. At this time, the Circline fluorescent lamp 214 can be on to assist in positioning the material. Next, the analyst is prompted to adjust the incident Circline fluorescent lamp 214 via the Variable Auto-transformer to a white level reading of approximately 0.9. The sub-stage transmitted light bank 218 should either be turned off at this time or masked using a piece of light-blocking, black construction paper placed over the 3 inch by 3 inch opening 224.

The analyst is now prompted to ensure that the detection threshold is set to the proper level for detection of the projections using the Detection window which is displayed on the computer monitor screen. Typically, the threshold is set using the white mode at a point approximately near the middle of the 8-bit gray-level range (e.g. 127). If necessary, the threshold level can be adjusted up or down so that the resulting detected binary will optimally encompass the projections shown in the acquired image with respect to their boundaries with the surrounding land region.

After the algorithm automatically performs several binary image processing steps on the detected binary of the projections, the analyst will be given an opportunity to re-check projection detection and correct any inaccuracies. The analyst can toggle both the 'control' and 'b' keys simultaneously to re-check projection detection against the underlying acquired gray-scale image. If necessary, the analyst can select from a set of binary editing tools (e.g. draw, reject, etc.) to make any minor adjustments. If care is taken to ensure proper illumination and detection in the previously described steps, little or no correction at this point should be necessary.

Next, the analyst is prompted to turn off the incident Circline fluorescent lamp 214 and either turn on the sub-stage transmitted light bank or remove the light blocking mask. The sub-stage transmitted light bank is adjusted by the Variable Auto-transformer to a white level reading of approximately 0.97. At this point, the image focus can be optimized for the land areas of the material.

The algorithm, after performing additional operations on the resulting separate binary images for projections, land areas and open area, will then automatically perform measurements and output the data into a designated EXCEL spreadsheet file. The following measurement parameter data will be located in the EXCEL file after measurements and data transfer has occurred:

Land Area
Land Open Area
Land % Open Area
Projection Area
Projection Open Area
Projection % Open Area
Total % Open Area Following the transfer of data, the algorithm will direct the auto-stage 208 to move to the next field-of-view and the process of turning on the incident, Circline fluorescent lamp 214 and blocking the transmitted sub-stage lighting bank 218 will begin again. This process will repeat four times so that there will be five sets of data from five separate field-of-view images per single material replicate.

Multiple sampling replicates from a single material can be performed during a single execution of the QUIPS algorithm (Note: The Sample For—Next line in the algorithm needs to be adjusted to reflect the number of material replicate analyses to be performed per material). The final material mean spread value is usually based on an N=5 analysis from five, separate, material subsample replicates. A comparison between different materials can be performed using a Student's T analysis at the 90% confidence level.

Method for Determining Height of Projections

The height of the projections can be determined by using the image analysis measurement method described herein. The image analysis method determines a dimensional numeric height value for projections using specific image analysis measurements of both land areas and projections with underlying land regions in a sample and then calculating the projection height alone by difference between the two. The projection height method is performed using conventional optical image analysis techniques to detect cross-sectional regions of both land areas and projection structures and then measure a mean linear height value for each when viewed using a camera with incident lighting. The resulting measurement data are used to compare the projection height characteristics of different types of body-side intake layers.

Prior to performing image analysis measurements, the sample of interest must be prepared in such a way to allow visualization of a representative cross-section that passes thru the center of a projection. Cross-sectioning can be performed by anchoring a representative piece of the sample on at least one of its cross-machine running straight edges on a flat, smooth surface with a strip of tape such as ¾ inch SCOTCH® Magic™ tape produced by 3M. Cross-sectioning is then performed by using a new, previously unused single edge carbon steel blue blade (PAL) and carefully cutting in a direction away from and orthogonal to the anchored edge and thru the centers of at least one projection and preferably more if projections are arranged in rows running in the machine direction. Any remaining rows of projections located behind the cross-sectioned face of projections should be cut away and removed prior to mounting so that only cross-sectioned projections of interest are present. Such blades for cross-sectioning can be acquired from Electron Microscopy Sciences of Hatfield, Pa. (Cat. #71974). Cross-sectioning is performed in the machine-direction of the sample, and a fresh, previously unused blade should be used for each new cross-sectional cut. The cross-sectioned face can now be mounted so that the projections are directed upward away from the base mount using an adherent such as two-side tape so that it can be viewed using a video camera possessing an optical lens. The mount itself and any background behind the sample that will be viewed by the camera must be darkened using non-reflective black tape and black construction paper 317 (shown in FIG. 21), respectively. For a typical sample, enough cross-sections should be cut and mounted separately from which a total of six projection height values can be determined.

Figure 21:
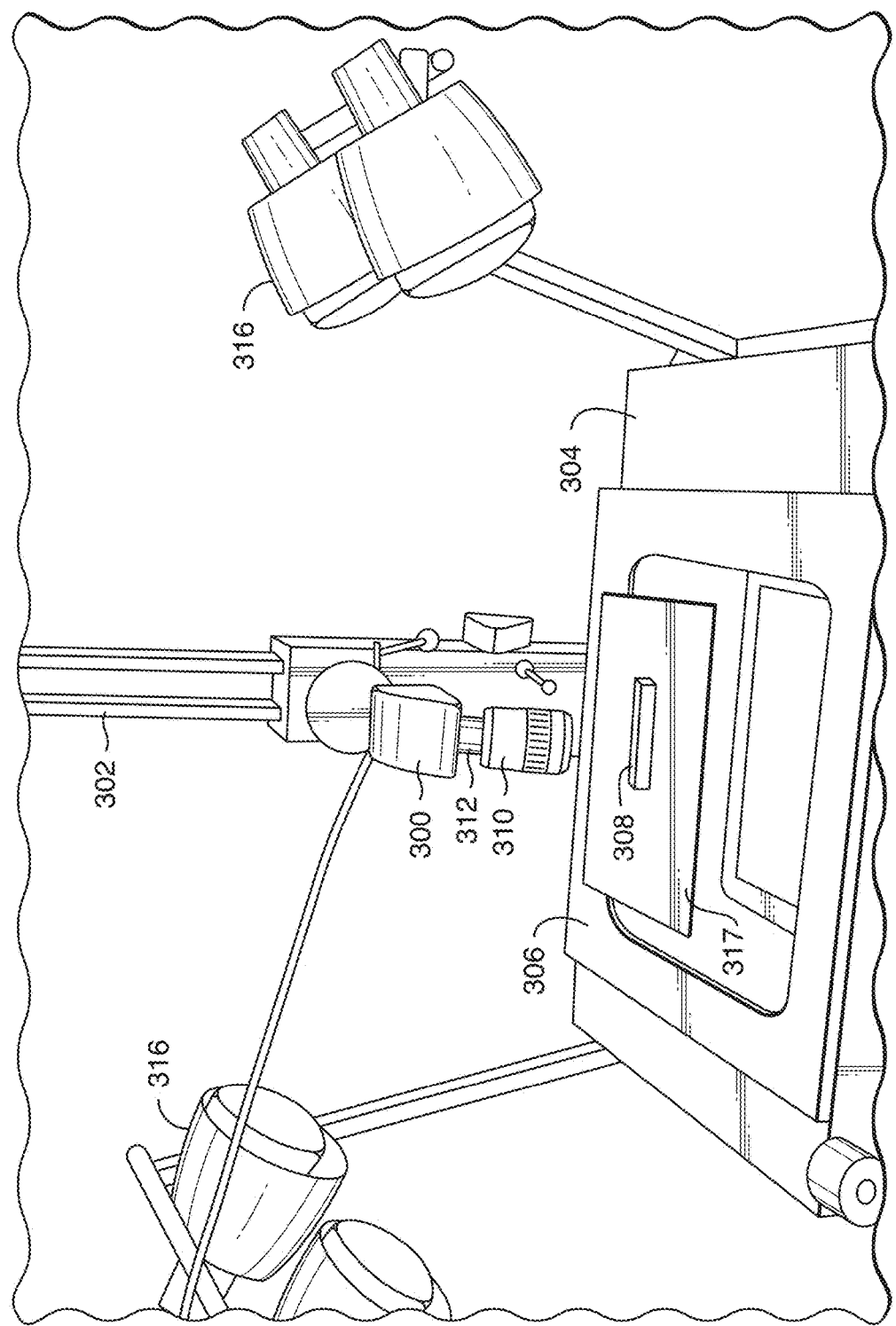
FIG. 21 is a perspective view of an exemplary illustration of a set-up of an imaging system used for determining projection height.

An exemplary setup for acquiring the images is representatively illustrated in FIG. 21. Specifically, a CCD video camera 300 (e.g., a Leica DFC 310 FX video camera operated in gray scale mode is available from Leica Microsystems of Heerbrugg, Switzerland) is mounted on a standard support 302 such as a Polaroid MP-4 Land Camera standard support available from Polaroid Resource Center in Cambridge, Miss. or equivalent. The standard support 302 is attached to a macro-viewer 304 such as a KREONITE macro-viewer available from Dunning Photo Equipment, Inc., having an office in Bixby, Okla. An auto stage 306 is placed on the upper surface of the macro-viewer 304. The auto stage 306 is used to move the position of a given sample for viewing by the camera 300. A suitable auto stage 306 is a Model H112, available from Prior Scientific Inc., having an office in Rockland, Mass.

The darkened sample mount 308 exposing the cross-sectioned sample face possessing land areas and projections is placed on the auto stage 306 under the optical axis of a 50 mm Nikon lens 310 with an f-stop setting of 2.8. The Nikon lens 310 is attached to the Leica DFC 310 FX camera 300 using a 30 mm extension tube 312 and a c-mount adaptor. The sample mount 308 is oriented so the sample cross-section faces flush toward the camera 300 and runs in the horizontal direction of the resulting image with the projections directed upward away from the base mount. The cross-sectional face is illuminated with incident, incandescent lighting 316 provided by two, 150 watt, GE Reflector Flood lamps. The two flood lamps are positioned so that they provide more illumination to the cross-sectional face than to the sample mount 308 beneath it in the image. When viewed from overhead directly above the camera 300 and underlying sample cross-section mount 308, the flood lamps 316 will be positioned at approximately 30 degrees and 150 degrees with respect to the horizontal plane running thru the camera 300. From this view the camera support will be at the 90 degree position. The illumination level of the lamps is controlled with a Variable Auto-transformer, type 3PN1010, available from Staco Energy Products Co. having an office in Dayton, Ohio.

The image analysis software platform used to perform measurements is a QWIN Pro (Version 3.5.1) available from Leica Microsystems, having an office in Heerbrugg, Switzerland. The system and images are also calibrated using the QWIN software and a standard ruler with metric markings at least as small as one millimeter. The calibration is performed in the horizontal dimension of the video camera image. Units of millimeters per pixel are used for the calibration.

Thus, the method for determining projection heights of a given sample includes the step of performing several, dimensional measurements. Specifically, an image analysis algorithm is used to acquire and process images as well as perform measurements using Quantimet User Interactive Programming System (QUIPS) language. The image analysis algorithm is reproduced below.

```
NAME = Height - Projection vs Land Regions - 1
PURPOSE = Measures height of projection and land regions
DEFINE VARIABLES & OPEN FILES
-- The following line is set to designate where measurement data will be stored.
Open File  (C:\Data\39291\Height\data.xls, channel #1)
FIELDS = 6
SAMPLE ID AND SET UP
Enter Results Header
File Results Header ( channel #1 )
File Line ( channel #1 )
Measure frame ( x 31, y 61, Width 1330, Height 978 )
Image frame ( x 0, y 0, Width 1392, Height 1040 )
-- Calvalue = 0.0083 mm/pixel
CALVALUE = 0.0083
Calibrate ( CALVALUE CALUNITS$ per pixel )
For ( REPLICATE = 1 to FIELDS, step 1 )
 Clear Feature Histogram #1
 Clear Feature Histogram #2
 Clear Accepts
 IMAGE ACQUISITION AND DETECTION
 PauseText ( "Position sample, focus image and set white level to 0.95." )
 Image Setup DC Twain [PAUSE] ( Camera 1, AutoExposure Off, Gain 0.00,
 ExposureTime 200.00 msec, Brightness 0, Lamp 49.99 )
 Acquire ( into Image0 )
  ACQOUTPUT = 0
  -- The following line can be optionally set-up for saving image files to a specific
  location.
  ACQFILE$ = "C:\Images\39291 - for Height\Text.
  2H_"+STR$(REPLICATE)+"s.jpg"
  Write image ( from ACQOUTPUT into file ACQFILE$ )
  Detect ( whiter than 104, from Image0 into Binary0 delineated )
```

```
IMAGE PROCESSING
Binary Amend (Close from Binary0 to Binary1, cycles 4, operator Disc, edge erode on)
Binary Amend (Open from Binary1 to Binary2, cycles 4, operator Disc, edge erode on)
Binary Identify (FillHoles from Binary2 to Binary3)
Binary Amend (Close from Binary3 to Binary4, cycles 15, operator Disc, edge erode on)
Binary Amend (Open from Binary4 to Binary5, cycles 20, operator Disc, edge erode on)
PauseText ( "Fill in projection & land regions that should be included, and reject over
  detected regions." )
Binary Edit [PAUSE] ( Draw from Binary5 to Binary6, nib Fill, width 2 )
PauseText ( "Select 'Land' region for measurement." )
Binary Edit [PAUSE] ( Accept from Binary6 to Binary7, nib Fill, width 2 )
PauseText ( "Select 'Projection' region for measurement." )
Binary Edit [PAUSE] ( Accept from Binary6 to Binary8, nib Fill, width 2 )
-- Combine land and projection regions with measurement grid.
Graphics ( Grid, 30 × 0 Lines, Grid Size 1334 × 964, Origin 21 × 21, Thickness 2,
Orientation 0.000000, to Binary15 Cleared )
Binary Logical ( C = A AND B : C Binary10, A Binary7, B Binary15 )
Binary Logical ( C = A AND B : C Binary11, A Binary8, B Binary15 )
MEASURE HEIGHTS
-- Land region only
Measure feature ( plane Binary10, 8 ferets, minimum area: 8, grey image: Image0 )
   Selected parameters: X FCP, Y FCP, Feret90
Feature Histogram #1 ( Y Param Number, X Param Feret90, from 0.0100 to 5.,
logarithmic, 20 bins )
Display Feature Histogram Results ( #1, horizontal, differential, bins + graph (Y axis
linear), statistics ) Data Window ( 1278, 412, 323, 371 )
-- Projection regions only (includes any underlying land material)
Measure feature ( plane Binary11, 8 ferets, minimum area: 8, grey image: Image0 )
   Selected parameters: X FCP, Y FCP, Feret90
Feature Histogram #2 ( Y Param Number, X Param Feret90, from 0.0100 to 10.,
logarithmic, 20 bins )
Display Feature Histogram Results ( #2, horizontal, differential, bins + graph (Y axis
linear), statistics ) Data Window ( 1305, 801, 297, 371 )
OUTPUT DATA
File ( "Land Height (mm)", channel #1 )
File Line ( channel #1 )
File Feature Histogram Results ( #1, differential, statistics, bin details, channel #1 )
File Line ( channel #1 )
File Line ( channel #1 )
File ( "Projection + Land Height (mm)", channel #1 )
File Line ( channel #1 )
File Feature Histogram Results ( #2, differential, statistics, bin details, channel #1 )
 File Line ( channel #1 )
 File Line ( channel #1 )
 File Line ( channel #1 )
Next ( REPLICATE )
Close File (channel #1)
END
```

The QUIPS algorithm is executed using the QWIN Pro software platform. The analyst is initially prompted to enter sample identification information which is sent to a designated EXCEL file to which the measurement data will also be subsequently sent.

The analyst is then prompted to position the mounted sample cross-section on the auto-stage 306 possessing the darkened background so the cross-sectional face is flush to the camera 300 with projections directed upward and the length running horizontally in the live image displayed on the video monitor screen. The analyst next adjusts the video camera 300 and lens' 310 vertical position to optimize the focus of the cross-sectional face. The illumination level is also adjusted by the analyst via the Variable Auto-transformer to a white level reading of approximately 0.95.

Once the analyst completes the above steps and executes the continue command, an image will be acquired, detected and processed automatically by the QUIPS algorithm. The analyst will then be prompted to fill-in the detected binary image, using the computer mouse, of any projection and/or land areas shown in the cross-sectional image that should have been included by the previous detection and image processing steps as well as rejecting any over detected regions that go beyond the boundaries of the cross-sectional structure shown in the underlying gray-scale image. To aid in this editing process, the analyst can toggle the 'control' and 'B' keys on the keyboard simultaneously to turn the overlying binary image on and off to assess how closely the binary matches with the boundaries of the sample shown in the cross-section. If the initial cross-sectioning sample preparation was performed well, little if any manual editing should be required.

The analyst is now prompted to "Select 'Land' region for measurement" using the computer mouse. This selection is performed by carefully drawing a vertical line down through one side of a single land area located between or adjacent to projections and then, with the left mouse button still depressed, moving the cursor beneath the land area to its opposite side and then drawing another vertical line upward. Once this has occurred, the left mouse button can be released and the land area to be measured should be filled in with a green coloring. If the vertical edges of the resulting selected region are skewed in any way, the analyst can reset to the original detected binary by clicking on the 'Undo' button located within the Binary Edit window and begin the selection process again until straight vertical edges on both sides of the selected land region are obtained.

Similarly, the analyst will next be prompted to "Select 'Projection' region for measurement." The top portion of a projection region adjacent to the previously selected land area is now selected in the same manner that was previously described for a land area selection.

The algorithm will then automatically perform measurements on both selected regions and output the data, in histogram format, into the designated EXCEL spreadsheet file. In the EXCEL file, the histograms for land and projection regions will be labeled "Land Height (mm)" and "Projection+Land Height (mm)," respectively. A separate set of histograms will be generated for each selection of land and projection region pairs.

The analyst will then again be prompted to position the sample and begin the process of selecting different land and projection regions. At this point, the analyst can either use the auto-stage joystick to move the same cross-section to a new sub-sampling position or an entirely different mounted cross-section obtained from the same sample can be positioned on the auto-stage 306 for measurement. The process for positioning the sample and selecting land and projection regions for measurement will occur six times for each execution of the QUIPS algorithm.

A single projection height value is then determined by calculating the numerical difference between the mean values of the separate land and projection region histograms for each single pair of measurements. The QUIPS algorithm will provide six replicate measurement sets of both land and projection regions for a single sample so that six projection height values will be generated per sample. The final sample mean spread value is usually based on an N=6 analysis from six, separate subsample measurements. A comparison between different samples can be performed using a Student's T analysis at the 90% confidence level.

EXAMPLES

Example 1

To demonstrate the process, apparatus and materials of the current disclosure, a series of fluid entangled body facing materials 28 were made as well as projection layers 94 without support layers 92. The samples were made on a spunlace production line at Textor Technologies PTY LTD in Tullamarine, Australia, in a fashion similar to that shown in FIG. 15 of the drawings with the exception being that only one projection fluid entangling device 158c was employed for forming the projections 90 in the texturizing zone 178. In addition, the projection layer 94 was pre-wetted upstream of the process shown in FIG. 15 and prior to the pre-entangling fluid entangling device 158a using conventional equipment. In this case, the pre-wetting was achieved through the use of a single injector set at a pressure of 8 bar. The pre-entangling fluid entangling device 158a was set at 45 bar, the lamination fluid entangling device 158b was set at 60 bar while the single projection fluid entangling device 158c pressure was varied as set forth in Tables 1 and 2 below at pressures of 140, 160 and 180 bar depending on the particular sample being run.

For the transport belt 152 in FIG. 15, the pre-entangling fluid device 158a was set at a height of 10 mm above the transport belt 152. For the lamination forming surface 180 the lamination fluid entangling device 158b was set at a height of 12 mm above the surface 180 as was the projection fluid entangling device 158c with respect to the projection forming surface 156.

The projection forming surface 156 was a 1.3 m wide steel texturizing drum having a diameter of 520 mm, a drum thickness of 3 mm and a hexagonal close packed pattern of 4 mm round forming holes 170 separated by 6 mm on a center-to-center spacing. The porous inner drum shell 174 was a 100 mesh (100 wires per inch in both directions/39 wires per centimeter in both directions) woven stainless steel mesh wire. The separation or gap between the exterior of the shell 174 and the inside of the drum 156 was 1.5 mm.

The process parameters that were varied were the aforementioned entangling fluid pressures (140, 160 and 180 bar) and the degree of overfeed (0%, 11%, 25% and 43%) using the aforementioned overfeed ratio of $OF=[(V_1/V_3)-1]\times 100$ where V1 is the input speed of the projection layer 94 and V3 is the output speed of the resultant body facing material 28.

All samples were run at an exit line or take-off speed (V3) of approximately 25 meters per minute (m/min) V1 is reported in the Tables 1 and 2 for the samples therein. V2 was held constant for all samples in Tables 1 and 2 at a speed equal to V3 or 25 meters per minute. The finished samples were sent through a line drier to remove excess water as is usual in the hydroentanglement process. Samples were collected after the drier and then labeled with a code (see Tables 1 and 2) to correspond to the process conditions used.

Relative to the materials made, as indicated below in Tables 1 and 2, some were made with a support layer 92 and others were not and when a support layer 92 was used, there were three variations including a spunbond web, a spunlace web and a through-air bonded carded web (TABCW). The spunbond support layer 92 was a 17 gsm polypropylene point bonded web made from 1.8 denier polypropylene spunbond fibers which were subsequently point bonded with an overall bond area per unit area of 17.5% made by Kimberly-Clark Australia of Milsons Point, Australia. The spunbond material was supplied and entered into the process in roll form with a roll width of approximately 130 centimeters. The spunlace support layer 92 was a 52 gsm spunlace material using a uniform mixture of 70 weight percent 1.5 denier, 40 mm long Viscose staple fibers and 30 weight percent 1.4 denier, 38 mm long Polyester (PET) staple fibers made by Textor Technologies PTY LTD of Tullamarine, Australia. The spunlace material was preformed and supplied in roll form and had a roll width of approximately 140 centimeters. The TABCW support layer 92 had a basis weight of 40 gsm and comprised a uniform mixture of 40 weight percent, 6 denier, 51 mm long PET staple fibers and 60 weight percent 3.8 denier, 51 mm long polyethylene sheath/polypropylene core bicomponent staple fibers made by Textor Technologies PTY LTD of Tullamarine, Australia. In the data below (see Tables 1 and 2) under the heading "support layer" the spunbond layer was identified as "SB", the spunlace layer was identified as "SL" and the TABCW layer was identified as "S". Where no support layer 92 was used, the term "None" appears. The basis weights used in the examples should not be considered a limitation on the basis weights that can be used as the basis weights for the support layers 92 may be varied depending on the end applications.

In all cases the projection layer 94 was a carded staple fiber web made from 100% 1.2 denier, 38 mm long polyester staple fibers available from the Huvis Corporation of Daejeon, Korea. The projection layer 94 carded web was manufactured in-line with the hydroentanglement process by Textor Technologies PTY LTD of Tullamarine, Australia, and had a width of approximately 140 centimeters. Basis weights varied as indicated in Tables 1 and 2 and ranged between 28 gsm and 49.5 gsm though other basis weights and ranges may be used depending upon the end application.

The projection layer 94 was identified as the "card web" in the data below in Tables 1 and 2.

Figure 22:
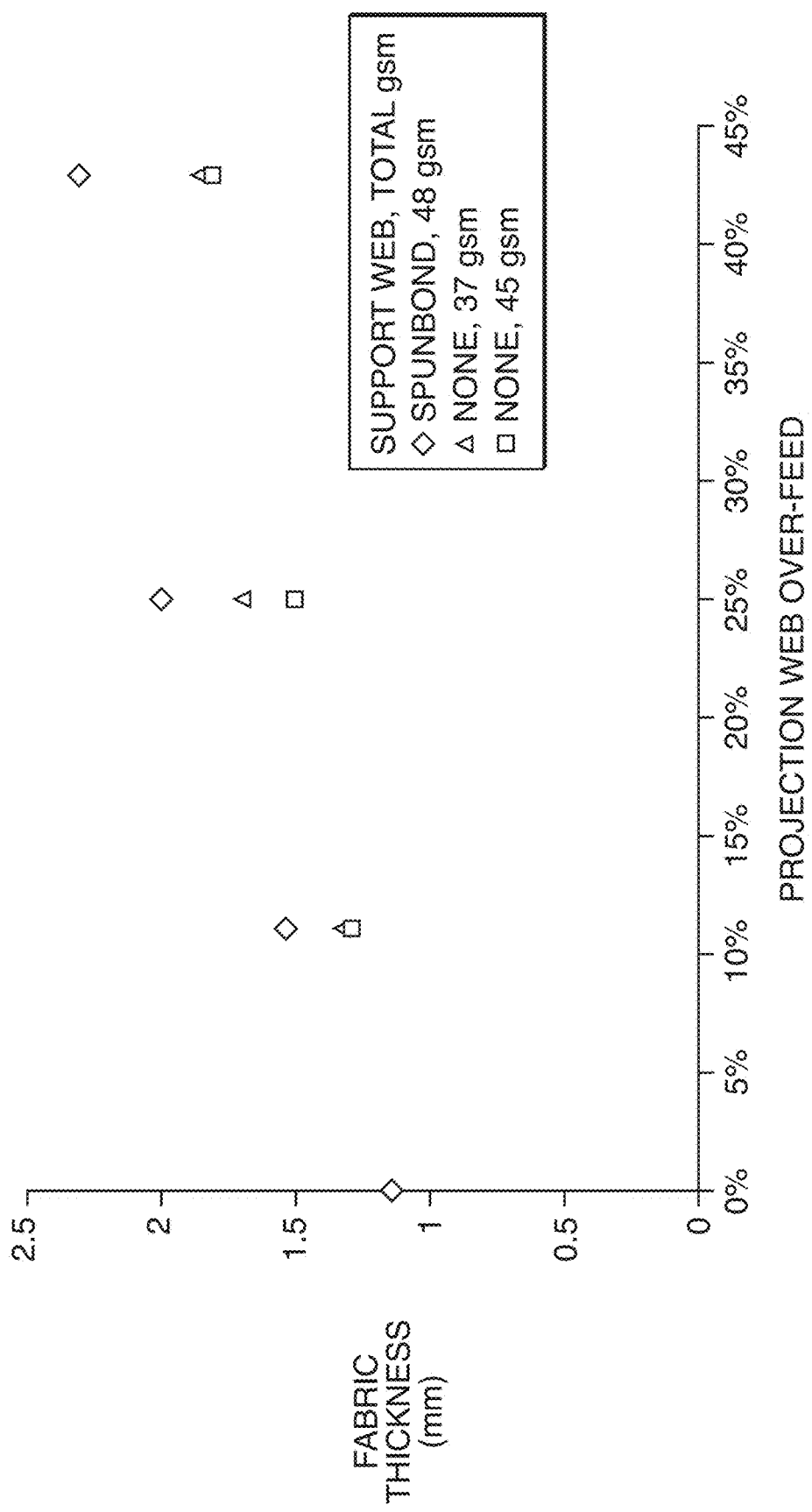
FIG. 22 is a graph depicting fabric thickness as a function of the overfeed ratio of the projection layer into a forming process.

The thickness of the materials set forth in Tables 1 and 2 below as well as in FIG. 22 were measured using a Mitutoyo model number ID-C1025B thickness gauge with a foot pressure of 345 Pa (0.05 psi). Measurements were taken at room temperature (about 20 degrees Celsius) and reported in millimeters using a round foot with a diameter of 76.2 mm (3 inches). Thicknesses for select samples (average of three samples) with and without support layers are shown in FIG. 22 of the drawings.

The tensile strength of the materials, defined as the peak load achieved during the test, was measured in both the Machine Direction (MD) and the cross-machine direction (CMD) using an Instron model 3343 tensile testing device running an Instron Series IX software module Rev. 1.16 with a +/−1 kN load cell. The initial jaw separation distance ("Gauge length") was set at 75 millimeters and the crosshead speed was set at 300 millimeters per minute. Samples were cut to 50 mm width by 300 mm length in the machine direction (MD) and each tensile strength test result reported was the average of two samples per code. Samples were evaluated at room temperature (about 20 degrees Celsius). Excess material was allowed to drape out the ends and sides of the apparatus. Cross machine direction (CMD) strengths and extensions were also measured and generally the CMD strengths were about one half to one fifth of MD strength and CMD extensions at peak load were about two to three times higher than in the MD direction. (The CMD samples were cut with the long dimension being taken in the CMD.) MD strengths were reported in Newtons per 50 mm width of material. (Results are shown in Tables 1 and 2) MD extensions for the material at peak load were reported as the percentage of the initial gauge length (initial jaw separation).

Extension measurements were also made and reported in the MD at a load of 10 Newtons (N). (See Tables 1 and 2 below and FIG. 23) Tables 1 and 2 show data based upon varying the support layer being used, the degree of overfeed being used and variances in the water pressure from the hydroentangling water jets.

As an example of the consequences of varying process parameters, high overfeed requires sufficient jet-pressure to drive the projection layer 94 into the projection forming surface 156 and to take up the excess material being overfed into the texturizing zone 178. If sufficient jet energy is not available to overcome the material's resistance to texturing then the material will fold and overlap itself and in the worst case may lap a roller prior to the texturing zone 178 requiring the process to be stopped. While the experiments were conducted at a line speed V3 of 25 m/min, this should not be considered a limitation as to the line speed as the equipment with similar materials was run at line speeds ranging from 10 to 70 meters per minute and speeds outside this range may be used depending on the materials being run.

The following tables (Tables 1 and 2) summarize the materials, process parameters, and test results. For the samples shown in Table 1, samples were made with and without support layers 92. Codes 1.1 through 3.6 used the aforementioned spunbond support layer 92. Codes 4.1 through 5.7 had no support layer 92. Jet pressures for each of the samples are listed in Tables 1 and 2.

TABLE 1

Experimental Parameters and test results, support layer 92 and no support layer 92, codes 1 to 5.

| CODE | Support Layer | Card web (gsm) | Overfeed | Card web Speed ($V_1$) (m/min) | Press. (bar) | Laminate* Weight (gsm) | Laminate* Thickness (mm) | Laminate* MD Strength (N/50 mm) | Laminate* Extension at Peak Load MD (%) | Laminate* MD Extension @10 N (%) |
|---|---|---|---|---|---|---|---|---|---|---|
| 1.1 | SB | 28 | 43% | 35.8 | 180 | 51 | 2.22 | 75.6 | 85.0 | 5.0 |
| 1.2 | SB | 28 | 43% | 35.8 | 160 | 52.2 | 2.33 | 65.8 | 82.1 | 3.5 |
| 1.3 | SB | 28 | 43% | 35.8 | 140 | 51.1 | 2.34 | 61.3 | 86.1 | 3.4 |
| 1.4 | SB | 28 | 11% | 27.8 | 140 | 46.3 | 1.47 | 95.5 | 53.0 | 4.9 |
| 1.5 | SB | 28 | 11% | 27.8 | 160 | 45.5 | 1.52 | 91.9 | 46.7 | 4.7 |
| 1.6 | SB | 28 | 11% | 27.8 | 180 | 46.7 | 1.61 | 109.1 | 49.8 | 5.0 |
| 1.7 | SB | 28 | 25% | 31.3 | 180 | 50.5 | 2.02 | 94.4 | 63.7 | 3.7 |
| 1.8 | SB | 28 | 25% | 31.3 | 160 | 50.7 | 1.97 | 82.1 | 62.2 | 5.6 |
| 1.9 | SB | 28 | 25% | 31.3 | 140 | 49.7 | 1.99 | 74.9 | 62.8 | 4.2 |
| 1.10 | SB | 28 | 0% | 25.0 | 140 | 42.9 | 1.08 | 104.4 | 35.8 | 3.0 |
| 1.11 | SB | 28 | 0% | 25.0 | 160 | 43.6 | 1.15 | 102.8 | 35.2 | 3.7 |
| 1.12 | SB | 28 | 0% | 25.0 | 180 | 44.1 | 1.17 | 97.5 | 35.7 | 5.0 |
| 2.1 | SB | 20 | 11% | 27.8 | 140 | 36.8 | 1.27 | 53.1 | 44.2 | 2.4 |
| 2.2 | SB | 20 | 11% | 27.8 | 160 | 36.2 | 1.27 | 52.5 | 62.1 | 2.9 |
| 2.3 | SB | 20 | 11% | 27.8 | 180 | 37.4 | 1.31 | 57.8 | 44.3 | 2.7 |
| 2.4 | SB | 20 | 25% | 31.3 | 180 | 39 | 1.55 | 53.4 | 56.6 | 2.4 |
| 2.5 | SB | 20 | 25% | 31.3 | 160 | 38 | 1.48 | 46.6 | 63.4 | 2.8 |
| 2.6 | SB | 20 | 25% | 31.3 | 140 | 38.8 | 1.46 | 39.7 | 30.4 | 2.3 |
| 2.7 | SB | 20 | 43% | 35.8 | 140 | 40.9 | 1.78 | 32.3 | 53.0 | 2.6 |
| 2.8 | SB | 20 | 43% | 35.8 | 160 | 41.4 | 1.82 | 35.7 | 77.2 | 2.7 |
| 2.9 | SB | 20 | 43% | 35.8 | 180 | 41.7 | 1.83 | 47.5 | 87.5 | 3.4 |
| 3.1 | SB | 38 | 25% | 31.3 | 180 | 62.2 | 2.52 | 97.3 | 64.8 | 2.2 |
| 3.2 | SB | 38 | 25% | 31.3 | 160 | 61 | 2.47 | 93.5 | 63.5 | 2.3 |
| 3.3 | SB | 38 | 25% | 31.3 | 140 | 60 | 2.32 | 83.9 | 68.2 | 2.4 |
| 3.4 | SB | 38 | 43% | 35.8 | 140 | 66.2 | 2.81 | 63.0 | 92.8 | 2.4 |
| 3.5 | SB | 38 | 43% | 35.8 | 160 | 65.4 | 2.81 | 78.6 | 86.5 | 2.3 |
| 3.6 | SB | 38 | 43% | 35.8 | 180 | 67.4 | 2.88 | 86.0 | 82.0 | 2.4 |
| 4.1 | None | 31.5 | 43% | 35.8 | 140 | 32.5 | 1.57 | 46.6 | 77.0 | 31.5 |
| 4.2 | None | 31.5 | 43% | 35.8 | 160 | 38.1 | 1.93 | 53.4 | 79.8 | 32.9 |
| 4.3 | None | 31.5 | 43% | 35.8 | 180 | 35.9 | 2.04 | 46.4 | 69.3 | 31.1 |
| 4.4 | None | 36.0 | 25% | 31.3 | 180 | 35.8 | 1.47 | 57.4 | 53.8 | 19.0 |
| 4.5 | None | 36.0 | 25% | 31.3 | 160 | 36.3 | 1.58 | 56.1 | 49.7 | 17.1 |

TABLE 1-continued

Experimental Parameters and test results, support layer 92 and no support layer 92, codes 1 to 5.

| CODE | Support Layer | Card web (gsm) | Overfeed | Card web Speed (V$_1$) (m/min) | Press. (bar) | Laminate* Weight (gsm) | Laminate* Thickness (mm) | Laminate* MD Strength (N/50 mm) | Laminate* Extension at Peak Load MD (%) | Laminate* MD Extension @10 N (%) |
|---|---|---|---|---|---|---|---|---|---|---|
| 4.6 | None | 36.0 | 25% | 31.3 | 140 | 35.9 | 2.03 | 60.6 | 54.0 | 18.4 |
| 4.7 | None | 40.5 | 11% | 27.8 | 140 | 38.8 | 1.3 | 69.0 | 41.3 | 15.1 |
| 4.8 | None | 40.5 | 11% | 27.8 | 160 | 38.2 | 1.33 | 72.4 | 41.4 | 9.9 |
| 4.9 | None | 40.5 | 11% | 27.8 | 180 | 37.6 | 1.31 | 72.3 | 36.6 | 8.4 |
| 5.1 | None | 38.5 | 43% | 35.8 | 140 | 43.2 | 2.16 | 51.7 | 72.1 | 28.7 |
| 5.2 | None | 38.5 | 43% | 35.8 | 160 | 44.1 | 2.2 | 54.2 | 76.1 | 26.0 |
| 5.3 | None | 38.5 | 43% | 35.8 | 180 | 43.2 | 2.3 | 50.4 | 74.2 | 24.1 |
| 5.4 | None | 46.0 | 25% | 31.3 | 180 | 40.5 | 1.77 | 67.5 | 51.8 | 13.6 |
| 5.5 | None | 46.0 | 25% | 31.3 | 160 | 46.5 | 2.02 | 60.0 | 58.2 | 16.5 |
| 5.6 | None | 46.0 | 25% | 31.3 | 140 | 45.8 | 1.99 | 61.1 | 54.8 | 20.2 |
| 5.7 | None | 49.5 | 11% | 27.8 | 140 | 43.6 | 1.52 | 74.0 | 36.8 | 9.2 |
| 5.8 | None | 49.5 | 11% | 27.8 | 160 | 45 | 1.54 | 75.6 | 35.9 | 8.4 |
| 5.9 | None | 49.5 | 11% | 27.8 | 180 | 47 | 1.71 | 70.8 | 39.1 | 8.9 |

*Note for codes 4.1 to 5.9 the "Laminate" was a single layer structure as no support layer 92 was present.

For Table 2, samples 6SL.1 through 6SL.6 were run on the same equipment under the same conditions as the samples in Table 1 with the aforementioned spunlace support layer 92 while samples 6S.1 through 6S.4 were run with the aforementioned through-air bonded carded web support layer 92. The projection layers 94 ("card webs") were made in the same fashion as those used in Table 1.

TABLE 2

Experimental parameters and test results code 6, alternative support layers 92.

| CODE | Support Layer | Card web (gsm) | Overfeed | Card web Speed (V$_1$) (m/min) | Texturizing Jet Press. (bar) | Laminate Weight (gsm) | Laminate Thickness (mm) | Laminate MD Strength (N/50 mm) | Laminate Extension at Peak Load MD (%) | Laminate MD Extension @10 N (%) |
|---|---|---|---|---|---|---|---|---|---|---|
| 6SL.1 | SL | 28 | 25% | 31.3 | 180 | 82.6 | 2.19 | 107.5 | 23.6 | 1.9 |
| 6SL.2 | SL | 28 | 25% | 31.3 | 160 | 80 | 2.11 | 103.6 | 23.6 | 1.9 |
| 6SL.3 | SL | 28 | 25% | 31.3 | 140 | 81.1 | 2.07 | 101.5 | 20.2 | 1.8 |
| 6SL.4 | SL | 28 | 43% | 35.8 | 140 | 85.4 | 2.16 | 86.7 | 20.2 | 1.7 |
| 6SL.5 | SL | 28 | 43% | 35.8 | 160 | 84.2 | 2.53 | 93.4 | 20.8 | 1.6 |
| 6SL.6 | SL | 28 | 43% | 35.8 | 180 | 83.7 | 2.55 | 103.3 | 22.4 | 1.4 |
| 6S.1 | S | 28 | 25% | 31.3 | 180 | 68.2 | 2.56 | 89 | 56 | 4.2 |
| 6S.2 | S | 28 | 25% | 31.3 | 160 | 70 | 2.57 | 70 | 56.7 | 2.2 |
| 6S.3 | S | 28 | 25% | 31.3 | 140 | 72.5 | 2.71 | 67.7 | 62 | 2.8 |
| 6S.4 | S | 28 | 43% | 35.8 | 140 | 78 | 2.63 | 48.5 | 57.8 | 2.8 |

As can be seen in Tables 1 and 2, the key quality parameter of fabric thickness depends predominantly on the amount of overfeed of the projection layer 94 into the texturizing zone 178. Relative to the data shown in Table 2 it can be seen that high overfeed ratios resulted in increased thickness. In addition, at the same overfeed ratios, higher fluid pressures resulted in higher thickness values which in turn indicates an increased projection 90 height. Table 2 shows the test results for samples made using alternative support layers 92. Code 6S used a 40 gsm through-air bonded carded web and code 6SL used a 52 gsm spunlaced material. These materials performed well and had good stability and appearance when compared to unsupported materials with no support layers 92.

FIG. 22 depicts the sample thickness in millimeters relative to the percentage of projection layer 94 overfeed for a body facing material 28 (represented by a diamond) versus two samples that did not have a support layer 92 (represented by a square and a triangle). All reported values were an average of three samples. As can be seen from the data in FIG. 22, as overfeed is increased, the thickness of the sample also increased showing the importance and advantage of using overfeed.

Figure 23:
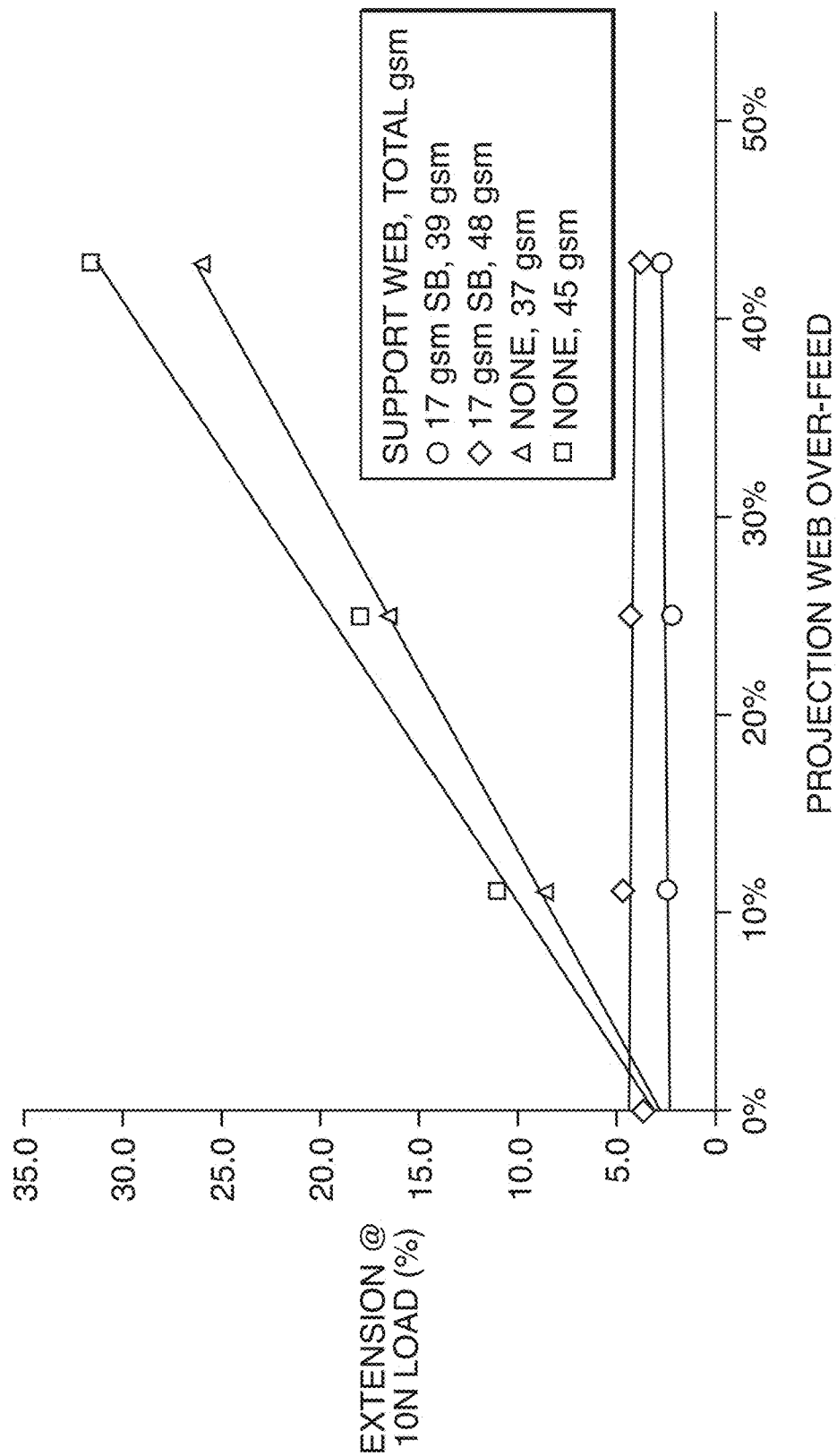
FIG. 23 is a graph depicting fabric extension at a 10N load as a function of the overfeed ratio of the projection layer into the forming process for body facing materials and unsupported projections layers.

FIG. 23 is a graph depicting the percentage of sample extension at a 10 Newton load relative to the amount of projection layer 94 overfeed for materials from Table 1. As can be seen from the graph in FIG. 23, when no support layer 92 was present, there was a dramatic increase in the machine direction extensibility of the resultant sample as the percentage of overfeed of material into the texturizing zone 178 was increased. In contrast, the sample with the spunbond support layer 92 experienced virtually no increase in its extension percentage as the overfeed ratio was increased.

This in turn resulted in the projection layer 94 having projections 90 which are more stable during subsequent processing and which are better able to retain their shape and height.

As can be seen from the data and the graphs, higher overfeed and hence greater projection height also decreased the MD tensile strength and increased the MD extension at peak load. This was because the increased texturing provided more material (in the projections) that did not immediately contribute to resisting the extension and generating the load and allowed greater extension before the peak load was reached.

A key benefit of the laminate of both a projection layer 94 and a support layer 92 compared to a single layer projection layer 94 with no support layer 92 can be that the support layer 92 can reduce excessive extension during subsequent processing and converting which can pull out the fabric texture and reduce the height of the projections. Without the support layer 92 being integrated into the projection forming process, it was very difficult to form webs with projections that could continue to be processed without the forces and tensions of the process acting upon the webs and negatively impacting the integrity of the projections, especially when low basis weight webs were desired. Other means can be used to stabilize the material such as thermal or adhesive bonding or increased entanglement but they tend to lead to a loss of fabric softness and an increased stiffness as well as increasing the cost. The fluid entangled body facing material 28 can provide softness and stability simultaneously. The difference between supported and unsupported textured materials is illustrated clearly in the last column of Table 1 which, for comparison, shows the extension of the samples at a load of 10N. The data is also displayed in FIG. 23. It can be seen that the sample supported by the spunbond support layer 92 extends only a few percent at an applied load of 10 Newtons (N) and the extension was almost independent of the overfeed. In contrast the unsupported projection layer 94 extended by up to 30% at a 10 Newton load and the extension at 10N was strongly dependent on the overfeed used to texture the material. Low extensions at 10N can be achieved for unsupported webs but only by having low overfeed, which results in low projection height, i.e., little texturing of the web.

Figure 24:
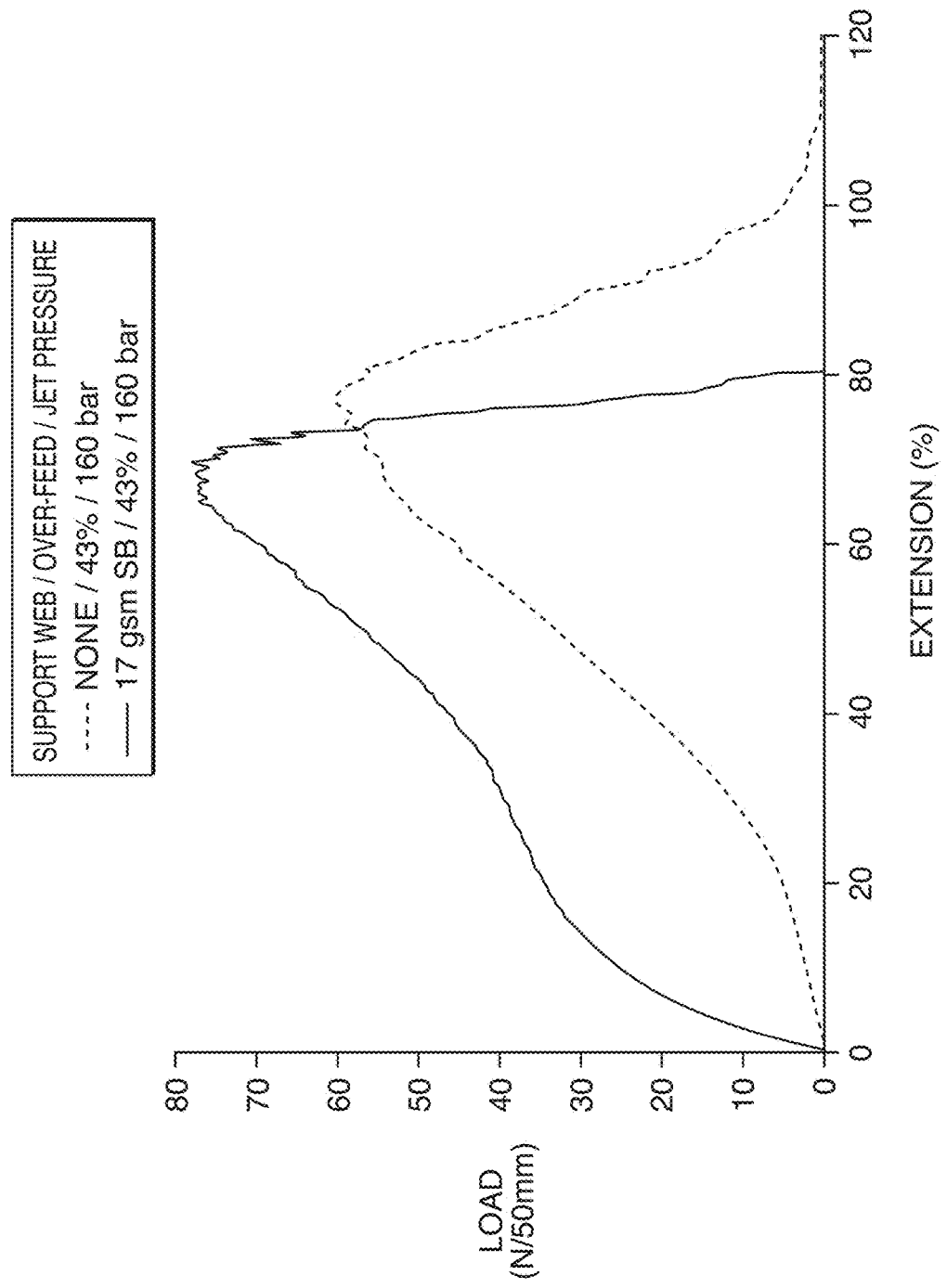
FIG. 24 is a graph depicting the load in Newtons per 50 mm width as a function of the percent extension comparing both a body facing material and an unsupported projection layer.

FIG. 24 shows an example of the load-extension curves obtained in tensile testing of samples in the machine direction (MD), which is the direction in which highest loads are most likely to be experienced in winding up the material and in further processing and converting. The samples shown were all made using an overfeed of 43% and approximately the same areal density (45 gsm). It can be seen that the sample containing the spunbond support layer 92 had a much higher initial modulus, the start of the curve was steep compared to that of the unsupported, single projection layer 94 by itself. This steeper initial part of the curve for the sample was also recoverable as the sample was elastic up to the point where the gradient starts to decrease. The unsupported sample has very low modulus and permanent deformation and loss of texture occurs at a lower load. FIG. 24 shows the load-extension curves for both a supported and unsupported fabric. Note the relative steepness of the initial part of the curve for the supported fabric/body facing material. This means that the unsupported sample is relatively easily stretched and a high extension is required to generate any tension in it compared to the supported sample. Tension is often required for stability in later processing and converting but the unsupported sample is more likely to suffer permanent deformation and loss of texture as a result of the high extension needed to maintain tension.

Figure 25:
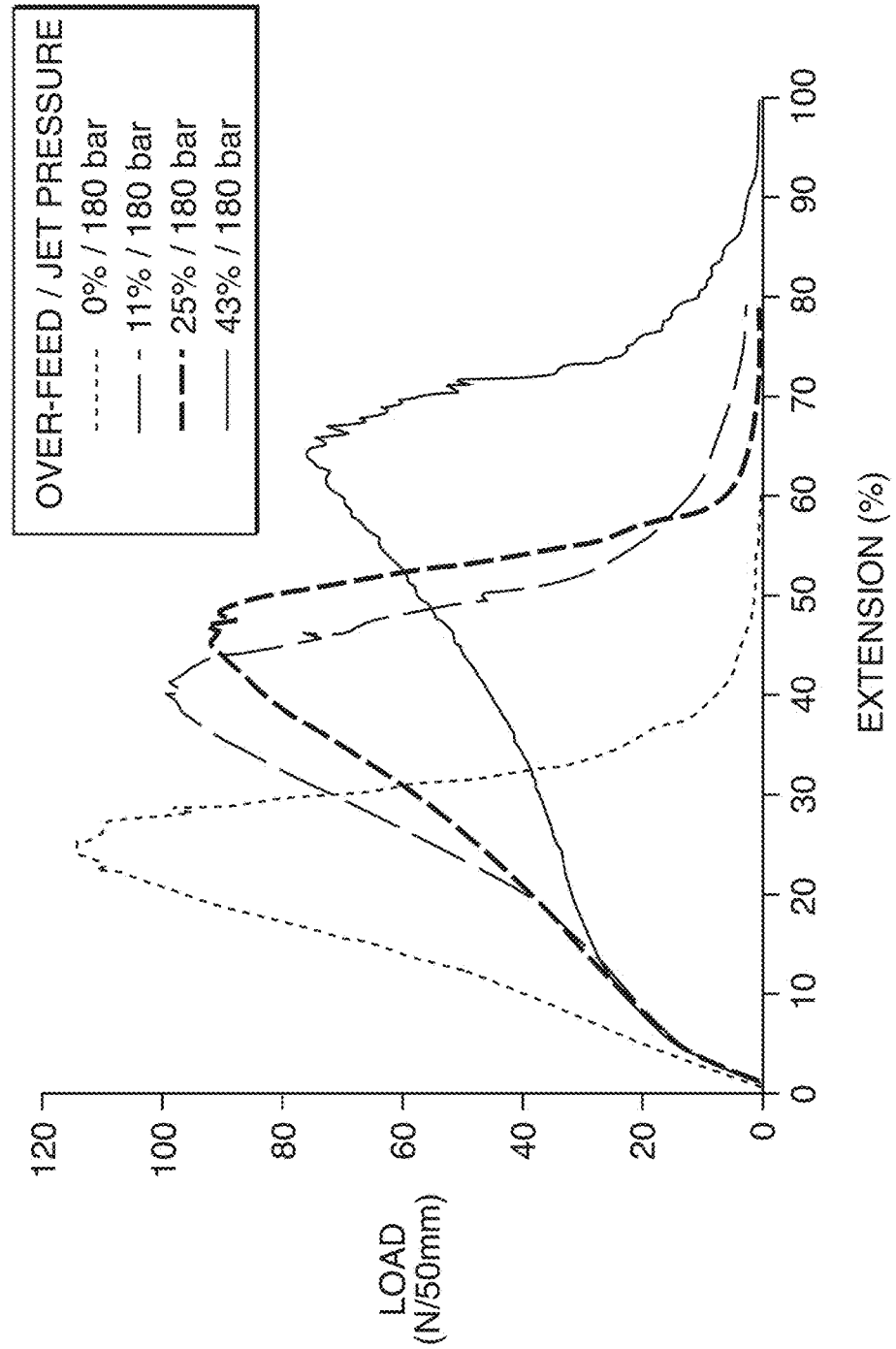
FIG. 25 is a graph depicting the load in Newtons per 50 mm width as a function of the percent extension for a series of body facing materials while varying the overfeed ratio.
Figure 26:
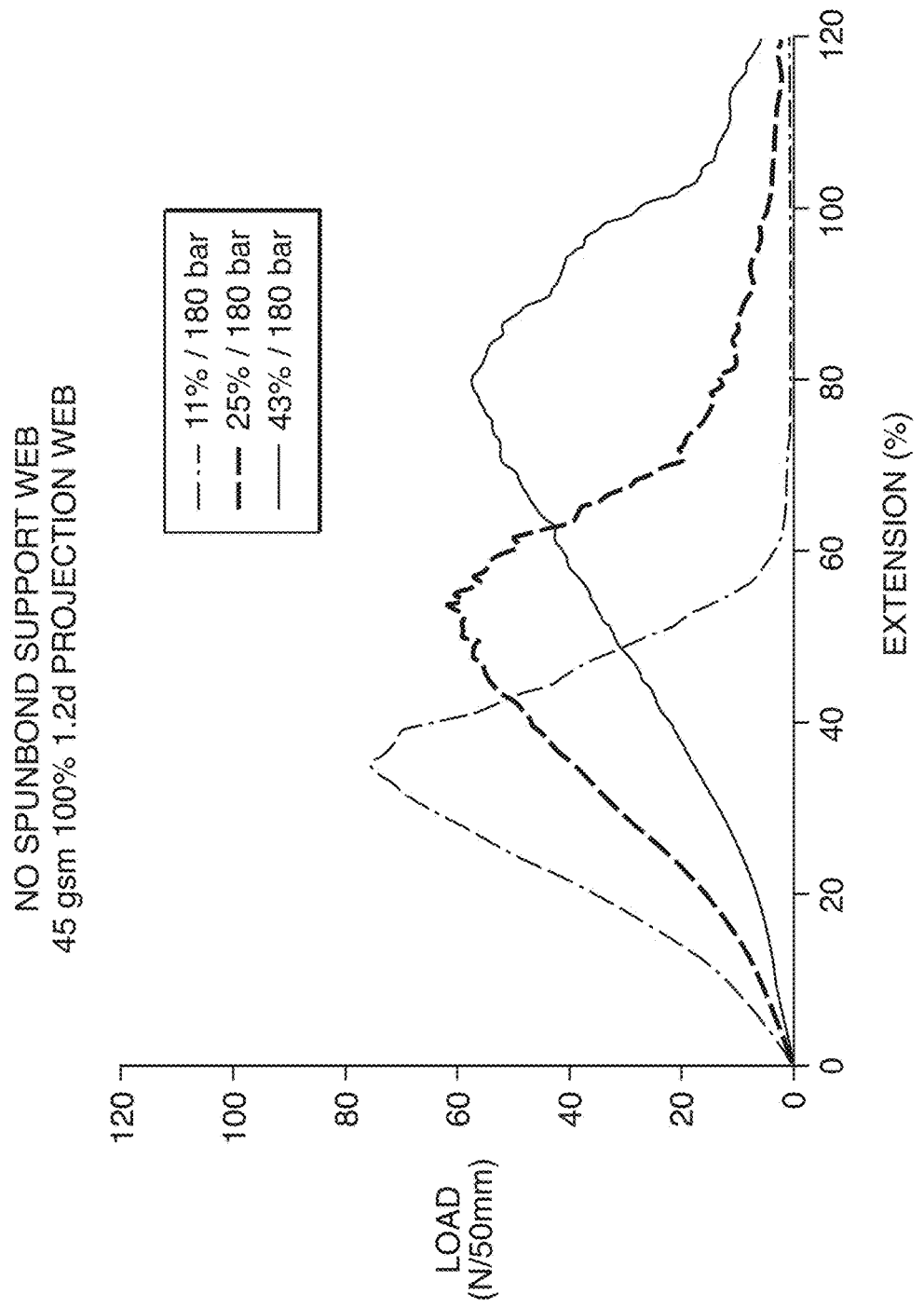
FIG. 26 is a graph depicting the load in Newtons per 50 mm width as a function of the percent extension for a series of 45 gsm projection layers while varying the overfeed ratio.

FIGS. 25 and 26 show the set of curves for a wider range of conditions. It can be seen that the samples with a low level of texturing from low overfeed were stiffer and stronger (despite being slightly lighter) but the absence of texture rendered them not useful in this context. All supported laminate samples had higher initial gradients compared to the unsupported samples.

Figure 27:
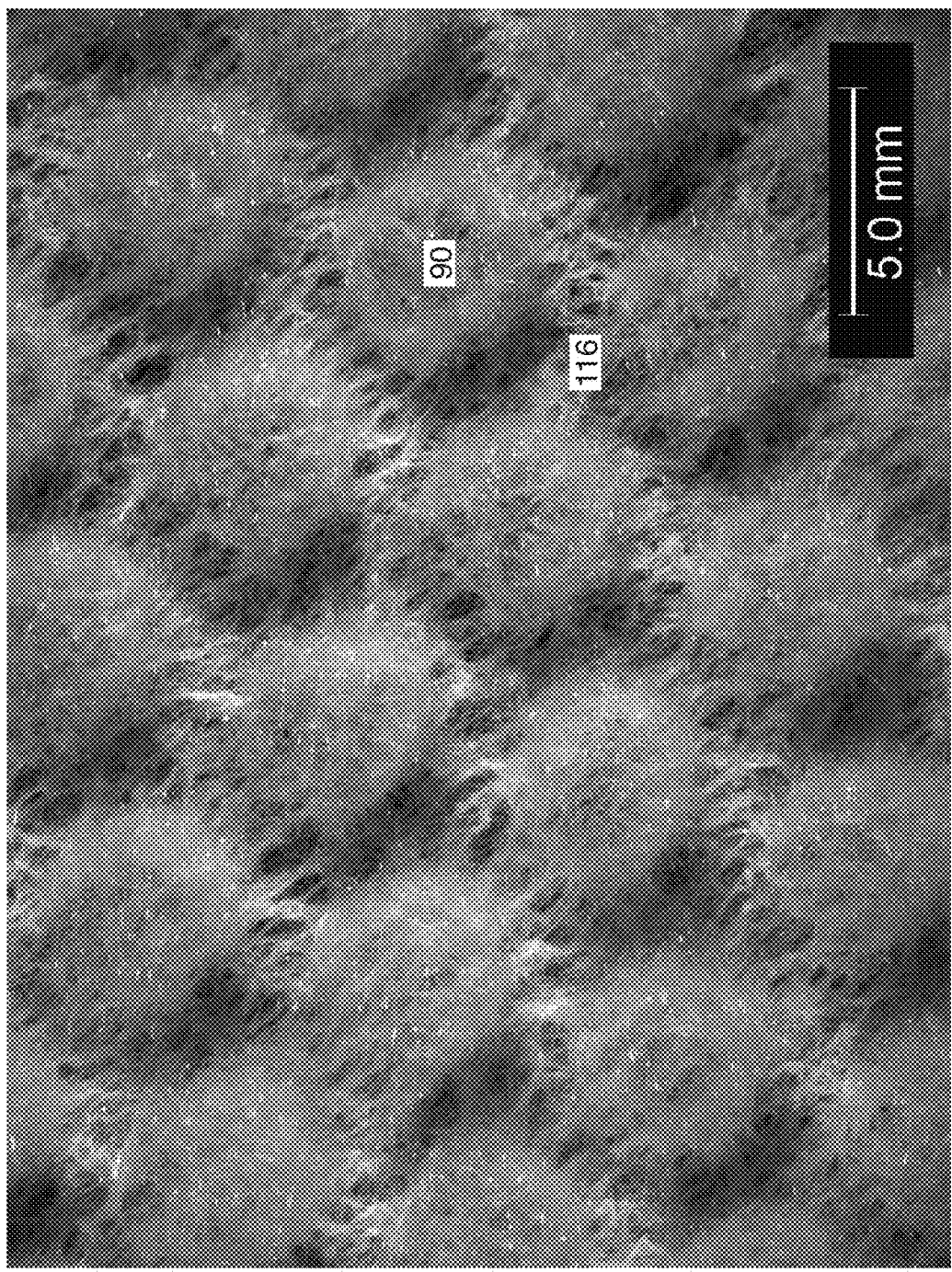
FIG. 27 is a photomicrograph in top view of a sample designated as code 3-6 in Table 1 of the specification.
Figure 27A:
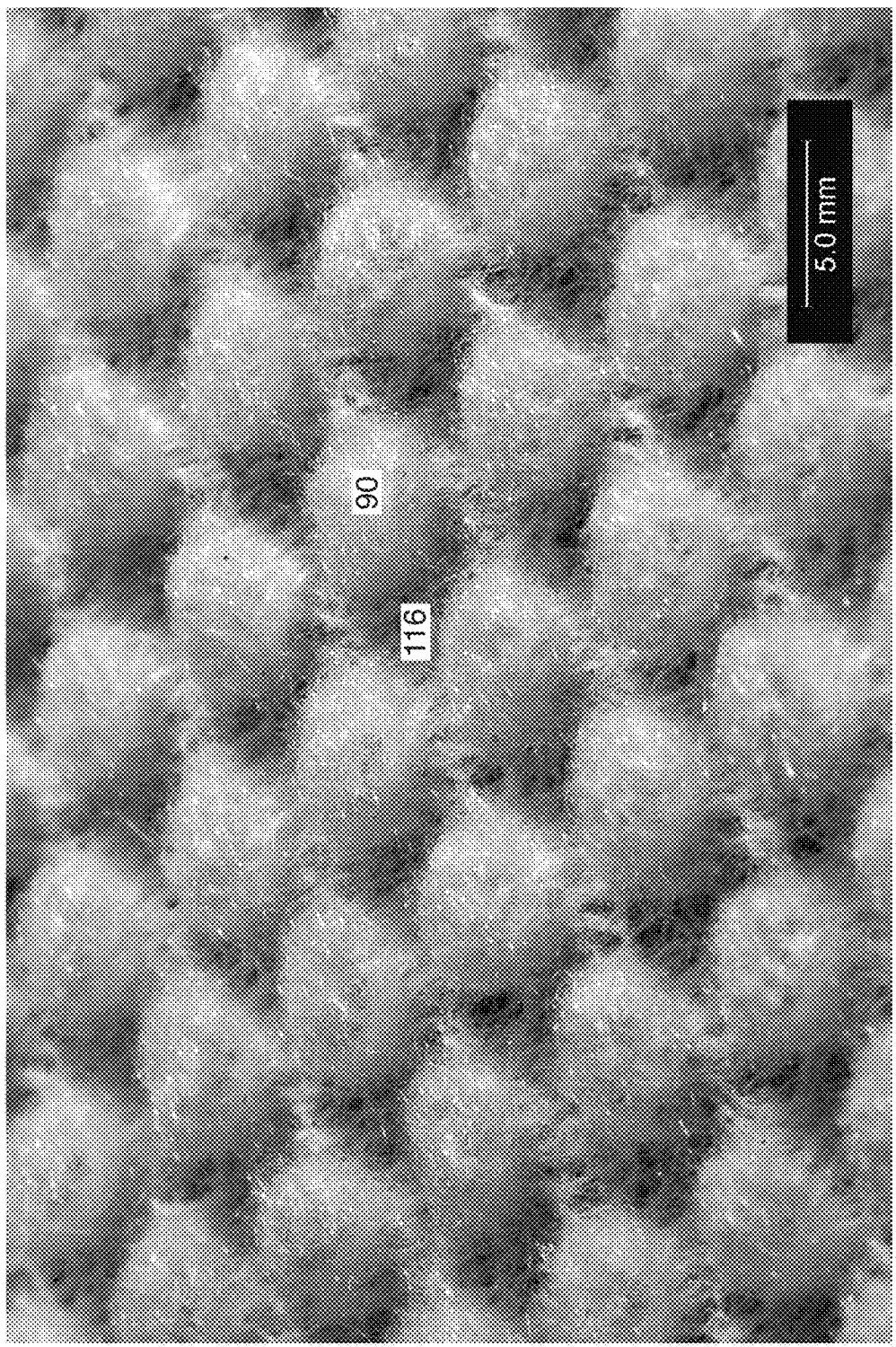
FIG. 27A is a photomicrograph of a sample designated as code 3-6 in Table 1 of the specification taken at a 45 degree angle.
Figure 28:
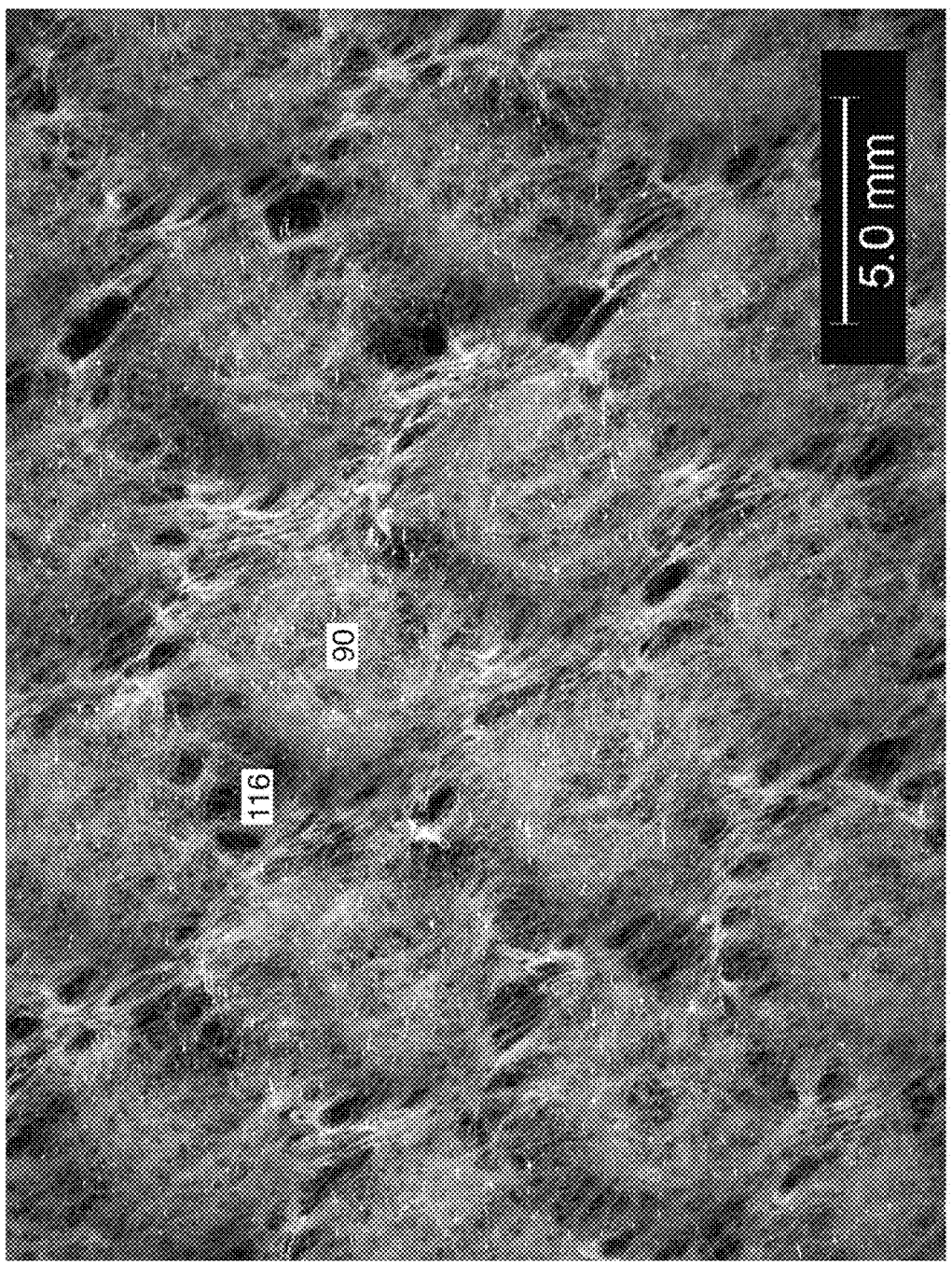
FIG. 28 is a photomicrograph in top view of a sample designated as code 5-3 in Table 1 of the specification.
Figure 28A:
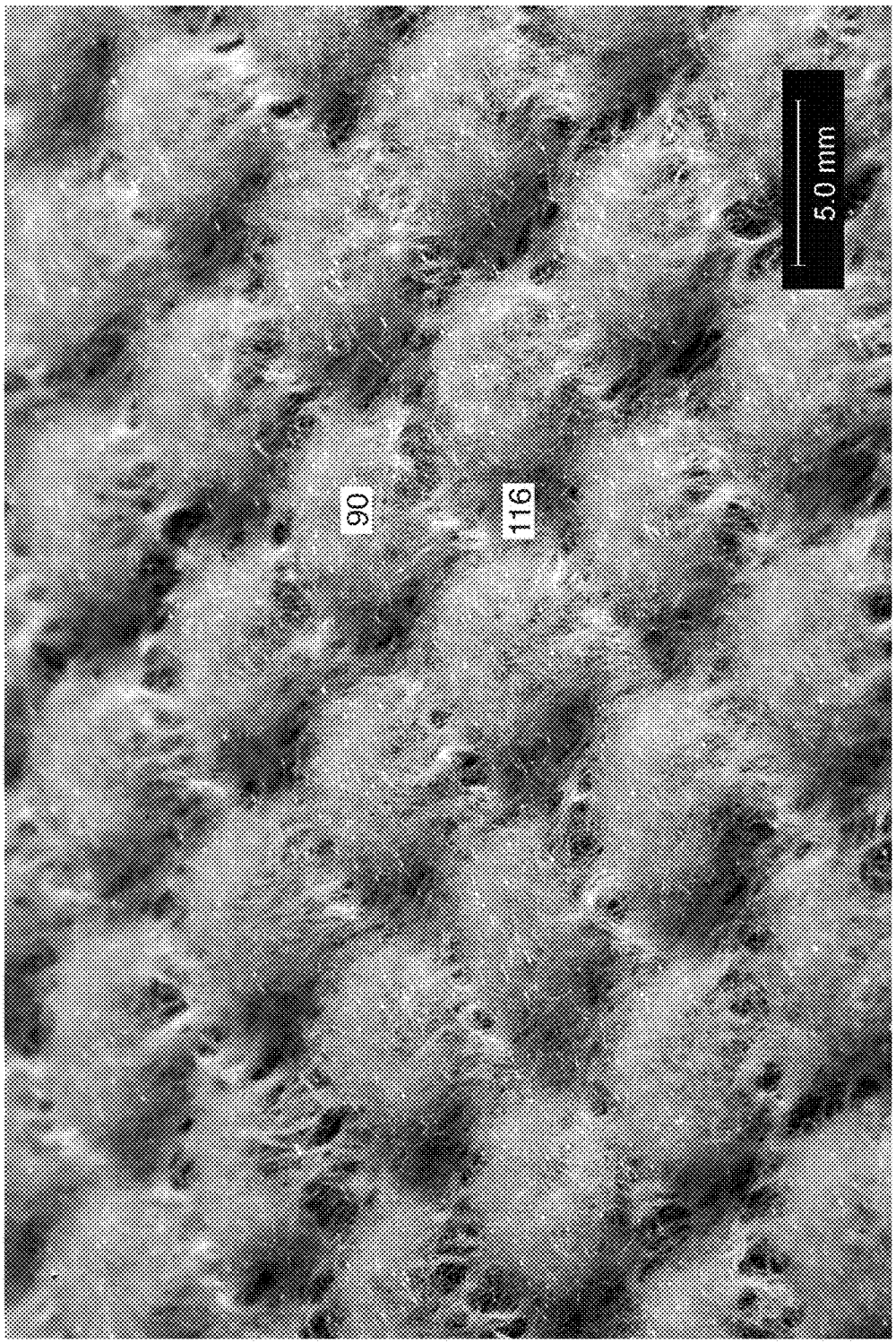
FIG. 28A is a photomicrograph of a sample designated as code 5-3 in Table 1 of the specification taken at a 45 degree angle.

The level of improvement in the overall quality of the body facing material 28 as compared to a projection layer 94 with no support layer 92 can be seen by comparing the photos of the materials shown in FIGS. 27, 27A, 28 and 28A. FIGS. 27 and 27A are photos of the sample represented by Code 3-6 in Table 1. FIGS. 28 and 28A are photos of the sample represented by Code 5-3 in Table 1. These codes were selected as they both had the highest amount of overfeed (43%), and jet pressure (180 bar) using comparable projection layer 94 basis weights (38 gsm and 38.5 gsm respectively) and thus the highest potential for good projection formation. As can be seen by the comparison of the two codes and accompanying photos, the supported web/laminate formed a much more robust and visually discernible projections and uniform material than the same projection layer without a support layer. It also had better properties as shown by the data in Table 1. As a result, the supported laminate is much more suitable for subsequent processing and use in such products as personal care absorbent articles.

Figure 29:
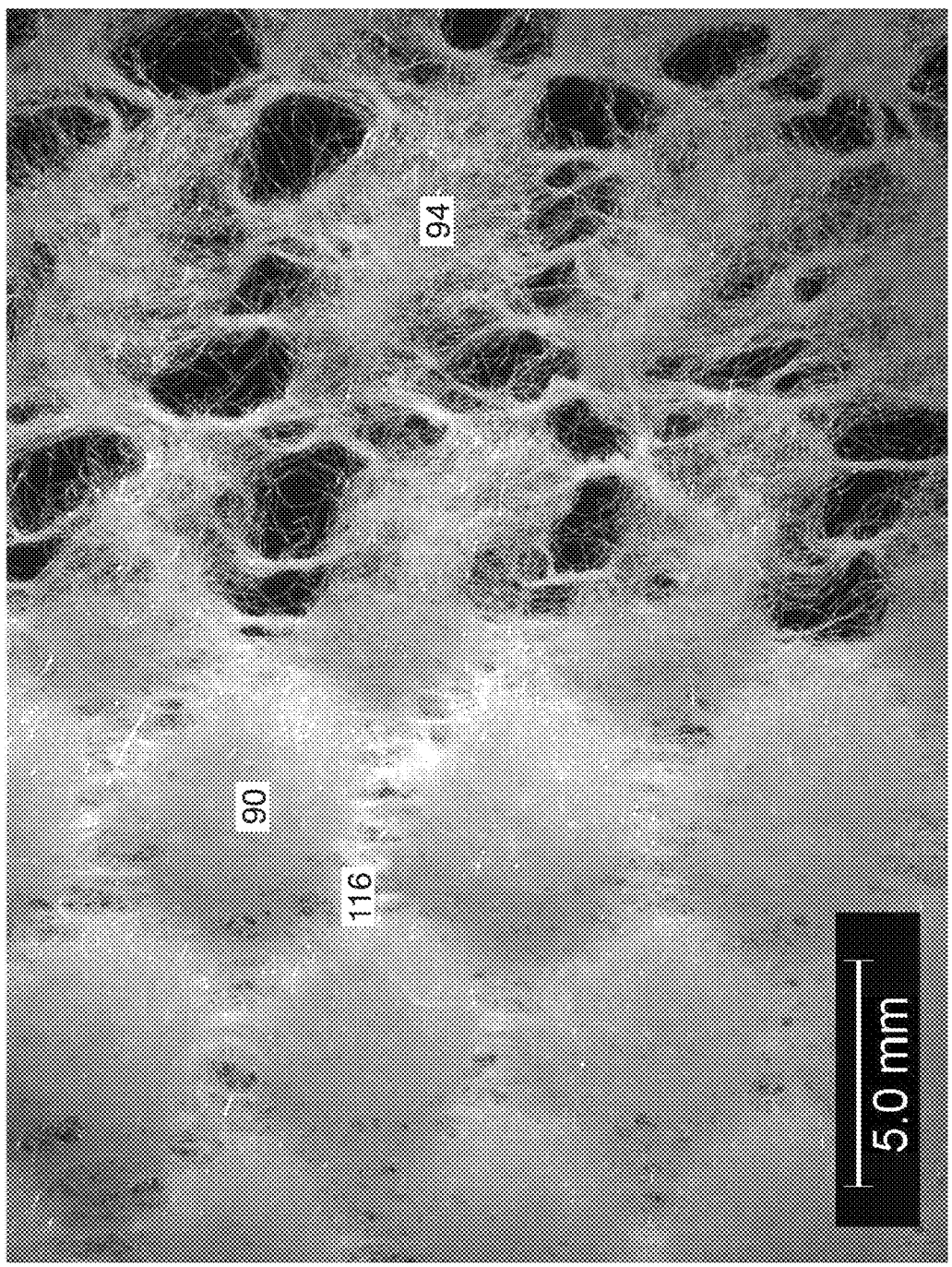
FIG. 29 is a photomicrograph showing the juxtaposition of a portion of a body facing material with and without a support layer backing the projection layer having been processed simultaneously on the same apparatus.

FIG. 29 is a photo at the interface of a projection layer 94 with and without a support layer 92. As can be seen in this photo, the supported projection layer 94 has a much higher level of integrity. This is especially important when the material is to be used in such end applications as personal care absorbent articles where it is necessary (often with the use of adhesives) to attach the projection layer 94 to subjacent layers of the product. With the unsupported projection layer, adhesive bleed through is a much higher threat. Such bleed through can result in fouling of the processing equipment and unwanted adhesion of layers thereby causing excessive downtime with manufacturing equipment. In use, the unsupported projection layer 94 is more likely to allow absorbed fluids taken in by the absorbent article (such as blood, urine, feces and menses) to flow back or "rewet" the top surface of the material thereby resulting in an inferior product.

Another advantage evident from visual observation of the samples (not shown) was the coverage and the degree of flatness of the back of the first surface 96 on the external side of the support layer 92 and thus the body facing material 28 resulting from the formation process when compared to the inner surface 102 of a projection layer 94 run through the same apparatus 150 without a support layer 92. Without the support layer 92, the external surface of the projection layer 94 opposite the projections 90 was uneven and relatively non-planar. In contrast, the same external surface of the body facing material 28 with the support layer 92 was smoother and much flatter. Providing such flat surfaces improves the ability to adhere the body facing material 28 to other materials in later converting. As noted in the exemplary product embodiments described herein, when body facing materials 28 according to the present disclosure are used in items such as personal care absorbent articles, having flat surfaces which readily interface with adjoining layers is important in the context of joining the body facing material 28 to other surfaces so as to allow rapid passage of body exudates through the various layers of the absorbent article. If good surface-to-surface contact between layers is not present, fluid transfer between the adjoining layers can be compromised.

Examples 2-11

In Examples 2-11 described herein, the following Table of Material Descriptions applies:

TABLE 3

Material Descriptions

| Material Code | Material Description |
|---|---|
| A | Body Facing Material: A dual layer fluid entangled body facing material having 1) a support layer of 17 gsm polypropylene point bonded web made from 1.8 denier polypropylene spunbond fibers which were subsequently point bonded with an overall bond area per unit area of 17.5% made by Kimberly-Clark Australia of Milsons Point, Australia and 2) a projection layer of 38 gsm carded staple fiber web made from 100% 1.2 denier, 38 mm long polyester staple fibers available from the Huvis Corporation of Daejeon, Korea. The projection layer has about 4.4% open area in the land areas and has less than about 0.2% open area in the projections. The projection layer has a projection diameter of about 4 mm. The web is made wettable with up to about 0.3% of 50:50 ratio of Ahcovel/SF-19 on the bottom of the support layer and up to about 0.12% of Ahcovel on the top of the projection layer. The web has a thickness of 2.4 mm when measured under a pressure of 0.345 kPa. The web has a total basis weight of 55 gsm. The web is available from Textor Technologies PTY LTD of Tullamarine, Australia. |
| B | Body Facing Material: A dual layer fluid entangled body facing material having 1) a support layer of 10 gsm polypropylene point bonded web made from 1.8 denier polypropylene spunbond fibers which were subsequently point bonded with an overall bond area per unit area of 17.5% made by Kimberly-Clark Australia of Milsons Point, Australia and 2) a projection layer of 38 gsm carded staple fiber web made from 100% 1.2 denier, 38 mm long polyester staple fibers available from the Huvis Corporation of Daejeon, Korea. The projection layer has about 8.4% open area in the land areas and has less than about 0.1% open area in the projections. The projection layer has a projection diameter of about 4 mm. The web is made wettable with up to about 0.3% of 50:50 ratio of Ahcovel/SF-19 on the bottom of the support layer and up to about 0.12% of Ahcovel on the top of the projection layer. The web has a thickness of 2.4 mm when measured under a pressure of 0.345 kPa. The web has a total basis weight of 48 gsm. The web is available from Textor Technologies PTY LTD of Tullamarine, Australia. |
| C | Body Facing Material: A dual layer fluid entangled body facing material having 1) a support layer of 10 gsm polypropylene point bonded web made from 1.8 denier polypropylene spunbond fibers which were subsequently point bonded with an overall bond area per unit area of 17.5% made by Kimberly-Clark Australia of Milsons Point, Australia and 2) a projection layer of 38 gsm carded staple fiber web made from 100% 1.2 denier, 38 mm long polyester staple fibers available from the Huvis Corporation of Daejeon, Korea. The projection layer has about 18.5% open area in the land areas and has less than about 0.5% open area in the projections. The projection layer has a projection diameter of about 4 mm. The web is made wettable with up to about 0.3% of 50:50 ratio of Ahcovel/SF-19 on the bottom of the support layer and up to about 0.12% of Ahcovel on the top of the projection layer. The web has a thickness of 2.3 mm when measured under a pressure of 0.345 kPa. The web has a total basis weight of 48 gsm. The web is available from Textor Technologies PTY LTD of Tullamarine, Australia. |
| D | Body Facing Material: A dual layer fluid entangled body facing material having 1) a support layer of 10 gsm polypropylene point bonded web made from 1.8 denier polypropylene spunbond fibers which were subsequently point bonded with an overall bond area per unit area of 17.5% made by Kimberly-Clark Australia of Milsons Point, Australia and 2) a projection layer of 38 gsm carded staple fiber web made from 100% 1.2 denier, 38 mm long polyester staple fibers available from the Huvis Corporation of Daejeon, Korea. The projection layer has greater than about 20% open area in the land areas and has less than about 1% interstitial fiber-to-fiber spacing in the projections. The projection layer has a projection diameter of about 4 mm. The web is made wettable with up to about 0.3% of 50:50 ratio of Ahcovel/SF-19 on the bottom of the support layer and up to about 0.12% of Ahcovel on the top of the projection layer. The web has a thickness of 2.1 mm when measured under a pressure of 0.345 kPa. The web has a total basis weight of 48 gsm. The web is available from Textor Technologies PTY LTD of Tullamarine, Australia. |
| E | Secondary Liner: A 13.5 gsm white wettable spunbond web composed of random laid continuous polypropylene round filaments. The web is made wettable with up to about 0.5% of a 52:18:30 ratio of Ahcovel/Glucopon/SF-19 using a foaming system. |
| F | Acquisition Layer: A 50 gsm through-air bonded-carded web composed of homogenous blend of 40% ES FiberVisions 7 denier T-118 hollow polypropylene fibers and 60% ES FiberVisions 3 denier ESC-233 bicomponent fibers. The web has a thickness of 1.15 mm when measured under a pressure of 0.345 kPa. The fibers are available from ES FiberVisions Corp., Duluth, GA, U.S.A |
| G | Acquisition Layer: A 50 gsm through-air bonded-carded web composed of homogenous blend of 40% ES FiberVisions 7 denier T-118 hollow polypropylene fibers and 60% ES FiberVisions 17 denier Varde bicomponent fibers. The web has a thickness of 1.09 mm when measured under a pressure of 0.345 kPa. The fibers are available from ES FiberVisions Corp., Duluth, GA, U.S.A |

TABLE 3-continued

Material Descriptions

| Material Code | Material Description |
|---|---|
| H | Acquisition Layer: A 50 gsm through-air bonded-carded web composed of homogenous blend of 50% ES FiberVisions 3 denier ESC-233 bicomponent fibers and 50% ES FiberVisions 1.5 denier ESC-215 bicomponent fibers. The web has a thickness of 2.27 mm when measured under a pressure of 0.345 kPa. The fibers are available from ES FiberVisions Corp., Duluth, GA, U.S.A |
| I | Acquisition Layer: A 50 gsm through-air bonded-carded web composed of homogenous blend of 50% Kelheim 3 denier Rayon Galaxy fibers and 50% ES FiberVisions 1.5 denier ESC-215 bicomponent fibers. The web has a thickness of 0.57 mm when measured under a pressure of 0.345 kPa. The Kelheim fibers are available from Kelheim Fibers GmbH, Regensburger StraBe 109, 93309 Kelheim, Germany. The ES FiberVisions fibers are available from ES FiberVisions Corp., Duluth, GA, U.S.A |
| J | Fluid Transfer Layer: A white 16.6 gsm 100% elemental chlorine free, single ply, low porosity creped wadding, water-cut-on-machine. This material is available from Cellu Tissue - Natural Dam, Gouverneur, N.Y., U.S.A. |
| K | Fluid Transfer Layer: A 10 gsm white wettable spunbond-meltblown-spunbond web with the spunbond layers composed of 10 gsm random laid continuous polypropylene round filaments and the meltblown layer composed of 10.4% meltblown fibers. The web is made wettable with up to 0.5% of a 52:18:30 ratio of Ahcovel/Glucopon/SF-19 using a foaming system. |
| L | Fluid Transfer Layer: A 45 gsm layered spunlace material composed of an 15 gsm spunbond polypropylene layer and a homogeneous 30 gsm hydraulically entangled (on the spunbond material) layer composed of about 48% *Radiata* Pine pulp supplied by J. Carter Holt Harvey Pulp and Paper and about 52% 6d polyester fibers supplied by Huvis. This material has a thickness of 0.32 mm when measured under a pressure of 0.345 kPa. |
| M | Fluid Transfer Layer: Commercially available Scott Towels Select-A-Size from Kimberly-Clark Corporation, Neenah, WI. |
| N | Absorbent Body: A slightly hourglass shaped, flat absorbent pad air formed on commercially available equipment (such as from Curt Joa., Sheboygan Falls, WI 53085) of a pulp fluff/superabsorbent material homogenous mixture with uniform thickness, density, and basis weight on a 12 gsm white spunbond-meltblown-spunbond backing sheet with a pad length of 287 mm and a pad width of 102 mm. The absorbent body contained 50% superabsorbent material (SanDia SANWET KC990L, available from San-Dia Polymers, Ltd, Tokyo, Japan) and 50% pulp fluff (Weyerhaeuser 7.5% moisture CF-416 Southern Softwood Kraft fluff pulp, available from Weyerhaeuser Company, Geneva, Switzerland). |
| O | Absorbent Body: A rectangular, flat absorbent pad air formed on commercially available equipment (such as from Curt Joa., Sheboygan Falls, WI 53085) of a pulp fluff/superabsorbent material homogenous mixture with uniform thickness, density, and basis weight on a 12 gsm white spunbond-meltblown-spunbond backing sheet with a pad length of 287 mm and a pad width of 102 mm. The absorbent body contained 70% superabsorbent material (EVONIK SXM-9500, available from Evonik Stockhausen Inc., GmbH, Greensboro, NC, U.S.A.) and 30% pulp fluff (Weyerhaeuser 7.5% moisture CF-416 Southern Softwood Kraft fluff pulp, available from Weyerhaeuser Company, Geneva, Switzerland). |
| P | Body Facing Material: A single layer fluid entangled body facing material without any support layer and a total basis weight of 44 gsm constructed from a carded staple fiber made from 100% 1.2 denier, 38 mm long polyester staple fibers available from the Huvis Corporation of Daejeon, Korea. The single layer material has projections on a single side of the material with a projection diameter of about 4 mm. The single layer material has about 17.8% open area in the land areas and has less than about 2.0% open area in the projections. The web has a thickness of 2.2 mm when measured under a pressure of 0.345 kPa. The web is available from Textor Technologies PTY LTD of Tullamarine, Australia |
| Q | Commercially available Kotex Natural Balance Ultra Thin Regular With Wings feminine hygiene product manufactured by Kimberly-Clark Corporation. |
| R | Commercially available Always ® Ultra Thin Long Super without wings products manufactured by the Procter & Gamble Company, Cincinnati, OH. |
| S | Acquisition Layer: 125 gsm airlaid with 16% PP/PE binder fibers and 84% Southern Softwood Kraft pulp. |
| T | Absorbent Body: 200 gsm Airlaid with 16% PP/PE binder fiber and 84% Southern Softwood Kraft pulp and 15% superabsorbent material. |
| U | Body Facing Material: A dual layer fluid entangled body facing material having 1) a support layer of 10 gsm polypropylene point bonded web made from 1.8 denier polypropylene spunbond fibers which were subsequently point bonded with an overall bond area per unit area of 17.5% made by Kimberly-Clark Australia of Milsons Point, Australia and 2) a projection layer of 38 gsm carded staple fiber web made from 100% 1.2 denier, 38 mm long polyester staple fibers available from the Huvis Corporation of Daejeon, Korea. The projection layer has about 16.5% open area in the land areas and has less than about 0.25% open area in the projections. The projection layer has a projection diameter of about 4 mm. The web is made wettable with up to about 0.3% of 50:50 ratio of Ahcovel/SF-19 on the bottom of the support layer and up to about 0.12% of |

TABLE 3-continued

Material Descriptions

| Material Code | Material Description |
|---|---|
| | Ahcovel on the top of the projection layer. The web has a thickness of 2.5 mm when measured under a pressure of 0.345 kPa. The web has a total basis weight of 48 gsm. The web is available from Textor Technologies PTY LTD of Tullamarine, Australia. |

Fecal Material Simulant:

The following is a description of the fecal material simulant utilized in some of the examples described herein.

Fecal Material Simulant Ingredients:
- Dannon® All Natural Lowfat Yogurt (1.5% milkfat grade A), Vanilla with other natural flavor, in 32 oz container.
- McCormick Ground Turmeric
- Great Value® 100% liquid egg whites
- Knox® Original Gelatin—unflavored and in powder form
- DAWN® Ultra Concentrated original scent dishwashing liquid
- Distilled Water Note: All fecal material simulant ingredients can be purchased at grocery stores such as Wal-Mart® or on-line retailers. Some of the fecal material simulant ingredients are perishable food items and should be incorporated into the fecal material simulant at least two weeks prior to their expiration date.

Fecal Material Simulant Mixing Equipment:
- Laboratory Scale with an accuracy to 0.01 gram
- 500 mL beaker
- Small lab spatula
- Stop watch
- IKA®-WERKE Eurostar Power Control-Visc with R 1312 Turbine stirrer available from IKA® Works, Inc., Wilmington, N.C., USA.

Fecal Material Simulant Mixing Procedure:
1. A 4-part mixture is created at room temperature by adding, in the following order, the following fecal material simulant ingredients (which are at room temperature) to the beaker at a temperature between 21° C. and 25° C.: 57% yogurt, 3% turmeric, 39.6% egg white and 0.4% gelatin. For example, for a total mixture weight of 200.0 g, the mixture will have 114.0 g of the yogurt, 6.0 g of the turmeric, 79.2 g of the egg whites, and 0.8 g of the gelatin using the laboratory scale.
2. The 4-part mixture should be stirred to homogeneity using the IKA®-WERKE Eurostar stirrer set to a speed of 50 RPM. Homogeneity will be reached in approximately 5 minutes (using the stop watch). The beaker position can be adjusted during stirring so the entire mixture is stirred uniformly. If any of the mixture material clings to the inside wall of the beaker, the small spatula is used to scrap the mixture material off the inside wall and place it into the center part of the beaker.
3. A 1.3% DAWN solution is made by adding 1.3 gram of DAWN Ultra Concentrated into 98.7 gram of distilled water. The IKA®-WERKE Eurostar and the R 1312 Turbine stirrer is used to mix the solution for 5 minutes at a speed of 50 RPM.
4. An amount of 2.0 grams of the 1.3% DAWN solution is added to 200 grams of the 4-part mixture obtained from Step 2 for a total combined weight of 202 grams of fecal material simulant. The 2.0 grams of the 1.3% DAWN solution is stirred into the homogenous 4-part mixture carefully and only to homogeneity (approximately 2 minutes) at a speed of 50 RPM, using the IKA®-WERKE Eurostar stirrer. Final viscosity of the final fecal material simulant should be 390±40 cP (centipoise) when measured at a shear rate of 10 s$^{-1}$ and temperature of 37° C.
5. The fecal material simulant is allowed to equilibrate for about 24 hours in a refrigerator at a temperature of 7° C. It can be stored in a lidded and airtight container and refrigerated for up to 5 days at around 7° C. Before use, the fecal material simulant should be brought to equilibrium with room temperature. It should be noted that multiple batches of fecal material simulant of similar viscosity can be combined together. For example, five batches of fecal material simulant of similar viscosity and each 200 grams can be combined into one common container for a total volume of 1000 cc. It will take approximately 1 hour for 1000 cc of fecal material simulant to equilibrate with room temperature.

Method to Determine the Viscosity of the Fecal Material Simulant:

The viscosity of the fecal material simulant is determined utilizing a Brookfield rheometer. The final viscosity of the fecal material simulant should be 390±40 cP (centipoise) when measured at a shear rate of 10 s$^{-1}$ and a temperature of 37° C.

Equipment:
- LV-model of the Brookfield DV-III ULTRA Rheometer with a spindle # SCA-28
- Rheocalc software provided by Brookfield Method:
1. Gently invert (2 to 3 times by hand with slow rocking for approximately 5 seconds) the sealed container of the fecal material simulant prior to loading it into the cartridge to reduce accumulation of particles on the bottom.
2. Per the instructions found in the Operator's Manual for the Rheometer, the fecal material simulant is added, in an amount of 17 mL, to the cartridge via syringe and placed in the Thermoset which is maintained at a constant temperature of 37° C.
3. Rheocalc is programmed to run at 30 second intervals between each RPM (revolutions per minute) starting at 0.01 RPM followed by 0.03, 0.07, 0.10, 0.50, 1.00, 3.00, 7.00, 10.0, 20.0, 50.0, 100.0, and 200.0 and going down to 100.0, 50.0, 20.0, 7.00, 3.00, 1.00, 0.50, 0.10, 0.07, 0.03, and 0.01.
4. The viscosity as a function of shear rate curve can be established from the Rheocalc data. From that curve the viscosity at a shear rate of 10/s can be determined
5. The test is repeated three times using three different batches of fecal material simulant to establish the range of viscosity for the simulant at 10/s.

Experimental Absorbent Composites:

Experimental absorbent composites are utilized in some examples described herein. The following is a description of how the experimental absorbent composites are prepared.

Materials:
- Outer Cover: Berry Plastics XP-8695H Inner Cover Film available from Berry Plastics, Evansville, Ind., USA.
- Body facing material, secondary liner, absorbent body, acquisition layer, and fluid transfer layer are unique to each example and specific materials are noted for each example as described herein.
- Construction Adhesive: H2525A available from Bostik Inc., U.S.A.
- Construction Adhesive Glue Gun Nozzle: unibody spray nozzle with a 0.012 inch orifice diameter as available as manufacturing part No. 152168 from Nordson Corp., U.S.A.

Material Preparation:
1. Body facing material (if present in the composite): Cut to a minimum size of 16 inches long by 6.5 inches wide.
2. Secondary Liner (if present in the composite): Cut to a minimum size of 16 inches long by 6.5 inches wide.
3. Acquisition Layer (if present in the composite): Cut to a size of 6 inches long by 4 inches wide.
4. Fluid Transfer Layer (if present in the composite): Cut to a size of 11.3 inches long by 4 inches wide.
5. Outer Cover: Cut to a minimum size of 16 inches long by 6.5 inches wide.

Assembly Instructions for an Experimental Absorbent Composite Having a Body Facing Material, Absorbent Body and Outer Cover:
1. Attach the absorbent body, centered in both the length and the width directions, to the outer cover using 15 gsm of construction adhesive to attach the backing sheet of the absorbent body to the outer cover.
2. Apply 17.5 gsm of construction adhesive to the entire exposed surface of the absorbent composite constructed so far, which includes the exposed outer cover and absorbent body.
3. Attach the body facing material, centered in both the length and width directions, to the absorbent composite, which includes the outer cover and the absorbent body.
4. Smooth out any wrinkles in the body facing material and ensure that it is tacked down to the adhesive.
5. Ensure that all the materials present in the composite are adhered into place by pressing firmly on the perimeter 1.5 inches.
6. Cut out the assembled absorbent composite. Finished size should be 6 inches wide by 15.5 inches long.
7. Mark the insult zone 6 inches from the back end of the absorbent body with a single, small dot using a permanent marker. The dot should be placed on the cross directional midline of the absorbent body.

Assembly Instructions for an Experimental Absorbent Composite Having a Body Facing Material, Fluid Transfer Layer, Absorbent Body and Outer Cover:
1. Attach the absorbent body, centered in both the length and the width directions, to the outer cover using 15 gsm of construction adhesive to attach the backing sheet of the absorbent body to the outer cover.
2. Attach the fluid transfer layer to the absorbent body using 11 gsm of construction adhesive. The midline of the width of the fluid transfer layer should align with the midline of the width of the absorbent body.
3. Apply 17.5 gsm of construction adhesive to the entire exposed surface of the absorbent composite constructed so far, which includes the exposed outer cover, absorbent body components, and the fluid transfer layer.
4. Attach the body facing material, centered in both the length and width directions, to the absorbent composite which includes the outer cover, the absorbent body and the fluid transfer layer.
5. Follow steps 4-7 listed above for an experimental absorbent composite having a body facing material, absorbent body and outer cover.

Assembly Instructions for an Experimental Absorbent Composite Having a Body Facing Material, Acquisition Layer, Absorbent Body and Outer Cover:
1. Attach the absorbent body, centered in both the length and the width directions, to the outer cover using 15 gsm of construction adhesive to attach the backing sheet of the absorbent body to the outer cover.
2. Apply 17.5 gsm of construction adhesive to the entire exposed surface of the absorbent composite constructed so far, which includes the exposed outer cover and absorbent body.
3. Bond the acquisition layer to the body facing material using the construction adhesive. The acquisition layer and body facing material should be aligned on the midline of the width of the body facing material.
4. Attach the body facing material and the acquisition layer to the absorbent composite which includes the outer cover and the absorbent body.
5. Follow steps 4-7 listed above for an experimental absorbent composite having a body facing material, absorbent body and outer cover.

Assembly Instructions for an Experimental Absorbent Composite Having a Body Facing Material, Acquisition Layer, Fluid Transfer Layer, Absorbent Body and Outer Cover:
1. Attach the absorbent body, centered in both the length and the width directions, to the outer cover using 15 gsm of construction adhesive to attach the backing sheet of the absorbent body to the outer cover.
2. Attach the fluid transfer layer to the absorbent body using 11 gsm of construction adhesive. The midline of the width of the fluid transfer layer should align with the midline of the width of the absorbent body.
3. Apply 17.5 gsm of construction adhesive to the entire exposed surface of the absorbent composite constructed so far, which includes exposed outer cover, absorbent body components, and the fluid transfer layer.
4. Bond the acquisition layer to the body facing material using the construction adhesive. The acquisition layer and body facing material should be aligned on the midline of the width of the body facing material.
5. Attach the body facing material and the acquisition layer to the absorbent composite which includes the outer cover, the absorbent body and the fluid transfer layer. The acquisition layer and fluid transfer layer should be aligned on the midline of the width of the absorbent composite.
6. Follow steps 4-7 listed above for an experimental absorbent composite having a body facing material, absorbent body and an outer cover.

Assembly Instructions for an Experimental Absorbent Composite Having a Body Facing Material, Secondary Liner, Acquisition Layer, Fluid Transfer Layer, Absorbent Body and Outer Cover:

1. Attach the absorbent body, centered in both the length and the width directions, to the outer cover using 15 gsm of construction adhesive to attach the backing sheet of the absorbent body to the outer cover.
2. Attach the fluid transfer layer to the absorbent body using 11 gsm of construction adhesive. The midline of the width of the fluid transfer layer should align with the midline of the width of the absorbent body.
3. Apply 17.5 gsm of construction adhesive to the entire exposed surface of the absorbent composite constructed so far, which includes exposed outer cover, absorbent body components, and the fluid transfer layer.
4. Bond the secondary liner to the body facing material with the construction adhesive. The secondary liner should be aligned on the midline of the width of the body facing material.
5. Bond the acquisition layer to the secondary liner using the construction adhesive. The acquisition layer, body facing material, and secondary liner should be aligned on the midline of the width of the body facing material.
6. Attach the body facing material, secondary liner and the acquisition layer to the absorbent composite which includes the outer cover, the absorbent body and the fluid transfer layer. The acquisition layer and fluid transfer layer should be aligned on the midline of the width of the absorbent composite.
7. Follow steps 4-7 listed above for an experimental absorbent composite having a body facing material, absorbent body and an outer cover.

Assembly Instructions for an Experimental Absorbent Composite Having a Secondary Liner, Acquisition Layer, Fluid Transfer Layer, Absorbent Body and Outer Cover:

1. Attach the absorbent body, centered in both the length and the width directions, to the outer cover using 15 gsm of construction adhesive to attach the backing sheet of the absorbent body to the outer cover.
2. Attach the fluid transfer layer to the absorbent body using 11 gsm of construction adhesive. The midline of the width of the fluid transfer layer should align with the midline of the width of the absorbent body.
3. Apply 17.5 gsm of construction adhesive to the entire exposed surface of the absorbent composite constructed so far, which includes exposed outer cover, absorbent body components, and the fluid transfer layer.
4. Bond the acquisition layer to the secondary liner using the construction adhesive. The acquisition layer and the secondary liner should be aligned on the midline of the width of the secondary liner.
5. Attach the secondary liner and the acquisition layer to the absorbent composite which includes the outer cover, the absorbent body and the fluid transfer layer. The acquisition layer and fluid transfer layer should be aligned on the midline of the width of the absorbent composite.
6. Smooth out any wrinkles in the secondary liner and ensure that it is tacked down to any adhesive not covered by the acquisition layer.
7. Follow steps 5-7 listed above for an experimental absorbent composite having a body facing material, absorbent body and an outer cover.

Figure 30:
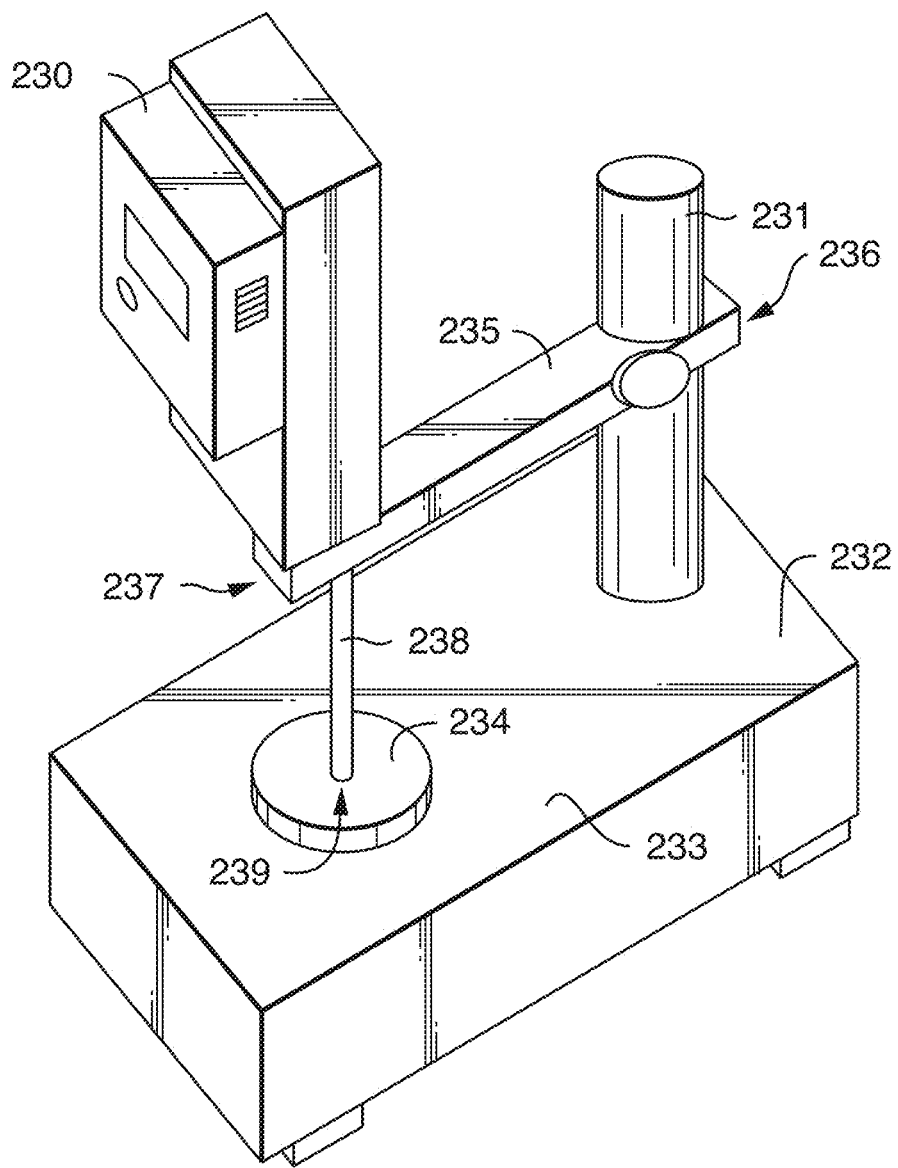
FIG. 30 is a perspective view of an exemplary illustration of a set-up of a Digital Thickness Gauge.
Figure 31:
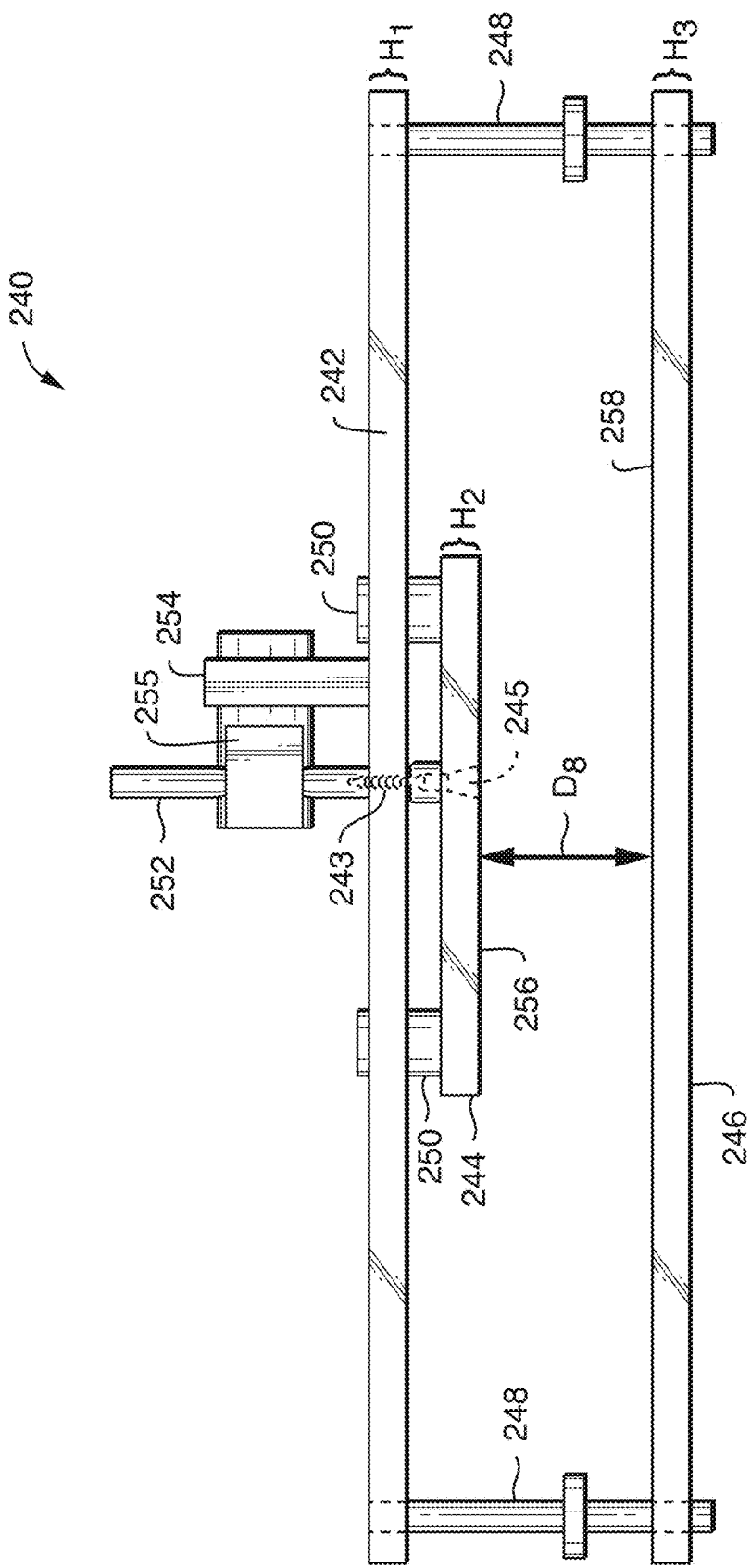
FIG. 31 is a side view of an exemplary illustration of a set-up of an injection apparatus.
Figure 32:
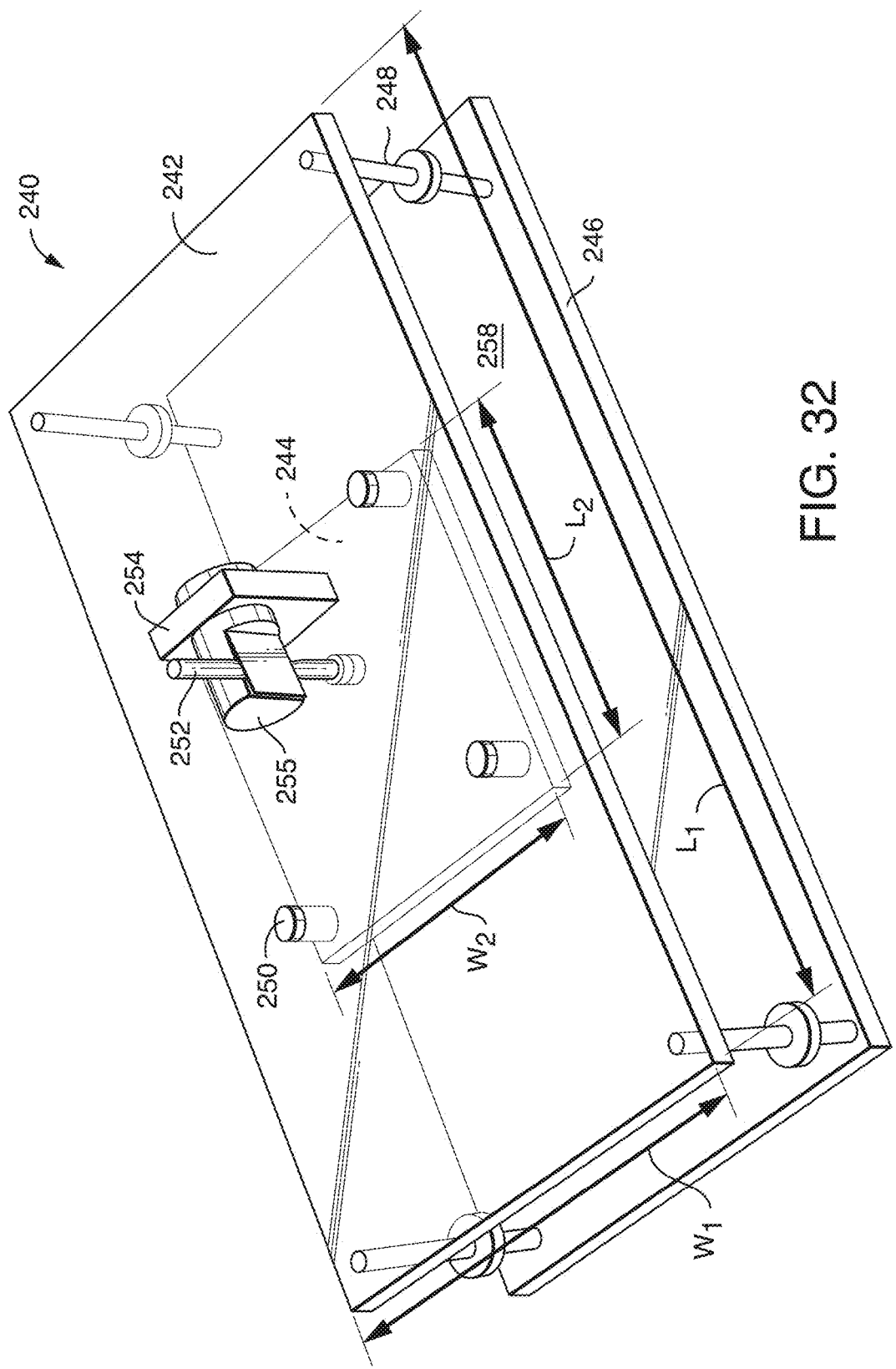
FIG. 32 is a perspective view of an exemplary illustration of a set-up of the injection apparatus of FIG. 31.
Figure 33:
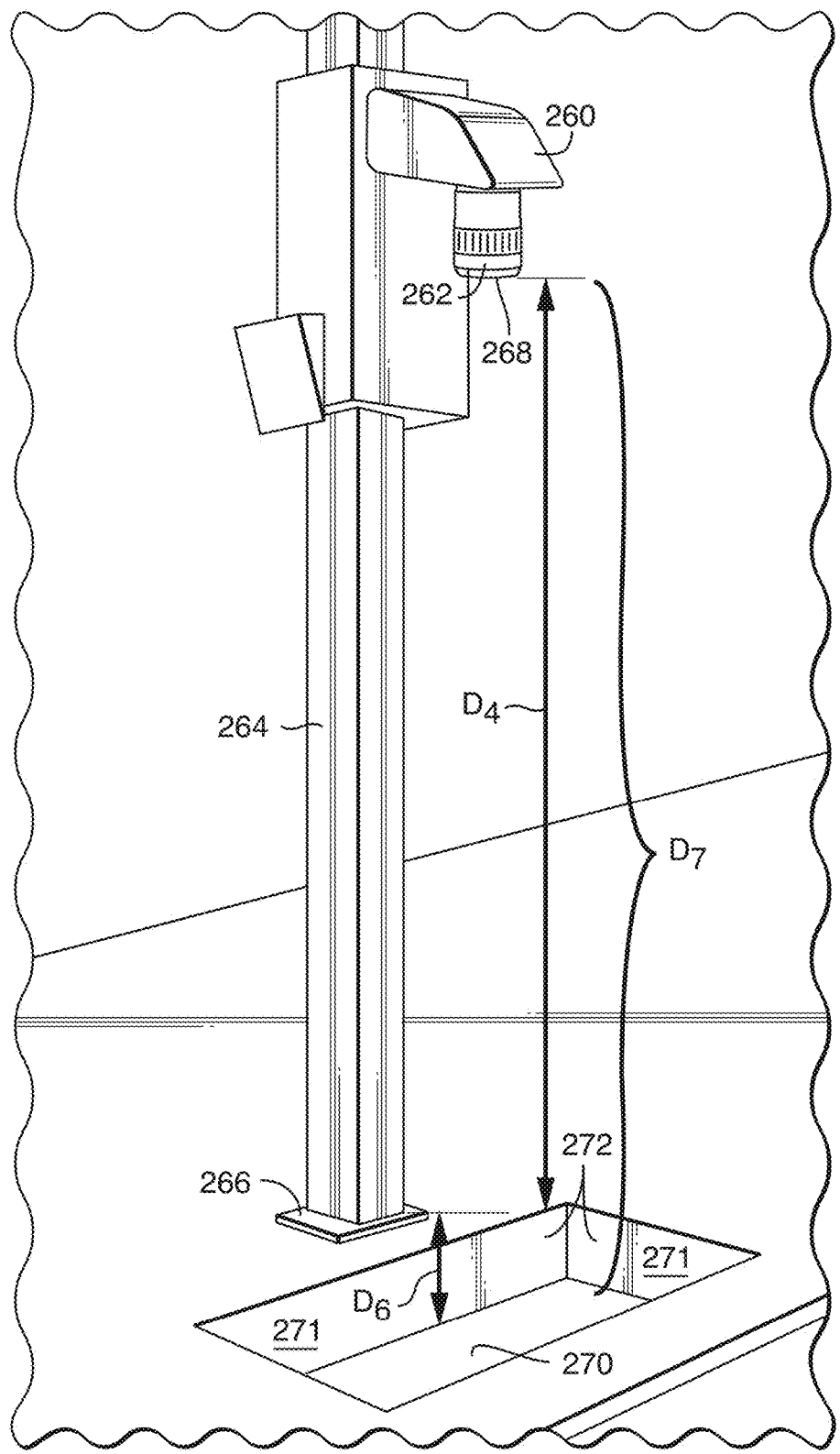
FIG. 33 is a perspective view of an exemplary illustration of a set-up of an imaging system.
Figure 34:
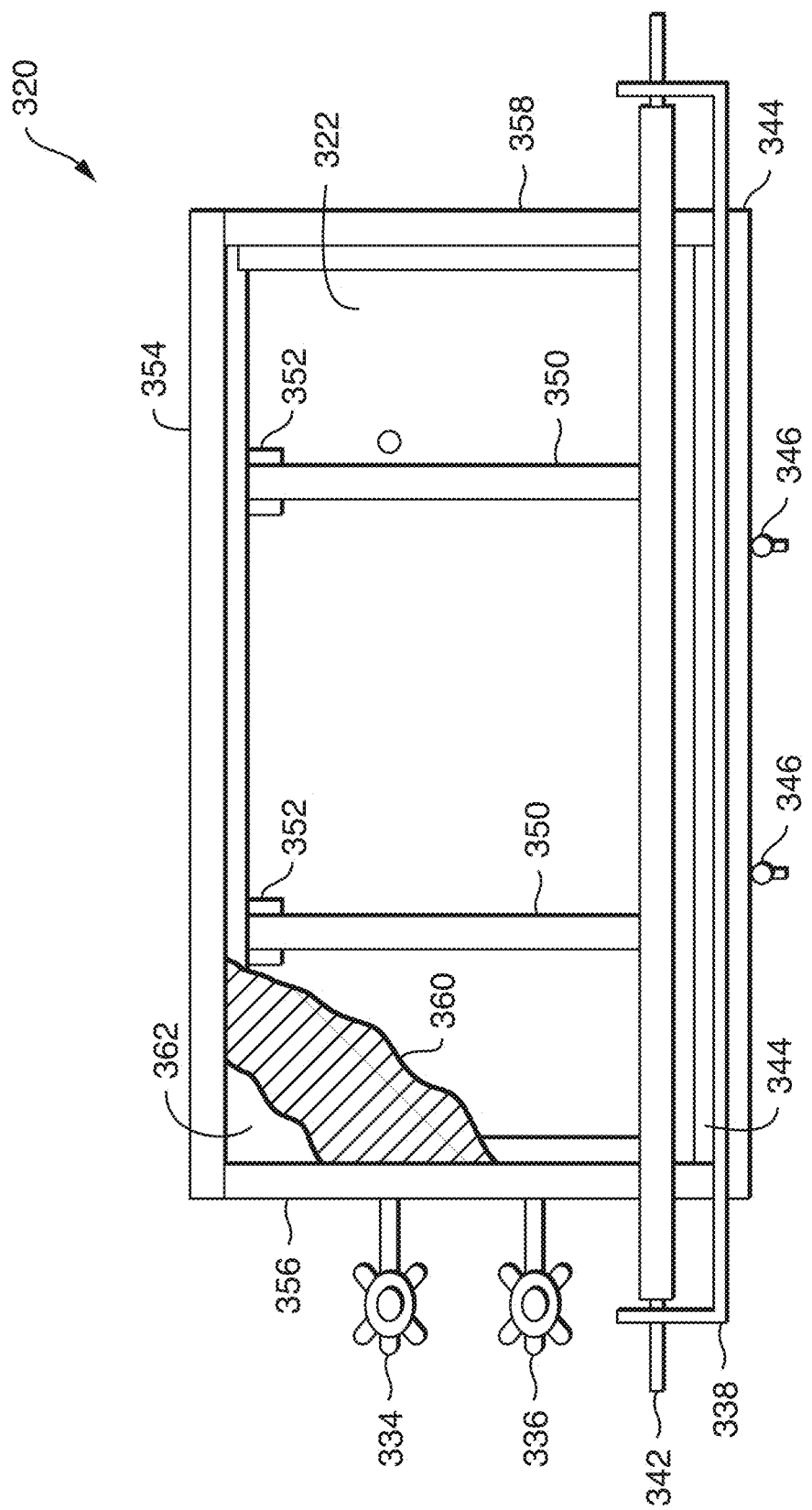
FIG. 34 is a top view of an exemplary illustration of a set-up of a vacuum box.
Figure 35:
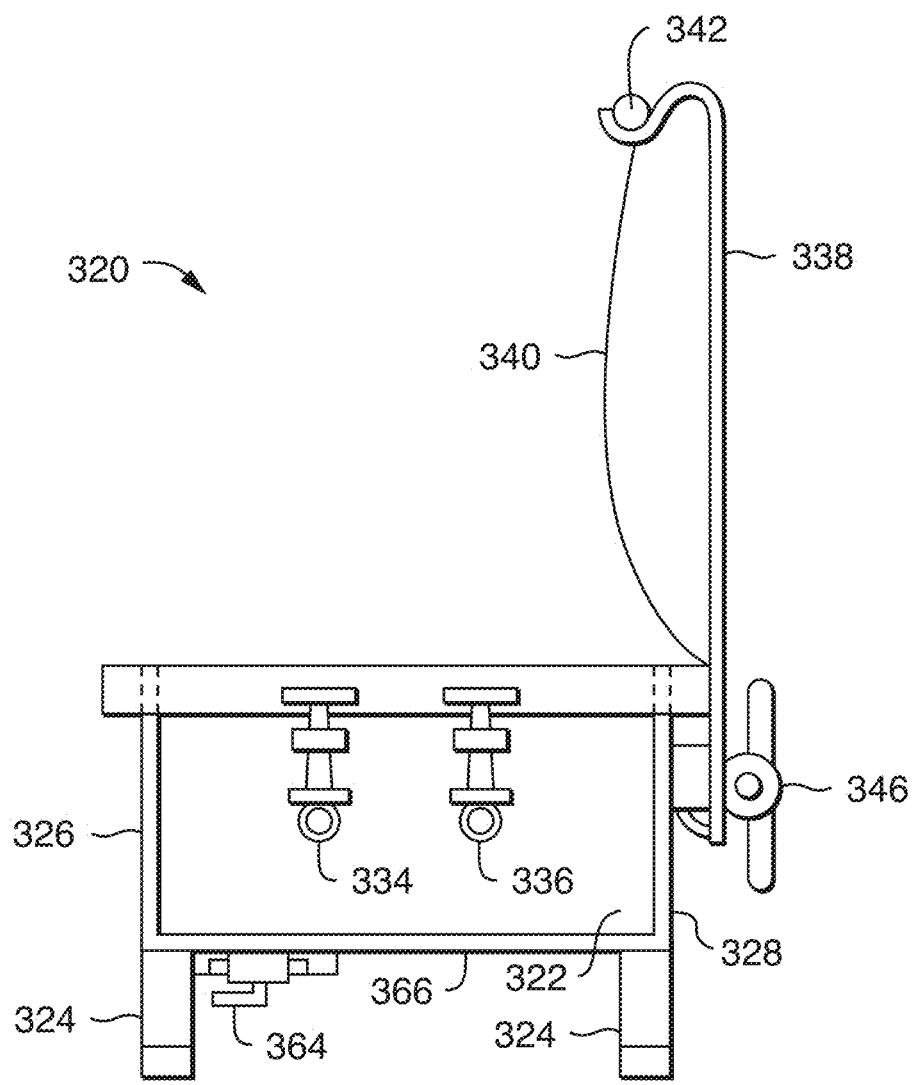
FIG. 35 is a side view of the exemplary illustration of the vacuum box of FIG. 34.
Figure 36:
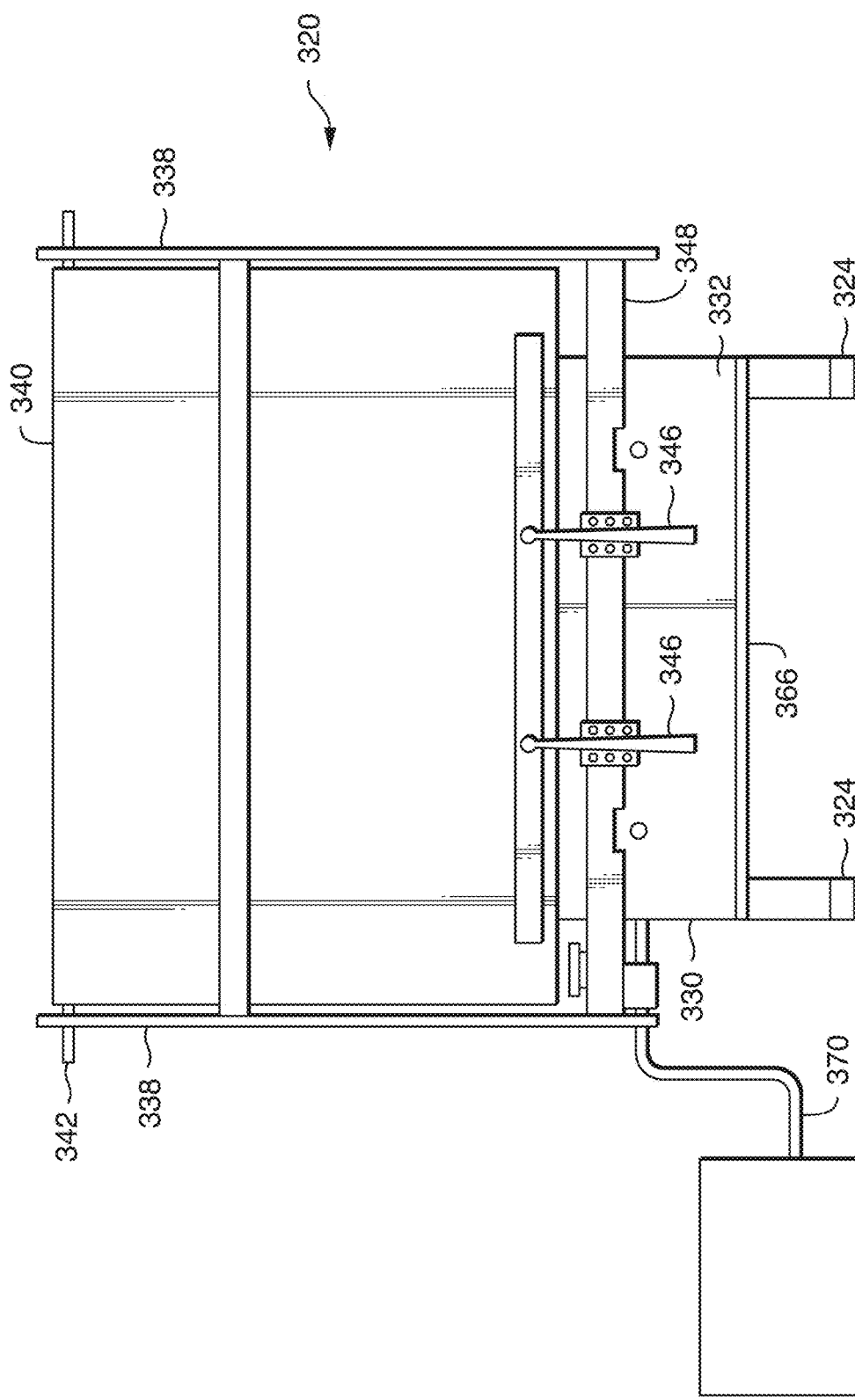
FIG. 36 is a rear view of the exemplary illustration of the vacuum box of FIG. 34.

Fecal Material Simulant Surface Spread and Fecal Material Simulant Surface Residual:

Testing Equipment and Supplies:
  Injection Apparatus (an exemplary set-up is illustrated in FIGS. 31 and 32)
  Balance with an accuracy to 0.01
  Electronic Digital Caliper (VWR International Model 62379-531)
  Digital Thickness Gauge (Mitutoyo Type IDF-1050E, and exemplary set-up is illustrated in FIG. 30)
  Vacuum Box (an exemplary set-up is illustrated in FIGS. 34-36)
  Digital Cooking Timer, readable to 1 second
  Digital Camera (an exemplary set-up is illustrated in FIG. 33)
  Ruler
  Fecal Material Simulant, as described herein, utilized at room temperature
  Scott® paper towels (Mega Roll Choose A Size)
  Absorbent composites for each absorbent composite test code as described herein Equipment Set-Up:
1. Pre-weigh a single paper towel which, as described below, will be used to wipe the middle plate 244 of the injection apparatus 240 clean of fecal material simulant.
2. Pre-weigh four sheets of paper towels which, as described below, will be placed on top of the absorbent composite when the absorbent composite is transitioned to the vacuum box.
3. With reference to FIG. 30, a Digital Thickness Gauge is set-up to obtain the bulk measurement of an absorbent composite. The Digital Thickness Gauge includes a granite base 232 having a clamp shaft 231 where the top surface 233 of the granite base 232 is flat and smooth. A suitable granite base 232 is a Starret Granite Base, model 653G (available from The L.S. Starrett Company, having a place of business located in Athol, Mass., U.S.A.) or equivalent. A clamp arm 235 is secured to the clamp shaft 231 at one end 236 of the clamp arm 235, and the digital thickness gauge 230 is secured to the clamp arm 235 at the opposing end 237. Extending downward from the digital thickness gauge 230 is a vertically-movable plunger 238. Attached to the distal end 239 of the plunger 238 is a circular platen 234 having a diameter of 76.2 mm. The platen 234 is constructed of acrylic and is flat and smooth on at least the bottom surface. The thickness and weight of the platen 234 is configured such that the digital thickness gauge 230 provides a pressure of 0.05 psi (0.345 kPa). To zero the Digital Thickness Gauge 230, ensure the granite surface 233 is clean of debris and position the platen 234 and plunger 238 such that the bottom surface of the platen 234 just touches the granite surface 233. After the Digital Thickness Gauge 230 is zeroed, lift the platen 234 and insert an absorbent composite between the platen 234 and the granite surface 233. The absorbent composite must have a size dimension of at least 90 mm by 102 mm. Lower the platen 234 and plunger 238 such that the bottom surface of the platen 234 just touches the surface of the absorbent composite as illustrated in FIG. 30. A pressure of 0.05 psi (0.345 kPa) is applied to the absorbent composite when the platen 234 is lowered. Measure and record the bulk of 5 absorbent composites for each absorbent composite test code. Calculate an average bulk for the absorbent composite test code by averaging the bulk of the 5 absorbent composites measured for each absorbent composite test code.
4. With reference to FIGS. 31 and 32, an injection apparatus 240 is set-up to deliver 10 cc of fecal material simulant at a rate of 15 cc per sec. The injection apparatus 240 has a top plate 242, a middle plate 244, and a bottom plate 246. The top plate 242 has a height H1 of 12.42 mm, the middle plate 244 has a height H2 of 12.2 mm, and the bottom plate has a height H3 of 12.2 mm. The top plate 242 and the bottom plate 246 each have a length L1 of 305 mm and a width W1 of 165 mm. The top plate 242 is positioned over, aligned with, and connected to the bottom plate 246 through the use of four threaded rods containing plastic thumb knobs 248 located near the corners of each of the top plate 242 and the bottom plate 246. Located between the top plate 242 and the bottom plate 246, the middle plate 244 has a length L2 of 152 mm and a width W2 of 102 mm and is suspended from the center of the top plate 242 with the use of four bolts 250 located near the corners of the middle plate 244. The injection apparatus 240 has a fecal material simulant injection tube 252 located above and positioned perpendicular to the top plate 242. The fecal material simulant injection tube 252 has a length of 7 inches and an inside diameter of 6.4 mm. The tube is made with Norprene® to allow for delivery of the fecal material simulant through the tubing and onto the absorbent composite. The fecal material simulant injection tube 252 connects to the top plate 242, via a hose barbed fitting 243 having a diameter of 0.25 inches. The hose barbed fitting 243 passes through the top plate 242, via a hole cut into the top plate 242, and to the middle plate 244, to deliver the fecal material simulant, via a hole cut through the middle plate 244, to the absorbent composite which is placed upon the surface of the bottom plate 246. The hose barbed fitting 243 is threaded into the middle plate 244 to create a seal. The hole cut through the middle plate 244 has an opening that is shaped like a cone 245 with a 0.88 inch diameter. The hose barbed fitting is manufactured by Parker with a manufacturing number of 125HB-3-4 and is available from MSC Industrial Supply Company. The fecal material simulant injection tube 252 is held in place on the top plate 242 of the injection apparatus 240 with a valve clamp block 254 containing a solenoid pinch valve 255 which can open to allow the fecal material simulant to pass through the tube 252 and close to prevent the fecal material simulant from passing through the tube 252. The solenoid pinch valve is a two-way, normally closed valve with 24 VDC. The solenoid pinch valve is available from NResearch, Inc., part number 648P012.

5. With reference to FIG. 33, a digital camera 260 operated in color mode is set up to visually record the appearance of an absorbent composite following delivery of fecal material simulant. The digital camera 260 is a Pixelink (Model: PL-A742) possessing a 1280×1024 pixel array and operating at a 10.2 Hertz frame rate in color mode. A Pentax TV lens 262 (Model: C6Z1218M3-2) is attached to the Pixelink camera 260 using a c-mount adaptor. The Pentax lens 262 system allows the focus of the lens 262 to be adjusted using accompanying software loaded onto the system computer. The camera/lens 262 system is connected to the computer via an ieee 1394 firewire (not shown). The camera 260 and lens 262 are attached to a VP-400 Bencher camera support 264. The Pentax lens face 268 is positioned at a distance D4 of 94 cm above the base 266 of the VP-Bencher camera support 264. An illuminated absorbent composite well 270 is located at a distance D6 of 16 cm below the base 266 of the VP-400 mount post 264. The distance D7 from the front face of the Pantex lens 262 to the absorbent composite is 110 cm. The absorbent composite well 270 is illuminated on all four sides 272 with a series of 18 Sylvania GE miniature fluorescent lights with an output of 8 watts per bulb. A ⅛" thick frosted glass diffuser plate 271 is located between the bulbs and the composite well 270. The camera 260 should be kept at the same distance and settings for all images to eliminate variability between absorbent composites. A ruler is placed in the absorbent composite well 270 and is also captured in the digital image of the absorbent composite for later spatial calibration reference when determining the spread size of the fecal material simulant on the absorbent composite. The images are acquired in JPEG format.

6. With reference to FIGS. 34-36, a vacuum apparatus 320 is prepared. The vacuum apparatus 320 comprises a vacuum chamber 322 supported on four leg members 324. The vacuum chamber 322 includes a front wall member 326, a rear wall member 328, and two side wall members 330 and 332. The wall members are sufficiently thick to withstand the anticipated vacuum pressures (5 inches of water), and are constructed and arranged to provide a chamber having outside dimensions measuring 23.5 inches (59.7 cm) in length, 14 inches (35.6 cm) in width and 8 inches (203 cm) in depth. A vacuum pump (not shown) operably connects with the vacuum chamber 322 through an appropriate vacuum line conduit and a vacuum valve 334. In addition, a suitable air bleed line connects into the vacuum chamber 322 through an air bleed valve 336. A hanger assembly 338 is suitably mounted on the rear wall 328 and is configured with S-curved ends to provide a convenient resting place for supporting a latex dam sheet 340 in a convenient position away from the top of the vacuum apparatus 320. A suitable hanger assembly 338 can be constructed from 0.25 inch (0.64 cm) diameter stainless steel rod. The latex dam sheet 340 is looped around a dowel member 342 to facilitate grasping and to allow a convenient movement and positioning of the latex dam sheet 340. In the illustrated position, the dowel member 342 is shown supported in a hanger assembly 338 to position the latex dam sheet 340 in an open position away from the top of the vacuum chamber 322. A bottom edge of the latex dam sheet 340 is clamped against a rear edge support member 344 with suitable securing means, such as toggle clamps 346. The toggle clamps 346 mounted on the rear wall member 328 with suitable spacers 348 which provide an appropriate orientation and alignment of the toggle clamps 346 for the desired operation. Two support shafts 350 are 1.5 inches in diameter and are removably mounted within the vacuum chamber 322 by means of support brackets 352. The support brackets 352 are generally equally spaced along the front wall member 326 and the rear wall member 328 and arranged in cooperating pairs. In addition, the support brackets 352 are constructed and arranged to suitably position the uppermost portions of the support shafts 350 flush with the top of the front, rear and side wall members of the vacuum chamber 322. Thus, the support shafts 350 are positioned substantially parallel with one another and are generally aligned with the side wall members 330 and 332. In addition to the rear edge support member 344, the vacuum apparatus 320 includes a front support member 354 and two side support members 356 and 358. Each side support member measures about 1 inch (2.5 cm) in width and about 1.25 inches (3.2 cm) in height. The lengths of the support members are constructed to suitably surround the periphery of the open top edges of the vacuum chamber 322, and are positioned to protrude above the top edges of the chamber wall members by a distance of about 0.5 inches. A layer of egg crating type material 360 is positioned on top of the support shafts 350 and the top edges of the wall members of the vacuum chamber 322. The egg crate material extends over a generally rectangular area measuring 23.5 inches (59.7 cm) by 14 inches (35.6 cm) and has a depth measurement of about 0.38 inches (1.0 cm). The individual cells of the egg crating structure measure about 0.5 inch square, and the thin sheet material comprising the egg crating is composed of a suitable material, such as polystyrene. For example, the egg crating material can be McMaster-Carr Supply Catalog No. 1624K14 translucent diffuser panel material (available from McMaster-Carr Supply Company, having a place of business in Atlanta, Ga., U.S.A.). A layer of 6 mm (0.24 inch) mesh TEFLON coated screening 362 (available from Eagle Supply and Plastics, Inc., having a place of business in Appleton, Wis., U.S.A.) which measures 23.5 inches (59.7 cm) by 14 inches (35.6 cm), is placed on top of the egg crating material 360. A suitable drain line and a drain valve 364 connect to the bottom plate member 366 of the vacuum chamber 322 to provide a convenient mechanism for draining liquid from the vacuum chamber 322. The various wall members and support members of the vacuum apparatus 320 may be composed of a suitable non-corroding, moisture resistant material, such as polycarbonate plastic. The various assembly joints may be affixed by solvent welding and/or fasteners, and the finished assembly of the vacuum apparatus 320 is constructed to be water-tight. A vacuum gauge 368 operably connects through a conduit 370 into the vacuum chamber 322. A suitable vacuum gauge 368 is a Magnahelic differential gauge capable of measuring a vacuum of 0-50 inches of water, such as a No. 2050C gauge available from Dwyer Instrument Incorporated (having a place of business in Michigan City, Ind., U.S.A.).

Delivery of Fecal Material Simulant and Determination of Residual Fecal Material Simulant:

1. Adjust the positioning of the top plate 242 of the injection apparatus 240 relative to the bottom plate 246 of the injection apparatus 240 using the height adjustable screws 248 to raise and lower the top plate 242 of the injection apparatus 240. The top plate 242 of the injection apparatus 240 should be raised and lowered for each absorbent composite test code based upon the average bulk of each absorbent composite test code. As the middle plate 244 is attached to the top plate 242, raising and lowering the top plate 242 will also raise and lower the middle plate 244. The top plate 242 of the injection apparatus 240 should be raised and lowered for each absorbent composite test code so that the distance D8 between the bottom surface 256 of the middle plate 244 and the top surface 258 of the bottom plate 246 is equivalent to the average bulk of the absorbent composite test code being evaluated. After adjusting the position of the top plate 242 to set the distance D8 a level should be placed on top of the top plate 242 to ensure the top plate 242 is level. If the top plate 242 is not level then the height adjustable screws 248 should be adjusted to ensure the top plate 242 is level while maintaining the distance D8.

2. Position an absorbent composite of an absorbent composite test code between the middle plate 244 and the bottom plate 246 of the injection apparatus 240. Align the insult zone of the absorbent composite underneath the fecal material simulant injection tubing 252.

3. Zero the digital cooking thermometer.

4. Inject 10 cc of the fecal material simulant at a rate of 15 cc/sec through the fecal material simulant injection tube 252 to deliver the fecal material simulant to the insult zone of the absorbent composite.

5. Upon delivery of the fecal material simulant to the insult zone of the absorbent composite, start the digital cooking timer and allow the absorbent composite to remain undisturbed for two minutes.

6. After the two minutes have elapsed, raise the top plate 242 and middle plate 244 of the injection apparatus 240, carefully remove the absorbent composite from the injection apparatus 240, keeping the absorbent composite flat and free from any additional contact with the surfaces of the middle plate 244 and top plate 242. The absorbent composite possessing a fecal material simulant stain is placed into the illuminated absorbent composite well 270, under the optical axis of the Pentax lens 262.

7. The absorbent composite is in a flat configuration and any macro-sized wrinkles are removed by gentle manual manipulation by the analyst. The absorbent composite is oriented so the machine-direction (MD) runs in the horizontal direction of the resulting image. The absorbent composite is illuminated with fluorescent lighting. The lights are connected to a standard 110 volt energy source and are fully illuminated. Align the ruler with the absorbent composite and photograph the absorbent composite located in the absorbent composite well 270 using the digital camera 260. The ruler is placed such that it is displayed just beneath the absorbent composite in the image (length-wise in the machine direction). The digital image of the absorbent composite is used to determine, as described below, the area of spread of the fecal material simulant.

8. The four sheets of pre-weighed paper towels are placed on the egg crate material and the mesh TEFLON coated screen of the vacuum apparatus. The four sheets are placed with the graphics facing down towards the vacuum chamber. The four sheets are then folded in half and then folded in half again. The absorbent composite is then placed upside down on top of the four sheets of paper towels. The latex dam sheet is then placed over the absorbent composite and the four sheets of paper towels as well as the entire egg crate material and TEFLON coated screen so that the latex dam sheet created a seal when a vacuum is drawn on the vacuum apparatus.

9. Apply vacuum pressure to the combination of the absorbent composite and four sheets of pre-weighed paper towels at 5 inches of water (0.18 psi) for 1 minute.

10. After the 1 minute has elapsed, the latex dam sheet is rolled back and the absorbent composite and four sheets of pre-weighed paper towels are removed from the vacuum apparatus. Remove the four sheets of pre-weighed paper towels from the absorbent composite and re-weigh the four sheets of pre-weighed paper towels. Determine the amount of simulated fecal material transferred to the four sheets of pre-weighed paper towels by subtracting the pre-weighed weight of the four sheets of paper towels from the re-weighed weight of the four sheets of paper towels.
11. Utilize the single pre-weighed paper towel to remove any simulated fecal material simulant remaining on the middle plate 244 of the injection apparatus 240. Wipe the middle plate 244 with the pre-weighed paper towel to remove any remaining fecal material simulant and re-weigh the single paper towel. Determine the amount of fecal material simulant that remained on the middle plate 244 by subtracting the pre-weighed weight of the single paper towel from the re-weighed weight of the single paper towel.
12. Determine the total amount of residual fecal material simulant by adding together the amount of fecal material transferred to the four sheets of pre-weighed paper towels and the amount of fecal material simulant remaining on the middle plate 244 of the injection apparatus 240.
13. Clean the injection apparatus middle plate 244 between each injection of fecal material simulant.
14. Repeat the above procedure for each absorbent composite of each absorbent composite test code.

Determination of Area of Spread of Fecal Material Simulant:

The area of spread of a fecal material simulant stain on a given combination of absorbent article components can be determined by using the image analysis measurement method described herein. Generally, the image analysis measurement method determines a dimensional numeric value of area for a fecal material simulant stain via a combination of specific image analysis measurement parameters. The area of spread is determined using conventional optical image analysis techniques to detect stain regions and measure such parameters as the area when viewed using a camera with incident lighting. An image analysis system, controlled by an algorithm, can detect and measure several other dimensional properties of a fecal material simulant stain. The resulting measurement data can be used to compare the efficacy of different combinations of absorbent article layers with respect to restricting and minimizing the area of spread of a fecal material simulant.

The method for determining the area of spread of fecal material simulant on a given absorbent composite includes the step of acquiring a digital image of the absorbent composite following an insult with fecal material simulant, such as described above (see the method for the Delivery of Fecal Material Simulant). Following the acquisition of the digital image of the absorbent composite, determining the area of spread of fecal material simulant on a given absorbent composite includes the step of performing multiple, dimensional measurements. The image analysis software platform used to perform the dimensional measurements is a QWIN Pro (Version 3.5.1) available from Leica Microsystems, having an office in Heerbrugg, Switzerland. The system and images are also accurately calibrated using the QWIN software and a standard ruler with metric markings at least as small as one millimeter which is placed next to the sample during image acquisition. The calibration is performed in the horizontal dimension of the video camera image. Units of centimeters per pixel are used for the calibration. Specifically, an image analysis algorithm is used to process digital images as well as perform measurements using Quantimet User Interactive Programming System (QUIPS) language. The image analysis algorithm is reproduced below.

```
NAME = Coverage-Size - BM on Diapers - 2a
PURPOSE = Measures the coverage and size of BM on body-side liner of absorbent product
ENTER SAMPLE ID & OPEN DATA FILE
  PauseText ( "Enter EXCEL data file name now." )
  Input ( FILENAME$ )
  OPENFILE$ = "C:\Data\36775\"+FILENAME$+".xls"
  Open File ( OPENFILE$, channel #CHAN )
CALIBRATE IMAGE
  - Calvalue = 0.0258 cm/px
  CALVALUE = 0.0258
  Calibrate ( CALVALUE CALUNITS$ per pixel )
  Enter Results Header
  File Results Header ( channel #1 )
  File Line ( channel #1 )
  REPLICATE = 0
  SAMPLE = 0
  ACQOUTPUT = 0
SET-UP
  Image frame ( x 0, y 0, Width 1280, Height 1024 )
  Measure frame ( x 31, y 61, Width 1218, Height 962 )
For ( SAMPLE = 1 to 156, step 1 )
  PauseText ( "Enter complete image file title." )
  Input ( TITLE$ )
  File ( TITLE$, channel #1 )
  File Line ( channel #1 )
  ACQUIRE IMAGE
  ACQOUTPUT = 0
  -- Comment: The following line must be set to read from the directory where images are located.
  Read image [PAUSE] (from file C:\Images\36775 \area
    Set\codeA3full1.jpg into Colour0)
  Colour Transform (RGB to HSI, from Colour0 to Colour0)
  Image Window (Auto Size, Auto Colour, No Auto Lut, Fit Image to Window, No
    Warning Before Image Overwrite, Do Not Load and Save Annotation with Image, Do
    Not Save Microscope Data with Image, Do Not Load and Save Reference Data with
    Image)
  DETECTION AND IMAGE PROCESSING
    PauseText ("Select optimal color detection")
    Colour Detect [PAUSE] (HSI+: 134-183, 140-255, 88-255, from Colour0 into Binary0)
    Binary Identify (EdgeFeat from Binary0 to Binary0)
    Binary Amend (Close from Binary0 to Binary1, cycles 8, operator Disc, edge erode on)
```

```
Binary Identify (FillHoles from Binary1 to Binary2)
Binary Amend (Open from Binary2 to Binary3, cycles 8, operator Disc, edge erode on )
PauseText ( "Edit and select only those regions that should be measured." )
Binary Edit [PAUSE] (Accept from Binary3 to Binary4, nib Fill, width 2)
MEASURE FEATURE PARAMETERS
Measure feature ( plane Binary4, 32 ferets, minimum area: 75, grey image: Colour0 )
    Selected parameters: Area, X FCP, Y FCP
File Line ( channel #1 )
File Feature Results ( channel #1 )
File Line ( channel #1 )
File Line ( channel #1 )
Next ( SAMPLE )
Close File ( channel #1 )
END
```

The QUIPS algorithm is executed using the QWIN Pro software platform. The analyst is initially prompted to enter in the EXCEL output data file name. This is followed by a prompting to enter the absorbent composite test code information which is sent to the EXCEL file.

The analyst is now prompted to enter the complete digital image file title which can be obtained from the host computer directory listing of the digital images to be analyzed. The directory containing the images is typically placed on the host computer's hard drive and can be accessed on the desktop screen via MS Windows. The image file title information is now automatically sent to the EXCEL file. Next, the same digital image file title can also be pasted into the Read Image window prompt. This will now read the digital image from the directory into the QWIN software display. The digital image will show the absorbent composite and any fecal material simulant stain in color. Note that the code line in the algorithm associated with reading the digital image must be pre-set to read from the designated host computer hard drive directory containing the files to be analyzed prior to algorithm execution.

The analyst is now prompted to "Select optimal color detection" by adjusting the detection threshold, if necessary, in order to obtain the optimal detection that is possible. The hue-saturation-intensity color detection mode is used in the Coverage-Size—BM on Diapers—2a algorithm. Typically, only the saturation and/or the intensity levels will need slight adjustments to optimize detection. The detection settings for the algorithm can be pre-determined before analyzing a set of images using QWIN and the hue-saturation-intensity color detection mode within the QUIPS algorithm with a couple of representative images. Settings can be considered optimized when the stain is covered by the overlaying detection binary with respect to its outer boundaries and areas within said boundaries. The degree of match between the overlaying binary and stain images can be checked during optimization by toggling the binary on and off using the 'control' and 'B' keys.

After detection and a series of automatic digital image processing steps, the analyst is asked to "Edit and select only those regions that should be measured." This is performed by simply using the computer mouse to manually select the fecal material simulant stain region to be measured. The user can toggle the 'control' and 'B' keys on the keyboard simultaneously to turn the overlying binary image on and off. A fit between the binary image and fecal material simulant stain is considered good when the binary image closely matches with the fecal material simulant stain with respect to its boundaries and regions within said boundaries.

The algorithm will then automatically perform measurements and output the data into the designated EXCEL spreadsheet file. The following primary measurement parameter data will be located in the EXCEL file after measurements and data transfer has occurred:

Area

Multiple digital image replicates from a single or multiple absorbent composites can be performed during a single execution of the QUIPS algorithm. The final sample mean spread value is usually based on an N=5 analysis from five, separate, absorbent composites of an absorbent composite test code. A comparison between different samples can be performed using a Student's T analysis at the 90% confidence level.

Example 2

The area of spread of fecal material simulant on an absorbent composite can be measured. This measurement can provide an understanding of how well a given absorbent composite design can minimize the surface spread of fecal material across a body contacting surface of an absorbent composite. The area of spread, measured in $cm^2$, of the fecal material simulant can be determined after a 10 cc insult of fecal material simulant, as described herein, at 15 cc/sec.

In this example, eight different experimental absorbent composite test codes were evaluated for the area of spread of fecal material simulant on the body contacting surface of the absorbent composite test code. Five absorbent composites for each absorbent composite test code were assembled by hand according to Table 4 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Area of Spread of Fecal Material Simulant test method described herein.

TABLE 4

Experimental Absorbent Composite Test Codes:

| Absorbent Composite Test Code | Body Facing Material | Secondary Liner | Acquisition Layer | Acquisition Layer Basis Weight (gsm) | Fluid Transfer Layer | Absorbent Body |
|---|---|---|---|---|---|---|
| 1 | A | N/A | G | 50 | K | O |
| 2 | B | N/A | G | 50 | K | O |
| 3 | C | N/A | G | 50 | K | O |
| 4 | D | N/A | G | 50 | K | O |
| 5 | A | N/A | N/A | N/A | K | O |
| 6 | B | N/A | N/A | N/A | K | O |
| 7 | C | N/A | N/A | N/A | K | O |
| 8 | D | N/A | N/A | N/A | K | O |

It should be noted that "N/A" means that for the absorbent composite test code in question, that particular material is not present. Thus, for example, for Absorbent Composite Test Code 1, the absorbent composites assembled had Body Facing Material "A" (as described in Table 3) adhesively bonded to Acquisition Layer "G" (as described in Table 3) without an additional layer of material between the two components. It should be understood that Body Facing Material "A" would be the body contacting surface of Absorbent Composite Test Code 1. Additionally, as an example, Absorbent Composite Test Code 5 is an absorbent composite assembled with Body Facing Material "A" (as described in Table 3) adhesively bonded to Fluid Transfer Layer "K" (as described in Table 3) without any additional layers between the two components. It should be understood that Body Facing Material "A" would be the body contacting surface of Absorbent Composite Test Code 5.

With regards to the absorbent composites assembled, the body facing material is adhesively bonded to the body facing surface of the acquisition layer or the body facing surface of the fluid transfer layer, depending on the absorbent composite test code. If present, the garment facing surface of the acquisition layer is adhesively bonded to the fluid transfer layer. The fluid transfer layer is adhesively bonded to the absorbent body. The absorbent body is adhesively bonded to the outer cover (as described in Table 3). The absorbent composites did not have any waist or leg elastics and did not have any containment flaps.

Figure 37:
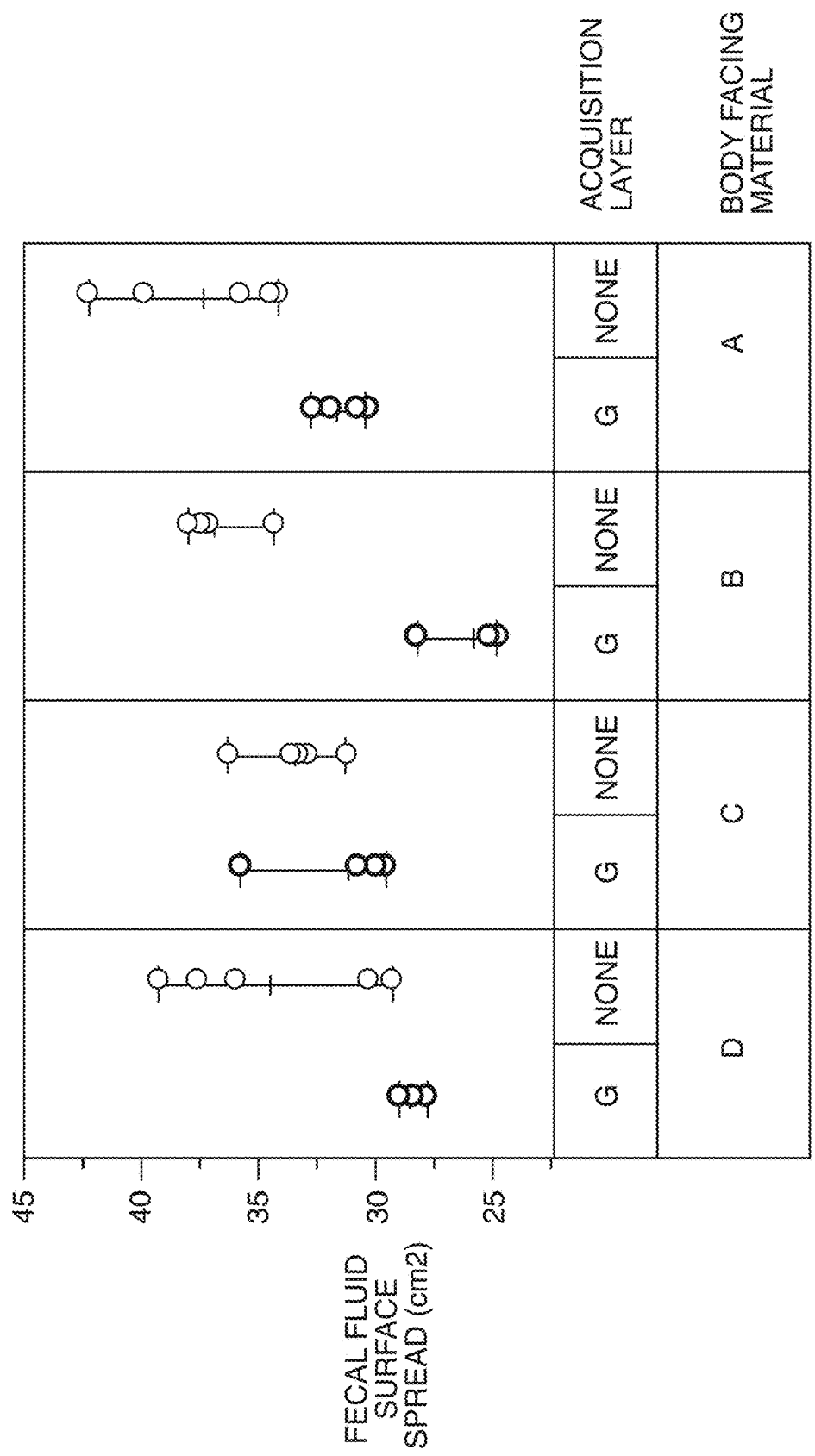
FIG. 37 is a graph depicting the area of spread of fecal material simulant on various absorbent composites.

As illustrated in FIG. 37, the design of the absorbent composite has an impact on the amount of area of spread of fecal material simulant in an absorbent composite test code. As illustrated in FIG. 37, the absorbent composite test codes that had an acquisition layer present as part of their design had lower area of spread of fecal material simulant than the absorbent composite test codes that did not have an acquisition layer present as part of their design. As illustrated in FIG. 37, with regards to the absorbent composite test codes containing an acquisition layer, the absorbent composite test codes having a body facing material 28 with land areas having from about 5% to about 10% open area reduced the area of spread of fecal material simulant to a greater extent than the remaining absorbent composite test codes which also contained an acquisition layer as part of their design.

Example 3

The area of spread of fecal material simulant on an absorbent composite can be measured. This measurement can provide an understanding of how well a given absorbent composite design can minimize the surface spread of fecal material across a body contacting surface of an absorbent composite. The area of spread, measured in $cm^2$, of the fecal material simulant can be determined after a 10 cc insult of fecal material simulant, as described herein, at 15 cc/sec.

In this example, twenty different experimental absorbent composite test codes were evaluated for the area of spread of fecal material simulant on the body contacting surface of the absorbent composite test code. Five absorbent composites for each absorbent composite test code were assembled by hand according to Table 5 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Area of Spread of Fecal Material Simulant test method described herein.

TABLE 5

Experimental Absorbent Composite Test Codes

| Absorbent Composite Test Code | Body Facing Material | Secondary Liner | Acquisition Layer | Acquisition Layer Basis Weight (gsm) | Fluid Transfer Layer | Absorbent Body |
|---|---|---|---|---|---|---|
| 1 | A | N/A | F | 50 | J | N |
| 2 | A | N/A | F/F | 100 | J | N |
| 3 | C | N/A | F | 50 | J | N |
| 4 | C | N/A | F/F | 100 | J | N |
| 5 | N/A | E | F | 50 | J | N |
| 6 | A | N/A | G | 50 | J | N |
| 7 | A | N/A | G/G | 100 | J | N |
| 8 | C | N/A | G | 50 | J | N |
| 9 | C | N/A | G/G | 100 | J | N |
| 10 | N/A | E | G | 50 | J | N |
| 11 | A | N/A | F | 50 | J | O |
| 12 | A | N/A | F/F | 100 | J | O |

TABLE 5-continued

Experimental Absorbent Composite Test Codes

| Absorbent Composite Test Code | Body Facing Material | Secondary Liner | Acquisition Layer | Acquisition Layer Basis Weight (gsm) | Fluid Transfer Layer | Absorbent Body |
|---|---|---|---|---|---|---|
| 13 | C | N/A | F | 50 | J | O |
| 14 | C | N/A | F/F | 100 | J | O |
| 15 | N/A | E | F | 50 | J | O |
| 16 | A | N/A | G | 50 | J | O |
| 17 | A | N/A | G/G | 100 | J | O |
| 18 | C | N/A | G | 50 | J | O |
| 19 | C | N/A | G/G | 100 | J | O |
| 20 | N/A | E | G | 50 | J | O |

It should be noted that "N/A" means that for the absorbent composite test code in question, that particular material is not present. Thus, for example, for Absorbent Composite Test Code 1, the absorbent composites assembled had Body Facing Material "A" (as described in Table 3) adhesively bonded to Acquisition Layer "F" (as described in Table 3) without an additional layer of material between the two components. It should be understood that Body Facing Material "A" would be the body contacting surface of Absorbent Composite Test Code 1. Additionally, as an example, Absorbent Composite Test Code 5 is an absorbent composite assembled with Liner "E" (as described in Table 3) adhesively bonded to Acquisition Layer "F" (as described in Table 3). It should be understood that Liner "E" would be the body contacting surface of Absorbent Composite Test Code 5. It should also be noted that some absorbent composite test codes contained a double layer of acquisition layers as noted in Table 5 above.

With regards to the absorbent composites assembled, the body facing material or secondary liner, depending on the absorbent composite test code, is adhesively bonded to the body facing surface of the acquisition layer. The garment facing surface of the acquisition layer is adhesively bonded to the fluid transfer layer and the fluid transfer layer is adhesively bonded to the absorbent body. The absorbent body is adhesively bonded to the outer cover (as described in Table 3). The absorbent composites did not have any waist or leg elastics and did not have any containment flaps.

Figure 38:
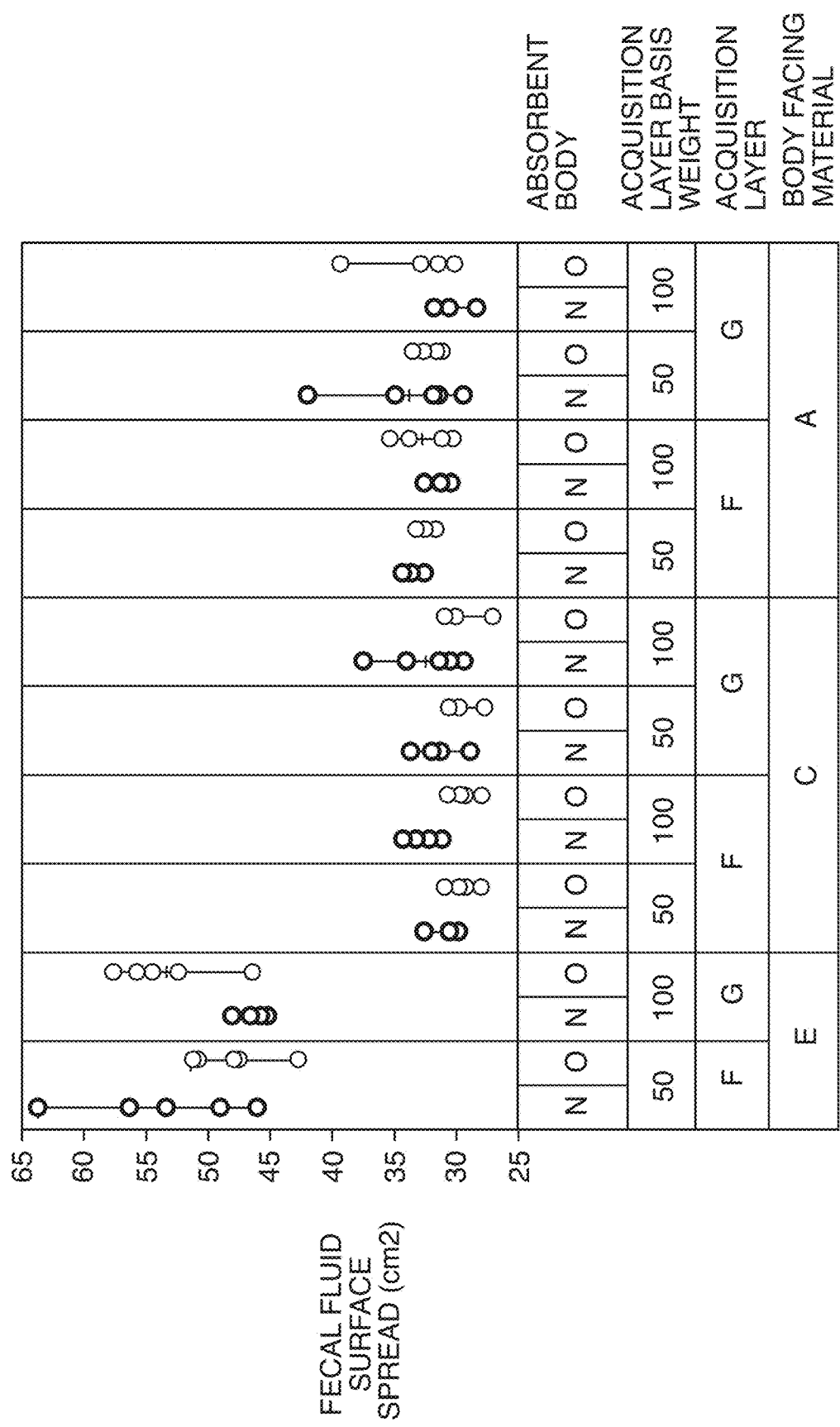
FIG. 38 is a graph depicting the area of spread of fecal material simulant on various absorbent composites.

As illustrated in FIG. 38, the design of the absorbent composite has an impact on the amount of area of spread of fecal material simulant in an absorbent composite test code. As illustrated in FIG. 38, the absorbent composite test codes with the body facing material (Material Codes "A" and "C") as the body contacting surface had lower area of spread of fecal material simulant than the absorbent composite test codes that had the secondary liner material (Material Code "E") as the body contacting surface.

Example 4

The area of spread of fecal material simulant on an absorbent composite can be measured. This measurement can provide an understanding of how well a given absorbent composite design can minimize the surface spread of fecal material across a body contacting surface of an absorbent composite. The area of spread, measured in cm$^2$, of the fecal material simulant can be determined after a 10 cc insult of fecal material simulant, as described herein, at 15 cc/sec.

In this example, six different experimental absorbent composite test codes were evaluated for the area of spread of fecal material simulant on the body contacting surface of the absorbent composite test code. Five absorbent composites for each absorbent composite test code were assembled by hand according to Table 6 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Area of Spread of Fecal Material Simulant test method described herein.

TABLE 6

Experimental Absorbent Composite Test Codes:

| Absorbent Composite Test Code | Body Facing Material | Secondary Liner | Acquisition Layer | Acquisition Layer Basis Weight (gsm) | Fluid Transfer Layer | Absorbent Body |
|---|---|---|---|---|---|---|
| 1 | A | N/A | I | 50 | J | N |
| 2 | C | N/A | I | 50 | J | N |
| 3 | N/A | E | I | 50 | J | N |
| 4 | A | N/A | H | 50 | J | N |
| 5 | C | N/A | H | 50 | J | N |
| 6 | N/A | E | H | 50 | J | N |

It should be noted that "N/A" means that for the absorbent composite test code in question, that particular material is not present. Thus, for example, for Absorbent Composite Test Code 1, the absorbent composites assembled had Body Facing Material "A" (as described in Table 3) adhesively bonded to Acquisition Layer "I" (as described in Table 3) without any additional layer of material between the two components. It should be understood that Body Facing Material "A" would be the body contacting surface of Absorbent Composite Test Code 1. Additionally, as an example, Absorbent Composite Test Code 3 is an absorbent composite assembled with Liner "E" (as described in Table 3) adhesively bonded to Acquisition Layer "I" (as described in Table 3). It should be understood that Liner "E" would be the body contacting surface of Absorbent Composite Test Code 3.

With regards to the absorbent composites assembled, the body facing material or secondary liner, depending on the absorbent composite test code, is adhesively bonded to the body facing surface of the acquisition layer. The garment facing surface of the acquisition layer is adhesively bonded to the fluid transfer layer and the fluid transfer layer is adhesively bonded to the absorbent body. The absorbent body is adhesively bonded to the outer cover (as described in Table 3). The absorbent composites did not have any waist or leg elastics and did not have any containment flaps.

Figure 39:
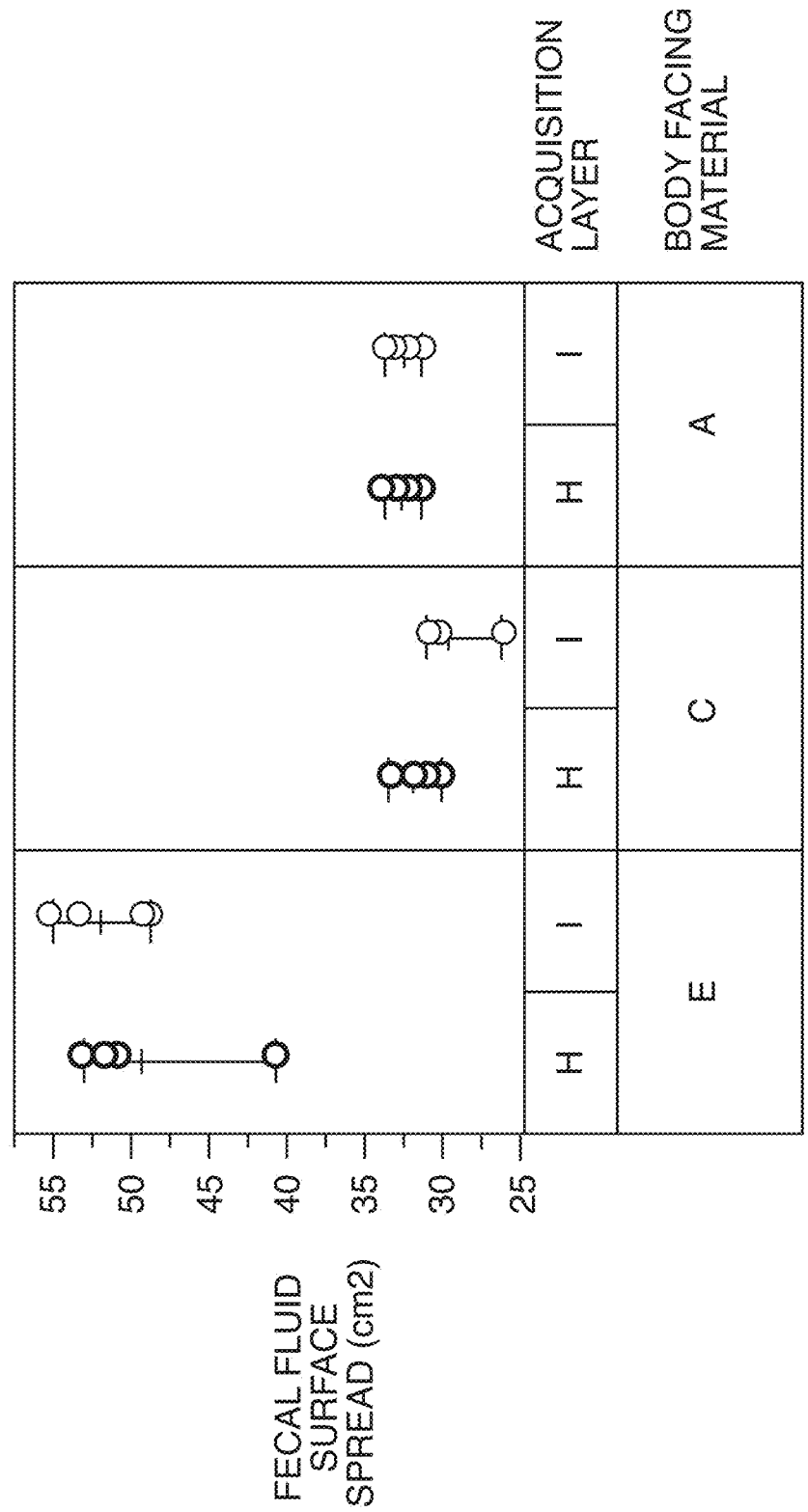
FIG. 39 is a graph depicting the area of spread of fecal material simulant on various absorbent composites.

As illustrated in FIG. 39, the design of the absorbent composite has an impact on the amount of area of spread of fecal material simulant in an absorbent composite test code. As illustrated in FIG. 39, the absorbent composite test codes with the body facing material (Material Codes "A" and "C") as the body contacting surface had lower area of spread of fecal material simulant than the absorbent composite test codes that had the secondary liner material (Material Code "E") as the body contacting surface.

Example 5

The amount of residual fecal material on the body contacting surface of an absorbent composite can be measured. This measurement can provide an understanding of how well a given absorbent composite design can minimize the amount of residual fecal material pooling on the surface of the body contacting surface. The amount of residual fecal material can be determined, as described herein, by measuring the weight, in grams, of the fecal material simulant that can be removed from the body contacting surface of the absorbent composite after two minutes.

In this example, eight different experimental absorbent composite test codes were evaluated for the amount of residual fecal material simulant on the body contacting surface of the absorbent composite test code. Five absorbent composites for each absorbent composite test code were assembled by hand according to Table 7 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Fecal Material Simulant Surface Residual test method described herein.

TABLE 7

Experimental Absorbent Composite Test Codes:

| Absorbent Composite Test Code | Body Facing Material | Secondary Liner | Acquisition Layer | Acquisition Layer Basis Weight (gsm) | Fluid Transfer Layer | Absorbent Body |
| --- | --- | --- | --- | --- | --- | --- |
| 1 | A | N/A | G | 50 | K | O |
| 2 | B | N/A | G | 50 | K | O |
| 3 | C | N/A | G | 50 | K | O |
| 4 | D | N/A | G | 50 | K | O |
| 5 | A | N/A | N/A | N/A | K | O |
| 6 | B | N/A | N/A | N/A | K | O |
| 7 | C | N/A | N/A | N/A | K | O |
| 8 | D | N/A | N/A | N/A | K | O |

It should be noted that "N/A" means that for the absorbent composite test code in question, that particular material is not present. Thus, for example, for Absorbent Composite Test Code 1, the absorbent composites assembled had Body Facing Material "A" (as described in Table 3) adhesively bonded to Acquisition Layer "G" (as described in Table 3) without any additional layers of material between the two components. It should be understood that Body Facing Material "A" would be the body contacting surface of Absorbent Composite Test Code 1. Additionally, as an example, Absorbent Composite Test Code 5 is an absorbent composite assembled with Body Facing Material "A" (as described in Table 3) adhesively bonded to Fluid Transfer Layer "K" (as described in Table 3) without any additional layers between the two components. It should be understood that Body Facing Material "A" would be the body contacting surface of Absorbent Composite Test Code 5.

With regards to the absorbent composites assembled, the body facing material is adhesively bonded to the body facing surface of the acquisition layer or the body facing surface of the fluid transfer layer, depending on the absorbent composite test code. If present, the garment facing surface of the acquisition layer is adhesively bonded to the fluid transfer layer. The fluid transfer layer is adhesively bonded to the absorbent body. The absorbent body is adhesively bonded to the outer cover (as described in Table 3). The absorbent composites did not have any waist or leg elastics and did not have any containment flaps.

Figure 40:
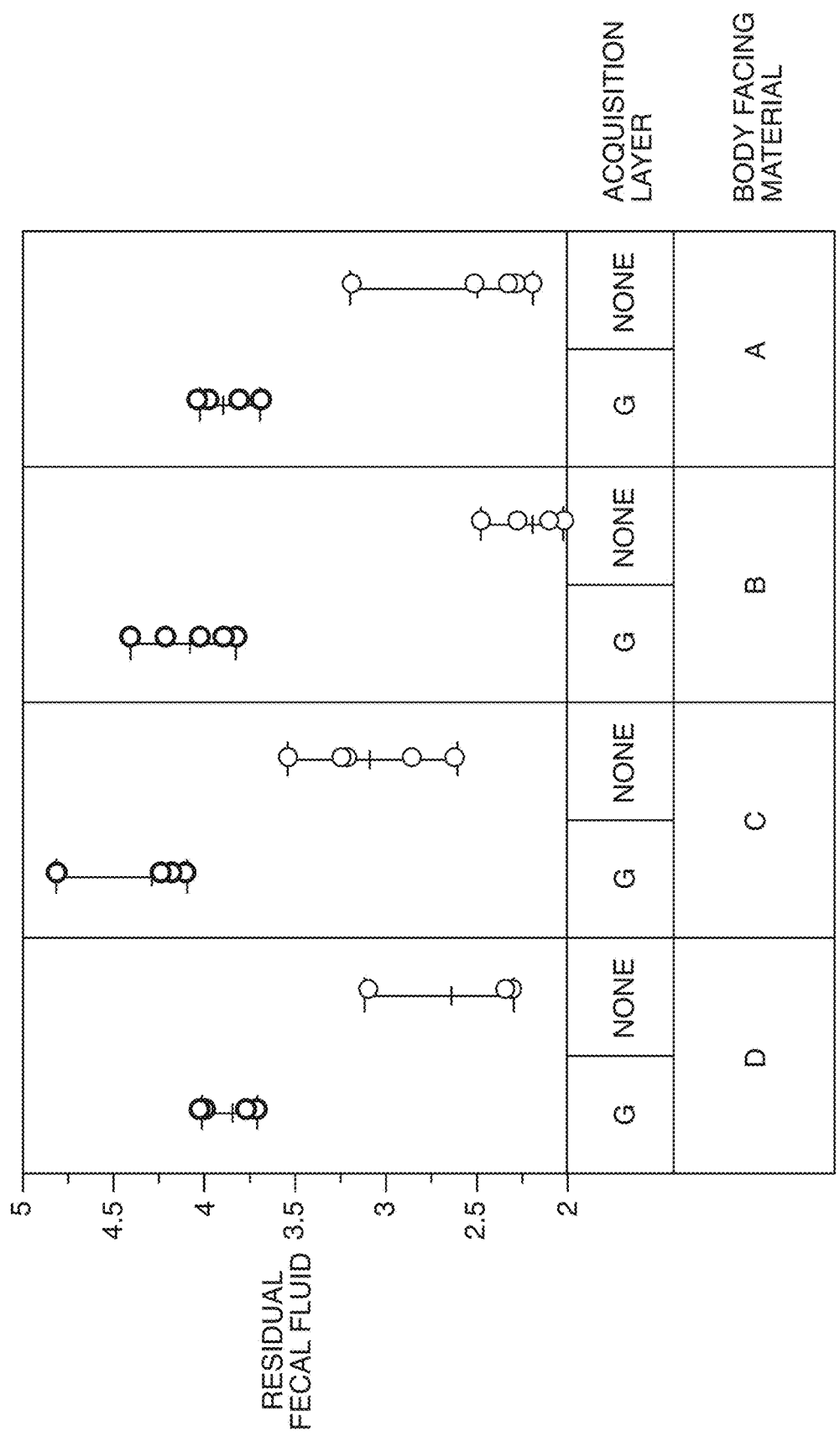
FIG. 40 is a graph depicting the residual amount of fecal material simulant on various absorbent composites.

As illustrated in FIG. 40, the design of the absorbent composite has an impact on the amount of residual fecal material simulant on the surface of an absorbent composite test code. As illustrated in FIG. 40, the absorbent composite test codes that had an acquisition layer present as part of their design had a larger amount of residual fecal material simulant on the surface of the body contacting surface of the absorbent composite than the absorbent composite test codes that did not have an acquisition layer present as part of their design.

Example 6

The amount of residual fecal material on the body contacting surface of an absorbent composite can be measured. This measurement can provide an understanding of how well a given absorbent composite design can minimize the amount of residual fecal material pooling on the surface of the body contacting surface. The amount of residual fecal material can be determined, as described herein, by measuring the weight, in grams, of the fecal material simulant that can be removed from the body contacting surface of the absorbent composite after two minutes.

In this example, twelve different experimental absorbent composite test codes were evaluated for the residual amount of fecal material simulant on the body contacting surface of the absorbent composite test code. Five absorbent composites for each absorbent composite test code were assembled by hand according to Table 8 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Fecal Material Simulant Surface Residual test method described herein.

TABLE 8

Experimental Absorbent Composite Test Codes:

| Absorbent Composite Test Code | Body Facing Material | Secondary Liner | Acquisition Layer | Fluid Transfer Layer | Absorbent Body |
|---|---|---|---|---|---|
| 1 | B | N/A | N/A | K | O |
| 2 | C | N/A | N/A | K | O |
| 3 | D | N/A | N/A | K | O |
| 4 | B | N/A | N/A | K | N |
| 5 | C | N/A | N/A | K | N |
| 6 | D | N/A | N/A | K | N |
| 7 | B | N/A | N/A | N/A | O |
| 8 | C | N/A | N/A | N/A | O |
| 9 | D | N/A | N/A | N/A | O |
| 10 | B | N/A | N/A | N/A | N |
| 11 | C | N/A | N/A | N/A | N |
| 12 | D | N/A | N/A | N/A | N |

It should be noted that "N/A" means that for the absorbent composite test code in question, that particular material is not present. Thus, for example, for Absorbent Composite Test Code 1, the absorbent composites assembled had Body Facing Material "B" (as described in Table 3) adhesively bonded to Fluid Transfer Layer "K" (as described in Table 3) without any additional layers of material between the two components. It should be understood that Body Facing Material "B" would be the body contacting surface of Absorbent Composite Test Code 1. Additionally, as an example, Absorbent Composite Test Code 7 is an absorbent composite assembled with Body Facing Material "B" (as described in Table 3) adhesively bonded to Absorbent Body "M" (as described in Table 3) without any additional layers between the two components. It should be understood that Body Facing Material "B" would be the body contacting surface of Absorbent Composite Test Code 7.

With regards to the absorbent composites assembled, the body facing material is adhesively bonded to the body facing surface of the fluid transfer layer or the body facing surface of the absorbent body, depending on the absorbent composite test code. If present, the fluid transfer layer is adhesively bonded to the absorbent body. The absorbent body is adhesively bonded to the outer cover (as described in Table 3). The absorbent composites did not have any waist or leg elastics and did not have any containment flaps.

Figure 41:
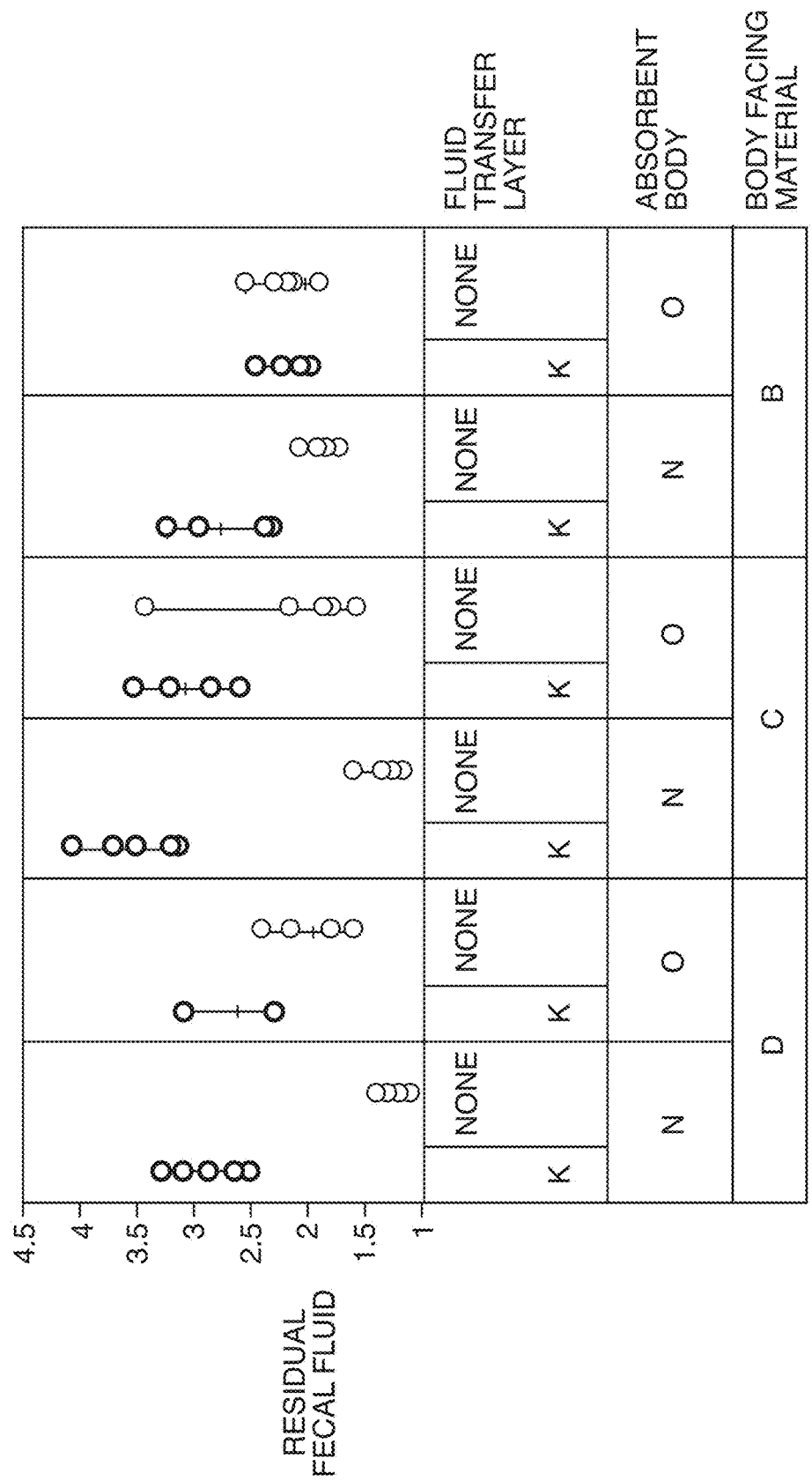
FIG. 41 is a graph depicting the residual amount of fecal material simulant on various absorbent composites.

As illustrated in FIG. 41, the design of the absorbent composite has an impact on the amount of residual fecal material simulant on the surface of an absorbent composite test code. As illustrated in FIG. 41, the absorbent composite test codes that did not contain an acquisition layer and a fluid transfer layer as part of their design had a lower amount of residual fecal material simulant on the surface of the body contacting surface of the absorbent composite than the absorbent composite test codes that did not have an acquisition layer present but did have a fluid transfer layer present as part of their design.

Example 7

The amount of residual fecal material on the body contacting surface of an absorbent composite can be measured. This measurement can provide an understanding of how well a given absorbent composite design can minimize the amount of residual fecal material pooling on the surface of the body contacting surface. The amount of residual fecal material can be determined, as described herein, by measuring the weight, in grams, of the fecal material simulant that can be removed from the body contacting surface of the absorbent composite after two minutes.

In this example, four different experimental absorbent composite test codes were evaluated for the residual amount of fecal material simulant on the body contacting surface of the absorbent composite test code. Five absorbent composites for each absorbent composite test code were assembled by hand according to Table 9 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Fecal Material Simulant Surface Residual test method described herein.

TABLE 9

Experimental Absorbent Composite Test Codes:

| Absorbent Composite Test Code | Body Facing Material | Secondary Liner | Acquisition Layer | Fluid Transfer Layer | Absorbent Body |
|---|---|---|---|---|---|
| 1 | D | N/A | N/A | J | O |
| 2 | D | N/A | N/A | L | O |
| 3 | D | N/A | N/A | M | O |
| 4 | D | N/A | N/A | K | O |

It should be noted that "N/A" means that for the absorbent composite test code in question, that particular material is not present. Thus, for example, for Absorbent Composite Test Code 1, the absorbent composites assembled had Body Facing Material "D" (as described in Table 3) adhesively bonded to Fluid Transfer Layer "J" (as described in Table 3) without any additional layers of material between the two components. It should be understood that Body Facing Material "D" would be the body contacting surface of Absorbent Composite Test Code 1. Additionally, as an example, Absorbent Composite Test Code 3 is an absorbent composite assembled with Body Facing Material "D" (as described in Table 3) adhesively bonded to Fluid Transfer Layer "M" (as described in Table 3) without any additional layers between the two components. It should be understood that Body Facing Material "D" would be the body contacting surface of Absorbent Composite Test Code 3.

With regards to the absorbent composites assembled, the body facing material is adhesively bonded to the body facing surface of the fluid transfer layer. The fluid transfer layer is adhesively bonded to the absorbent body. The absorbent body is adhesively bonded to the outer cover (as described in Table 3). The absorbent composites did not have any waist or leg elastics and did not have any containment flaps.

Figure 42:
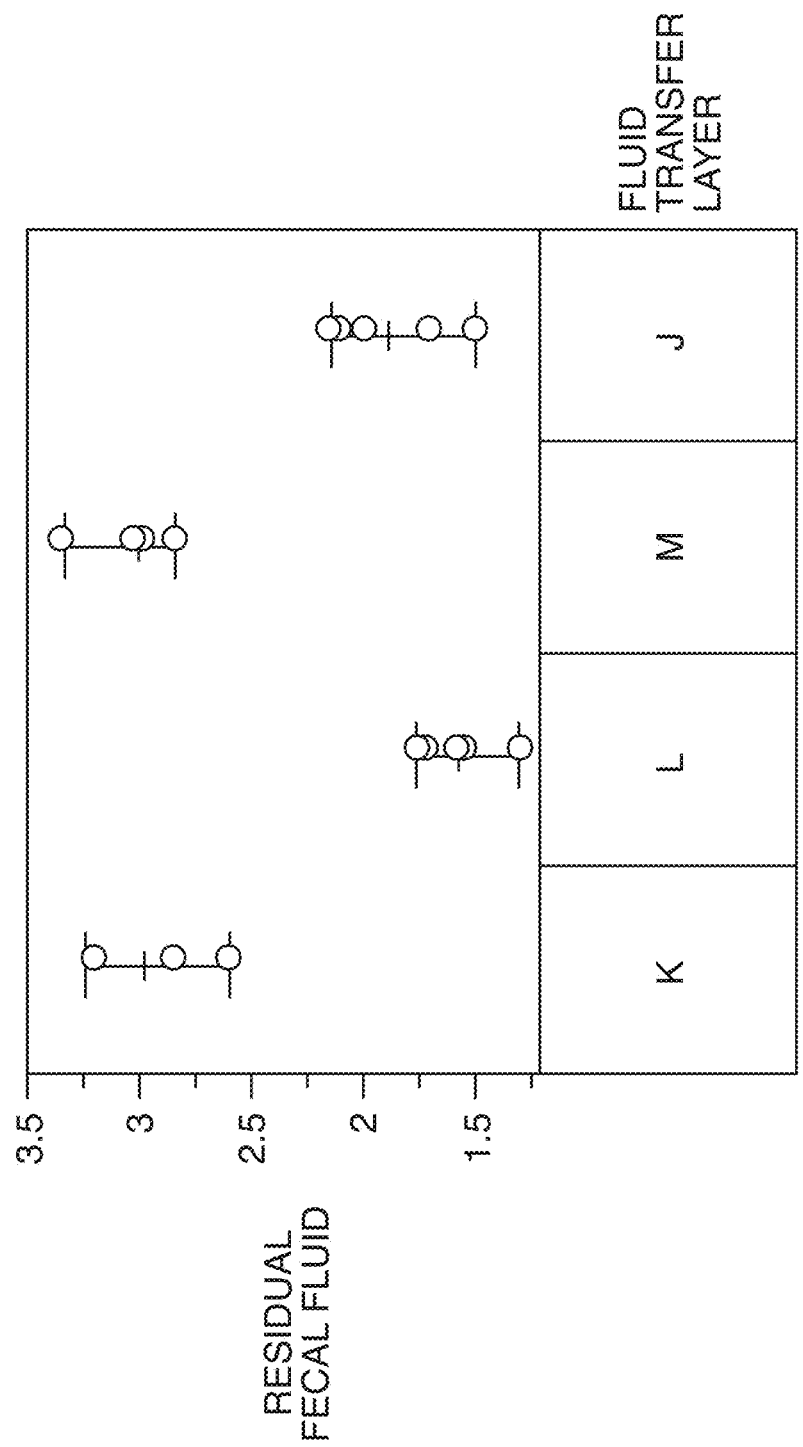
FIG. 42 is a graph depicting the residual amount of fecal material simulant on various absorbent composites.

As illustrated in FIG. 42, the design of the absorbent composite has an impact on the amount of residual fecal material simulant on the surface of an absorbent composite test code. As illustrated in FIG. 42, the absorbent composite test codes that had a fluid transfer layer composed of a tissue material or a hydroentangled material as part of their design had a lower amount of residual fecal material simulant on the surface of the body contacting surface of the absorbent composite than the absorbent composite test codes that had the Scott Towel or a material having polymeric materials as the fluid transfer layer as part of their design.

Example 8

The amount of residual fecal material on the body contacting surface of an absorbent composite can be measured. This measurement can provide an understanding of how well a given absorbent composite design can minimize the amount of residual fecal material pooling on the surface of the body contacting surface. The amount of residual fecal material can be determined, as described herein, by measuring the weight, in grams, of the fecal material simulant that can be removed from the body contacting surface of the absorbent composite after two minutes.

In this example, six different experimental absorbent composite test codes were evaluated for the residual amount of fecal material simulant on the body contacting surface of the absorbent composite test code. Five absorbent composites for each absorbent composite test code were assembled by hand according to Table 10 below, utilizing the corresponding material descriptions listed in Table 3: Material Descriptions above. Each absorbent composite was subjected to the delivery of a 10 cc insult of fecal material simulant, as described herein, at 15 cc/sec and each absorbent composite of each absorbent composite test code was analyzed according to the Area of Spread of Fecal Material Simulant test method described herein.

facing surface of the acquisition layer is adhesively bonded to the fluid transfer layer and the fluid transfer layer is adhesively bonded to the absorbent body. The absorbent body is adhesively bonded to the outer cover (as described in Table 3). The absorbent composites did not have any waist or leg elastics and did not have any containment flaps.

Figure 43:
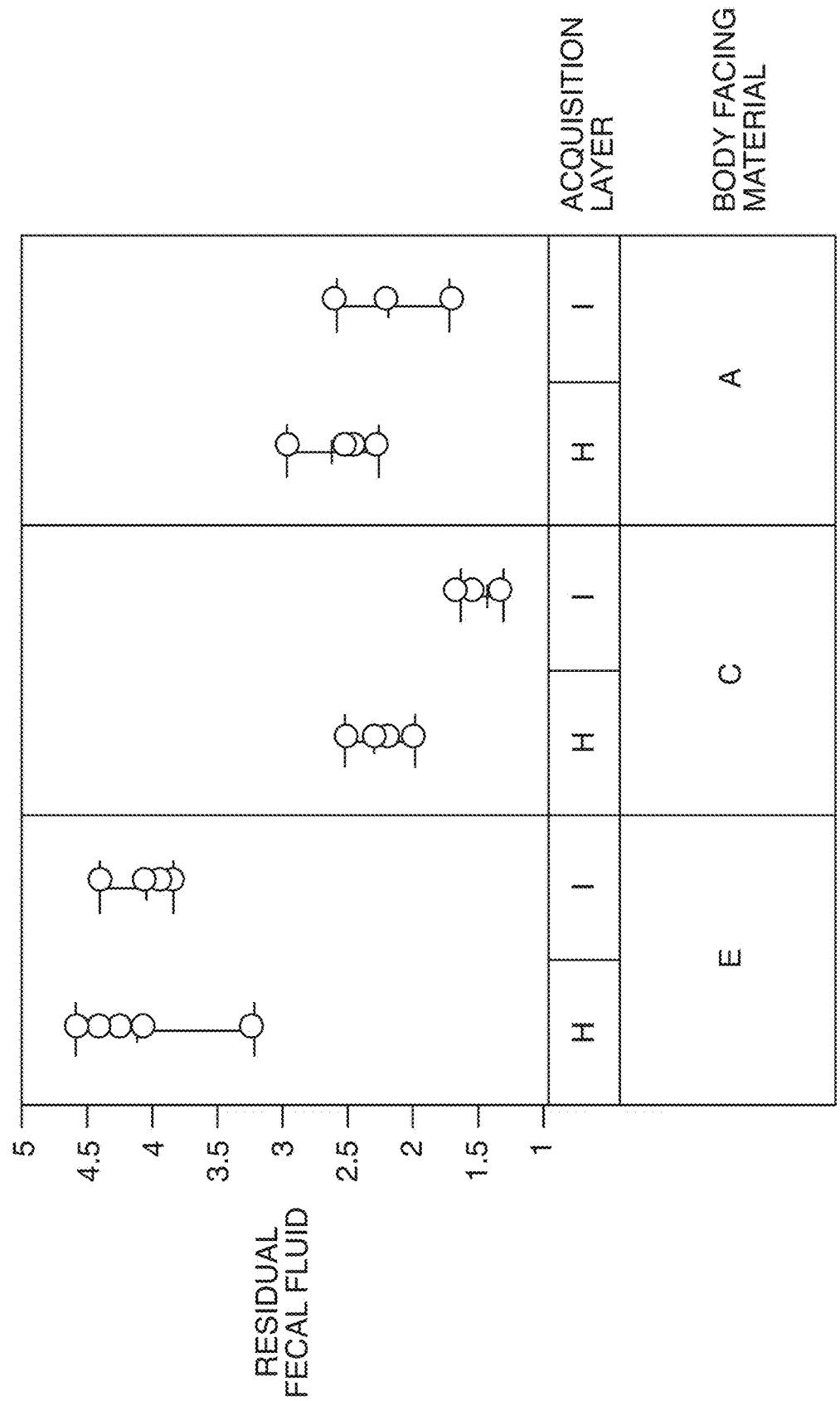
FIG. 43 is a graph depicting the residual amount of fecal material simulant on various absorbent composites.

As illustrated in FIG. 43, the design of the absorbent composite has an impact on the amount of residual fecal material simulant on the surface of an absorbent composite test code. As illustrated in FIG. 43, the absorbent composite test codes with the body facing material (Material Codes "A" and "C") as the body contacting surface had a lower amount of residual fecal material simulant on the surface of the absorbent composite test codes than the absorbent composite test codes that had the secondary liner material (Material Code "E") as the body contacting surface. From the information gathered in Example 2, it would have been expected that absorbent composite test codes 1, 2, 4 and 5 also would have had a larger amount of residual fecal material simulant on the surface of the body contacting surface of the absorbent composite test codes. However, as illustrated in FIG. 43, absorbent composite test codes 1, 2, 4 and 5, which each have an acquisition layer present in their design, still had a lower amount of residual fecal material simulant on the surface of the body contacting surface of the absorbent composite test codes. As illustrated in FIGS. 40 and 43, if an acquisition layer is present in the design of the absorbent composite, the composition of the acquisition layer has an impact on the amount of residual fecal material simulant on the body contacting surface of the absorbent composite. As illustrated in FIG. 43, an acquisition layer

TABLE 10

Experimental Absorbent Composite Test Codes:

| Absorbent Composite Test Code | Body Facing Material | Secondary Liner | Acquisition Layer | Acquisition Layer Basis Weight (gsm) | Fluid Transfer Layer | Absorbent Body |
|---|---|---|---|---|---|---|
| 1 | A | N/A | I | 50 | J | N |
| 2 | C | N/A | I | 50 | J | N |
| 3 | N/A | E | I | 50 | J | N |
| 4 | A | N/A | H | 50 | J | N |
| 5 | C | N/A | H | 50 | J | N |
| 6 | N/A | E | H | 50 | J | N |

It should be noted that "N/A" means that for the absorbent composite test code in question, that particular material is not present. Thus, for example, for Absorbent Composite Test Code 1, the absorbent composites assembled had Body Facing Material "A" (as described in Table 3) adhesively bonded to Acquisition Layer "I" (as described in Table 3) without any additional layers of material between the two components. It should be understood that Body Facing Material "A" would be the body contacting surface of Absorbent Composite Test Code 1. Additionally, as an example, Absorbent Composite Test Code 3 is an absorbent composite assembled with Liner "E" (as described in Table 3) adhesively bonded to Acquisition Layer "I" (as described in Table 3). It should be understood that Liner "E" would be the body contacting surface of Absorbent Composite Test Code 3.

With regards to the absorbent composites assembled, the body facing material or secondary liner, depending on the absorbent composite test code, is adhesively bonded to the body facing surface of the acquisition layer. The garment having smaller fiber denier can have a lower amount of residual fecal material simulant on the body contacting surface of an absorbent composite than absorbent composites containing an acquisition layer with larger fiber denier as part of its design.

Example 9

One-Cycle compression testing can be performed to measure the compression resiliency of projections on single layer projection layers and dual layer body facing materials having a support layer and a projection layer. Using measurements of the thickness of the unsupported projection layer and the dual layer body facing material during loading and unloading, the percent resiliency can be determined.

In this example, an unsupported projection layer and two different body facing materials were evaluated, following their removal from an absorbent composite, for the percent resiliency of the unsupported projection layer and the dual layer body facing materials. Each absorbent composite was assembled by hand according to Table 11 below, utilizing the corresponding materials descriptions listed in Table 3: Material Descriptions above. Each unsupported projection layer and each dual layer body facing material was analyzed according to the Percent Resiliency-One Cycle Compression test method described herein.

TABLE 11

Experimental Absorbent Composite Test Codes:

| Absorbent Composite Test Code | Experimental Liner | Absorbent Body |
|---|---|---|
| 1 | A | O |
| 2 | C | O |
| 3 | P | O |

With regards to the absorbent composites assembled, the experimental liner is adhesively bonded to the body facing surface of the absorbent body. The garment facing surface of the Absorbent body is adhesively bonded to the outer cover. The absorbent composites do not have any waist or leg elastics and does not have any containment flaps.

Figure 44:
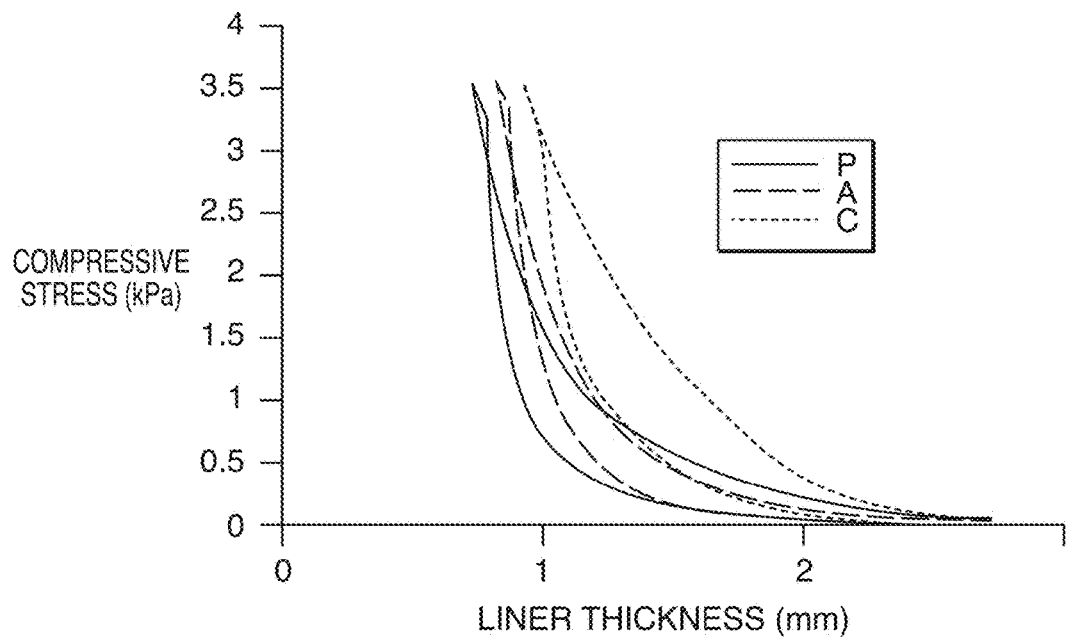
FIG. 44 is a graph depicting the compressive stress versus thickness for an unsupported projection layer and two body facing materials under a one-cycle loading and unloading.

FIG. 44 illustrates the compressive stress versus liner thickness curves under the one-cycle loading and unloading for the unsupported projection layer and the two body facing materials tested.

Percent resiliency is calculated according to the following equation:

% Resiliency=[(Thickness at 0.483 kPa unloading)/ (Thickness at 0.483 kPa loading)]×100%

Table 12 provides a summary of the liner thicknesses at 0.483 kPa during the loading and unloading and the percent resiliency for the unsupported projection layer and the two body facing materials tested.

TABLE 12

Body Facing Material thickness (mm) under 0.483 kPa (0.07 psi) during loading and unloading and Percent Resiliency

| Liner | P | A | C |
|---|---|---|---|
| During Loading (mm) | 1.56 | 1.44 | 1.91 |
| During Unloading (mm) | 1.08 | 1.19 | 1.47 |
| % Resiliency | 69 | 83 | 77 |

As indicated in Table 12, and as illustrated in FIG. 44, the percent resiliency of the single layer unsupported projection layer is around 69%. As further indicated in Table 12, and as further illustrated in FIG. 44, the percent resiliency of a liner, such as a projection layer having projections, can be improved by combining a projection layer with a support layer to produce the body facing material.

Percent Resiliency—One Cycle Compression Test Method
1. Use "freeze off" spray to carefully remove the unsupported projection layer or body facing material with projections from an absorbent composite.
2. From the unsupported projection layer or body facing material, cut a 38 mm by 25 mm test sample.
3. The upper and lower platens made of stainless steel are attached to a tensile tester (Model: Alliance RT/1 manufactured by MTS System Corporation, a business having a location in Eden Prairie, Minn. U.S.A.)
4. The top platen has a diameter of 57 mm while the lower platen has a diameter of 89 mm. The upper platen is connected to a 100 N load cell while the lower platen is attached to the base of the tensile tester.
5. TestWorks Version 4 software program provided by MTS is used to control the movement of the upper platen and record the load and the distance between the two platens.
6. The upper platen is activated to slowly move downward and touch the lower platen until the compression load reaches around 5000 g. At this point, the distance between the two platens is zero.
7. The upper platen is then set to move upward (away from the lower platen) until the distance between the two platens reaches 15 mm
8. The crosshead reading shown on TestWorks Version 4 software program is set to zero.
9. A test sample is placed on the center of the lower platen with the projections facing toward the upper platen.
10. The upper platen is activated to descend toward the lower platen and compress the test sample at a speed of 25 mm/min. The distance that the upper platen travels is indicated by the crosshead reading. This is a loading process.
11. When 345 gram force (about 3.5 kPa) is reached, the upper platen stops moving downward and returns at a speed of 25 mm/min to its initial position where the distance between the two platens is 15 mm. This is an unloading process.
12. The compression load and the corresponding distance between the two platens during the loading and unloading are recorded on a computer using TestWorks Version 4 software program provided by MTS.
13. The compression load is converted to the compression stress by dividing the compression force by the area of the test sample.
14. The distance between the two platens at a given compression stress represents the thickness under that particular compression stress.
15. A total of three test samples are tested for each test sample code to get representative loading and unloading curves for each test sample code.

Example 10

To measure the resistance to stretching and the associated collapse of projections, the percent extension under varying loads of an unsupported projection layer and a dual layer body facing material can be measured.

In this example, an unsupported projection layer and two different dual layer body facing materials were evaluated, following their removal from an absorbent composite, for the percent extension under varying loads of the unsupported projection layer and the body facing material. Each absorbent composite was assembled by hand according to Table 13 below, utilizing the corresponding material descriptions listed in Table 3: Material Descriptions above. Each unsupported projection layer and body facing material was analyzed according to the Load vs. Percent Extension test method described herein.

TABLE 13

Experimental Absorbent Composite Test Codes:

| Absorbent Composite Test Code | Body Facing Material | Absorbent Body |
|---|---|---|
| 1 | A | O |
| 2 | C | O |
| 3 | P | O |

With regards to the absorbent composites assembled, the unsupported projection layer or body facing material is adhesively bonded to the body facing surface of the absorbent body. The garment facing surface of the absorbent body is adhesively bonded to the outer cover. The absorbent composites do not have any waist or leg elastics and does not have any containment flaps.

Figure 45:
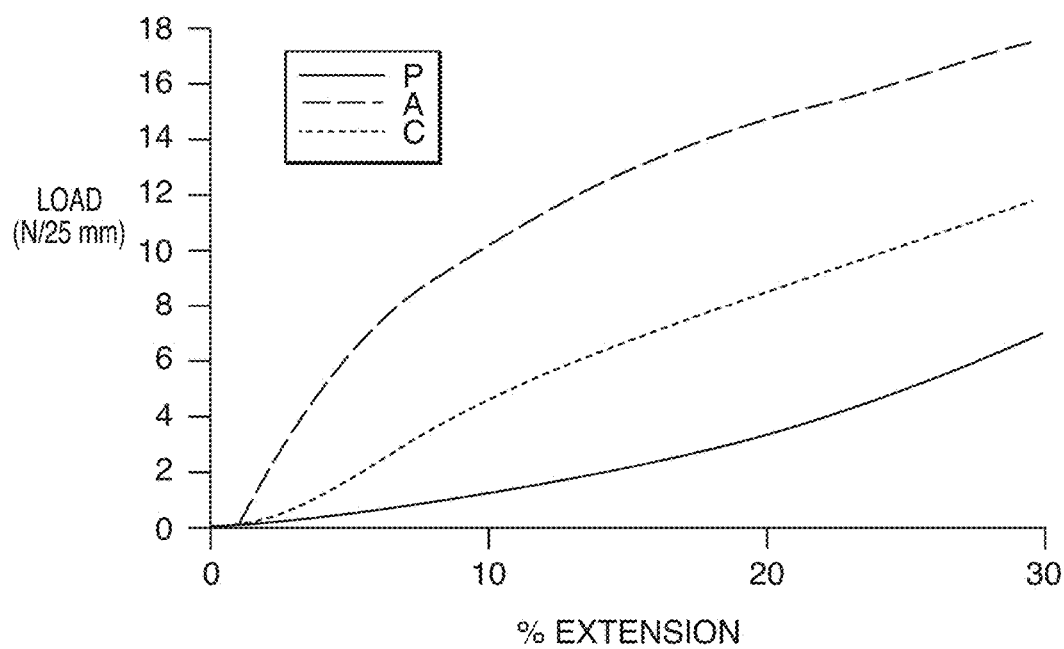
FIG. 45 is a graph depicting the load (N/25 mm) versus percent extension for an unsupported projection layer and two different body facing materials.

FIG. 45 illustrates the load (N/25 mm) versus percent extension for the unsupported projection layer and the two body facing materials tested.

Table 14 provides a summary of the load versus percent extension for the unsupported projection layer and the two body facing materials tested.

TABLE 14

Load (N/25 mm) vs. % Extension at Various Loads

| Load | % Extension | | |
|---|---|---|---|
| (Newton/25 mm width) | P | A | C |
| 0 | 0 | 0 | 0 |
| 2.0 | 14 | 1.9 | 5.4 |
| 4.0 | 23 | 3.2 | 8.8 |
| 6.0 | 28 | 4.7 | 13 |

As illustrated in FIG. 45 and as summarized in Table 14, at a given load, the percent elongation of a dual layer body facing material is less than that of a single layer unsupported projection layer. This demonstrates the benefit of incorporating a support layer into a body facing material to provide support to the projection layer of the body facing material. The dual layer body facing material can have an improved resistance to stretching and maintenance of the height of the projections of the body facing material.

Tensile Force Versus Percent Tensile Strain Test Method
1. Use "freeze off" spray to carefully remove the unsupported projection layer or the body facing material with projections from an absorbent composite.
2. Once the unsupported projection layer or body facing material is removed from the absorbent composite, a 25 mm wide by 150 mm long test sample is cut from the unsupported projection layer or body facing material. The length direction of the test sample is the machine direction of the unsupported projection layer or body facing material and absorbent composite.
3. The test sample is clamped between two jaws of the Load vs Percent Extension test equipment (Model: Alliance RT/1 manufactured by MTS System Corporation, a business having a location in Eden Prairie, Minn., U.S.A.) The initial separation between the two jaws is 125 mm
4. The upper jaw is activated to travel away from the lower jaw at a speed of 3.75 cm/min
5. The upper jaw travels about 38 mm before it is stopped.
6. The percent extension versus load curve is recorded on a computer using TestWorks Version 4 software program provided by MTS.
7. A total of three samples are tested for each test sample to obtain an average curve.

Example 11

The intake and rewet of feminine hygiene absorbent composites and commercially available products utilizing simulated menses can be evaluated as described herein.

In this example, three different body facing materials and two commercially available feminine hygiene products were evaluated for their intake and rewet capabilities. Each experimental feminine pad absorbent composite was assembled by hand according to Table 15 below, utilizing the corresponding material descriptions listed in Table 3: Material Descriptions above. Each body facing material and absorbent composite was analyzed according to the Intake/Rewet test method described herein utilizing menses simulant as described herein. With regards to the absorbent composites assembled, the body facing material is adhesively bonded to the body facing surface of the acquisition layer. The adhesive is applied, in a 1.5 to 2 inch width to the center portion of the body facing material, to the support layer of the body facing material (i.e., non-projection side of the body facing material). The garment facing surface of the acquisition layer is adhesively bonded to the absorbent body.

TABLE 15

Experimental Feminine Pad Absorbent Composite Test Codes:

| Test Code | Body Facing Material | Acquisition Layer | Absorbent Body |
|---|---|---|---|
| 1 | B | S | T |
| 2 | C | S | T |
| 3 | U | S | T |

Test Codes 4 and 5 are material codes, Q and R, respectively, as described in Table 3: Material Descriptions above. Each of the commercially available products was analyzed according to the Intake/Rewet test method described herein utilizing menses simulant as described herein.

Table 16 provides a summary of the intake and rewet values for the three body facing materials tested and the two commercially available products tested.

TABLE 16

Intake/Rewet Values:

| | | Test Code | | | | |
|---|---|---|---|---|---|---|
| | | 1 | 2 | 3 | 4 | 5 |
| Intake 1 | Avg | 7.59 | 7.08 | 7.68 | 11.09 | 8.56 |
| | Std | 0.3 | 0.34 | 0.34 | 0.67 | 0.59 |
| Intake 2 | Avg | 14.46 | 10.79 | 11.22 | 31.4 | 21.07 |
| | Std | 1.25 | 0.61 | 0.99 | 3.69 | 3.28 |
| Rewet | Avg | 1.65 | 1.56 | 1.63 | 1.66 | 1.95 |
| | Std | 0.07 | 0.08 | 0.06 | 0.05 | 0.06 |

As summarized in Table 16, the second intake time is less than and therefore faster than the commercially available products. This indicates that the body facing material can capture the fluid faster and can decrease the probability of leakage caused by slow fluid capture by the commercially available products. Typically, intake times are improved at the expense of rewet amount. In this case, while the second intake time is faster with the body facing materials, no increase in rewet amount compared to the commercial products is found.

Menses Simulant Preparation:
The menstrual simulant was prepared using porcine blood and egg white from chicken eggs per the following protocol as published in IP.com on Aug. 6, 2010, reference number IPCOM000198395D. This procedure is a batch process that can produce 2.5 L to 4.0 L of fluid. Menses simulant can be purchased from Cocalico Biologicals, Reamstown Pa.

1. Apparatus:
   1.1. Stirrer and stand
   1.2. Stirring rod with 3" diameter flat blade
   1.3. 3 L reaction vessel
   1.4. Plastic strainer
   1.5. Preparatory centrifuge
   1.6. Hematocrit centrifuge
   1.7. Motorized pipettor
2. Materials and supplies:
   2.1 Fresh jumbo chicken eggs
   2.2 Defibrinated porcine blood
   2.3 Defibrinated porcine plasma
   2.4 Parafilm
   2.5 Micro-hematocrit capillary tubes
   2.6 Critoseal sealant (Oxford Labware)
3. Protocol
   3.1. Collection, separation and processing of thick egg white
      3.1.1. Using fresh, jumbo chicken eggs, one at a time, remove the egg from its shell and place in a yolk-separator set on the rim of a 250 mL beaker. Allow the egg white to pass through the yolk-separator and into the 250 mL beaker, and then discard the yolk. Remove any chalazae from the egg white using a rounded soup spoon and transfer the egg white to a 600 mL beaker. This process is continued until 12 eggs have been processed and collected in the 600 mL beaker.
      3.1.2. Transfer the egg whites from 12 eggs into the plastic filter/collection bowl and allow the thin egg white to drain through the filter into the collection bowl for 10 minutes. Tip the filter bowl from side to side every 3-4 minutes during this process to facilitate drainage of the thin egg white. Discard the thin egg white.
      3.1.3. Place a clean collection bowl under the filter bowl containing the retained thick egg white and, using the back of a soup spoon, press the thick egg white through the openings in the filter bowl and into the collection bowl.
      3.1.4. Place the processed thick egg white in a 1.5 or 2 L beaker
      3.1.5. Repeat the processing of 12 eggs until sufficient thick egg white has been collected.
   3.2. Preparation of porcine blood plasma
      3.2.1. Pour porcine blood into 750 mL plastic centrifuge buckets (maximum 500 mL in each bucket) and place buckets in carriers. Centrifuge buckets must be filled in pairs.
      3.2.2. Carefully balance pairs of buckets, in their carriers, on a beam balance by transferring blood from one bucket to the other. Then place buckets and carriers in the centrifuge.
      3.2.3. Centrifuge the balanced buckets at 3500 rpm for 60 minutes at room temperature.
      3.2.4. Carefully remove plasma from each bucket using a 10 mL pipette and a pipette motor and place in a 1 L beaker. Keep tip of pipette at least 5 mm above the packed red blood cell layer to avoid aspirating the red cells and contaminating the plasma.
      3.2.5. Alternatively, defibrinated porcine plasma may be purchased from Cocalico Biologicals, Inc.
         3.2.5.1. If purchased plasma is used, place the plasma in 750 mL centrifuge buckets and balance the buckets, as described above.
         3.2.5.2. Centrifuge the plasma at 3500 rpm for 30 minutes at room temperature. This procedure will separate the plasma from any precipitate that may be present.
         3.2.5.3. Decant the clarified plasma by carefully pouring the fluid into a 1 L beaker. Preparation of packed porcine red blood cells
      3.2.6. Follow the procedure above for preparation of porcine blood plasma.
      3.2.7. Remove the remaining plasma supernatant from each bucket containing packed red blood cells and a thin layer of plasma using a 10 mL pipette as described in section 4.2.4 above.
      3.2.8. A thin buff-colored layer of white cells (known as the "buffy coat") remains at the top of the packed red cell layer. Remove this layer by aspirating it into a 3 mL plastic Pasteur pipette while drawing the tip of the pipette across the surface of the red cell layer.
      3.2.9. Transfer the contents of the centrifuge buckets to a 1 L beaker and mix gently with a rubber spatula.
      3.2.10. Remove a small aliquot of the mixed pack red cell and measure the hematocrit, in triplicate, as described in section 5 below.
   3.3. Blending of processed egg white and blood plasma
      3.3.1. Pour a volume of processed thick egg white into the 3 L-reaction vessel. This volume may be between 1000 mL and 1600 mL.
      3.3.2. Pour a volume of porcine blood plasma into the 3 L-reaction vessel. This volume must be equal to 75% of the volume of thick egg white.
      3.3.3. Stir the mixture briefly (10-20 seconds) with a large rubber spatula.
      3.3.4. Lower the 3" diameter flat, SS stirring disc into the mixture. The stirring disc must be centered in the reaction vessel and 5 inches below the surface of the mixture.
      3.3.5. Turn on the stirrer, adjust the stirrer speed to 1000 rpm, and stir the mixture for 1 hour.
      3.3.6. Stop the stirrer and remove the stirring rod and disc.
      3.3.7. Using a rubber spatula, remove any foam that may have formed on the surface of the mixture during stirring.
      3.3.8. Transfer the blended mixture to a 3-4 L beaker.
   3.4. Addition and mixing of packed red cell
      3.4.1. Measure the hematocrit of the packed red cells using the procedure described in section 5 below.
      3.4.2. Calculate the amount of packed red cells to be added to the egg white/plasma mixture using one of the following equations.
         3.4.2.1. If the packed cells are to be added by volume, use the following equation to calculate that volume:

$$pRBC volume = \frac{0.3 \times (eggwhite/plasma) volume}{Hematocrit(pRBC) - 0.3}$$

3.4.2.2. If the packed cells are to be added by weight, use the following equation to calculate that weight:

$$pRBC grams = \frac{0.321 \times (eggwhite/plasma) grams}{Hematocrit(pRBC) - 0.3}$$

3.4.3. Add the calculated amount of packed red blood cells to the egg white/plasma mixture and stir with a rubber spatula for 1 minute.

3.5. Filling of Fenwal storage bags.

3.5.1. Cut the access tubing on the Fenwal storage bags to a length of approximately 24 inches.

3.5.2. Attach the cut end of the storage bag tubing to the outflow of a large plastic beaker.

3.5.3. Pour the required fluid volume into the funnel and allow the fluid to fill the bag by gravity flow.

3.5.4. Using a large syringe, remove all air bubbles from the bag.

3.5.5. Measure the hematocrit of the contents of the bag using the procedure described in section 5 below.

3.5.6. Seal the bag by tying a double knot in the tubing about 2 to 3 inches from the bag, or use Fenwal metal tubing clips, and cut off the excess tubing.

4. Hematocrit testing:

4.1. Insure that the blood or simulant to be tested is at room temperature and well mixed.

4.2. Place a small aliquot (0.1 to 0.2 mL) of the fluid to be tested in a small cup or on a piece of Parafilm.

4.3. Draw the fluid up into a Hematocrit tube, leaving about 15 mm of air at the top of the tube.

4.4. Hold your finger on the top of the Hematocrit tube (to prevent the flow of fluid out of the tube) and seal the tube by placing the bottom of the tube in the Hemoseal stand.

4.5. Place the filled, sealed tubes in the Hematocrit Centrifuge with the sealed end facing away from the center of the centrifuge.

4.6. Centrifuge the tubes for 3 minutes.

4.7. Read the hematocrit of each tube using the built-in hematocrit reader.

Intake/Rewet Test Method

Figure 46A:
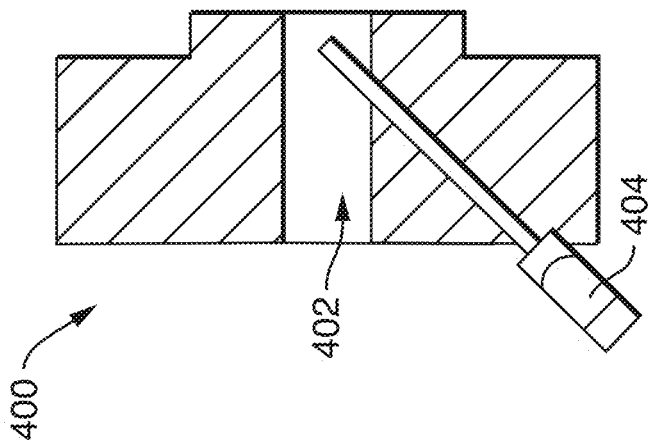
FIG. 46A is a cross-sectional view of the rate block of FIG. 46.
Figure 46:
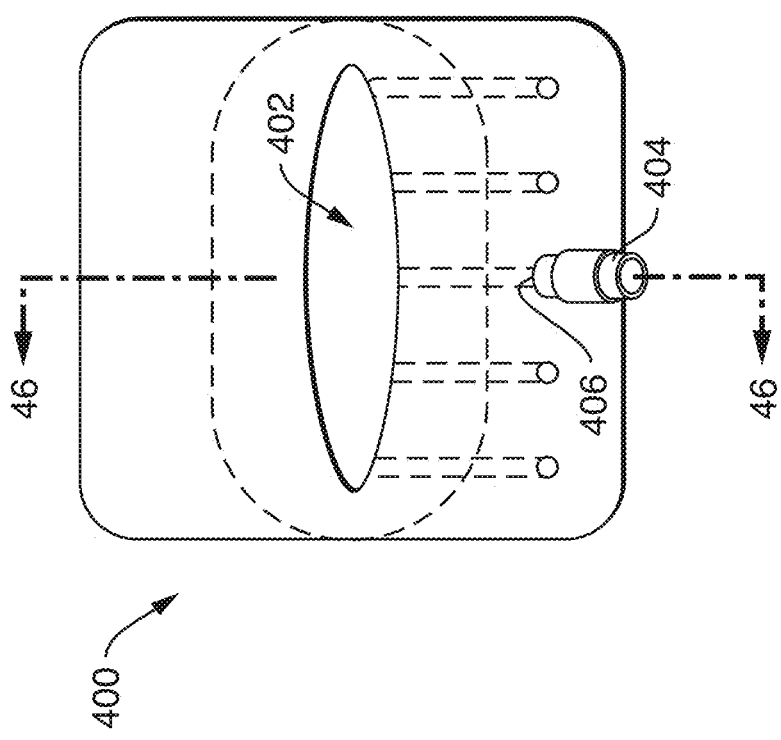
FIG. 46 is a top down view of an embodiment of a rate block.

The prepared absorbent composites are laid flat on the testing surface. The top of the absorbent composite is then insulted with a first 2 mL gush of room temperature menses simulant (24 mL/min), followed by a 2 minute, 55 second pause, followed by a 3 mL trickle (0.3 mL/min), and then a second 2 mL gush (24 mL/min). The menses simulant is administered through a cannula 404 in a rate block 400 that is placed at the center crotch of the test product. The rate block 400 is made of a non-electrostatic material called Ertalyte. This material allows simulant to pass along its surface without attracting it. The opening 402 is oval shaped and measures 60 mm long (L3)×13 mm wide (W3) with its ends 404 consisting of 4-mm diameter half circles. As shown in FIG. 46 and FIG. 46A, the cannula 404 is inserted through a small center hole 406 offset in the top of the rate block 400 to allow the cannula 404 to be at an angle with respect to the oval opening 402 and to allow the fluid to be applied through the center of the rate block 400 oval opening 402.

The first and second Intake values are measured with a stopwatch during the first and second 2 mL gush, respectively. The stopwatch is started when the gush starts and is stopped when the fluid from the gush is completely absorbed by the absorbent composite. Rewet values are determined after complete penetration of the second 2 mL gush. The measure rewet values, two pieces of blotting paper (Verigood grade, white, 300 g/m², 48.26 by 60.96 cm stock, 250 sheets per ream, Georgia-Pacific Corp. part number 411-01-12, or equivalent) are placed to cover the insulted absorbent composite. A foot that covers the absorbent composite is lowered against the blotter paper to create a pressure load of 1.0 psi for 3 minutes and the amount of fluid transferred to the blotting paper is determined gravimetrically. The pressure used in this test has been shown to correlate well with the pressure applied to feminine hygiene pads during use.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   an outer cover;
   a body facing material; and
   an absorbent body disposed between the outer cover and the body facing material,
   wherein the body facing material comprises:
   a first layer comprising a first plurality of fibers and having a first surface and an opposed second surface;
   a second layer comprising a second plurality of fibers and having an inner surface and an opposed outer surface, wherein portions of the second surface of the first layer are in contact with the inner surface of the second layer, wherein at least a portion of the first plurality of fibers or the second plurality of fibers are fluid-entangled with at least a portion of the other of the first plurality of fibers or the second plurality of fibers;
   a plurality of hollow projections formed from at least a portion of the second plurality of fibers, the plurality of hollow projections extending from the outer surface of the second layer in a direction away from the first layer;
   a plurality of apertures within the second layer; and
   a land area, wherein the plurality of hollow projections are surrounded by the land area.

2. The absorbent article of claim 1, wherein the plurality of apertures within the second layer extend from the inner surface to the outer surface.

3. The absorbent article of claim 1, further comprising a plurality of apertures within the first layer.

4. The absorbent article of claim 3, wherein:
the plurality of apertures within the second layer extend from the inner surface to the outer surface, and
the plurality of apertures within the first layer extend from the first surface to the second surface.

5. The absorbent article of claim 3, wherein at least one of the plurality of apertures within the second layer aligns with at least one of the plurality of apertures within the first layer.

6. The absorbent article of claim 1, wherein the body facing material has a basis weight of between about 25 grams per square meter and about 100 grams per square meter.

7. The absorbent article of claim 1, wherein a portion of the plurality of apertures within the second layer are located in the plurality of hollow projections.

8. The absorbent article of claim 7, wherein the portion of the plurality of apertures within the second layer are located in side walls of the plurality of hollow projections.

9. An absorbent article comprising:
an outer cover;
a body facing material; and
an absorbent body disposed between the outer cover and the body facing material,
wherein the body facing material comprises:
a first layer comprising a plurality of fibers and having a first surface and an opposed second surface;
a second layer comprising a plurality of fibers and having an inner surface and an opposed outer surface, wherein portions of the second surface of the first layer are in contact with the inner surface of the second layer;
a plurality of hollow projections formed from a first portion of the plurality of fibers of the second layer, the plurality of hollow projections extending from the outer surface of the second layer in a direction away from the first layer;
a plurality of apertures within the second layer; and
a and area, wherein the plurality of hollow projections are surrounded by the land area,
wherein a second portion of the plurality of fibers of the second layer are fluid-entangled with at least a portion of the plurality of fibers of the First layer, the second portion of the plurality of fibers of the second layer being different from the first portion of the plurality of fibers of the second layer.

10. The absorbent article of claim 9, wherein the plurality of apertures within the second layer extend from the inner surface to the outer surface.

11. The absorbent article of claim 9, further comprising a plurality of apertures within the first layer.

12. The absorbent article of claim 11, wherein:
the plurality of apertures within the second layer extend from the inner surface to the outer surface, and
the plurality of apertures within the first layer extend from the first surface to the second surface.

13. The absorbent article of claim 11, wherein at least one of the plurality of apertures within the second layer aligns with at least one of the plurality of apertures within the first layer.

14. The absorbent article of claim 9, wherein the second layer has less fiber-to-fiber bonding or fiber entanglement than the first layer.

15. An absorbent article comprising:
an outer cover;
a body facing material; and
an absorbent body disposed between the outer cover and the body facing material,
wherein the body facing material comprises:
a first layer comprising a first plurality of fibers and having a first surface and an opposed second surface;
a second layer comprising a second plurality of fibers and having an inner surface and an opposed outer surface, wherein portions of the second surface of the first layer are in contact with the inner surface of the second layer, wherein at least some of the first plurality of fibers or the second plurality of fibers are fluid-entangled with at least some of the other of the first plurality of fibers or the second plurality of fibers; and
a plurality of hollow projections formed from at least a portion of the second plurality of fibers, the plurality of projections extending from the outer surface of the second layer in a direction away from the first layer; and
a plurality of apertures within the second layer,
wherein each of the plurality of hollow projections has a round shape when the laminate web is viewed from a top view.

16. The absorbent article of claim 15, further comprising a plurality of apertures within the first layer.

17. The absorbent article of claim 16, wherein:
the plurality of apertures within the second layer extend from the inner surface to the outer surface, and
the plurality of apertures within the first layer extend from the first surface to the second surface.

* * * * *